(12) United States Patent
Jungmichel et al.

(10) Patent No.: US 12,161,673 B2
(45) Date of Patent: Dec. 10, 2024

(54) MAGE-A4 PEPTIDE DUAL T CELL ENGAGERS

(71) Applicant: CDR-LIFE AG, Schlieren (CH)

(72) Inventors: Stephanie Jungmichel, Zürich (CH); Fabian Bert Scheifele, Mägenwil-Aargau (CH); Anna Maria Sobieraj, Zürich (CH); Philipp Robert Richle, Zürich (CH); Hannes Merten, Zürich (CH); Leonardo Borras, Birmensdorf (CH); Christian Valdemar Vinge Leisner, Thalwil (CH)

(73) Assignee: CDR-LIFE AG, Horgen (CH)

( * ) Notice: Subject to any disclaimer, the term of this patent is extended or adjusted under 35 U.S.C. 154(b) by 0 days.

(21) Appl. No.: 18/466,103

(22) Filed: Sep. 13, 2023

(65) Prior Publication Data

US 2024/0091262 A1    Mar. 21, 2024

Related U.S. Application Data

(60) Provisional application No. 63/406,475, filed on Sep. 14, 2022.

(51) Int. Cl.
| | |
|---|---|
| *C07K 16/30* | (2006.01) |
| *A61K 35/17* | (2015.01) |
| *A61K 39/00* | (2006.01) |
| *A61K 39/395* | (2006.01) |
| *C07K 16/38* | (2006.01) |
| *C12N 15/63* | (2006.01) |
| *C07K 16/28* | (2006.01) |

(52) U.S. Cl.
CPC .......... *A61K 35/17* (2013.01); *A61K 39/4611* (2023.05); *A61K 39/4631* (2023.05); *A61K 39/464499* (2023.05); *C07K 16/30* (2013.01); *C12N 15/63* (2013.01); *A61K 2239/29* (2023.05); *A61K 2239/57* (2023.05); *C07K 16/2809* (2013.01); *C07K 16/2833* (2013.01); *C07K 2317/622* (2013.01)

(58) Field of Classification Search
CPC ................ C07K 16/2833; C07K 16/30; C07K 14/70539; A61K 2039/505; A61K 39/001186; A61K 2239/29
See application file for complete search history.

(56) References Cited

U.S. PATENT DOCUMENTS

| | | | |
|---|---|---|---|
| 6,710,172 B1 | 3/2004 | Chaux et al. | |
| 7,199,231 B1 | 4/2007 | Guagler et al. | |
| 7,311,914 B2 | 12/2007 | Zhang et al. | |
| 8,003,770 B2 | 8/2011 | Shiku et al. | |
| 9,802,997 B2 | 10/2017 | Mahr et al. | |
| 10,738,132 B2 * | 8/2020 | Desjarlais | C07K 16/2896 |
| 10,859,566 B2 | 12/2020 | Flechtner et al. | |
| 11,098,115 B2 | 8/2021 | Willemsen et al. | |
| 11,286,289 B2 | 3/2022 | Tribble et al. | |
| 11,497,768 B2 | 11/2022 | Shiku et al. | |
| 11,505,590 B2 | 11/2022 | Hayes et al. | |
| 11,912,771 B2 | 2/2024 | Sobieraj et al. | |
| 2005/0033031 A1 | 2/2005 | Couto | |
| 2011/0219464 A1 | 9/2011 | Domon et al. | |
| 2018/0088140 A1 | 3/2018 | Grabert et al. | |
| 2018/0118827 A1 * | 5/2018 | Moore | C07K 16/2809 |
| 2019/0092834 A1 | 3/2019 | Hayes et al. | |
| 2019/0144521 A1 | 5/2019 | Tribble et al. | |
| 2020/0400674 A1 | 12/2020 | Williams | |
| 2020/0408769 A1 | 12/2020 | Kumaki et al. | |
| 2021/0032361 A1 | 2/2021 | Hutt et al. | |
| 2021/0032370 A1 | 2/2021 | Pszolla et al. | |
| 2021/0061914 A1 | 3/2021 | Jooss et al. | |
| 2021/0147550 A1 | 5/2021 | Jooss et al. | |
| 2021/0230278 A1 | 7/2021 | Weinzierl et al. | |
| 2021/0238543 A1 | 8/2021 | Renes et al. | |
| 2022/0119479 A1 | 4/2022 | Conroy et al. | |
| 2022/0324939 A1 | 10/2022 | Bowerman et al. | |
| 2022/0340894 A1 | 10/2022 | Sobieraj et al. | |
| 2022/0380472 A1 | 12/2022 | Sobieraj et al. | |
| 2023/0159612 A1 | 5/2023 | Ellinger et al. | |

FOREIGN PATENT DOCUMENTS

| | | |
|---|---|---|
| CN | 108866098 A | 11/2018 |
| CN | 110333352 A | 10/2019 |
| WO | WO 2009/155725 A1 | 12/2003 |
| WO | WO 2004/016740 A2 | 2/2004 |
| WO | WO 2005/016950 A1 | 2/2005 |
| WO | WO 2007/101661 A1 | 9/2007 |
| WO | WO 2008/110348 A1 | 9/2008 |

(Continued)

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Murphy et al., Journal of Immunological Methods, vol. 463, p. 127-133, 2018.*
AACR 2021—Abstract LB167: A powerful discovery platform for the generation of high affinity and specificity TCR-like antibodies for immunotherapies in solid tumor, Jul. 1, 2021, Proceedings: AACR Annual Meeting 2021, 81(13): Supplement.
AACR 2022—Abstract 2891: Enhanced anti-tumor responses with a novel dual pMHC T-cell engager bispecific antibody, Jun. 15, 2022, Proceedings: AACR Annual Meeting 2022, 82(12): Supplement.

(Continued)

*Primary Examiner* — Hong Sang
(74) *Attorney, Agent, or Firm* — LATHROP GPM LLP; James H. Velema, Esq.; Michael J. Spellberg, Esq.

(57) ABSTRACT

Described herein are antigen binding proteins with specificity to Melanoma-Associated Antigen A4 (MAGE-A4) peptide-MHC (pMHC). Also described are multispecific antigen binding proteins comprising an antigen binding domain with specificity to CD3, and at least one MAGE-A4 pMHC antigen binding domain. Methods of treating cancer with the same are also described.

40 Claims, 42 Drawing Sheets

Specification includes a Sequence Listing.

(56) References Cited

FOREIGN PATENT DOCUMENTS

| | | |
|---|---|---|
| WO | WO 2008/144757 A1 | 11/2008 |
| WO | WO 2009/000098 A2 | 12/2008 |
| WO | WO 2009/000099 A2 | 12/2008 |
| WO | WO 2009/155726 A1 | 12/2009 |
| WO | WO 2016/086196 A2 | 6/2016 |
| WO | WO 2016/199140 A1 | 12/2016 |
| WO | WO 2016/199141 A1 | 12/2016 |
| WO | WO 2017/175006 A1 | 10/2017 |
| WO | WO 2017/201493 A1 | 11/2017 |
| WO | WO 2018/178307 A1 | 10/2018 |
| WO | WO 2019/012138 A1 | 1/2019 |
| WO | WO 2019/171064 A1 | 9/2019 |
| WO | WO 2020/109616 A1 | 6/2020 |
| WO | WO 2020/243315 A1 | 12/2020 |
| WO | WO 2021/016585 A1 | 1/2021 |
| WO | WO 2021/046316 A2 | 3/2021 |
| WO | WO 2021/112676 A2 | 6/2021 |
| WO | WO 2021/116469 A2 | 6/2021 |
| WO | WO 2021/122875 A1 | 6/2021 |
| WO | WO 2021/216972 A1 | 10/2021 |
| WO | WO 2021/224913 A1 | 11/2021 |
| WO | WO 2021/229234 A1 | 11/2021 |
| WO | WO 2021/229235 A1 | 11/2021 |
| WO | WO 2022/105924 A1 | 5/2022 |
| WO | WO 2022/190007 A1 | 9/2022 |
| WO | WO 2022/190009 A1 | 9/2022 |
| WO | WO 2022/235662 A1 | 11/2022 |
| WO | WO 2022/262678 A1 | 12/2022 |
| WO | WO 2023/011268 A1 | 2/2023 |
| WO | WO 2023/011273 A1 | 2/2023 |
| WO | WO 2023/014809 A2 | 2/2023 |
| WO | WO 2023/044402 A1 | 3/2023 |

OTHER PUBLICATIONS

Al-Lazikani et al., "Standard conformations for the canonical structures of immunoglobulins", JMB, 1997, 273(4): 927-948.

Almagro et al., "Progress and Challenges in the Design and Clinical Development of Antibodies for Cancer Therapy", Front Immunol., Jan. 2018, 8: 1751.

Arimilli et al., "Refolding and reconstitution of functionally active complexes of human leukocyte antigen DR2 and myelin basic protein peptide from recombinant alpha and beta polypeptide chains", J Biol Chem., Jan. 13, 1995, 270(2): 971-977.

Augsberger et al., "Targeting intracellular WT1 in AML with a novel RMF-peptide-MHC-specific T-cell bispecific antibody", Blood, Immunobiology and Immuotherapy, Dec. 23, 2021, 138(25): 2655-2669.

AYYAR rabbit scFv, Appl Microbiol Biotechnol., Dec. 24, 2014, 99(6): 2693-2703.

Bird et al., "Single-chain antigen-binding proteins", Science, 1988, 242(4877): 423-426.

Brown et al., "Tolerance of single, but not multiple, amino acid replacements in antibody VH CDR 2: a means of minimizing B cell wastage from somatic hypermutation?", J. Immunol., May 1996, 156(9): 3285-3291.

Chaudhary et al., "A rapid method of cloning functional variable-region antibody genes in *Escherichia coli* as single-chain immunotoxins", PNAS, 1990, 87(3): 1066-1070.

Chiu et al., "Antibody Structure and Function: The Basis for Engineering Therapeutics", Antibodies (Basel), Dec. 2019, 8(4): 55.

Cooper et al., "T-cell clones can be rendered specific for CD19: toward the selective augmentation of the graft-versus-B-lineage leukemia effect", Blood, 2003, 101(4): 1637-1644.

Davari et al., "Development of a CD8 co-receptor independent T-cell receptor specific for tumor-associated antigen MAGE-A4 for next generation T-cell-based immunotherapy", Journal for Immuno Therapy of Cancer, Feb. 17, 2021, 9(3): e002035.

Davis et al., "Ligand recognition by alpha beta T cell receptors", Annu Rev Immunol., 1998, 16: 523-544.

Gertz et al., "Accuracy and coverage assessment of *Oryctolagus cuniculus*(rabbit) genes encoding immunoglobulins in the whole genome sequence assembly (OryCun2.0) and localization of theIGHlocus to chromosome 20", Immunogenetics, Aug. 8, 2013, 65(10): 749-762.

Grossman et al., "Toward a Shared Vision for Cancer Genomic Data", N Engl J Med., 2016, 375: 1109-1112.

Gupta, "Cancer Associated Testis Antigens", Proteomics of Spermatogenesis, Jan. 2005, 777-794.

Heeley et al., "Mutations Flanking The Polyglutamine Repeat In The Modulatory Domain Of Rat Glucocorticoid Receptor Lead To An Increase In Affinity For Hormone", Endocr Res, 2002, 28(3): 217-229.

Honegger et al., "Yet another numbering scheme for immunoglobulin variable domains: an automatic modeling and analysis tool," J Mol Biol, Jun. 8, 2001; 309(3): 657-670.

Hossler, "Optimal and consistent protein glycosylation in mammalian cell culture", Glycobiology, Jun. 3, 2009, 19(9): 936-949.

International Search Report and Written Opinion for PCT International Patent Application No. PCT/EP2022/085689, dated Mar. 23, 2023.

International Search Report and Written Opinion for PCT International Patent Application No. PCT/EP2023/075190, dated Jan. 3, 2024.

International Search Report and Written Opinion for PCT International Patent Application No. PCT/IB2022/052117, dated Aug. 1, 2022.

International Search Report and Written Opinion for PCT International Patent Application No. PCT/IB2022/052119, dated Aug. 3, 2022.

Janeway et al., "Immunobiology: The immune system in Health and Disease", 5th edition, 2001.

Jungmichael et al., "Abstract 2891: Enhanced anti-tumor responses with a novel dual pMHC T-cell engager bispecific antibody", Power Presentations—Proffered Abstracts, Jun. 15, 2022, Cancer Res., 2022, 82(Suppl. 12): 2891.

Kim et al., "Hybrid restriction enzymes: zinc finger fusions to Fok I cleavage domain", PNAS, 1996, 93(3): 1156-1160.

Lefranc et al., "IMGT unique numbering for immunoglobulin and T cell receptor variable domains and Ig superfamily V-like domains," Dev Comp Immunol, Jan. 2003, 27(1): 55-77.

Liljeblad et al., "Analysis of agalacto-IgG in rheumatoid arthritis using surface plasmon resonance", Glyco Journ., 2000, 17: 323-329.

Liu et al., "N-terminal glutamate to pyroglutamate conversion in vivo for human IgG2 antibodies", J Biol Chem., Apr. 1, 2011, 286(13): 11211-11217.

Liu et al., "Design of polydactyl zinc-finger proteins for unique addressing within complex genomes", PNAS USA, 1997, 94(11): 5525-5530.

Lydard et al., "Generation of diversity", Immunology, 2011, Section D: Antibodies, 76-85.

MacCallum et al., "Antibody-antigen interactions: Contact analysis and binding site topography", J. Mol. Biol., 1996, 262: 732-745.

Maus et al., "Antibody-modified T cells: CARs take the front seat for hematologic malignancies", Blood, 2014, 123(17): 2625-2635.

Popkov et al., "Rabbit Immune Repertoires as Sources for Therapeutic Monoclonal Antibodies: The Impact of Kappa Allotype-correlated Variation in Cysteine Content on Antibody Libraries Selected by Phage Display", Journal Of Molecular Biology, Jan. 10, 2003, 325(2): 325-335.

Rodenko et al., "Generation of peptide-MHC class I complexes through UV-mediated ligand exchange", Nat. Protoc., 2006, 1(3): 1120-1132.

Roosnek et al., "T cell activation by a bispecific anti-CD3/anti-major histocompatibility complex class I antibody", European Journal of Immunology, Jun. 1990, 20(6): 1393-1396.

Rudikoff et al., "Single amino acid substitution altering antigen-binding specificity", Proc. Natl. Acad. Sci. USA, Mar. 1982, 79(6): 1979-1983.

Rudolph et al., "How TCRs bind MHCs, peptides, and coreceptors", Annu Rev Immunol., 2006, 24: 419-466.

(56) References Cited

OTHER PUBLICATIONS

Saito et al., "High expression of MAGE-A4 and MHC class I antigens in tumor cells and induction of MAGE-A4 immune responses are prognostic markers of CHP-MAGE-A4 cancer vaccine", Vaccine, Oct. 14, 2014, 32(45): 5901-5907.
Sampei et al., "Antibody engineering to generate SKY59, a long-acting anti-C5 recycling antibody", PLOS One, Dec. 2018, 13(12): 1-20.
Sanderson et al., "Preclinical evaluation of an affinity-enhanced MAGE-A4-specific T-cell receptor for adoptive T-cell therapy", Oncoimmunology, Nov. 24, 2019, 9(1): 1682381.
Sang et al., "MAGE-A family: Attractive targets for cancer immunotherapy", Vaccine, Nov. 3, 2011, 29(47), 8496-8500.
Schoonjans et al., "A new model for intermediate molecular weight recombinant bispecific and trispecific antibodies by efficient heterodimerization of single chain variable domains through fusion to a Fab-chain", Biomolecular Engineering, 2001, 17(6): 193-202.
Schoonjans et al., "Fab Chains As an Efficient Heterodimerization Scaffold for the Production of Recombinant Bispecific and Trispecific Antibody Derivatives", J. Immunology, 2000, 165(12): 7050-7057.
Shichijo et al., "Detection of mage-4 protein in lung cancers", 1995, International Journal of Cancer (Pred. Oncol.), 64(3): 158-165.
Tian et al., "CD8+ T Cell Activation Is Governed by TCR-Peptide/MHC Affinity, Not Dissociation Rate", J Immunol., 2007, 179(5): 2952-2960.
U.S. Appl. No. 17/690,089 2022/0340894, filed Mar. 9, 2022 Oct. 27, 2022, Anna Maria Sobieraj, Rabbit-Derived Antigen Binding Protein Nucleic Acid Libraries And Methods Of Making The Same.
U.S. Appl. No. 17/690,526 2022/0380472 U.S. Pat. No. 11,912,771, filed Mar. 9, 2022 Dec. 1, 2022 Feb. 17, 2024, Anna Maria Sobieraj, Mage-A4 Peptide-MHC Antigen Binding Proteins.
U.S. Appl. No. 18/404,536, filed Jan. 4, 2024, Anna Maria Sobieraj, Mage-A4 Peptide-MHC Antigen Binding Proteins.
U.S. Appl. No. 18/466,103, filed Sep. 13, 2023, Stephanie Jungmichael, Mage-A4 Peptide Dual T Cell Engagers.

* cited by examiner

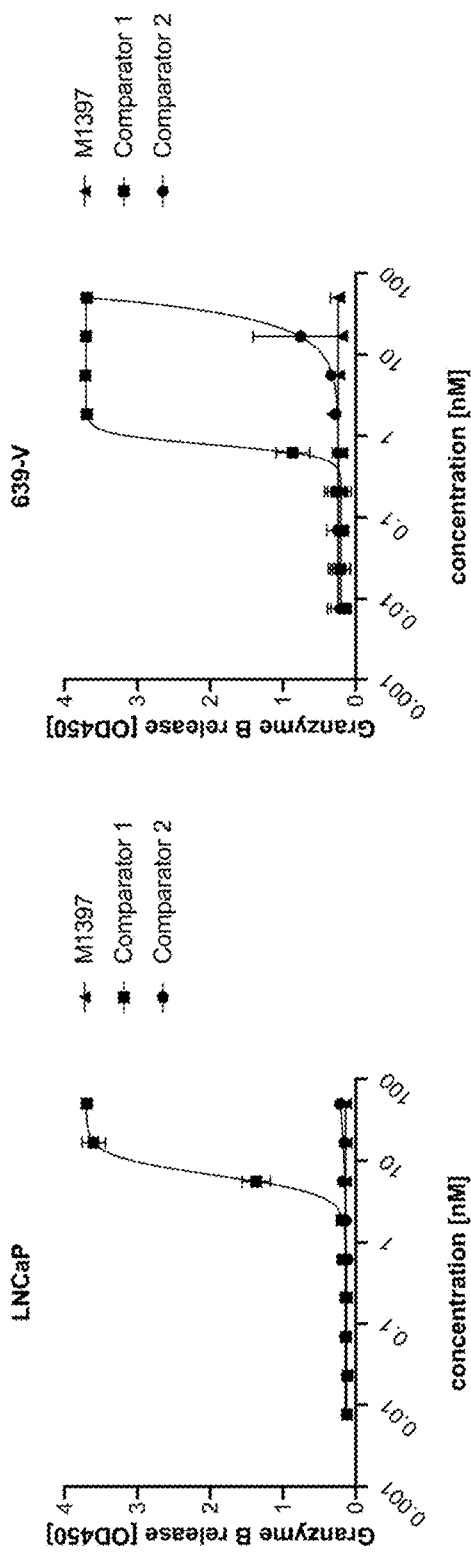
Figure 14E
Figure 14F
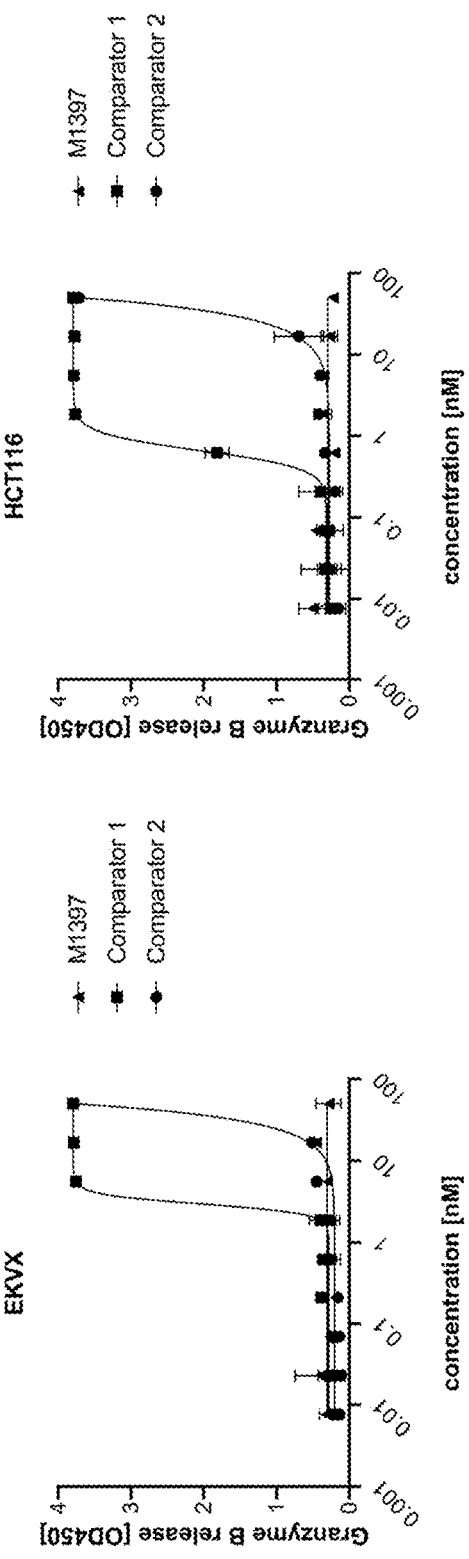
Figure 14G
Figure 14H

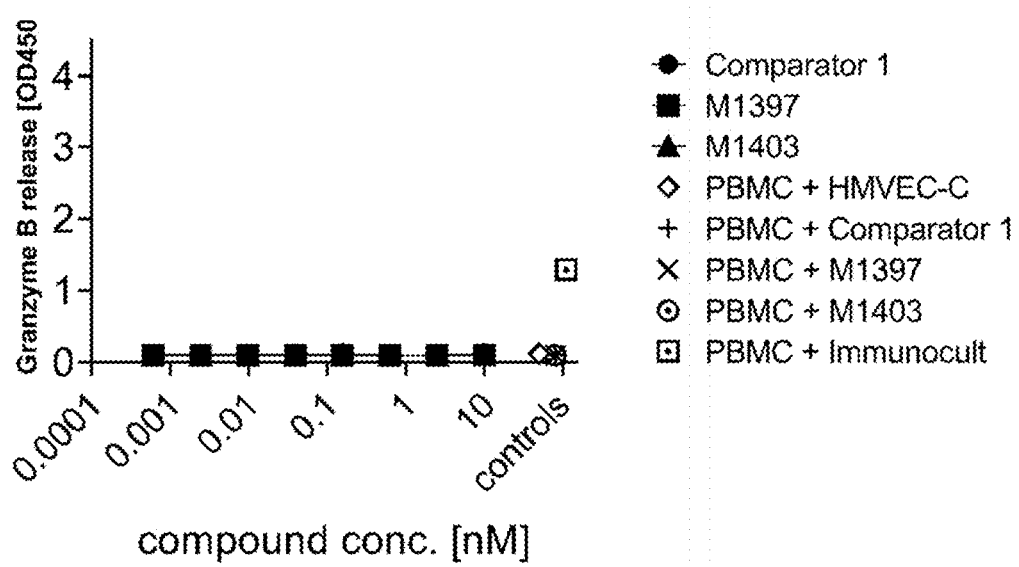
Figure 15A HMVEC-C
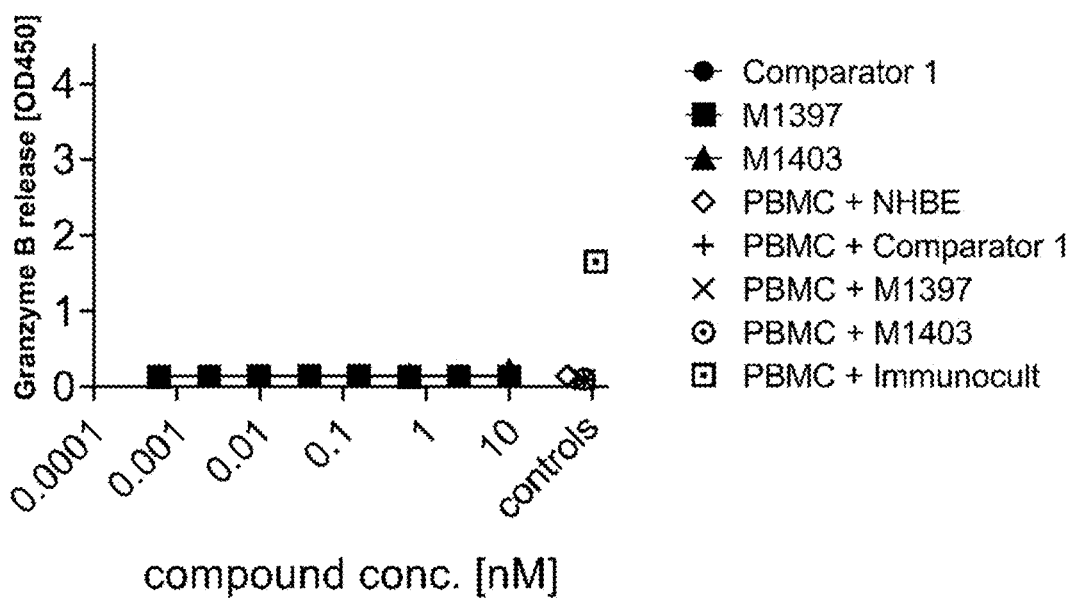
Figure 15B NHBE

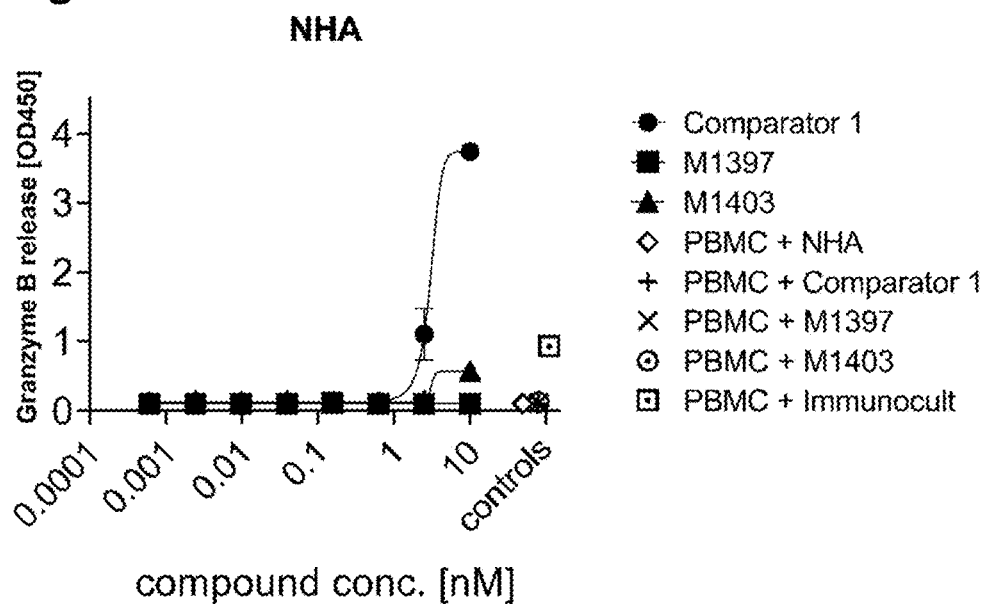

MAGE-A4 PEPTIDE DUAL T CELL ENGAGERS

RELATED APPLICATIONS

This application claims the benefit of U.S. Provisional Application Ser. No. 63/406,475, filed Sep. 14, 2022, the entire disclosure of which is hereby incorporated herein by reference.

SEQUENCE LISTING

The instant application contains a Sequence Listing which has been submitted electronically in XML format and is hereby incorporated by reference in its entirety. Said XML file, created on Sep. 12, 2023, is named 743750_CDR9-010_ST26.xml and is 91,215 bytes in size.

BACKGROUND

Melanoma-Associated Antigen A4 (MAGE-A4) peptide-MHC (pMHC) expression is present in a number of cancers, including non-small cell lung cancer (NSCLC), melanoma, bladder, head and neck, and gastroesophageal cancers (Grossman et al. N Engl J Med. 2016. 375: 1109-1112). Therefore, it represents an attractive target for TCR-based T cell therapy. Unfortunately, TCR molecules possess low affinity for their pMHC targets. Moreover, TCR-based T cell therapies are laborious and costly to develop and use. In contrast, isolated monoclonal antibodies offer substantially higher binding affinities for their target with potentially reduced off-target activity. However, it is difficult to generate monoclonal antibodies against pMHC targets due to the small epitope of the bound peptide in the HLA.

Accordingly, there is a need in the art for novel antigen binding proteins which are suitable as therapeutics and specifically recognize target MAGE-A4 pMHC with high affinity while retaining high specificity (i.e., low to no off-target effects on healthy tissue), have favorable drug-like properties and can be produced in sufficient quantity and quality at reasonable costs.

SUMMARY

The present disclosure relates to antigen binding proteins and multispecific antigen binding proteins which specifically bind to Melanoma-Associated Antigen A4 (MAGE-A4) peptide-MHC (pMHC). The present antigen binding proteins and multispecific antigen binding proteins comprise enhanced binding affinity to the target MAGE-A4 pMHC and/or enhanced stability, with low off-target binding to non-target MAGE-A4 pMHC or other molecules. The multispecific antigen binding proteins may further comprise a Fab domain which specifically binds to a cell surface protein of an immune cell (e.g., CD3), the Fab domain comprising a heavy chain and a light chain; at least a first pMHC binding domain operably linked to the heavy chain, wherein the first pMHC binding domain binds to first target peptide-MHC (pMHC) complex; and c) at least a second pMHC binding domain operably linked to the light chain, wherein the second pMHC binding domain binds to a second pMHC complex. Bivalent targeting of pMHCs with the bispecific antigen binding proteins of the invention results in increased cancer cell killing compared to their monovalent bispecific counterparts, while the overall specificity against cells bearing the same HLA but not expressing the target protein is not substantially affected.

Preferably, the antigen binding proteins of the invention lack an Fc domain and are therefore not recognized through Fc-receptors on effector cells, such as the Fc-receptor FcγRIII on macrophages and activated neutrophils, or inhibiting receptors such as FcγRIIb, and on FcγRIIa complexes on non-cytotoxic cells such as platelets and B-cells. For bispecific T-cell engagers, Fc-mediated immune functions are unwanted to avoid antigen-independent cytokine release syndrome (CRS) due to crosslinking of CD3 and Fcγ receptors followed by nonspecific activation of immune cells. Rather, the Fab domain of the antigen binding protein serves as a specific heterodimerization scaffold to which the additional pMHC binding domains are linked. The natural and efficient heterodimerization properties of the heavy chain (Fd fragment) and light chain (L) of a Fab fragment makes the Fab fragment a useful scaffold. Additional binding domains may be in several different formats, including, but not limited to, another Fab domain, an scFv, or an sdAb. Moreover, in certain contexts, an Fc-containing antigen binding protein may be disadvantageous due to increased half-life. An extended half-life may lead to increased toxicity from, among other things, excess cytokine release from immune cells. The extended half-life may also promote T cell exhaustion. The antigen binding proteins of the disclosure lacking an Fc domain may possess reduced cytotoxicity in part due to a shorter half-life relative to an Fc-containing antigen binding protein.

Further to being highly specific for their target, the antigen binding proteins of the invention demonstrate favorable drug-like properties, such as intrinsic stability and/or general physical and chemical stability.

In one aspect, the disclosure provides an antigen binding protein which specifically binds to Melanoma-Associated Antigen A4 (MAGE-A4) peptide-MHC (pMHC), comprising: (i) an antibody heavy chain variable (VH) domain comprising an amino acid sequence that is at least about 90%, 95%, 96%, 97%, 98% or 100% identical to the amino acid sequence of SEQ ID NO: 10, and an antibody light chain variable (VL) domain comprising an amino acid sequence that is at least about 90%, 95%, 96%, 97%, 98% or 100% identical to the amino acid sequence of SEQ ID NO: 15; (ii) a VH domain comprising an amino acid sequence that is at least about 90%, 95%, 96%, 97%, 98% or 100% identical to the amino acid sequence of SEQ ID NO: 20, and a VL domain comprising an amino acid sequence that is at least about 90%, 95%, 96%, 97%, 98% or 100% identical to the amino acid sequence of SEQ ID NO: 25; (iii) a VH domain comprising an amino acid sequence that is at least about 90%, 95%, 96%, 97%, 98% or 100% identical to the amino acid sequence of SEQ ID NO: 30, wherein the VH domain comprises a C amino acid at position 44 of SEQ ID NO: 30, and a VL domain comprising an amino acid sequence that is at least about 90%, 95%, 96%, 97%, 98% or 100% identical to the amino acid sequence of SEQ ID NO: 35, wherein the VL domain comprises a C amino acid at position 102 of SEQ ID NO: 35; or (iv) a VH domain comprising an amino acid sequence that is at least about 90%, 95%, 96%, 97%, 98% or 100% identical to the amino acid sequence of SEQ ID NO: 40, wherein the VH domain comprises a Y amino acid at position 47, a R amino acid at position 71, and a N amino acid at position 73 of SEQ ID NO: 40, and a VL domain comprising an amino acid sequence that is at least about 90%, 95%, 96%, 97%, 98% or 100% identical to the amino acid sequence of SEQ ID NO: 45

In certain embodiments, the MAGE-A4 pMHC complex is a GVYDGREHTV (SEQ ID NO: 3) HLA-A*02 complex.

In certain embodiments, the MAGE-A4 pMHC complex is a GVYDGREHTV (SEQ ID NO: 3) HLA-A*02:01 complex.

In certain embodiments, the antigen binding protein remains at least 94% monomeric at a concentration of about 1 mg/mL (e.g., 0.90 to 1.10 mg/mL) to about 10 mg/mL (e.g., 9.9 to 10.1 mg/mL) during storage at 4° C. in PBS for at least two weeks as determined by SEC-HPLC, such as 94%, 95%, 96%, 97%, 98% or 99%. In certain embodiments, the antigen binding protein remains at least 80% monomeric at a concentration of about 1 mg/mL (e.g., 0.90 to 1.10 mg/mL) to about 10 mg/mL (e.g., 9.9 to 10.1 mg/mL) during storage at 37° C. in PBS for at least two weeks as determined by SEC-HPLC. In certain embodiments, the antigen binding protein remains at least 95% monomeric at a concentration of about 1 mg/mL (e.g., 0.90 to 1.10 mg/mL) to about 10 mg/mL (e.g., 9.9 to 10.1 mg/mL) during storage at 37° C. in PBS for at least two weeks as determined by SEC-HPLC. In certain embodiments, the antigen binding protein remains at least 94% monomeric at a concentration of about 1 mg/mL and about 10 mg/mL during storage at 4° C. in PBS for at least two weeks as determined by SEC-HPLC, such as 94%, 95%, 96%, 97%, 98% or 99%.

In certain embodiments, the antigen binding protein comprises a full-length immunoglobulin or an antibody fragment such as a Fab, a Fab', a F(ab')$_2$, a scFv or a Fv fragment.

In certain embodiments, the VH domain comprising an HCDR1 amino acid sequence of SNYAMS (SEQ ID NO: 11), an HCDR2 amino acid sequence of IVSSGGTTYYAX$_1$X$_2$X$_3$KG (SEQ ID NO: 6), wherein X$_1$ corresponds to amino acid S or D, X$_2$ corresponds to amino acid W or S, and X$_3$ corresponds to amino acid A or V, and an HCDR3 amino acid sequence of DLYYGPX$_4$TX$_5$YX$_6$X$_7$X$_8$NL (SEQ ID NO: 7), wherein X$_4$ corresponds to amino acid T, N, or S, X$_5$ corresponds to amino acid D or is absent, X$_6$ corresponds to amino acid S or F, X$_7$ corresponds to amino acid A or V, and X$_8$ corresponds to amino acid F or A; and the VL domain comprising an LCDR1 amino acid sequence of TADTLSRSYAS (SEQ ID NO: 16), an LCDR2 amino acid sequence of RDTSRPS (SEQ ID NO: 17), and an LCDR3 amino acid sequence of ATX$_9$X$_{10}$X$_{11}$SGSNFQX$_{12}$ (SEQ ID NO: 8), wherein X$_9$ corresponds to amino acid S or R, X$_{10}$ corresponds to amino acid D or P, X$_{11}$ corresponds to amino acid G, S, or F, and X$_{12}$ corresponds to amino acid L or A.

In certain embodiments, the antigen binding protein is linked to or combined with a detectable label, a therapeutic agent or a PK modifying moiety.

In certain embodiments, the antigen binding protein is chemically or biologically modified. In certain embodiments, the antigen binding protein is glycosylated, PEGylated, PASylated, XTENylated or HESylated.

In one aspect, the disclosure provides a chimeric antigen receptor (CAR) comprising the antigen binding protein described above.

In another aspect, the disclosure provides an immune cell expressing the CAR described above. In certain embodiments, the immune cell is a T cell.

In another aspect, the disclosure provides a multispecific antigen binding protein comprising the antigen binding protein described above.

In certain embodiments, the multispecific antigen binding protein is bispecific or trispecific.

In certain embodiments, the multispecific antigen binding protein further comprises at least one additional binding domain. In certain embodiments, the additional binding domain is an immune cell engager, in particular a CD3-binding domain or a CD16a-binding domain.

In certain embodiments, the multispecific antigen binding protein further comprises a third antigen binding domain. In certain embodiments, the third antigen binding domain binds to HLA-A*02/MAGE-A4. In certain embodiments, the third antigen binding domain is identical to the first MAEG-A4 pMHC antigen binding domain as defined above.

In certain embodiments, said third antigen binding domain comprises: an antibody heavy chain variable (VH) domain comprising an HCDR1 amino acid sequence of SNYAMS (SEQ ID NO: 11), an HCDR2 amino acid sequence of IVSSGGTTYYAX$_1$X$_2$X$_3$KG (SEQ ID NO: 6), wherein X$_1$ corresponds to amino acid S or D, X$_2$ corresponds to amino acid W or S, and X$_3$ corresponds to amino acid A or V, and an HCDR3 amino acid sequence of DLYYGPX$_4$TX$_5$YX$_6$X$_7$X$_8$NL (SEQ ID NO: 7), wherein X$_4$ corresponds to amino acid T, N, or S, X$_5$ corresponds to amino acid D or is absent, X$_6$ corresponds to amino acid S or F, X$_7$ corresponds to amino acid A or V, and X$_8$ corresponds to amino acid F or A; and an antibody light chain variable (VL) domain comprising an LCDR1 amino acid sequence of TADTLSRSYAS (SEQ ID NO: 16), an LCDR2 amino acid sequence of RDTSRPS (SEQ ID NO: 17), and an LCDR3 amino acid sequence of ATX$_9$X$_{10}$X$_{11}$SGSNFQX$_{12}$ (SEQ ID NO: 8), wherein X$_9$ corresponds to amino acid S or R, X$_{10}$ corresponds to amino acid D or P, X$_{11}$ corresponds to amino acid G, S, or F, and X$_{12}$ corresponds to amino acid L or A.

In certain embodiments, said third antigen binding domain comprises: i) an antibody heavy chain variable (VH) domain comprising an amino acid sequence that is at least about 90%, 95%, 96%, 97%, 98% or 100% identical to the amino acid sequence of SEQ ID NO: 10, and an antibody light chain variable (VL) domain comprising an amino acid sequence that is at least about 90%, 95%, 96%, 97%, 98% or 100% identical to the amino acid sequence of SEQ ID NO: 15; ii) a VH domain comprising an amino acid sequence that is at least about 90%, 95%, 96%, 97%, 98% or 100% identical to the amino acid sequence of SEQ ID NO: 20, and a VL domain comprising an amino acid sequence that is at least about 90%, 95%, 96%, 97%, 98% or 100% identical to the amino acid sequence of SEQ ID NO: 25; iii) a VH domain comprising an amino acid sequence that is at least about 90%, 95%, 96%, 97%, 98% or 100% identical to the amino acid sequence of SEQ ID NO: 30, and a VL domain comprising an amino acid sequence that is at least about 90%, 95%, 96%, 97%, 98% or 100% identical to the amino acid sequence of SEQ ID NO: 35; or iv) a VH domain comprising an amino acid sequence that is at least about 90%, 95%, 96%, 97%, 98% or 100% identical to the amino acid sequence of SEQ ID NO: 40, and a VL domain comprising an amino acid sequence that is at least about 90%, 95%, 96%, 97%, 98% or 100% identical to the amino acid sequence of SEQ ID NO: 45.

In one aspect, the disclosure provides a multispecific antigen binding protein comprising: a) a first antigen binding domain which specifically binds to CD3; b) a second antigen binding domain which specifically binds to Melanoma-Associated Antigen A4 (MAGE-A4) peptide-MHC (pMHC), the second antigen binding domain comprising: b1) an antibody heavy chain variable (VH) domain comprising an HCDR1 amino acid sequence of SNYAMS (SEQ ID NO: 11), an HCDR2 amino acid sequence of IVSSGGTTYYAX$_1$X$_2$X$_3$KG (SEQ ID NO: 6), wherein X$_1$ corresponds to amino acid S or D, $X_2$ corresponds to amino acid W or S, and $X_3$ corresponds to amino acid A or V, and an HCDR3 amino acid sequence of DLYYGPX$_4$TX$_5$YX$_6$X$_7$X$_8$NL (SEQ ID NO: 7), wherein $X_4$ corresponds to amino acid T, N, or S, $X_5$ corresponds to amino acid D or is absent, $X_6$ corresponds to amino acid S or F, $X_7$ corresponds to amino acid A or V, and $X_8$ corresponds to amino acid F or A; and b2) an antibody light chain variable (VL) domain comprising an LCDR1 amino acid sequence of TADTLSRSYAS (SEQ ID NO: 16), an LCDR2 amino acid sequence of RDTSRPS (SEQ ID NO: 17), and an LCDR3 amino acid sequence of ATX$_9$X$_{10}$X$_{11}$SGSNFQX$_{12}$ (SEQ ID NO: 8), wherein $X_9$ corresponds to amino acid S or R, $X_{10}$ corresponds to amino acid D or P, $X_{11}$ corresponds to amino acid G, S, or F, and $X_{12}$ corresponds to amino acid L or A.

In certain embodiments, the MAGE-A4 peptide-MHC (pMHC) is a GVYDGREHTV (SEQ ID NO: 3) HLA-A*02 complex.

In certain embodiments, the multispecific antigen binding protein remains at least 94%, 95%, 96%, 97%, 98%, 99% or 100% monomeric after incubation for 14 days at 4° C. in PBS as determined by SEC-HPLC.

In certain embodiments, the multispecific antigen binding protein further comprises a third antigen binding domain, in particular, said third binding domain being identical to said second binding domain.

In certain embodiments, the multispecific antigen binding protein comprises: c) a third antigen binding domain which specifically binds to MAGE-A4 pMHC, the third antigen binding domain comprising: c1) a VH domain comprising an HCDR1 amino acid sequence of SNYAMS (SEQ ID NO: 11), an HCDR2 amino acid sequence of IVSSGGTTYYAX$_1$X$_2$X$_3$KG (SEQ ID NO: 6), wherein $X_1$ corresponds to amino acid S or D, $X_2$ corresponds to amino acid W or S, and $X_3$ corresponds to amino acid A or V, and an HCDR3 amino acid sequence of DLYYGPX$_4$TX$_5$YX$_6$X$_7$X$_8$NL (SEQ ID NO: 7), wherein $X_4$ corresponds to amino acid T, N, or S, $X_5$ corresponds to amino acid D or is absent, $X_6$ corresponds to amino acid S or F, $X_7$ corresponds to amino acid A or V, and $X_8$ corresponds to amino acid F or A; and c2) a VL domain comprising an LCDR1 amino acid sequence of TADTLSRSYAS (SEQ ID NO: 16), an LCDR2 amino acid sequence of RDTSRPS (SEQ ID NO: 17), and an LCDR3 amino acid sequence of ATX$_9$X$_{10}$X$_{11}$SGSNFQX$_{12}$ (SEQ ID NO: 8), wherein $X_9$ corresponds to amino acid S or R, $X_{10}$ corresponds to amino acid D or P, $X_{11}$ corresponds to amino acid G, S, or F, and $X_{12}$ corresponds to amino acid L or A.

In certain embodiments, the second and third antigen binding domains comprises: (i) a VH comprising an HCDR1 sequence comprising the amino acid sequence of SNYAMS (SEQ ID NO: 11), an HCDR2 sequence comprising the amino acid sequence of IVSSGGTTYYADSVKG (SEQ ID NO: 12), and an HCDR3 sequence comprising the amino acid sequence of DLYYGPNTDYSAANL (SEQ ID NO: 13); and a VL comprising an LCDR1 sequence comprising the amino acid sequence of TADTLSRSYAS (SEQ ID NO: 16), an LCDR2 sequence comprising the amino acid sequence of RDTSRPS (SEQ ID NO: 17), and an LCDR3 sequence comprising the amino acid sequence of ATRPSSGSNFQA (SEQ ID NO: 18); (ii) a VH comprising an HCDR1 sequence comprising the amino acid sequence of SNYAMS (SEQ ID NO: 21), an HCDR2 sequence comprising the amino acid sequence of IVSSGGTTYYADSVKG (SEQ ID NO: 22), and an HCDR3 sequence comprising the amino acid sequence of DLYYGPSTYFVANL (SEQ ID NO: 23); and a VL comprising an LCDR1 sequence comprising the amino acid sequence of TADTLSRSYAS (SEQ ID NO: 26), an LCDR2 sequence comprising the amino acid sequence of RDTSRPS (SEQ ID NO: 27), and an LCDR3 sequence comprising the amino acid sequence of ATRPSSGSNFQL (SEQ ID NO: 28); (iii) a VH comprising an HCDR1 sequence comprising the amino acid sequence of SNYAMS (SEQ ID NO: 31), an HCDR2 sequence comprising the amino acid sequence of IVSSGGTTYYASWAKG (SEQ ID NO: 32), and an HCDR3 sequence comprising the amino acid sequence of DLYYGPTTYSAANL (SEQ ID NO: 33); and a VL comprising an LCDR1 sequence comprising the amino acid sequence of TADTLSRSYAS (SEQ ID NO: 36), an LCDR2 sequence comprising the amino acid sequence of RDTSRPS (SEQ ID NO: 37), and an LCDR3 sequence comprising the amino acid sequence of ATRDFSGSNFQL (SEQ ID NO: 38); or (iv) a VH comprising an HCDR1 sequence comprising the amino acid sequence of SNYAMS (SEQ ID NO: 41), an HCDR2 sequence comprising the amino acid sequence of IVSSGGTTYYASWAKG (SEQ ID NO: 42), and an HCDR3 sequence comprising the amino acid sequence of DLYYGPTTYSAFNL (SEQ ID NO: 43); and a VL comprising an LCDR1 sequence comprising the amino acid sequence of TADTLSRSYAS (SEQ ID NO: 46), an LCDR2 sequence comprising the amino acid sequence of RDTSRPS (SEQ ID NO: 47), and an LCDR3 sequence comprising the amino acid sequence of ATRPSSGSNFQA (SEQ ID NO: 48).

In certain embodiments, the second and third antigen binding domains comprise: (i) an antibody heavy chain variable (VH) domain comprising an amino acid sequence that is at least about 90%, 95%, 96%, 97%, 98% or 100% identical to the amino acid sequence of SEQ ID NO: 10, and an antibody light chain variable (VL) domain comprising an amino acid sequence that is at least about 90%, 95%, 96%, 97%, 98% or 100% identical to the amino acid sequence of SEQ ID NO: 15; (ii) a VH domain comprising an amino acid sequence that is at least about 90%, 95%, 96%, 97%, 98% or 100% identical to the amino acid sequence of SEQ ID NO: 20, and a VL domain comprising an amino acid sequence that is at least about 90%, 95%, 96%, 97%, 98% or 100% identical to the amino acid sequence of SEQ ID NO: 25; (iii) a VH domain comprising an amino acid sequence that is at least about 90%, 95%, 96%, 97%, 98% or 100% identical to the amino acid sequence of SEQ ID NO: 30, and a VL domain comprising an amino acid sequence that is at least about 90%, 95%, 96%, 97%, 98% or 100% identical to the amino acid sequence of SEQ ID NO: 35; or (iv) a VH domain comprising an amino acid sequence that is at least about 90%, 95%, 96%, 97%, 98% or 100% identical to the amino acid sequence of SEQ ID NO: 40, and a VL domain comprising an amino acid sequence that is at least about 90%, 95%, 96%, 97%, 98% or 100% identical to the amino acid sequence of SEQ ID NO: 45.

In certain embodiments, any one or more of the first, second, and third antigen binding domain comprises an antibody fragment. In certain embodiments, the antibody fragment comprises a Fab fragment, a F(ab')$_2$ fragment, a Fab' fragment, an Fv fragment, a single chain variable fragment (scFv), and a single domain antibody fragment.

In certain embodiments, the immune cell or CD3 antigen binding domain is a Fab fragment, wherein the Fab fragment comprises a heavy chain comprising a CH1 domain and the VH, and a light chain comprising a CL domain and the VL.

In certain embodiments, the CH1 domain comprises at least 5 amino acids of an antibody hinge region. In certain embodiments, the CH1 domain comprises an amino acid sequence EPKSC (SEQ ID NO: 88) of an antibody hinge region.

In certain embodiments, the MAGE-A4 pMHC antigen binding domains comprise an scFv.

In certain embodiments, the second antigen binding domain is operably linked to the C-terminus of the Fab domain heavy chain or the N-terminus of the Fab domain heavy chain. In certain embodiments, the third antigen binding domain is operably linked to the C-terminus of the Fab domain heavy chain or the N-terminus of the Fab domain heavy chain.

In certain embodiments, a) the second antigen binding domain comprises an scFv being linked to the C-terminus of the Fab domain heavy chain and the third antigen binding domain comprises an scFv being linked to the C-terminus of the Fab domain light chain; b) the second antigen binding domain comprises an scFv being linked to the N-terminus of the Fab domain heavy chain and the third antigen binding domain comprises an scFv being linked to the N-terminus of the Fab domain light chain; c) the second antigen binding domain comprises an scFv being linked to the N-terminus of the Fab domain heavy chain and the third antigen binding domain comprises an scFv being linked to the C-terminus of the Fab domain light chain; or d) the second antigen binding domain comprises an scFv being linked to the C-terminus of the Fab domain heavy chain and the third antigen binding domain comprises an scFv being linked to the N-terminus of the Fab domain light chain.

In certain embodiments, the scFv is linked to the Fab domain with an amino acid linker. In certain embodiments, the amino acid linker comprises (GGGGS)n (SEQ ID NO: 73), wherein n is an integer between 1 and 5. In certain embodiments, the amino acid linker comprises the amino acid sequence GGGGS (SEQ ID NO: 74), GGGGSGGGGSGGGGS (SEQ ID NO: 75), GGGGSGGGGSGGGGSGGGGS (SEQ ID NO: 76), GGGGSGGGGSGGGGSGGGGAS (SEQ ID NO: 77), or GGGGGSGGGGSGGGGSGGGGS (SEQ ID NO: 78).

In certain embodiments, the second and/or third antigen binding domain VH and VL are joined with an amino acid linker. In certain embodiments, the amino acid linker comprises (GGGGS)n (SEQ ID NO: 73), wherein n is an integer between 1 and 5. In certain embodiments, the amino acid linker comprises the amino acid sequence GGGGS (SEQ ID NO: 74), GGGGSGGGGSGGGGS (SEQ ID NO: 75), GGGGSGGGGSGGGGSGGGGS (SEQ ID NO: 76), GGGGSGGGGSGGGGSGGGGAS (SEQ ID NO: 77), or GGGGGSGGGGSGGGGSGGGGS (SEQ ID NO: 78).

In certain embodiments, the multispecific antigen binding protein does not comprise an Fc domain.

In certain embodiments, the multispecific antigen binding protein comprises a (scFv)$_2$, (scFv)$_3$, BiTE, BIKE, Dart, diabody, tribody, Fab$_2$, Fab$_3$, Fab$_4$, scFv-Fab-scFv or minibody-scFv.

In certain embodiments, the multispecific antigen binding protein comprises a molecular weight of about 75 kDa to about 100 kDa or about 110 kDa. In certain embodiments, the antigen binding protein has increased serum half-life relative to an antigen binding protein with a molecular weight of <about 75 kDa.

In certain embodiments, the CD3 antigen binding domain comprises: a1) a VH comprising an HCDR1 sequence comprising the amino acid sequence of STYAMN (SEQ ID NO: 51), an HCDR2 sequence comprising the amino acid sequence of RIRSKYNNYATYYADSVKG (SEQ ID NO: 52), and an HCDR3 sequence comprising the amino acid sequence of HGNFGDSYVSWFAY (SEQ ID NO: 53); and a2) a VL comprising an LCDR1 sequence comprising the amino acid sequence of GSSTGAVTTSNYAN (SEQ ID NO: 56), an LCDR2 sequence comprising the amino acid sequence of GTNKRAP (SEQ ID NO: 57), and an LCDR3 sequence comprising the amino acid sequence of ALWYSNHWV (SEQ ID NO: 58).

In certain embodiments, the CD3 antigen binding domain comprises: a VH comprising an amino acid sequence that is at least about 90% identical (e.g., 90%, 91%, 92%, 93%, 94%, 95%, 96%, 97%, 98%, 99%, or 100% identical) to the amino acid sequence of SEQ ID NO: 50, and a VL comprising an amino acid sequence that is at least about 90% identical (e.g., 90%, 91%, 92%, 93%, 94%, 95%, 96%, 97%, 98%, 99%, or 100% identical) to the amino acid sequence of SEQ ID NO: 55.

In certain embodiments, the CD3 antigen binding domain comprises: a heavy chain comprising an amino acid sequence that is at least about 90% identical (e.g., 90%, 91%, 92%, 93%, 94%, 95%, 96%, 97%, 98%, 99%, or 100% identical) to the amino acid sequence of SEQ ID NO: 49, and a light chain comprising an amino acid sequence that is at least about 90% identical (e.g., 90%, 91%, 92%, 93%, 94%, 95%, 96%, 97%, 98%, 99%, or 100% identical) to the amino acid sequence of SEQ ID NO: 54.

In certain embodiments, the multispecific antigen binding protein comprises: (i) a first polypeptide chain comprising an amino acid sequence set forth in SEQ ID NO: 9 and a second polypeptide chain comprising an amino acid sequence set forth in SEQ ID NO: 14; (ii) a first polypeptide chain comprising an amino acid sequence set forth in SEQ ID NO: 19 and a second polypeptide chain comprising an amino acid sequence set forth in SEQ ID NO: 24; (iii) a first polypeptide chain comprising an amino acid sequence set forth in SEQ ID NO: 29 and a second polypeptide chain comprising an amino acid sequence set forth in SEQ ID NO: 34; or (iv) a first polypeptide chain comprising an amino acid sequence set forth in SEQ ID NO: 39; and a second polypeptide chain comprising an amino acid sequence set forth in SEQ ID NO: 44, or a variant of said sequences being at least 90%, 95%, 96%, 97%, 98% or 99% identical thereto while retaining antigen specificity (i.e., retaining specificity to GVYDGREHTV (SEQ ID NO: 3) HLA-A*02 complex and to CD3).

In certain embodiments, the MAGE-A4 pMHC binding domain, such as the second antigen binding domain and/or the third antigen binding domain above, in particular when in scFv format, comprise a variable heavy chain having a polar amino acid at position 11, 89 and/or 108, according to Kabat numbering. In certain embodiments, the Fab domain comprises a variable heavy chain having a polar amino acid at position 11, 89 and/or 108, according to Kabat numbering.

In certain embodiments, the variable heavy chain comprises: leucine (L) or serine (S) at amino acid position 11, according to Kabat numbering; valine (V), serine (S), or threonine (T) at amino acid position 89, according to Kabat numbering; and/or leucine (L), serine (S), or threonine (T) amino acid position 108, according to Kabat numbering.

In certain embodiments, the polar amino acid is serine (S) and/or threonine (T).

In certain embodiments, the variable heavy chain comprises serine (S) at amino acid position 11, serine (S) or threonine (T) at amino acid position 89, and serine (S) or threonine (T) at amino acid position 108, according to Kabat numbering.

In certain embodiments, the variable heavy chain comprises serine (S) at amino acid position 11, serine (S) at amino acid position 89, and serine (S) at amino acid position 108, according to Kabat numbering.

In one aspect, the disclosure provides a multispecific antigen binding protein comprising: a) a first antigen binding domain which specifically binds to CD3, the first antigen binding domain comprising: a1) a VH comprising an HCDR1 sequence comprising the amino acid sequence of STYAMN (SEQ ID NO: 51), an HCDR2 sequence comprising the amino acid sequence of RIRSKYNNYATYY-ADSVKG (SEQ ID NO: 52), and an HCDR3 sequence comprising the amino acid sequence of HGNFGDSYVSW-FAY (SEQ ID NO: 53); and a2) a VL comprising an LCDR1 sequence comprising the amino acid sequence of GSST-GAVTTSNYAN (SEQ ID NO: 56), an LCDR2 sequence comprising the amino acid sequence of GTNKRAP (SEQ ID NO: 57), and an LCDR3 sequence comprising the amino acid sequence of ALWYSNHWV (SEQ ID NO: 58); and b) a second antigen binding domain which specifically binds to Melanoma-Associated Antigen A4 (MAGE-A4) peptide-MHC (pMHC).

In certain embodiments, the second antigen binding domain comprises: b1) an antibody heavy chain variable (VH) domain comprising an HCDR1 amino acid sequence of SNYAMS (SEQ ID NO: 11), an HCDR2 amino acid sequence of IVSSGGTTYYAX$_1$X$_2$X$_3$KG (SEQ ID NO: 6), wherein X$_1$ corresponds to amino acid S or D, X$_2$ corresponds to amino acid W or S, and X$_3$ corresponds to amino acid A or V, and an HCDR3 amino acid sequence of DLYYGPX$_4$TX$_5$YX$_6$X$_7$X$_8$NL (SEQ ID NO: 7), wherein X$_4$ corresponds to amino acid T, N, or S, X$_5$ corresponds to amino acid D or is absent, X$_6$ corresponds to amino acid S or F, X$_7$ corresponds to amino acid A or V, and X$_8$ corresponds to amino acid F or A; and b2) an antibody light chain variable (VL) domain comprising an LCDR1 amino acid sequence of TADTLSRSYAS (SEQ ID NO: 16), an LCDR2 amino acid sequence of RDTSRPS (SEQ ID NO: 17), and an LCDR3 amino acid sequence of ATX$_9$X$_{10}$X$_{11}$SGSNFQX$_{12}$ (SEQ ID NO: 8), wherein X$_9$ corresponds to amino acid S or R, X$_{10}$ corresponds to amino acid D or P, X$_{11}$ corresponds to amino acid G, S, or F, and X$_{12}$ corresponds to amino acid L or A.

In certain embodiments, the CD3 binding domain comprises: —a VH comprising an amino acid sequence that is at least about 90% identical (such as 95%, 96%, 97%, 98% or 99% identical) to the amino acid sequence of SEQ ID NO: 50, and —a VL comprising an amino acid sequence that is at least about 90% identical (such as 95%, 96%, 97%, 98% or 99% identical) to the amino acid sequence of SEQ ID NO: 55.

In certain embodiments, the CD3 binding domain comprises: —a VH comprising an amino acid sequence that is at least about 90% identical (such as 95%, 96%, 97%, 98% or 99% identical) to the amino acid sequence of SEQ ID NO: 49, and —a VL comprising an amino acid sequence that is at least about 90% identical (such as 95%, 96%, 97%, 98% or 99% identical) to the amino acid sequence of SEQ ID NO: 54.

In certain embodiments, multispecific antigen binding protein further comprises a third antigen binding domain.

In certain embodiments, the multispecific antigen binding protein comprises: c) a third antigen binding domain which specifically binds to MAGE-A4 pMHC, said third antigen binding domain comprising: c1) a VH domain comprising an HCDR1 amino acid sequence of SNYAMS (SEQ ID NO: 11), an HCDR2 amino acid sequence of IVSSGGTTYYAX$_1$X$_2$X$_3$KG (SEQ ID NO: 6), wherein X$_1$ corresponds to amino acid S or D, X$_2$ corresponds to amino acid W or S, and X$_3$ corresponds to amino acid A or V, and an HCDR3 amino acid sequence of DLYYGPX$_4$TX$_5$YX$_6$X$_7$X$_8$NL (SEQ ID NO: 7), wherein X$_4$ corresponds to amino acid T, N, or S, X$_5$ corresponds to amino acid D or is absent, X$_6$ corresponds to amino acid S or F, X$_7$ corresponds to amino acid A or V, and X$_8$ corresponds to amino acid F or A; and c2) a VL domain comprising an LCDR1 amino acid sequence of TADTLSRSYAS (SEQ ID NO: 16), an LCDR2 amino acid sequence of RDTSRPS (SEQ ID NO: 17), and an LCDR3 amino acid sequence of ATX$_9$X$_{10}$X$_{11}$SGSNFQX$_{12}$ (SEQ ID NO: 8), wherein X$_9$ corresponds to amino acid S or R, X$_{10}$ corresponds to amino acid D or P, X$_{11}$ corresponds to amino acid G, S, or F, and X$_{12}$ corresponds to amino acid L or A.

In one aspect, the disclosure provides a multispecific antigen binding protein binding to MAGE-A4-pMHC and to CD3 comprising: (i) a first polypeptide chain comprising an amino acid sequence set forth in SEQ ID NO: 9, and a second polypeptide chain comprising an amino acid sequence set forth in SEQ ID NO: 14; (ii) a first polypeptide chain comprising an amino acid sequence set forth in SEQ ID NO: 19 and a second polypeptide chain comprising an amino acid sequence set forth in SEQ ID NO: 24; (iii) a first polypeptide chain comprising an amino acid sequence set forth in SEQ ID NO: 29 and a second polypeptide chain comprising an amino acid sequence set forth in SEQ ID NO: 34; or (iv) a first polypeptide chain comprising an amino acid sequence set forth in SEQ ID NO: 39; and a second polypeptide chain comprising an amino acid sequence set forth in SEQ ID NO: 44, or a variant of said sequences being at least 90%, 95%, 96%, 97%, 98% or 99% identical thereto while retaining antigen specificity (i.e., retaining specificity to GVYDGREHTV (SEQ ID NO: 3) HLA-A*02 complex and to CD3).

In one aspect, the disclosure provides a multispecific antigen binding protein binding to GVYDGREHTV (SEQ ID NO: 3) HLA-A*02 complex and to CD3 comprising: (i) a first polypeptide chain comprising an amino acid sequence set forth in SEQ ID NO: 9 and a second polypeptide chain comprising an amino acid sequence set forth in SEQ ID NO: 14; (ii) a first polypeptide chain comprising an amino acid sequence set forth in SEQ ID NO: 19 and a second polypeptide chain comprising an amino acid sequence set forth in SEQ ID NO: 24; (iii) a first polypeptide chain comprising an amino acid sequence set forth in SEQ ID NO: 29 and a second polypeptide chain comprising an amino acid sequence set forth in SEQ ID NO: 34; or (iv) a first polypeptide chain comprising an amino acid sequence set forth in SEQ ID NO: 39; and a second polypeptide chain comprising an amino acid sequence set forth in SEQ ID NO: 44.

In certain embodiments of the multispecific antigen binding protein described herein, said MAGE-A4 peptide-MHC (pMHC) is a GVYDGREHTV (SEQ ID NO: 3) HLA-A*02 complex.

In certain embodiments of the multispecific antigen binding protein described herein, the multispecific antigen binding protein remains at least 94%, 95%, 96%, 97%, 98%, 99% or 100% monomeric after incubation for 14 days at 4° C. at 1 mg/mL and/or 10 mg/mL in PBS as determined by SEC-HPLC.

In certain embodiments of the multispecific antigen binding protein described herein, the multispecific antigen binding protein shows efficacy (e.g., cytotoxicity) on target positive tumor cells as determined by an LDH cytotoxicity assay.

In certain embodiments of the multispecific antigen binding protein described herein, the multispecific antigen binding protein shows tumor growth inhibition and tumor eradication in a cell line-derived mouse non-small cell lung cancer (NSCLC) xenograft model.

In certain embodiments, the multispecific antigen binding protein is chemically or biologically modified. In certain embodiments, the multispecific antigen binding protein is glycosylated, PEGylated, HESylated, PASylated or XTE-Nylated.

In certain embodiments, the multispecific antigen binding protein is linked to or combined with a functional entity such as a detectable label, a therapeutic agent or a PK modifying moiety.

In certain embodiments, the functional entity is a toxin.

In certain embodiments of the multispecific antigen binding protein described herein, the light chain and/or heavy chain comprises an N-terminal and/or C-terminal truncation of 1, 2, 3, 4, or 5 amino acids.

In certain embodiments of the multispecific antigen binding protein described herein, the light chain comprises an N-terminal truncation of 1 or 2 amino acids.

In certain embodiments of the multispecific antigen binding protein described herein, the multispecific antigen binding protein comprises a pyroglutamate (pE) at position 1 instead of glutamine (Q) or glutamate (E) of the light chain and/or heavy chain.

In certain embodiments of the multispecific antigen binding protein described herein, the multispecific antigen binding protein comprises a pyroglutamate (pE) at position 1 instead of glutamine (Q) or glutamate (E) of the light chain.

In certain embodiments, the antigen binding protein is for use in diagnostics.

In certain embodiments, the multispecific antigen binding protein described above is for use in a method for inhibiting growth or proliferation of cancer cells.

In certain embodiments, the multispecific antigen binding protein described above is for use in a method of redirecting a T cell to a MAGE-A4-expressing cancer cell.

In certain embodiments, the antigen binding protein described above, or the multispecific antigen binding protein described above, is for use as medicament.

In one aspect, the disclosure provides a nucleic acid encoding the antigen binding protein described above, or the multispecific antigen binding protein described above.

In one aspect, the disclosure provides a vector comprising the nucleic acid described above.

In one aspect, the disclosure provides a host cell population comprising the vector described above.

In one aspect, the disclosure provides a kit comprising the antigen binding protein described above, or the multispecific antigen binding protein described above.

In one aspect, the disclosure provides a method of manufacturing the antigen binding protein described above, or the multispecific antigen binding protein described above, comprising the steps of: (i) cultivating the host cell described above under conditions allowing expression of the antigen binding protein or the multispecific antigen binding protein; (ii) recovering the antigen binding protein or the multispecific antigen binding protein; and optionally (iii) further purifying and/or modifying and/or formulating the antigen binding protein or the multispecific antigen binding protein.

In one aspect, the disclosure provides a pharmaceutical composition comprising the antigen binding protein described above, or the multispecific antigen binding protein described above, and a pharmaceutically acceptable buffer.

In one aspect, the disclosure provides a use of the antigen binding protein described above, the multispecific antigen binding protein described above, or the pharmaceutical composition described above in the manufacture of a medicament.

In one aspect, the disclosure provides a use of the antigen binding protein described above, the CAR described above, the immune cell described above, the multispecific antigen binding protein described above, the cell described above, or the pharmaceutical composition described above in the treatment of a disease, in particular cancer.

In one aspect, the disclosure provides a method of treating a MAGE-A4 pMHC-expressing cancer in a patient in need thereof comprising administering to the patient a therapeutically effective amount of the antigen binding protein described above, the CAR described above, the immune cell described above, the multispecific antigen binding protein described above, the cell described above, or the pharmaceutical composition described above.

In certain embodiments, the cancer is selected from the group consisting of head & neck squamous cancer (HNSC), non-small cell lung carcinoma (NSCLC), triple negative breast cancer, urothelial carcinoma, high-grade endometrial cancers including uterine carcinosarcoma (UCS; in particular UCEC subgroup), myxoid/round cell liposarcoma, gastric or gastroesophageal junction (GEJ) adenocarcinoma, epithelial ovarian cancer, such as high grade serous ovarian carcinoma, synovial sarcoma, bladder urothelial carcinoma (BLCA), in particular transitional cell carcinoma, testicular germ cell tumors (TGCT) and cervical squamous carcinoma (CESC).

In certain embodiments, the cancer is of squamous origin, such as head and neck squamous cell carcinoma (HNSCC) or squamous NSCLC.

In one aspect, the disclosure provides a method for selecting patients eligible for treatment with a MAGE-A4 antagonist comprising the sequential steps of: (i) obtaining a tumor sample from a patient; (ii) adding an anti-MAGEA4 detection antibody to the sample; (iii) incubating said detection antibody and the sample; (iv) detecting said detection antibody bound to the sample; and (v) selecting the patient for treatment with a MAGE-A4 antagonist if said detection antibody is bound by the sample.

In certain embodiments, the detection antibody is OTI1F9, E7O1U or the antigen binding protein described herein.

In certain embodiments, the method further comprises the step of performing RNA sequencing for detection of total MAGE-A4.

In certain embodiments, the MAGE-A4 antagonist is the antigen binding protein of described herein, the CAR described herein, the immune cell described herein, the multispecific antigen binding protein described herein, or the pharmaceutical composition described herein in the treatment of a disease, in particular cancer.

BRIEF DESCRIPTION OF THE DRAWINGS

The foregoing and other features and advantages of the present invention will be more fully understood from the following detailed description of illustrative embodiments taken in conjunction with the accompanying drawings. The patent or application file contains at least one drawing executed in color. Copies of this patent or patent application publication with color drawing(s) will be provided by the Office upon request and payment of the necessary fee.

FIG. 6A shows the data for incubation at 4° C., FIG. 6B for incubation at 37° C.

FIG. 8A: Dual engager M1397 and Comparator 1 in U2OS; FIG. 8B: Dual engager M1403 and Comparator 1 in U2OS; FIG. 8C: Dual engager M1397 and Comparator 1 in NCI-H1703; FIG. 8D: Dual engager M1403 and Comparator 1 in NCI-H1703; FIG. 8E: Dual engagers M1397 and M1403 and Comparator 1 in A375; FIG. 8F: Dual engager M1397 and Comparator 1 in PANC-1; FIG. 8G: Dual engager M1403 and Comparator 1 in PANC-1; FIG. 8H: Dual engager M1397 and Comparator 1 in MDA-MB-231; FIG. 8I: Dual engager M1397 and Comparator 1 in MDA-MB-231; FIG. 8J: Dual engager M1397 and Comparator 1 in NCI-H441; FIG. 8K: Dual engager M1403 and Comparator 1 in NCI-H441.

FIG. 10B: M1403 and Comparator 1 in U2OS; FIG. 10C: M1397 and Comparator 1 in NCI-H1703; FIG. 10D: M1403 and Comparator 1 in NCI-H1703) and MAGE-A4-negative HLA-A*02:01-positive cancer cells (FIG. 10E: M1397 and Comparator 1 in PANC-1; FIG. 10F: M1403 and Comparator 1 in PANC-1; FIG. 10G: M1397 and Comparator 1 in MDA-MB-231; FIG. 10H: M1403 and Comparator 1 in MDA-MB-231; FIG. 10I: M1397 and Comparator 1 in NCI-H441; FIG. 10J: M1403 and Comparator 1 in NCI-H441).

FIGS. 14A-14H show Granzyme B release upon treatment with dual T cell engager M1397, Comparator 1 or Comparator 2 of antigen-negative cancer cell lines KLE, LNCaP, KMRC-2, KMRC-3, 639-V, EKVX and HCT116 (FIGS. 14B-14H). Antigen-positive cell line NCI-H1703 served as a positive control (FIG. 14A).

FIGS. 15A-15C show safety of dual engagers M1397 and M1403 or Comparator 1 in HLA-A*02:01-positive primary cells. FIG. 15A: HMVEC-C cells; FIG. 15B: NHBE cells; FIG. 15C: NHA cells.

FIG. 16A: in HCM_679 cells; FIG. 16B: in HCM_639 cells; FIG. 16C: in HCM_745 cells; FIG. 16D: in HCM_746 cells; FIG. 16E: in HMVEC-L_73809 cells; FIG. 16F: in HCF_251 cells; FIG. 16G: in RPTEC_82573 cells; FIG. 16H: in NHLF_19232 cells; FIG. 16I: in NHLF_76039 cells; FIG. 16J: in NHA_72445 cells; FIG. 16K: in NHBE_35497 cells; FIG. 16L: in RPTEC_49985 cells; FIG. 16M: in HAoSMC_735 cells.

DETAILED DESCRIPTION

Figure 1A:
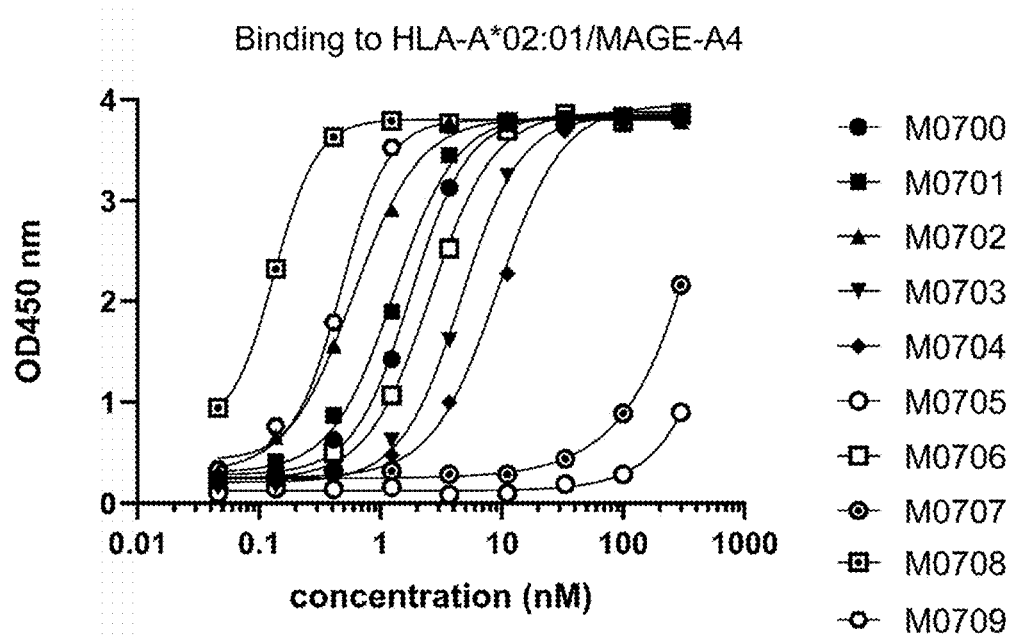
FIGS. 1A-1D depict the binding of antibodies to HLA-A*02:01/MAGE-A4 (FIGS. 1A and 1B) or control complex HLA-A*02:01/peptide mix (FIGS. 1C and 1D), as determined by direct ELISA.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein is well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

Antigen Binding Proteins

"MAGE-A4" stands for "Melanoma-associated antigen 4" which is a member of the MAGE family of Cancer Testis Antigens (CTAs). The MAGE A family of proteins encompasses 12 highly homologous genes clustered at Xq28 and characterized by the presence of a conserved domain (MAGE Homology Domain, MHD). Human MAGE-A4 is described in UniProt (www.uniprot.org) accession no. P43358 (entry version 163). "MAGE-A4$_{p230-239}$" or "203-239 peptide" refers to the MAGE-A4 derived peptide having the amino acid sequence GVYDGREHTV (SEQ ID NO: 3) at position 230-239 of the MAGE-A4 protein.

"CD3", the cluster of differentiation 3 co-receptor (or co-receptor complex) of the T cell receptor, is a complex composed of four distinct chains. In mammals, the complex contains a CD3γ (gamma) chain/subunit, a CD3δ (delta) chain/subunit, and two CD3ε (epsilon) chains/subunits. Reference to CD3 as the cell surface protein of an immune cell is made herein throughout. The term "CD3" refers to any native CD3 from any vertebrate source, including primates. In certain embodiments, the antigen binding proteins of the disclosure specifically bind to human CD3, in particular to the CD3ε (epsilon) chain/subunit of CD3 (see e.g., UniProt (www.uniprot.org) accession no. P07766 (version 189), or NCBI (www.ncbi.nlm.nih.gov/) RefSeq NP 000724.1.) The CD3 molecule may be the full-length, unprocessed CD3 molecule or a fragment or variant thereof that e.g., results from processing in the cell. For example, such variants may be naturally occurring variants like splice variants or allelic variants. In certain embodiments, the antigen binding proteins disclosed herein bind to an epitope of CD3 that is conserved among the CD3 antigens from different species, such as non-human primates (e.g., cynomolgus monkeys) or rodents (e.g., mice, rats). In certain embodiments, the antigen binding proteins are not cross-reactive with a CD3 antigen from rodents (e.g., mouse or rat) or minipigs.

As used herein, the term "antibody" or "antigen binding protein" refers to an immunoglobulin molecule or immunoglobulin derived molecule that specifically binds to, or is immunologically reactive with an antigen or epitope, and includes both polyclonal and monoclonal antibodies, as well as functional antibody fragments, including but not limited to fragment antigen-binding (Fab) fragments, F(ab')$_2$ fragments, Fab' fragments, Fv fragments, recombinant IgG (rIgG) fragments, single chain variable fragments (scFv) and single domain antibodies (e.g., sdAb, sdFv, nanobody, VHH) fragments. The antibody may thus be a single domain antibody or comprise at least one variable light and at least one variable heavy chain. In one embodiment, at least one variable light and at least one variable heavy chain are displayed as a single polypeptide chain. The term "antibody" or "antigen binding protein" includes germline derived antibodies. The term "antibody" or "antigen binding protein" includes genetically engineered or otherwise modified forms of immunoglobulins, such as intrabodies, peptibodies, chimeric antibodies, fully human antibodies, humanized antibodies, heteroconjugate antibodies (e.g., bispecific antibodies, diabodies, triabodies, tetrabodies, tandem di-scFv, tandem tri-scFv) and the like. Unless otherwise stated, the term "antibody" or "antigen binding protein" should be understood to encompass functional antibody fragments thereof.

In certain embodiments, the antigen binding protein is multispecific (i.e., binds to two or more different target molecules or to two or more epitopes on the same target molecule). In certain embodiments, the antigen binding protein is bispecific and e.g., binds to two different target molecules or to two epitopes on the same target molecule. In certain embodiments, the antibody is trispecific and e.g., binds to at least three different target molecules.

The antigen binding protein may be monovalent or multivalent, i.e., having one or more antigen binding sites. Non-limiting examples of monovalent antigen binding proteins include scFv, Fab, scFab, dAb, VHH, V(NAR), DARPins, affilins and nanobodies. A multivalent antigen binding protein can have two, three, four or more antigen binding sites. Non-limiting examples of multivalent antigen binding proteins include full-length immunoglobulins, F(ab')$_2$ fragments, bis-scFv (or tandem scFv or BiTE), DART, diabodies, scDb, DVD-Ig, IgG-scFab, scFab-Fc-scFab, IgG-scFv, scFv-Fc, scFv-fc-scFv, Fv$_2$-Fc, FynomABs, quadroma, CrossMab, DuoBody, triabodies and tetrabodies. In some embodiments, the multivalent antigen binding protein is bivalent, i.e., two binding sites are present. In some embodiments, the multivalent antigen binding protein is bispecific, i.e., the antigen binding protein is directed against two different targets or two different target sites on one target molecule. In some embodiments, the multivalent antigen binding protein includes more than two, e.g., three or four different binding sites for three or four, respectively, different antigens. Such antigen binding protein is multivalent and multispecific, in particular tri- or tetra-specific, respectively.

In some embodiments, the antigen binding proteins are multispecific (e.g., bispecific), such as, without being limited to, diabodies, single-chain diabodies, DARTs, BiTEs, BIKEs, tandem scFvs or IgG-like asymmetric heterobispecific antibodies. In certain embodiments, one or the binding specificities of the multispecific antigen binding protein is an immune cell engager (i.e., comprising binding affinity to a cell surface protein of an immune cell). Examples of immune cells that may be recruited include, but are not limited to, T cells, B cells, natural killer (NK) cells, natural killer T (NKT) cells, neutrophil cells, monocytes, and macrophages. Examples of surface proteins that may be used to recruit immune cells includes, but are limited to, CD3, TCRα, TCRβ, CD16, NKG2D, CD94/NKG2C, NKp30, NKp46, CD89, CD64, and CD32. In certain embodiments, the immune cell target antigen is CD3.

As used herein, the term "monoclonal antibody" refers to an antibody obtained from a population of substantially homogeneous antibodies, i.e., antibodies that bind to the same epitope and/or are identical in sequence. A population of polyclonal antibodies, in contrast, will bind to multiple epitopes and comprises antibodies of different sequences. A monoclonal antibody preparation may or may not comprise to a minor extent variant antibodies, e.g., due to naturally occurring mutations. Such variants may e.g., be generated through posttranslational modifications, such as clipping at the N-terminal or C-terminal end of the light and/or heavy chain, or pyroglutamate formation on the N terminus of the polypeptide chain (see e.g., Liu Y D, et al. J Biol Chem. 2011 Apr. 1; 286(13):11211-7). Depending on the methods and antibody used, the percentage of variants in the mixture varies, and may involve substantially all antibodies produced, or a very low percentage.

As used herein, a "single-chain variable fragment" (scFv) is an antigen binding protein comprising a heavy chain variable domain (VH) linked to a light chain variable domain (VL). The VH and VL domains of the scFv are linked via any appropriate art recognized linker. Such linkers include, but are not limited to, repeated GGGGS (SEQ ID NO: 74) amino acid sequences or variants thereof. The scFv is generally free of antibody constant domain regions, although an scFv of the disclosure may be linked or attached to antibody constant domain regions (e.g., antibody Fc domain) to alter various properties of the scFv, including, but not limited to, increased serum or tissue half-life. An scFv generally has a molecular weight of about 25 kDa and a hydrodynamic radius of about 2.5 nm.

As used herein, a "Fab fragment" or "Fab" or "Fab domain" is an antibody fragment comprising a light chain fragment comprising a variable light (VL) domain and a constant domain of the light chain (CL), and variable heavy (VH) domain and a first constant domain (CH1) of the heavy chain. A F(ab')$_2$ comprises two antigen-binding regions joined at the hinge through disulfides.

As used herein, a "VHH", "nanobody", "heavy-chain only antibody", "single domain antibody", or "sdAb" is an antigen binding protein comprising a single heavy chain variable domain derived from the species of the Camelidae family, which includes camels, llama, alpaca. A VHH generally has a molecular weight of about 15 kDa.

The antigen binding proteins of the disclosure may comprise one or more linkers for linking the domains of the antigen binding protein (e.g., linking a VH and VL to form a scFv, or linking multiple binding domains to form a multispecific antigen binding protein).

Illustrative examples of linkers include glycine polymers (Gly)$_n$; glycine-serine polymers (GlynSer)$_n$, where n is an integer of at least one, two, three, four, five, six, seven, or eight; glycine-alanine polymers; alanine-serine polymers; and other flexible linkers known in the art.

Glycine and glycine-serine polymers are relatively unstructured, and therefore may be able to serve as a neutral tether between domains of fusion proteins such as the antigen binding proteins described herein. Glycine accesses significantly more phi-psi space than other small side chain amino acids, and is much less restricted than residues with longer side chains (Scheraga, Rev. Computational Chem. 1: 1173-142 (1992)). A person skilled in the art will recognize that design of an antigen binding protein in particular embodiments can include linkers that are all or partially flexible, such that the linker can include flexible linker stretches as well as one or more stretches that confer less flexibility to provide a desired structure.

Linker sequences can however be chosen to resemble natural linker sequences, for example, using the amino acid stretches corresponding to the beginning of human CH1 and Cκ sequences or amino acid stretches corresponding to the lower portion of the hinge region of human IgG.

The design of the peptide linkers connecting VL and VH domains in the scFv moieties are flexible linkers generally composed of small, non-polar or polar residues such as, e.g., Gly, Ser and Thr. A particularly exemplary linker connecting the variable domains of the scFv moieties is the (Gly$_4$Ser)$_4$ linker (SEQ ID NO: 76), where 4 is the exemplary number of repeats of the motif.

Linkers connecting the scFv antigen binding proteins to the Fab domain are also envisioned. In certain embodiments, the scFv antigen binding proteins are linked to the CH1 and CL domains of the Fab with a Gly-Ser linker. In certain embodiments, the linker comprises the amino acid sequence GGGGS (SEQ ID NO: 74). In certain embodiments, the amino acid linker comprises the amino acid sequence GGGGSGGGGSGGGGS (SEQ ID NO: 75), GGGGSGGGGSGGGGSGGGGS (SEQ ID NO: 76), GGGGSGGGGSGGGGSGGGGAS (SEQ ID NO: 77), or GGGGGSGGGGSGGGGSGGGGS (SEQ ID NO: 78).

Other exemplary linkers include, but are not limited to the following amino acid sequences: GGG; DGGGS (SEQ ID NO: 79); TGEKP (SEQ ID NO: 80) (Liu et al, Proc. Natl. Acad. Sci. 94: 5525-5530 (1997)); GGRR (SEQ ID NO: 81); (GGGGS)$_n$(SEQ ID NO: 73) wherein n=1, 2, 3, 4 or 5 (Kim et al, Proc. Natl. Acad. Sci. 93: 1156-1160 (1996)); EGKSSGSGSESKVD (SEQ ID NO: 82) (Chaudhary et al., Proc. Natl. Acad. Sci. 87: 1066-1070 (1990)); KESGSVSSEQLAQFRSLD (SEQ ID NO: 83) (Bird et al., Science 242:423-426 (1988)), GGRRGGGS (SEQ ID NO: 84); LRQRDGERP (SEQ ID NO: 85); LRQKDGGGSERP (SEQ ID NO: 86); and GSTSGSGKPGSGEGSTKG (SEQ ID NO: 87) (Cooper et al, Blood, 101(4): 1637-1644 (2003)). Alternatively, flexible linkers can be rationally designed using a computer program capable of modeling the 3D structure of proteins and peptides or by phage display methods.

The antibodies may comprise a variable light (VL) domain and a variable heavy (VH) domain. Each VL and VH domain further comprises a set of three CDRs.

As used herein, the term "complementarity determining region" or "CDR" refers to non-contiguous sequences of amino acids within antibody variable regions, which confer antigen specificity and affinity. In general, there are three CDRs in each heavy chain variable domain (HCDR1, HCDR2, HCDR3) and three CDRs in each light chain variable domain (LCDR1, LCDR2, LCDR3). "Framework regions" or "FRs" are known in the art to refer to the non-CDR portions of the variable domains of the heavy and light chains. In general, there are four FRs in each heavy chain variable domain (HFR1, HFR2, HFR3, and HFR4), and four FRs in each light chain variable domain (LFR1, LFR2, LFR3, and LFR4). Accordingly, an antibody variable region amino acid sequence can be represented by the formula FR1-CDR1-FR2-CDR2-FR3-CDR3-FR4. Each segment of the formula, i.e., FR1, CDR1, FR2, CDR2, FR3, CDR3, and FR4, represents a discrete amino acid sequence (or a polynucleotide sequence encoding the same) that can be mutated, including one or more amino acid substitutions, deletions, and insertions. In certain embodiments, an antibody variable light chain amino acid sequence can be represented by the formula LFR1-LCDR1-LFR2-LCDR2-LFR3-LCDR3-LFR4. In certain embodiments, an antibody variable heavy chain amino acid sequence can be represented by the formula HFR1-HCDR1-HFR2-HCDR2-HFR3-HCDR3-HFR4.

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia"

numbering scheme), MacCallum et al., J. Mol. Biol. 262: 732-745 (1996), "Antibody-antigen interactions: Contact analysis and binding site topography," J. Mol. Biol. 262, 732-745. ("Contact" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Pluckthun A, "Yet another numbering scheme for immunoglobulin variable domains: an automatic modeling and analysis tool," J Mol Biol, 2001 Jun. 8; 309(3):657-70, ("AHo" numbering scheme).

The boundaries of a given CDR or FR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Table 1, below, lists exemplary position boundaries of LCDR1, LCDR2, LCDR3 and HCDR1, HCDR2, HCDR3 of an antibody, as identified by Kabat, Chothia, and Contact schemes, respectively. For HCDR1, residue numbering is listed using both the Kabat and Chothia numbering schemes. CDRs are located between FRs, for example, with LCDR1 located between LFR1 and LFR2, and so forth. It is noted that because the shown Kabat numbering scheme places insertions at H35A and H35B, the end of the Chothia HCDR1 loop when numbered using the shown Kabat numbering convention varies between H32 and H34, depending on the length of the loop.

TABLE 1

Exemplary Position Boundaries of CDRs

| CDR | Kabat | Chothia | Contact |
|---|---|---|---|
| LCDR1 | L24--L34 | L24--L34 | L30--L36 |
| LCDR2 | L50--L56 | L50--L56 | L46--L55 |
| LCDR3 | L89--L97 | L89--L97 | L89--L96 |
| HCDR1 (Kabat Numbering[1]) | H31--H35B | H26--H32 ... 34 | H30--H35B |
| HCDR1 (Chothia Numbering[2]) | H31--H35 | H26--H32 | H30--H35 |
| HCDR2 | H50--H65 | H52--H56 | H47--H58 |
| HCDR3 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al. (1997), J. Mol. Biol. 273: 927-948

Thus, unless otherwise specified, a "CDR" or "complementary determining region," or individual specified CDRs (e.g., HCDR1, HCDR2), of a given antibody or fragment thereof, such as a variable domain thereof, should be understood to encompass a (or the specific) complementary determining region as defined by any of the known schemes. Likewise, unless otherwise specified, an "FR" or "framework region," or individual specified FRs (e.g., "HFR1," "HFR2") of a given antibody or fragment thereof, such as a variable domain thereof, should be understood to encompass a (or the specific) framework region as defined by any of the known schemes. In some instances, the scheme for identification of a particular CDR or FR is specified, such as the CDR as defined by the Kabat, Chothia, or Contact method. In other cases, the particular amino acid sequence of a CDR or FR is given.

In certain embodiments, the antigen binding proteins disclosed here are rabbit-derived antigen binding proteins. In certain embodiments, the antigen binding proteins are humanized. As used herein, the term "humanized" or "humanization" refers to an antigen binding protein that has been altered to make it more like a human antibody. Non-human antigen binding proteins, such as rabbit antigen binding proteins, would elicit a negative immune reaction if administered to a human for therapy. It is therefore advantageous to humanize the rabbit antigen binding proteins for later therapeutic use.

In certain embodiments, the antigen binding proteins are humanized through resurfacing (i.e., remodel the solvent-accessible residues of the non-human framework such that they become more human-like). Resurfacing strategies are described in more detail in WO2004/016740, WO2008/144757, and WO2005/016950, each of which is incorporated herein by reference.

In certain embodiments, the antigen binding proteins are humanized through CDR grafting (i.e., inserting the rabbit antigen binding protein CDRs into a human antibody acceptor framework). Grafting strategies and human acceptor frameworks are described in more detail in WO2009/155726, incorporated herein by reference.

As used herein, "sequence identity" between two polypeptides is determined by comparing the amino acid sequence of one polypeptide to the sequence of a second polypeptide. Similarly, "sequence identity" between two polynucleotides is determined by comparing the nucleotide sequence of one polynucleotide to the sequence of a second polynucleotide. The terms "% identical", "% identity" or similar terms are intended to refer, in particular, to the percentage of nucleotides or amino acids (as applicable) which are identical after the sequences to be compared have been aligned to yield maximum identity, potentially introducing gaps. Said percentage may be purely statistical, and the differences between the two sequences may be but are not necessarily randomly distributed over the entire length of the sequences to be compared. Comparisons of two sequences are usually carried out by comparing the sequences, after optimal alignment, with respect to a segment or "window of comparison", in order to identify local regions of corresponding sequences. For example, the optimal alignment for a comparison may be carried out manually or with the aid of the local homology algorithm by Smith and Waterman, 1981, Ads App. Math. 2, 482, with the aid of the local homology algorithm by Needleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using the algorithms (GAP, BESTFIT, FASTA, BLAST P, BLAST N and TFASTA in Wisconsin Genetics Software Package, Genetics Computer Group, 575 Science Drive, Madison, Wis., or Clustal Omega). In some embodiments, percent identity of two sequences is determined using the BLASTN or BLASTP algorithm, as available on the United States National Center for Biotechnology Information (NCBI) website (e.g., at blast.ncbi.nlm.nih.gov/Blast.cgi?PAGE_TYPE=BlastSearch&BLAST_SPEC=blast2seq& LINK_LOC=align2seq). Typically, the % identity is determined over the entire length of the reference sequence on which the analysis is performed.

A variant polypeptide, such as an antigen binding protein, may contain one or more substitutions (e.g., conservative substitutions), insertions, or deletions relative to the reference sequence. In certain embodiments, the variant polypeptide comprises one, two or three substitutions, insertions and/or deletions relative to the reference sequence. Substitutions, insertions, or deletions may result in the change of one or more biophysical parameters but particularly preferred are tolerated changes so that the polypeptide retains the desired activity. In some embodiments, the variant polypeptide comprises one or more tolerated substitutions, such as conservative substitutions. In certain embodiments, such variant polypeptide maintains physically, biologically, chemically and/or functionally the properties of the corresponding reference sequence.

"Specifically recognizes" or "specifically binds" refers to the ability of the antigen binding proteins to bind selectively to the antigen in contrast to non-specific interactions with unrelated proteins which do not comprise the binding epitope. Suitable assays for determining the specific binding are described below. In certain embodiments, the equilibrium dissociation constant ($K_D$) of an antigen binding protein to an unrelated protein is less than about 50-fold lower than the one of the antigen binding protein to its antigen, as e.g., determined by SPR.

As used herein, the term "affinity" (or "binding affinity" as used interchangeably herein) refers to the strength of the interaction between an antibody's antigen binding site and the epitope to which it binds. As readily understood by those skilled in the art, an antibody or antigen binding protein affinity may be reported as an equilibrium dissociation constant ($K_D$) in molarity (M). The equilibrium dissociation constant $K_D$ is calculated from the association rate constant $k_a$ (having the unit $M^{-1}s^{-1}$) and the dissociation rate constant $k_d$ (having the unit $s^{-1}$) by $k_d/k_a$. The antibodies of the disclosure may have $K_D$ values in the range of $10^{-8}$ to $10^{-14}$ M.

The ability of an antibody to bind to a specific antigenic determinant (e.g., a target peptide-MHC) can be measured either through an enzyme-linked immunosorbent assay (ELISA) or other techniques familiar to one of skill in the art, e.g., surface plasmon resonance (SPR) technique (conducted e.g. using a BIAcore instrument) (Liljeblad et al., Glyco J 17, 323-329 (2000)), and traditional binding assays (Heeley, Endocr Res 28, 217-229 (2002)). Generally, kinetic rate constants can be determined at temperatures in the range of 15° C. to 37° C. The present specification makes reference to kinetic rate constants determined by SPR throughout. Typically, in embodiments pertaining to each reference to SPR throughout the present specification, association rate constant values, dissociation rate constant values and equilibrium dissociation constant values recited herein are determined by SPR at 25° C. SPR based on the monovalent antigen binding protein. Preferably, the SPR-based system used is a Biacore SPR system. The skilled person will appreciate that the binding parameters can be measured in the context of the monovalent or bivalent bi-, tri- or multi-specific constructs.

In certain embodiments, the antigen binding protein is not a T cell receptor (TCR), including but not limited to, a soluble TCR. As used herein, the term "T cell receptor" or "TCR" refers to a heterodimeric protein comprised of two different chains (TCRα and TCRβ), which structurally belong to the immunoglobulin (Ig) superfamily. The extracellular portion of each chain is composed of variable ("Vα" and "Vβ") and constant ("Cα" and "Cβ") domains, and a hinge region, where the formation of a stabilizing disulfide bond occurs. The intracellular region forms a non-covalent interaction with another transmembrane protein, CD3, which in the case of the correct target recognition leads to a series of conformational changes and a first T cell activation signal. Recognition and binding of peptide-MHC (pMHC) by a TCR is governed by the six hypervariable loops, termed complementarity determining regions (CDRs), located on the variable domains of the TCRα (CDRα1, CDRα2, CDRα3) and TCRβ (CDRβ1, CDRβ2, CDRβ3). CDR3 loops (CDRα3 and CDRβ3) lead the recognition of the processed antigen with the support of CDRα1 and CDRβ1, that have been implicated in the recognition of the N- and C-terminal amino acids of the presented peptide, respectively (Rudolph et al. Annu Rev Immunol. 24:419-66. 2006). Recognition of the MHC is typically achieved through the interaction with CDRα2 and CDRβ2. The high sequence diversity of the TCR is achieved through V(D)J recombination process, in which the variable domain is generated from a combination of genes: V (variable) and J (joining) for both TCRα and TCRβ, and an additional D (diversity) gene for TCRβ. The high antigen specificity of the TCR is controlled by the thymic maturation process, in which the self-reacting T cells are negatively selected. TCR affinity towards the specific pMHC and the functional avidity are the key factors controlling T-cell activation. A critical role in antigen recognition, however, is played by the affinity, i.e., the strength of binding between the TCR and the cell-displayed pMHC (Tian et al. J Immunol. 179:2952-2960. 2007). The physiological affinities of TCRs range from 1 μM to 100 μM (Davis et al. Annu Rev Immunol. 16:523-544. 1998), which, in comparison to antibodies, is relatively low.

As used herein, the term "peptide-MHC" or "pMHC" or "pMHC complex" as used interchangeably herein refers to a major histocompatibility complex (MHC) molecule (MHC-I or -II) with an antigenic peptide bound in a peptide binding pocket of the MHC. As is known in the art, MHC molecules present peptides, in particular antigenic peptides, on the surface of cells to be recognized by immune cells. Accordingly, as will be appreciated by a skilled artisan, the term "pMHC" as used herein refers to a complex of an MHC molecule and a peptide, in particular an antigenic peptide, presented by the MHC molecule. This is commonly known as MHC-restricted antigen presentation. Accordingly, the peptide targeted by the pMHC binding domains is an MHC-restricted peptide. The peptide can thus be considered as target peptide or target antigenic peptide. Further, in accordance with the present disclosure, the terms "target pMHC binding domain" and "pMHC binding domain" may be used interchangeably herein, and in any case refer to the at least first and at least second pMHC binding domains referred to herein throughout. The terms "target peptide/antigen presented by an MHC molecule/complex" and "MHC restricted target peptide/antigen", or similar expressions used throughout the present specification, may be used interchangeably herein.

In certain embodiments, the MHC is a human MHC. While MHCs occur in all vertebrates, the MHC in human is known as HLA (human leukocyte antigen). HLA is highly polygenic and can be broadly divided into three classes of MHC molecules, class I, class II and class III. Moreover, HLA genes have the highest level of polymorphism of the human genome. The target peptide may be presented on an MHC class I complex (such as of serotype HLA-A, HLA-B, HLA-C, HLA-E, HLA-F, HLA-G, HLA-K or HLA-L, or their respective subtypes) or an MHC class II complex (such as the serotypes HLA-DP, HLA-DQ, HLA-DR, DM or DO, or their respective subtypes). The HLA-A protein constitutes the alpha chain of the respective class I MHC (major histocompatibility complex) protein, which further comprises a beta 2 microglobulin subunit. "HLA-A2", "HLA-A*02", "HLA-A02", or "HLA-A*2" as used interchangeably herein refers to a human leukocyte antigen serotype in the HLA-A serotype group 2. Each of the serotypes comprise different subtypes. HLA-A*02:01 (also referred to as HLA-A0201, HLA-A02.01, or HLA-A201) is a specific subtype of the HLA-A*02 protein. "MAGE-A4 pMHC" refers to a complex of an HLA-A*02 molecule and a MAGE-A4 derived peptide (also referred to herein as a "MAGE-A4 peptide"), specifically GVYDGREHTV (SEQ ID NO: 3). "MAGE-A8 pMHC" refers to a complex of an HLA-A*02 molecule and a MAGE-A8 derived peptide (also referred to herein as a "MAGE-A8 peptide"), specifically GLYDGREHSV (SEQ ID NO: 71). "MAGE-B4 pMHC" refers to a complex of an HLA-A*02 molecule and a MAGE-B4 derived peptide (also referred to herein as a "MAGE-B4 peptide"), specifically GIYDGKRHLI (SEQ ID NO: 72).

As used herein, the term "PBS" refers to phosphate buffered saline. PBS is a pH-adjusted blend of phosphate buffers and saline solutions. In certain embodiments, the PBS comprises about 100-150 mM NaCl, about 1-5 mM KCl, about 1-10 mM $Na_2HPO_4$, and 1-5 mM $KH_2PO_4$. In certain embodiments, the PBS comprises 130 mM NaCl, 10 mM $Na_2HPO_4$, and pH of 6.0.

MAGE-A4 Peptide-MHC and Antigen Binding Proteins Thereto

The antigen binding proteins and multispecific antigen binding proteins described herein possess binding specificity to a MAGE-A4 peptide-MHC.

In certain embodiments, provided are isolated antigen binding proteins that bind to HLA-presented GVYDGREHTV (SEQ ID NO: 3), i.e., the isolated antigen binding protein is not associated or bound to the surface of a cell, such as a T cell. Isolated antigen binding proteins are separated from a component of its natural environment. In certain embodiments, the isolated antigen binding protein is purified to greater than 95% or 99% purity as determined by, for example, electrophoretic methods (e.g., SDS-PAGE, isoelectric focusing (IEF), capillary electrophoresis) or chromatography (e.g., ion exchange or reverse phase HPLC, affinity chromatography, size exclusion chromatography). In certain embodiments, the antigen binding protein is not a soluble TCR (e.g., a TCR lacking one or more of a transmembrane domain, an intracellular signaling domain, and constant domains). In certain embodiments, the antigen binding protein is a monoclonal antibody, in particular an antibody fragment such as a scFv.

The target peptide may be presented on an MHC class I complex (such as of serotype HLA-A, HLA-B, HLA-C, HLA-E, HLA-F, HLA-G, HLA-K or HLA-L, or their respective subtypes) or an MHC class II complex (such as the serotypes HLA-DP, HLA-DQ, HLA-DR, DM or DO, or their respective subtypes). Each of the serotypes comprise different subtypes. In one embodiment, the antigen binding protein targets a peptide bound to an HLA-A2 pMHC complex, also termed HLA-A*02, in particular HLA-A*02: 01.

The antigen binding proteins possess surprisingly high binding affinity while retaining high specificity for the target (i.e., low affinity to no binding for pMHCs displaying non-related peptides, or beta-2-microglobulin). As used herein, a "non-related peptide" corresponds to a peptide which does not comprise the binding epitope of the antigen binding protein of the disclosure. In certain embodiments, the affinity of an antigen binding protein to an unrelated peptide MHC is less than about 50-fold lower than binding of the antigen binding protein to HLA-presented GVYDGREHTV (SEQ ID NO: 3), as e.g., determined by SPR.

In certain embodiments, the antigen binding protein comprises specificity for a MAGE-A4 peptide amino acid sequence set forth in SEQ ID NO: 3 (GVYDGREHTV) which corresponds to amino acids 230-239 of MAGE-A4.

In certain embodiments, the antigen binding proteins bind related HLA-displayed MAGE-A4, MAGE-A8 and MAGE-B4 peptides in a similar affinity range. Accordingly, the disclosure provides an antigen binding protein comprising binding specificity to MAGE-A4 pMHC, MAGE-A8 pMHC, and MAGE-B4 pMHC, in particular MAGE-A4 derived GVYDGREHTV (SEQ ID NO: 3), MAGE-A8 derived GLYDGREHSV (SEQ ID NO: 71) and MAGE-B4 derived GIYDGKRHLI (SEQ ID NO: 72).

In certain embodiments, the MAGE-A4 peptide, said MAGE-A8 peptide, and/or said MAGE-B4 peptide is in complex with an HLA-A*02 polypeptide.

In certain embodiments, the HLA-A*02 polypeptide comprises the amino acid sequence set forth in SEQ ID NO: 1.

In certain embodiments, the beta-2-microglobulin polypeptide comprises the amino acid sequence set forth in SEQ ID NO: 2.

Thus, in certain embodiments, the antigen binding protein comprises specificity for a HLA-A*02/MAGE-A4, in particular to the peptide GVYDGREHTV (SEQ ID NO: 3) displayed by HLA-A*02, more particularly by the HLA-A*02 subtype HLA-A*02:01.

In one aspect, the disclosure provides an antigen binding protein which specifically binds to Melanoma-Associated Antigen A4 (MAGE-A4) peptide-MHC (pMHC), comprising: an antibody heavy chain variable (VH) domain comprising an amino acid sequence that is at least about 90%, 95%, 96%, 97%, 98%, 99% or 100% identical to the amino acid sequence of SEQ ID NO: 10 or consists of the amino acid sequence of SEQ ID NO: 10, and an antibody light chain variable (VL) domain comprising an amino acid sequence that is at least about 90%, 95%, 96%, 97%, 98%, 99% or 100% identical to the amino acid sequence of SEQ ID NO: 15 or consists of the amino acid sequence of SEQ ID NO: 15.

In certain embodiments, such antigen binding protein is a scFv comprising or consisting of SEQ ID NO: 61, or a variant thereof that is at least about 90%, 95%, 96%, 97%, 98%, 99% or 100% identical to the amino acid sequence of SEQ ID NO: 61.

In one aspect, the disclosure provides an antigen binding protein which specifically binds to Melanoma-Associated Antigen A4 (MAGE-A4) peptide-MHC (pMHC), comprising: a VH domain comprising an amino acid sequence that is at least about 90%, 95%, 96%, 97%, 98%, 99% or 100% identical to the amino acid sequence of SEQ ID NO: 20 or consists of the amino acid sequence of SEQ ID NO: 20, and a VL domain comprising an amino acid sequence that is at least about 90%, 95%, 96%, 97%, 98%, 99% or 100% identical to the amino acid sequence of SEQ ID NO: 25 or consists of the amino acid sequence of SEQ ID NO: 25.

In certain embodiments, the antigen binding protein is a scFv comprising or consisting of SEQ ID NO: 62, or a variant thereof that is at least about 90%, 95%, 96%, 97%, 98%, 99% or 100% identical to the amino acid sequence of SEQ ID NO: 62.

In one aspect, the disclosure provides an antigen binding protein which specifically binds to Melanoma-Associated Antigen A4 (MAGE-A4) peptide-MHC (pMHC), comprising: a VH domain comprising an amino acid sequence that is at least about 90%, 95%, 96%, 97%, 98%, 99% or 100% identical to the amino acid sequence of SEQ ID NO: 30, wherein the VH domain comprises a C amino acid at position 44 of SEQ ID NO: 30, and a VL domain comprising an amino acid sequence that is at least about 90%, 95%, 96%, 97%, 98%, 99% or 100% identical to the amino acid sequence of SEQ ID NO: 35, wherein the VL domain comprises a C amino acid at position 102 of SEQ ID NO: 35.

In certain embodiments, the antigen binding protein comprises a VH domain consisting of an amino acid sequence of SEQ ID NO: 30, and a VL domain consisting of an amino acid sequence of SEQ ID NO: 35.

In certain embodiments, the antigen binding protein is a scFv comprising or consisting of SEQ ID NO: 63 or a variant thereof that is at least about 90%, 95%, 96%, 97%, 98%, 99% or 100% identical to the amino acid sequence of SEQ ID NO: 63.

In one aspect, the disclosure provides an antigen binding protein which specifically binds to Melanoma-Associated Antigen A4 (MAGE-A4) peptide-MHC (pMHC), comprising: a VH domain comprising an amino acid sequence that is at least about 90%, 95%, 96%, 97%, 98%, 99% or 100% identical to the amino acid sequence of SEQ ID NO: 40, wherein the VH domain comprises a Y amino acid at position 47, a R amino acid at position 71, and a N amino acid at position 73 of SEQ ID NO: 40, and a VL domain comprising an amino acid sequence that is at least about 90%, 95%, 96%, 97%, 98%, 99% or 100% identical to the amino acid sequence of SEQ ID NO: 45.

In certain embodiments, the antigen binding protein comprises a VH domain consisting of an amino acid sequence of SEQ ID NO: 40, and a VL domain consisting of an amino acid sequence of SEQ ID NO: 45.

In certain embodiments, the antigen binding protein is a scFv comprising or consisting of SEQ ID NO: 64, or a variant thereof that is at least about 90%, 95%, 96%, 97%, 98%, 99% or 100% identical to the amino acid sequence of SEQ ID NO: 62.

Additional exemplary MAGE-A4 pMHC antigen binding proteins are described in PCT/IB2022/052117, and filed Mar. 9, 2022, PCT/IB2022/052119, filed Mar. 9, 2022, the contents of each are incorporated herein by reference.

The antigen binding proteins may be monovalent or multivalent, such as e.g., bispecific or trispecific. In certain embodiments, the antigen binding protein is monovalent. In certain aspects, monovalent antigen binding proteins are provided which comprise the CDRs of the VL and/or VH sequences recited above. Such monovalent antigen binding proteins include, without being limited to, scFv, Fab, scFab, dAb, VHH, V(NAR), DARPins, affilins and nanobodies.

MAGE-A4 Peptide-MHC—Immune Cell Engaging Antigen Binding Proteins

The multispecific antigen binding proteins described herein possess at least one MAGE-A4 peptide-MHC binding domain and a binding domain with binding specificity to a cell surface protein of an immune cell (e.g., CD3 on the surface of a T cell or CD16a expressed on the surface of a NK cell). Alternatively, the multispecific antigen binding proteins described herein possess at least two MAGE-A4 peptide-MHC binding domains and optionally a binding domain with binding specificity to a cell surface protein of an immune cell (e.g., CD3 on the surface of a T cell, or CD16a expressed on the surface of a NK cell). In certain embodiments, the multispecific antigen binding protein comprises the MAGE-A4 peptide-MHC antigen binding protein described above.

With respect to dual pMHC engagement, targeting two MAGE-A4 peptide-MHC on the surface of a target cell (e.g., a cancer cell) improves target cell engagement through enhanced binding avidity. The enhanced binding avidity may in turn promote improved target cell killing relative to an antigen binding protein that only has one pMHC binding domain. The enhanced binding avidity created by at least two pMHC binding domains may be particularly useful when targeting pMHC complexes of low copy number on the surface of a target cell (e.g., cancer cell). The dual pMHC engaging multispecific binding protein is described in further detail in U.S. 63/289,380, filed Dec. 14, 2021, and U.S. 63/317,256, filed Mar. 7, 2022, the contents of each are incorporated herein by reference.

In certain embodiments, the multispecific antigen binding protein is bispecific or trispecific.

In certain embodiments, the multispecific antigen binding protein is bivalent or polyvalent, such as trivalent.

In certain embodiments, the multispecific antigen binding protein further comprises at least one additional binding domain.

In certain embodiments, the additional binding domain is an immune cell engager, in particular a CD3-binding domain or a CD16a-binding domain.

In certain embodiments, the multispecific antigen binding protein further comprises a third antigen binding domain.

In certain embodiments, the third antigen binding domain binds to HLA-A*02/MAGE-A4.

In certain embodiments, the third antigen binding domain is identical to the first HLA-A*02/MAGE-A4 antigen binding domain described above.

In certain embodiments, the multispecific antigen binding protein may bind to two (or more) different epitopes of HLA-A2/MAGE-A4.

In one aspect, the disclosure provides an multispecific antigen binding protein comprising: a) a first antigen binding domain which specifically binds to CD3; b) a second antigen binding domain which specifically binds to Melanoma-Associated Antigen A4 (MAGE-A4) peptide-MHC (pMHC), the second antigen binding domain comprising: b1) an antibody heavy chain variable (VH) domain comprising an HCDR1 amino acid sequence of SNYAMS (SEQ ID NO: 11), an HCDR2 amino acid sequence of IVSSGGTTYYAX$_1$X$_2$X$_3$KG (SEQ ID NO: 6), wherein X$_1$ corresponds to amino acid S or D, X$_2$ corresponds to amino acid W or S, and X$_3$ corresponds to amino acid A or V, and an HCDR3 amino acid sequence of DLYYGPX$_4$TX$_5$YX$_6$X$_7$X$_8$NL (SEQ ID NO: 7), wherein X$_4$ corresponds to amino acid T, N, or S, X$_5$ corresponds to amino acid D or is absent, X$_6$ corresponds to amino acid S or F, X$_7$ corresponds to amino acid A or V, and X$_8$ corresponds to amino acid F or A; and b2) an antibody light chain variable (VL) domain comprising an LCDR1 amino acid sequence of TADTLSRSYAS (SEQ ID NO: 16), an LCDR2 amino acid sequence of RDTSRPS (SEQ ID NO: 17), and an LCDR3 amino acid sequence of ATX$_9$X$_{10}$X$_{11}$SGSNFQX$_{12}$ (SEQ ID NO: 8), wherein X$_9$ corresponds to amino acid S or R, X$_{10}$ corresponds to amino acid D or P, X$_{11}$ corresponds to amino acid G, S, or F, and X$_{12}$ corresponds to amino acid L or A.

In certain embodiments, the MAGE-A4 peptide-MHC (pMHC) is a GVYDGREHTV (SEQ ID NO: 3) HLA-A*02 complex.

In certain embodiments, the multispecific antigen binding protein remains at least 94%, 95%, 96%, 97%, 98%, 99% or 100% monomeric after incubation for 14 days at 4° C. at 1 mg/ml and/or 10 mg/ml in PBS as determined by SEC-HPLC.

In certain embodiments, the multispecific antigen binding protein further comprises a third antigen binding domain, in particular, said third binding domain being identical to said second binding domain, i.e., the MAGE-A4 pMHC binding domain.

In certain embodiments, such multispecific antigen binding protein comprises: c) a third antigen binding domain which specifically binds to MAGE-A4 pMHC, the third antigen binding domain comprising: c1) a VH domain comprising an HCDR1 amino acid sequence of SNYAMS (SEQ ID NO: 11), an HCDR2 amino acid sequence of IVSSGGTTYYAX$_1$X$_2$X$_3$KG (SEQ ID NO: 6), wherein X$_1$ corresponds to amino acid S or D, X$_2$ corresponds to amino acid W or S, and X$_3$ corresponds to amino acid A or V, and an HCDR3 amino acid sequence of DLYYGPX$_4$TX$_5$YX$_6$X$_7$X$_8$NL (SEQ ID NO: 7), wherein X$_4$ corresponds to amino acid T, N, or S, X$_5$ corresponds to amino acid D or is absent, X$_6$ corresponds to amino acid S or F, X$_7$ corresponds to amino acid A or V, and X$_8$ corresponds to amino acid F or A; and c2) a VL domain comprising an LCDR1 amino acid sequence of TADTLSRSYAS (SEQ ID NO: 16), an LCDR2 amino acid sequence of RDTSRPS (SEQ ID NO: 17), and an LCDR3 amino acid sequence of ATX$_9$X$_{10}$X$_{11}$SGSNFQX$_{12}$ (SEQ ID NO: 8), wherein X$_9$ corresponds to amino acid S or R, X$_{10}$ corresponds to amino acid D or P, X$_{11}$ corresponds to amino acid G, S, or F, and X$_{12}$ corresponds to amino acid L or A.

In certain embodiments, the second and third antigen binding domains comprise:
(i) a VH comprising an HCDR1 sequence comprising the amino acid sequence of SNYAMS (SEQ ID NO: 11), an HCDR2 sequence comprising the amino acid sequence of IVSSGGTTYYADSVKG (SEQ ID NO: 12), and an HCDR3 sequence comprising the amino acid sequence of DLYYGPNTDYSAANL (SEQ ID NO: 13); and a VL comprising an LCDR1 sequence comprising the amino acid sequence of TADTLSRSYAS (SEQ ID NO: 16), an LCDR2 sequence comprising the amino acid sequence of RDTSRPS (SEQ ID NO: 17), and an LCDR3 sequence comprising the amino acid sequence of ATRPSSGSNFQA (SEQ ID NO: 18);
(ii) a VH comprising an HCDR1 sequence comprising the amino acid sequence of SNYAMS (SEQ ID NO: 21), an HCDR2 sequence comprising the amino acid sequence of IVSSGGTTYYADSVKG (SEQ ID NO: 22), and an HCDR3 sequence comprising the amino acid sequence of DLYYGPSTYFVANL (SEQ ID NO: 23); and a VL comprising an LCDR1 sequence comprising the amino acid sequence of TADTLSRSYAS (SEQ ID NO: 26), an LCDR2 sequence comprising the amino acid sequence of RDTSRPS (SEQ ID NO: 27), and an LCDR3 sequence comprising the amino acid sequence of ATRPSSGSNFQL (SEQ ID NO: 28);
(iii) a VH comprising an HCDR1 sequence comprising the amino acid sequence of SNYAMS (SEQ ID NO: 31), an HCDR2 sequence comprising the amino acid sequence of IVSSGGTTYYASWAKG (SEQ ID NO: 32), and an HCDR3 sequence comprising the amino acid sequence of DLYYGPTTYSAANL (SEQ ID NO: 33); and a VL comprising an LCDR1 sequence comprising the amino acid sequence of TADTLSRSYAS (SEQ ID NO: 36), an LCDR2 sequence comprising the amino acid sequence of RDTSRPS (SEQ ID NO: 37), and an LCDR3 sequence comprising the amino acid sequence of ATRDFSGSNFQL (SEQ ID NO: 38); or
(iv) a VH comprising an HCDR1 sequence comprising the amino acid sequence of SNYAMS (SEQ ID NO: 41), an HCDR2 sequence comprising the amino acid sequence of IVSSGGTTYYASWAKG (SEQ ID NO: 42), and an HCDR3 sequence comprising the amino acid sequence of DLYYGPTTYSAFNL (SEQ ID NO: 43); and a VL comprising an LCDR1 sequence comprising the amino acid sequence of TADTLSRSYAS (SEQ ID NO: 46), an LCDR2 sequence comprising the amino acid sequence of RDTSRPS (SEQ ID NO: 47), and an LCDR3 sequence comprising the amino acid sequence of ATRPSSGSNFQA (SEQ ID NO: 48).

In certain embodiments, the second and third antigen binding domains comprise:
(i) an antibody heavy chain variable (VH) domain comprising an amino acid sequence that is at least about 90%, 95%, 96%, 97%, 98%, 99% or 100% identical to the amino acid sequence of SEQ ID NO: 10, and an antibody light chain variable (VL) domain comprising an amino acid sequence that is at least about 90%, 95%, 96%, 97%, 98%, 99% or 100% identical to the amino acid sequence of SEQ ID NO: 15;
(ii) a VH domain comprising an amino acid sequence that is at least about 90%, 95%, 96%, 97%, 98%, 99% or 100% identical to the amino acid sequence of SEQ ID NO: 20, and a VL domain comprising an amino acid sequence that is at least about 90%, 95%, 96%, 97%, 98%, 99% or 100% identical to the amino acid sequence of SEQ ID NO: 25;
(iii) a VH domain comprising an amino acid sequence that is at least about 90%, 95%, 96%, 97%, 98%, 99% or 100% identical to the amino acid sequence of SEQ ID NO: 30, and a VL domain comprising an amino acid sequence that is at least about 90%, 95%, 96%, 97%, 98%, 99% or 100% identical to the amino acid sequence of SEQ ID NO: 35; or
(iv) a VH domain comprising an amino acid sequence that is at least about 90%, 95%, 96%, 97%, 98%, 99% or 100% identical to the amino acid sequence of SEQ ID NO: 40, and a VL domain comprising an amino acid sequence that is at least about 90%, 95%, 96%, 97%, 98%, 99% or 100% identical to the amino acid sequence of SEQ ID NO: 45.

In certain embodiments, any one or more of the first, second, and third antigen binding domain comprises an antibody fragment. In certain embodiments, the antibody fragment comprises a Fab fragment, a F(ab')$_2$ fragment, a Fab' fragment, an Fv fragment, a single chain variable fragment (scFv), and a single domain antibody fragment.

In certain embodiments, the MAGE-A4 pMHC antigen binding domains comprise an scFv. In certain embodiments, the multispecific antigen binding protein comprises at least one scFv comprising the amino acid sequence of SEQ ID NO: 61, SEQ ID NO: 62, SEQ ID NO: 63 and/or SEQ ID NO: 64, or a variant thereof that is at least about 90%, 95%, 96%, 97%, 98% or 99% identical to the amino acid sequence of SEQ ID NO: SEQ ID NO: 61, SEQ ID NO: 62, SEQ ID NO: 63 and/or SEQ ID NO: 64, respectively.

In certain embodiments, the immune cell or CD3 antigen binding domain is a Fab fragment, wherein the Fab fragment comprises a heavy chain comprising a CH1 domain and the VH, and a light chain comprising a CL domain and the VL.

In certain embodiments, the CH1 domain comprises at least 5 amino acids of an antibody hinge region. In certain embodiments, the CH1 domain comprises an amino acid sequence EPKSC (SEQ ID NO: 88) of an antibody hinge region.

In certain embodiments, the second antigen binding domain is operably linked to the C-terminus of the heavy chain or the N-terminus of the heavy chain.

In certain embodiments, the third antigen binding domain is operably linked to the C-terminus of the heavy chain or the N-terminus of the heavy chain.

In certain embodiments, the second antigen binding domain is operably linked to the C-terminus of the light chain or the N-terminus of the light chain.

In certain embodiments, the third antigen binding domain is operably linked to the C-terminus of the light chain or the N-terminus of the light chain.

In certain embodiments, a) the second antigen binding domain comprises an scFv linked to the C-terminus of the Fab domain heavy chain and the third antigen binding domain comprises an scFv linked to the C-terminus of the Fab domain light chain; b) the second antigen binding domain comprises an scFv linked to the N-terminus of the Fab domain heavy chain and the third antigen binding domain comprises an scFv linked to the N-terminus of the Fab domain light chain; c) the second antigen binding domain comprises an scFv linked to the N-terminus of the Fab domain heavy chain and the third antigen binding domain comprises an scFv linked to the C-terminus of the Fab domain light chain; or d) the second antigen binding domain comprises an scFv linked to the C-terminus of the Fab domain heavy chain and the third antigen binding domain comprises an scFv linked to the N-terminus of the Fab domain light chain.

In certain embodiments, the scFv is linked to the Fab domain with an amino acid linker.

In certain embodiments, the amino acid linker comprises (GGGGS)n (SEQ ID NO: 73), wherein n is an integer between 1 and 5. In certain embodiments, amino acid linker comprises the amino acid sequence GGGGS (SEQ ID NO: 74), GGGGSGGGGSGGGGS (SEQ ID NO: 75), GGGGSGGGGSGGGGSGGGGS (SEQ ID NO: 76), GGGGSGGGGSGGGGSGGGGAS (SEQ ID NO: 77), or GGGGGSGGGGSGGGGSGGGGS (SEQ ID NO: 78).

In certain embodiments, second and/or third antigen binding domain VH and VL are joined with an amino acid linker.

In certain embodiments, the amino acid linker comprises (GGGGS)n (SEQ ID NO: 73), wherein n is an integer between 1 and 5. In certain embodiments, the amino acid linker comprises the amino acid sequence GGGGS (SEQ ID NO: 74), GGGGSGGGGSGGGGS (SEQ ID NO: 75), GGGGSGGGGSGGGGSGGGGS (SEQ ID NO: 76), GGGGSGGGGSGGGGSGGGGAS (SEQ ID NO: 77), or GGGGGSGGGGSGGGGSGGGGS (SEQ ID NO: 78).

In certain embodiments, the multispecific antigen binding protein does not comprise an Fc domain.

In certain embodiments, the multispecific antigen binding protein comprises a (scFv)$_2$, (scFv)$_3$, BiTE, BIKE, Dart, diabody, tribody, Fab$_2$, Fab$_3$, Fab$_4$, scFv-Fab-scFv or minibody-scFv.

In certain embodiments, the multispecific antigen binding protein comprises a molecular weight of about 75 kDa to about 110 kDa.

In certain embodiments, the antigen binding protein has longer serum half-life relative to an antigen binding protein with a molecular weight of <about 75 kDa.

Suitable anti-CD3 binding domains for the multispecific antigen binding domains disclosed herein are known in the art, particularly T-cell activating CD-epsilon binding domains. Exemplary CD3 binding domains are disclosed in U.S. Pat. No. 6,750,325, WO2008079713, U.S. Pat. No. 7,635,475, WO2005040220, U.S. Pat. No. 7,728,114, WO9404679, U.S. Pat. No. 7,381,803, WO2008119567, WO2014110601, WO2014145806, WO2016086189 and/or WO2019195535A1, each of which is incorporated herein by reference. In certain embodiments, the CD3 domain does not cross-react with minipig CD3 or rodent CD3, in particular rat or mouse CD3.

In certain embodiments, the CD3 antigen binding domain comprises: a1) a VH comprising an HCDR1 sequence comprising the amino acid sequence of STYAMN (SEQ ID NO: 51), an HCDR2 sequence comprising the amino acid sequence of RIRSKYNNYATYYADSVKG (SEQ ID NO: 52), and an HCDR3 sequence comprising the amino acid sequence of HGNFGDSYVSWFAY (SEQ ID NO: 53); and a2) a VL comprising an LCDR1 sequence comprising the amino acid sequence of GSSTGAVTTSNYAN (SEQ ID NO: 56), an LCDR2 sequence comprising the amino acid sequence of GTNKRAP (SEQ ID NO: 57), and an LCDR3 sequence comprising the amino acid sequence of ALWYSNHWV (SEQ ID NO: 58).

In certain embodiments, the CD3 antigen binding domain comprises: a VH comprising an amino acid sequence that is at least about 90%, 95%, 96%, 97%, 98%, 99% or 100% identical to the amino acid sequence of SEQ ID NO: 50, and a VL comprising an amino acid sequence that is at least about 90%,%, 95%, 96%, 97%, 98%, 99% or 100% identical to the amino acid sequence of SEQ ID NO: 55.

In certain embodiments, the CD3 antigen binding domain comprises: a VH consisting of an amino acid sequence of SEQ ID NO: 50, and a VL consisting of an amino acid sequence of SEQ ID NO: 55.

In certain embodiments, the CD3 antigen binding domain comprises: a heavy chain comprising an amino acid sequence that is at least about 90%,%, 95%, 96%, 97%, 98%, 99% or 100% identical to the amino acid sequence of SEQ ID NO: 49, and a light chain comprising an amino acid sequence that is at least about 90%,%, 95%, 96%, 97%, 98%, 99% or 100% identical to the amino acid sequence of SEQ ID NO: 54.

In certain embodiments, the CD3 antigen binding domain comprises: a VH consisting of an amino acid sequence of SEQ ID NO: 49, and a VL consisting of an amino acid sequence of SEQ ID NO: 54.

In certain embodiments, the multispecific antigen binding protein comprises: a) a first antigen binding domain which specifically binds to CD3, the first antigen binding domain comprising: a1) a VH comprising an HCDR1 sequence comprising the amino acid sequence of STYAMN (SEQ ID NO: 51), an HCDR2 sequence comprising the amino acid sequence of RIRSKYNNYATYYADSVKG (SEQ ID NO: 52), and an HCDR3 sequence comprising the amino acid sequence of HGNFGDSYVSWFAY (SEQ ID NO: 53); and a2) a VL comprising an LCDR1 sequence comprising the amino acid sequence of GSSTGAVTTSNYAN (SEQ ID NO: 56), an LCDR2 sequence comprising the amino acid sequence of GTNKRAP (SEQ ID NO: 57), and an LCDR3 sequence comprising the amino acid sequence of ALWYSNHWV (SEQ ID NO: 58); and b) a second antigen binding domain which specifically binds to Melanoma-Associated Antigen A4 (MAGE-A4) peptide-MHC (pMHC). Embodiments of suitable second antigen binding domains have been described in detail above. Such multispecific antigen binding proteins may comprise a third binding domain which may be identical to the second binding domain. Possible formats and modifications have also been detailed above.

In one aspect, the disclosure provides an antigen binding protein which is multispecific, comprising: a) a single Fab domain which specifically binds CD3 on a T cell, the Fab domain comprising a heavy chain and a light chain and the CD3 antigen binding domain comprising a VH comprising an amino acid sequence that is at least about 90%, 95%, 96%, 97%, 98%, 99% or 100% identical to the amino acid sequence of SEQ ID NO: 50, and a VL comprising an amino acid sequence that is at least about 90%, 95%, 96%, 97%, 98%, 99% or 100% identical to the amino acid sequence of SEQ ID NO: 55; b) a MAGE-A4 pMHC binding domain operably linked to the C-terminus of the Fab heavy chain, comprising a VH comprising an amino acid sequence that is at least about 90%, 95%, 96%, 97%, 98%, 99% or 100% identical to the amino acid sequence of SEQ ID NO: 10 and a VL comprising an amino acid sequence that is at least about 90% identical to the amino acid sequence of SEQ ID NO: 15; and c) a MAGE-A4 pMHC binding domain operably linked to the C-terminus of the Fab light chain, comprising a VH comprising an amino acid sequence that is at least about 90%, 95%, 96%, 97%, 98%, 99% or 100% identical to the amino acid sequence of SEQ ID NO: 10 and a VL comprising an amino acid sequence that is at least about 90%, 95%, 96%, 97%, 98%, 99% or 100% identical to the amino acid sequence of SEQ ID NO: 15. In certain embodiments, said multispecific antigen binding protein is a bispecific Fab(scFv)$_2$, as e.g. shown in FIG. 4.

In one aspect, the disclosure provides an antigen binding protein which is multispecific, comprising: a) a single Fab domain which specifically binds CD3 on a T cell, the Fab domain comprising a heavy chain and a light chain and the CD3 antigen binding domain comprising a VH comprising an amino acid sequence that is at least about 90%, 95%, 96%, 97%, 98%, 99% or 100% identical to the amino acid sequence of SEQ ID NO: 50, and a VL comprising an amino acid sequence that is at least about 90%, 95%, 96%, 97%, 98%, 99% or 100% identical to the amino acid sequence of SEQ ID NO: 55; b) a MAGE-A4 pMHC binding domain operably linked to the C-terminus of the Fab heavy chain, comprising a VH comprising an amino acid sequence that is at least about 90%, 95%, 96%, 97%, 98%, 99% or 100% identical to the amino acid sequence of SEQ ID NO: 20 and a VL comprising an amino acid sequence that is at least about 90%, 95%, 96%, 97%, 98%, 99% or 100% identical to the amino acid sequence of SEQ ID NO: 25; and c) a MAGE-A4 pMHC binding domain operably linked to the C-terminus of the Fab light chain, comprising a VH comprising an amino acid sequence that is at least about 90%, 95%, 96%, 97%, 98%, 99% or 100% identical to the amino acid sequence of SEQ ID NO: 20 and a VL comprising an amino acid sequence that is at least about 90%, 95%, 96%, 97%, 98%, 99% or 100% identical to the amino acid sequence of SEQ ID NO: 25. In certain embodiments, said multispecific antigen binding protein is a bispecific Fab(scFv)$_2$, as e.g. shown in FIG. 4.

In one aspect, the disclosure provides an antigen binding protein which is multispecific, comprising: a) a single Fab domain which specifically binds CD3 on a T cell, the Fab domain comprising a heavy chain and a light chain and the CD3 antigen binding domain comprising a VH comprising an amino acid sequence that is at least about 90%, 95%, 96%, 97%, 98%, 99% or 100% identical to the amino acid sequence of SEQ ID NO: 50, and a VL comprising an amino acid sequence that is at least about 90%, 95%, 96%, 97%, 98%, 99% or 100% identical to the amino acid sequence of SEQ ID NO: 55; b) a MAGE-A4 pMHC binding domain operably linked to the C-terminus of the Fab heavy chain, comprising a VH comprising an amino acid sequence that is at least about 90%, 95%, 96%, 97%, 98%, 99% or 100% identical to the amino acid sequence of SEQ ID NO: 30 and a VL comprising an amino acid sequence that is at least about 90%, 95%, 96%, 97%, 98%, 99% or 100% identical to the amino acid sequence of SEQ ID NO: 35; and c) a MAGE-A4 pMHC binding domain operably linked to the C-terminus of the Fab light chain, comprising a VH comprising an amino acid sequence that is at least about 90%, 95%, 96%, 97%, 98%, 99% or 100% identical to the amino acid sequence of SEQ ID NO: 30 and a VL comprising an amino acid sequence that is at least about 90%, 95%, 96%, 97%, 98%, 99% or 100% identical to the amino acid sequence of SEQ ID NO: 35. In certain embodiments, said multispecific antigen binding protein is a bispecific Fab (scFv)$_2$, as e.g. shown in FIG. 4.

In one aspect, the disclosure provides an antigen binding protein which is multispecific, comprising: a) a single Fab domain which specifically binds CD3 on a T cell, the Fab domain comprising a heavy chain and a light chain and the CD3 antigen binding domain comprising a VH comprising an amino acid sequence that is at least about 90%, 95%, 96%, 97%, 98%, 99% or 100% identical to the amino acid sequence of SEQ ID NO: 50, and a VL comprising an amino acid sequence that is at least about 90%, 95%, 96%, 97%, 98%, 99% or 100% identical to the amino acid sequence of SEQ ID NO: 55; b) a MAGE-A4 pMHC binding domain operably linked to the C-terminus of the Fab heavy chain, comprising a VH comprising an amino acid sequence that is at least about 90%, 95%, 96%, 97%, 98%, 99% or 100% identical to the amino acid sequence of SEQ ID NO: 40 and a VL comprising an amino acid sequence that is at least about 90%, 95%, 96%, 97%, 98%, 99% or 100% identical to the amino acid sequence of SEQ ID NO: 45; and c) a MAGE-A4 pMHC binding domain operably linked to the C-terminus of the Fab light chain, comprising a VH comprising an amino acid sequence that is at least about 90%, 95%, 96%, 97%, 98%, 99% or 100% identical to the amino acid sequence of SEQ ID NO: 40 and a VL comprising an amino acid sequence that is at least about 90%, 95%, 96%, 97%, 98%, 99% or 100% identical to the amino acid sequence of SEQ ID NO: 45. In certain embodiments, said multispecific antigen binding protein is a bispecific Fab (scFv)$_2$, as e.g. shown in FIG. 4.

In certain embodiments, the multispecific antigen binding is a Fab(scFv)$_2$ comprising (a) a single Fab domain targeting CD3, the Fab domain comprising a heavy chain and a light chain, wherein the heavy chain comprises or consists of an amino acid sequence that is at least about 90%, 95%, 96%, 97%, 98%, 99% or 100% identical to the amino acid sequence of SEQ ID NO: 49 and the light chain comprises or consists of an amino acid sequence that is at least about 90%, 95%, 96%, 97%, 98%, 99% or 100% identical to the amino acid sequence of SEQ ID NO: 54; and (b) two scFvs targeting HLA-displayed SEQ ID NO: 3, each scFv comprising of consisting of an amino acid sequence that is at least about 90%, 95%, 96%, 97%, 98%, 99% or 100% identical to the amino acid sequence of SEQ ID NO: SEQ ID NO: 61, SEQ ID NO: 62, SEQ ID NO: 63 and/or SEQ ID NO: 64. In certain embodiments, one scFv is linked to the C-terminal end of the Fab heavy chain and the second one to the C-terminal end of the light chain, see the exemplary embodiment of FIG. 4.

In one aspect, the disclosure provides a multispecific antigen binding protein binding to GVYDGREHTV (SEQ ID NO: 3) HLA-A*02 complex and to CD3 comprising:

(i) a first polypeptide chain comprising or consisting of an amino acid sequence set forth in SEQ ID NO: 9 and a second polypeptide chain comprising an amino acid sequence set forth in SEQ ID NO: 14;

(ii) a first polypeptide chain comprising or consisting of an amino acid sequence set forth in SEQ ID NO: 19 and a second polypeptide chain comprising an amino acid sequence set forth in SEQ ID NO: 24;

(iii) a first polypeptide chain comprising or consisting of an amino acid sequence set forth in SEQ ID NO: 29 and a second polypeptide chain comprising an amino acid sequence set forth in SEQ ID NO: 34; or (iv) a first polypeptide chain comprising or consisting of an amino acid sequence set forth in SEQ ID NO: 39; and a second polypeptide chain comprising an amino acid sequence set forth in SEQ ID NO: 44;

or a variant of said sequences being at least 90%, 95%, 96%, 97%, 98% or 99% identical thereto while retaining antigen specificity (i.e., retaining specificity to GVYDGREHTV (SEQ ID NO: 3) HLA-A*02 complex and to CD3). In certain embodiments, the pMHC binding domain, in particular when in scFv format, comprise a variable heavy chain having a polar amino acid at position 11, 89 and/or 108, according to Kabat numbering.

In certain embodiments, the Fab domain comprises a variable heavy chain having a polar amino acid at position 11, 89 and/or 108, according to Kabat numbering.

In certain embodiments, the variable heavy chain comprises: leucine (L) or serine (S) at amino acid position 11, according to Kabat numbering; valine (V), serine (S), or threonine (T) at amino acid position 89, according to Kabat numbering; and/or leucine (L), serine (S), or threonine (T) amino acid position 108, according to Kabat numbering.

In certain embodiments, when leucine (L) is present at amino acid position 11, then serine (S) or threonine (T) are present at amino acid position 89, and serine (S) or threonine (T) are present at amino acid position 108, according to Kabat numbering.

In certain embodiments, when valine (V) is present at amino acid position 89, then serine (S) is present at amino acid position 11, and serine (S) or threonine (T) are present at amino acid position 108, according to Kabat numbering.

In certain embodiments, when leucine (L) is present at amino acid position 108, then serine (S) or threonine (T) are present at amino acid position 11, and serine (S) or threonine (T) are present at amino acid position 89, according to Kabat numbering.

In certain embodiments, the polar amino acid is serine (S) and/or threonine (T).

In certain embodiments, the variable heavy chain comprises serine (S) at amino acid position 11, serine (S) or threonine (T) at amino acid position 89, and serine (S) or threonine (T) at amino acid position 108, according to Kabat numbering.

In certain embodiments, the variable heavy chain comprises serine (S) at amino acid position 11, serine (S) at amino acid position 89, and serine (S) at amino acid position 108, according to Kabat numbering.

In certain embodiments, the Fab domain comprises a variable heavy chain having a serine (S) at position 113 deleted, according to Kabat numbering.

In certain embodiments, the pMHC binding domain, such as the first and/or the second pMHC binding domain, comprises a variable heavy chain having a serine (S) at position 113 deleted, according to Kabat numbering.

In certain embodiments, the Fab domain comprises a variable heavy chain having a serine (S) at position 112 deleted and a serine (S) at position 113 deleted, according to Kabat numbering.

In certain embodiments, the pMHC binding domain, such as the first and/or the second pMHC binding domain comprise a variable heavy chain having a serine (S) at position 112 deleted and a serine (S) at position 113 deleted, according to Kabat numbering.

In certain embodiments, the antigen binding protein comprises an S113A, S113G, or S113T substitution, according to Kabat numbering.

In certain embodiments, the antigen binding protein comprises an S113A, S113G, or S113T substitution, and wherein S112 is deleted, according to Kabat numbering.

In certain embodiments, the antigen binding protein comprises an S112A, S112G, or S112T substitution, according to Kabat numbering.

In certain embodiments, the antigen binding protein comprises an S112A, S112G, or S112T substitution, and wherein S113 is deleted, according to Kabat numbering.

In certain embodiments, the immune cell the multispecific antigen binding molecule binds to via the immune cell engager binding arm is selected from the group consisting of a T cell, a B cell, a natural killer (NK) cell, a natural killer T (NKT) cell, a neutrophil cell, a monocyte, and a macrophage. In certain embodiments, the immune cell is a T cell.

In certain embodiments, the Fab domain specifically binds to CD3 with a binding affinity between about 1 nM to about 100 nM (e.g., 1 nM, 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 26 nM, 27 nM, 28 nM, 29 nM, 30 nM, 31 nM, 32 nM, 33 nM, 34 nM, 35 nM, 36 nM, 37 nM, 38 nM, 39 nM, 40 nM, 41 nM, 42 nM, 43 nM, 44 nM, 45 nM, 46 nM, 47 nM, 48 nM, 49 nM, 50 nM, 51 nM, 52 nM, 53 nM, 54 nM, 55 nM, 56 nM, 57 nM, 58 nM, 59 nM, 60 nM, 61 nM, 62 nM, 63 nM, 64 nM, 65 nM, 66 nM, 67 nM, 68 nM, 69 nM, 70 nM, 71 nM, 72 nM, 73 nM, 74 nM, 75 nM, 76 nM, 77 nM, 78 nM, 79 nM, 80 nM, 81 nM, 82 nM, 83 nM, 84 nM, 85 nM, 86 nM, 87 nM, 88 nM, 89 nM, 90 nM, 91 nM, 92 nM, 93 nM, 94 nM, 95 nM, 96 nM, 97 nM, 98 nM, 99 nM, or 100 nM), as determined by SPR. In certain embodiments, the Fab domain specifically binds to CD3 with a binding affinity between about 1 nM to about 50 nM, as determined by SPR. In certain embodiments, the Fab domain specifically binds to CD3 with a binding affinity between about 20 nM to about 50 nM, as determined by SPR.

In certain embodiments, the Fab domain specifically binds to CD3 with a binding affinity of about 1 nM, of about 10 nM, or of about 50 nM, as determined by SPR.

In some embodiments, the association rate constant $k_a$ of the anti-CD3 binding domain is between about $1 \times 10^5$ to about $1 \times 10^7$ $M^{-1}s^{-1}$, such as at least $1 \times 10^6$ $M^{-1}s^{-1}$ or at least $2 \times 10^6$ $M^{-1}s^{-1}$. In some embodiments, the dissociation rate constant $k_d$ of the anti-CD3 binding domain is between about $1 \times 10^{-1}$ to about $1 \times 10^{-6}$ $s^{-1}$, such as at least $2 \times 10^3$ $s^{-1}$, or at least $3 \times 10^{-3}$ $s^{-1}$ or at least $4 \times 10^{-3}$ $s^{-1}$. Without being bound to theory, a fast dissociation rate, e.g., a $k_d$-value of $2-3 \times 10^{-3}$ $s^{-1}$, may lead to less T cell overactivation and in consequence, less cytokine release.

In one embodiment, the association rate constant $k_a$ and/or the dissociation rate constant $k_d$ are equivalent or similar for both CD3-heterodimers CD3εγ (epsilon/gamma)

and CD3εδ (epsilon/delta), i.e., there is no significant difference for either the $k_a$ or the $k_a$ or both of the anti-CD3 binding domain to CD3εγ (epsilon/gamma) and CD3εδ (epsilon/delta) when measured under the same conditions, in particular when determined by SPR at 25° C. In certain embodiments thereof, the association rate constant $k_a$ and/or the dissociation rate constant $k_d$ values that are within 1 fold of each other, 1.5 fold of each other, 2-fold of each other, 2.5-fold of each other or 3-fold of each other, i.e., association rate constant $k_a$ values of $1 \times 10^5$ $M^{-1}s^{-1}$ and $3 \times 10^5$ $M^{-1}s^{-1}$.

In certain embodiments, the pMHC binding domain binds the target MAGE-A4-pMHC complex with a binding affinity of about 100 pM to about 5 nM (e.g., about 100 pM, about 150 pM, about 200 pM, about 250 pM, about 300 pM, about 350 pM, about 400 pM, about 450 pM, about 500 pM, about 550 pM, about 600 pM, about 650 pM, about 700 pM, about 750 pM, about 800 pM, about 850 pM, about 900 pM, about 950 pM, about 1 nM (1,000 pM), about 2 nM, about 3 nM, about 4 nM, or about 5 nM). In certain embodiments, the pMHC binding domain binds the target pMHC complex with a binding affinity of about 100 pM to about 1 nM. In certain embodiments, the pMHC binding domain binds the target pMHC complex with a binding affinity of about 100 pM to about 400 pM.

In certain embodiments, the pMHC binding domains disclosed herein bind a pMHC displayed MAGE-A8 and MAGE-B4 peptide with a similar binding affinity as the pMHC displayed MAGE-A4 peptide. In certain embodiments, the pMHC binding domain binds a pMHC displayed MAGE-A8 peptide and/or a pMHC displayed MAGE-B4 peptide with a binding affinity of about 1.5 nM to about 2.5 nM, such as 1.6 nM, 1.7 nM, 1.8 nM, 1.9 nM, 2 nM, 2.1 nM, 2.2 nM, 2.3 nM, 2.4 nM or 2.5 nM. In certain embodiments, a pMHC binding domain binds a pMHC displayed MAGE-A8 peptide with a binding affinity of about 2.2 nM, as measured by SPR, and/or a pMHC displayed MAGE-B4 peptide with a binding affinity of about 1.9 nM. In certain embodiments, the pMHC binding domain binds a pMHC displayed MAGE-A4, MAGE-A8 and MAGE-B4 peptide with a similar binding affinity in the range of about 1.9 nM to about 2.2 nM. In certain embodiments, the MAGE-A8 peptide is GLYDGREHSV (SEQ ID NO: 71). In certain embodiments, the MAGE-B4 peptide is GIYDGKRHLI (SEQ ID NO: 72).

In some embodiments, the pMHC binding domain comprises an association rate constant $k_a$ towards the MAGE-A4 pMHC is between about $1 \times 10^5$ to about $1 \times 10^7$ $M^{-1}s^{-1}$, preferably between about $0.5 \times 10^6$ $M^{-1}s^{-1}$ to about $3 \times 10^6$ $M^{-1}s^{-1}$, such as at least $0.5 \times 10^6$ $M^{-1}s^{-1}$, at least $1 \times M^{-1}s^{-1}$, at least $2 \times 10^6$ $M^{-1}s^{-1}$ or at least $3 \times 10^6$ $M^{-1}s^{-1}$. In some embodiments, the pMHC binding domain comprises a dissociation rate constant $k_d$ towards the MAGE-A4 pMHC is between about $1 \times 10^{-1}$ to about $1 \times 10^{-6}$ $s^{-1}$, such as between about $1 \times 10^{-2}$ to about $1 \times 10^{-5} s^{-1}$, such as at least $2 \times 10^{-3}$ $s^{-1}$, at least $4 \times 10^{-3}$ $s^{-1}$, at least $6 \times 10^{-3}$ $s^{-1}$, at least $8 \times 10^{-3}$ $s^{-1}$, at least $2 \times 10^{-4}$ $s^{-1}$, at least $4 \times 10^{-4}$ $s^{-1}$, at least $6 \times 10^{-4}$ $s^{-1}$ or at least $8 \times 10^{-4}$ $s^{-1}$.

In certain embodiments, the antigen binding protein comprises a molecular weight of about 75 kDa to about 110 kDa (e.g., about 75 kDa, about 80 kDa, about 85 kDa, about 90 kDa, about 95 kDa, about 100 kDa, about 105 kDa or about 110 kDa). In certain embodiments, the antigen binding protein has increased serum half-life relative to an antigen binding protein with a molecular weight of <about 75 kDa.

An advantage of the antigen binding protein scaffolds of the disclosure is the intermediate molecular size of approximately 75-110 kDa. Blinatumomab, a bispecific T cell engager (BiTE), has shown excellent results in patients with relapsed or refractory acute lymphoblastic leukemia. Because of its small size (54 kDa), blinatumomab is characterized by a short serum half-life of several hours, and therefore continuous infusion is needed (see, U.S. Pat. No. 7,112,324 B1). The antigen binding proteins of the disclosure are expected to have significantly longer half-lives in comparison to smaller bispecific antibodies, such as BiTEs like blinatumomab, and thus, do not require continuous infusion due to their favorable half-life. An intermediate sized molecule may avoid kidney clearance and provide a half-life sufficient for improved tumor accumulation. While the antigen binding proteins of the disclosure have increased plasma half-life compared to other small bispecific formats, they still retain the tumor penetration ability.

The Fab domain of the antigen binding protein of the disclosure may serve as a specific heterodimerization scaffold to which the additional pMHC binding domains are linked. The natural and efficient heterodimerization properties of the heavy chain (Fd fragment) and light chain (L) of a Fab fragment makes the Fab fragment a useful scaffold. Additional binding domains may be in several different formats, including, but not limited to, another Fab domain, a scFv, or an sdAb.

Each chain of the Fab fragment can be extended at the N- or C-terminus with additional binding domains. The chains may be co-expressed in mammalian cells, where the host-cell Binding immunoglobulin protein (BiP) chaperone drives the formation of the heavy chain-light chain heterodimer (Fd:L). These heterodimers are stable, with each of the binders retaining their specific affinities. The two remaining pMHC binding domains may then be fused as scFvs or sdAbs to distinct Fab chains where each chain can be extended, e.g., at the C-terminus with an additional scFv or sdAb domain (see, for example, Schoonjans et al. J. Immunology, 165(12): 7050-7057, 2000; Schoonjans et al. Biomolecular Engineering, 17: 193-202, 2001.) An additional advantage of using Fabs as a heterodimerization unit is that Fab molecules are abundantly present in serum and therefore may be non-immunogenic when administered to a subject.

In certain embodiments, the (multispecific) antigen binding protein of the disclosure has one or more of the following properties: (i) it is capable of inhibiting tumor growth and eradicating tumor, e.g., in a cell line-derived mouse NSCLC xenograft model, such as exemplarily shown in Example 14; and/or (ii) it shows efficacy on target positive tumor cells as determined by an LDH cytotoxicity; and/or (iii) it shows efficacy on target positive tumor cells as e.g., determined by an IncuCyte S3 system; and/or (iv) it induces lower levels of the pro-inflammatory cytokine IFN gamma in both antigen-positive and antigen-negative cell lines (see e.g., Example 12 for exemplary assays) than comparator 1; and/or (v) it induces lower levels of pro-inflammatory cytokines IL-2, IL-6 and/or TNF alpha cytokine release (see e.g., Example 12 for exemplary assays) than comparator 1; (vi) it has T cell activating properties, see e.g., Example 12 for exemplary assays; and/or (vii) safety, as e.g., measured by Granzyme B release (for example in antigen-negative cancer cell line KLE (endometrial carcinoma), LNCaP (Lymph Node Carcinoma of the Prostate), KMRC-2 (clear cell renal cell carcinoma), KMRC-3 (clear cell renal cell carcinoma), 639-V (urothelial bladder cancer), EKVX (lung adenocarcinoma) and/or HCT116 (colorectal carcinoma), see e.g. Example 12) and/or reactivity in healthy tissues as e.g. determined by a T cell activation assay, see Examples 12 and 13 for exemplary assays and/or (viii) remains at least 94% monomeric, during storage at 4° C. at 1 mg/ml and/or 10 mg/ml in PBS for at least two weeks as determined by SEC-HPLC.

Also encompassed are variants of the sequences disclosed herein. A variant amino acid or nucleic acid sequence differs from its parental sequence by virtue of insertion (including addition), deletion and/or substitution of one or more amino acid residues or nucleobases, respectively, while retaining at least one desired property of the parent sequence disclosed herein, e.g., specific antigen binding, efficacy on target positive tumor cells, stability (e.g., serum stability, thermal stability, and/or storage stability), producibility (e.g., expression levels), safety (e.g., reactivity in healthy tissues, Granzyme B release, pro-inflammatory cytokine IFN gamma antigen-positive or antigen-negative cell lines, and/or low to no induction of pro-inflammatory cytokines IL-2, IL-6 and TNF alpha cytokine release), efficacy (e.g., tumor growth inhibition, tumor eradication, and/or T cell activating properties as e.g. determined in vitro), or binds MAGE-A4 GVYDGREHTV (SEQ ID NO: 3) HLA-A*02 complex, MAGE-A8 derived GLYDGREHSV (SEQ ID NO: 71) HLA-A*02 complex and MAGE-B4 derived GIYDGKRHLI (SEQ ID NO: 72) HLA-A*02 complex in a similar affinity range). In certain embodiments, the variant antigen binding protein retains binding to a GVYDGREHTV (SEQ ID NO: 3) HLA-A*02:01 complex of at least 50%, such as 60%, 70%, 80%, 90% or 95% of the equilibrium dissociation constant $K_D$ of the reference antigen binding protein (i.e., the corresponding antigen binding protein without said substitutions, insertions, and/or deletions) when measured under identical conditions. Variants may be artificially engineered or naturally occurring, such as e.g., allelic or splice variants. In some embodiments, the variant antigen binding protein comprises an amino acid sequence being at least about 80%, 85%, 90%, 95%, 96%, 97%, 98% or 99% identical to an amino acid sequence disclosed herein.

Thus, in certain embodiments, a variant antigen binding protein retains specific binding to the target (i.e., MAGE-A4 pMHC, in particular GVYDGREHTV (SEQ ID NO: 3) HLA-A*02:01 complex, or CD3, respectively) and/or competes with the antigen binding protein disclosed herein for binding to its target. In certain embodiments, the antigen binding protein retains stability and remains at least 94%, 95%, 96%, 97%, 98%, 99% or 100% monomeric after incubation for 14 days at 4° C. in PBS at 1 mg/ml and/or 10 mg/ml as determined by SEC-HPLC.

Reduction of Anti-Drug Antibody Binding

Anti-drug antibodies (ADAs) may affect the risk profile and efficacy of a biological drug. If neutralizing, they may block the drug's ability to bind to its target. It is therefore a regulatory requirement to test biologic drugs for the binding of anti-drug antibodies and their neutralizing potential. Anti-drug antibody assays are e.g., detailed in WO2007101661A1 (Hoffmann La Roche), WO2018178307A1 (Ablynx), WO2021046316A2 (Adverum Biotechnologies, Charles River), and US20180088140A1 (Genzyme Corporation), each of which is incorporated herein by reference.

Anti-drug antibodies binding to a tumor targeting domain of an antigen binding protein may lead to clustering of said antigen binding protein when each variable domain of the ADA binds to one tumor targeting domain of two antigen binding proteins. The two or more CD3 binding domains on said antigen binding protein cluster and overstimulate the targeted T cell in the absence of target engagement, thereby leading to off-target toxicity. Unspecific stimulation of the T-cells may lead to systemic cytokine release.

Generally, there is a need in the art to develop safer and more effective bispecific antibodies for cancer immunotherapy.

The inventors have found that certain mutations in the tumor antigen binding domain of a T cell engager reduce ADA response and at the same time reduce nonspecific T cell stimulation in the absence of target engagement. Thereby, a highly effective and safe approach for cancer immunotherapy is provided.

For such purpose, a variable heavy chain amino acid at position 11, 89, and/or 108, according to Kabat numbering, is substituted with a polar amino acid; and/or serine (S) at position 113 is deleted, according to Kabat numbering. Such substitution is particularly favorable when the binding domain is in scFv format. In case of a Fab(scFv)$_2$, one or both scFvs may comprise such substitution or deletion.

In certain embodiments, the polar amino acid is serine (S) and/or threonine (T).

In certain embodiments, the heavy chain amino acid is substituted with serine (S) at heavy chain amino acid position 11, serine (S) or threonine (T) at heavy chain amino acid position 89, and/or serine (S) or threonine (T) at heavy chain amino acid position 108, according to Kabat numbering.

In certain embodiments, the heavy chain amino acid is substituted with serine (S) at heavy chain amino acid position 11, serine (S) at heavy chain amino acid position 89, and serine (S) at heavy chain amino acid position 108, according to Kabat numbering.

In certain embodiments, further to the deletion of serine (s) at position 113, serine (S) at position 112, according to Kabat numbering, is deleted.

In certain embodiments, the method further comprises adding alanine (A), glycine (G) or threonine (T) at Kabat amino position 112 or 113, in particular alanine (A).

In certain embodiments, the method further comprises adding alanine (A) at Kabat amino position 112 or 113.

Expression of Antigen Binding Proteins

In one aspect, polynucleotides or nucleic acids encoding the antigen binding proteins (including the multispecific antigen binding proteins) disclosed herein are provided. Such polynucleotides or nucleic acids are typically isolated synthetic. Methods of making an antigen binding protein comprising expressing these polynucleotides are also provided.

Polynucleotides encoding the antigen binding proteins disclosed herein are typically inserted in a cloning vector or into an expression vector for introduction into host cells that may be used to produce the desired quantity of the antigen binding proteins. Accordingly, in certain aspects, the invention provides expression vectors comprising polynucleotides disclosed herein and host cells comprising these vectors and polynucleotides.

The term "vector" or "expression vector" is used herein to mean vectors used in accordance with the present invention as a vehicle for introducing into and expressing a desired gene in a cell. As known to those skilled in the art, such vectors may readily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

Numerous expression vector systems may be employed for the purposes of this invention. For example, one class of vector utilizes DNA elements which are derived from animal viruses such as bovine papilloma virus, polyoma virus, adenovirus, vaccinia virus, baculovirus, retroviruses (e.g., RSV, MMTV, MOMLV or the like), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals. In some embodiments, the cloned variable region genes are inserted into an expression vector along with the heavy and light chain constant region genes (e.g., human constant region genes) synthesized as discussed above.

In other embodiments, the antigen binding proteins may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980, which is incorporated by reference herein in its entirety for all purposes. Those skilled in the art will appreciate that such expression systems may be used to effectively produce the full range of polypeptides disclosed in the instant application.

More generally, once a vector or DNA sequence encoding an antigen binding protein has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Chapter 24.2, pp. 470-472 Vectors, Rodriguez and Denhardt, Eds. (Butterworths, Boston, Mass. 1988). Plasmid introduction into the host can be by electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), fluorescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

In one embodiment, a host cell line used for antibody expression is of mammalian origin. Those skilled in the art can determine particular host cell lines which are best suited for the desired gene product to be expressed therein. Exemplary host cell lines include, but are not limited to, DG44 and DUXB11 (Chinese hamster ovary lines, DHFR minus), HELA (human cervical carcinoma), CV-1 (monkey kidney line), COS (a derivative of CV-1 with SV40 T antigen), R1610 (Chinese hamster fibroblast) BALBC/3T3 (mouse fibroblast), HAK (hamster kidney line), SP2/O (mouse myeloma), BFA-1c1BPT (bovine endothelial cells), RAJI (human lymphocyte), 293 (human kidney) and the like. In one embodiment, the cell line provides for altered glycosylation, e.g., afucosylation, of the antibody expressed therefrom (e.g., PER.C6® (Crucell) or FUT8-knock-out CHO cell lines (Potelligent®) cells) (Biowa, Princeton, N.J.)). Host cell lines are typically available from commercial services, e.g., the American Tissue Culture Collection, or from published literature.

In vitro production allows scale-up to give large amounts of the desired polypeptides. Techniques for mammalian cell cultivation under tissue culture conditions are known in the art and include homogeneous suspension culture, e.g., in an airlift reactor or in a continuous stirrer reactor, or immobilized or entrapped cell culture, e.g., in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-) affinity chromatography.

Genes encoding the antigen binding proteins featured in the invention can also be expressed non-mammalian cells such as bacteria or yeast or plant cells. In this regard it will be appreciated that various unicellular non-mammalian microorganisms such as bacteria can also be transformed, i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the proteins can become part of inclusion bodies. The proteins must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms, although a number of other strains are commonly available. For expression in *Saccharomyces*, the plasmid Yrp7, for example (Stinchcomb et al., Nature, 282:39 (1979); Kingsman et al., Gene, 7:141 (1979); Tschemper et al., Gene, 10:157 (1980)), is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan.

Engineering and Optimization of Antigen Binding Proteins

The antigen binding proteins, including the multispecific antigen binding proteins, of the disclosure may be engineered or optimized. As used herein, "optimized" or "optimization" refers to the alteration of an antigen binding protein to improve one or more functional properties. Alteration includes, but is not limited to, deletions, substitutions, additions, and/or modifications of one or more amino acids within an antigen binding protein.

As used herein, the term "functional property" is a property of an antigen binding protein for which an improvement (e.g., relative to a conventional antigen binding protein, such as an antibody) is desirable and/or advantageous to one of skill in the art, e.g., in order to improve the manufacturing properties or therapeutic efficacy of a antigen binding protein. In one embodiment, the functional property is stability (e.g., thermal stability). In another embodiment, the functional property is solubility (e.g., under cellular conditions). In yet another embodiment, the functional property is aggregation behavior. In still another embodiment, the functional property is protein expression (e.g., in a prokaryotic cell). In yet another embodiment the functional property is refolding behavior following inclusion body solubilization in a manufacturing process. In certain embodiments, the functional property is not an improvement in antigen binding affinity. In another embodiment, the improvement of one or more functional properties has no substantial effect on the binding affinity of the antigen binding protein.

In certain embodiments, the antigen binding protein of the disclosure comprises an scFv and is optimized by identifying preferred amino acid residues to be substituted, deleted, and/or added at amino acid positions of interest (e.g., amino acid positions identified by comparing a database of scFv sequences having at least one desirable property, e.g., as selected with Quality Control (QC) assay, versus a database of mature antibody sequences, e.g., the Kabat database) in an antigen binding protein. Thus, the disclosure further provides "enrichment/exclusion" methods for selecting a particular amino acid residue. Still further, the disclosure provides methods of engineering antigen binding proteins (e.g., scFvs) by mutating particular framework amino acid positions identified using the "functional consensus" approach described herein. In certain embodiments, the framework amino acid positions are mutated by substituting the existing amino acid residue by a residue which is found to be an "enriched" residue using the "enrichment/exclusion" analysis methods described herein. In one aspect, the disclosure provides a method of identifying an amino acid position for mutation in a single chain antibody (scFv), the scFv having VH and VL amino acid sequences, the method comprising: a) entering the scFv VH, VL or VH and VL amino acid sequences into a database that comprises a multiplicity of antibody VH, VL or VH and VL amino acid sequences such that the scFv VH, VL or VH and VL amino acid sequences are aligned with the antibody VH, VL or VH and VL amino acid sequences of the database; b) comparing an amino acid position within the scFv VH or VL amino acid sequence with a corresponding position within the antibody VH or VL amino acid sequences of the database; c) determining whether the amino acid position within the scFv VH or VL amino acid sequence is occupied by an amino acid residue that is conserved at the corresponding position within the antibody VH or VL amino acid sequences of the database; and d) identifying the amino acid position within the scFv VH or VL amino acid sequence as an amino acid position for mutation when the amino acid position is occupied by an amino acid residue that is not conserved at the corresponding position within the antibody VH or VL amino acid sequences of the database. ScFv optimization is described in further detail in WO2008110348, WO2009000099, WO2009000098, and WO2009155725, all of which are incorporated herein by reference.

In certain embodiments, the antigen binding protein comprises an Fc domain which is modified such that it does not induce cytotoxic immune responses and/or does not activate complement. For example, one or more substitutions may be introduced into the Fc domain so that its ADCC/ADCP or CDC effector function is inactivated. Such antigen binding protein has the advantage of increased half-life when compared to antibody fragments with a molecular weight below 75 kDa, without mediating cytotoxic immune responses.

Chemical and/or Biological Modifications

In one aspect, the antigen binding protein (such as the multispecific antigen binding protein described above) is chemically and/or biologically modified. For example, the antigen binding protein may be glycosylated, phosphorylated, hydroxylated, PEGylated, HESylated, PASylated, XTENylated, sulfated, labeled with dyes and/or radioisotopes, conjugated with enzymes and/or toxins, and/or Albumin fusion technology. Likewise, any nucleic acid sequence, plasmid or vector and/or host cell described herein may be modified accordingly.

Such modification may for example be done to optimize pharmacodynamics, its water solubility or to lower its side effects. For example, PEGylation, PASylation, XTE-Nylation, HESylation and/or the fusion to serum albumin may be applied to slow down renal clearance, thereby increasing plasma half-life time of the antigen binding protein. In one embodiment, a modification adds a different functionality to the antigen binding protein, for example, a detection label for diagnostics or a toxin to combat cancer cells even more efficiently.

Alternatively, or additionally, in some embodiments, the antigen binding proteins and other polypeptides provided herein undergo co- and post-translational modifications as known in the art. Examples of post-translational modifications include, but are not limited to, disulfide bond formation, glycosylation, cyclization (such as e.g., N-terminal pyroglutamate formation), have a N-terminal or C-terminal residue removed or "clipped" (for example, C-terminal lysine residues are often removed during the manufacturing process), deamidation, isomerization, oxidation, glycation, acylation, fucosylation, peptide bond cleavage, non-reducible cross-linking, truncation, and/or have part or all of a signal sequence incompletely processed.

In certain embodiments, the CD3 antigen binding domain comprises an N-terminal truncation of 1 or more amino acids (e.g., a N-terminal truncation of 1, 2, 3, 4, or 5 amino acids). In certain embodiments, the CD3 antigen binding domain comprises a C-terminal truncation of 1 or more amino acids (e.g., a C-terminal truncation of 1, 2, 3, 4, or 5 amino acids). In certain embodiments, the N-terminal and/or C-terminal truncation is a truncation of the CD3 targeting Fab fragment of a heavy chain amino acid sequence of SEQ ID NO: 49 and a light chain amino acid sequence of SEQ ID NO: 54. In certain embodiments, the light chain amino acid sequence of SEQ ID NO: 54 comprises an N-terminal truncation of 1, 2, 3, 4, or 5 amino acids, such as 1 or 2 truncations. In certain embodiments, the heavy chain amino acid sequence of SEQ ID NO: 49 comprises an N-terminal truncation of 1, 2, 3, 4, or 5 amino acids, such as 1 or 2 truncations. In certain embodiments, the light chain amino acid sequence of SEQ ID NO: 54 comprises a C-terminal truncation of 1, 2, 3, 4, or 5 amino acids. In certain embodiments, the heavy chain amino acid sequence of SEQ ID NO: 49 comprises a C-terminal truncation of 1, 2, 3, 4, or 5 amino acids.

In certain embodiments, the (multispecific) antigen binding protein comprises a pyroglutamate (pE, pyrGlu, pyre or pGlu) instead of the N-terminal glutamine or the N-terminal glutamine. In certain embodiments, the light chain of the antigen binding protein comprises pyroglutamate (pE) instead of the N-terminal glutamine. In certain embodiments, the variant sequence of SEQ ID NO: 14, SEQ ID NO: 24, SEQ ID NO: 34, SEQ ID NO: 44, SEQ ID NO: 54, SEQ ID NO: 55, SEQ ID NO: 61 or SEQ ID NO: 62 comprises a pyroglutamate at amino acid position 1. In certain embodiments, the light chain of the antigen binding protein comprises pyroglutamate (pE) instead of the N-terminal glutamate. In certain embodiments, the variant sequence of SEQ ID NO: 9, SEQ ID NO: 10, SEQ ID NO: 19, SEQ ID NO: 20, SEQ ID NO: 29, SEQ ID NO: 30, SEQ ID NO: 39, SEQ ID NO: 40, SEQ ID NO: 49, SEQ ID NO: 50 or SEQ ID NO: 65 comprises a pyroglutamate at amino acid position 1. In certain embodiments, such pyroglutamate (pE) modification has no impact on the safety and/or efficacy of the (multi-specific) antigen binding protein.

In one embodiment, the antigen binding protein is glycosylated. Glycosylation refers to a process that attaches carbohydrates to proteins. In biological systems, this process is performed enzymatically within the cell as a form of co-translational and/or post-translational modification. A protein can also be chemically glycosylated. The carbohydrates may be N-linked to a nitrogen of asparagine or arginine side-chains; O-linked to the hydroxy oxygen of serine, threonine, tyrosine, hydroxylysine, or hydroxyproline side-chains; employ xylose, fucose, mannose, and N-acetylglucosamine attached to a phospho-serine; and/or adding mannose sugar to a tryptophan residue found in a specific recognition sequence. Glycosylation patterns may, e.g., be controlled by choosing appropriate cell lines, culturing media, protein engineering manufacturing modes and process strategies (see, HOSSLER, P. Optimal and consistent protein glycosylation in mammalian cell culture. Glycobiology 2009, vol. 19, no. 9, p. 936-949). In some embodiments, the glycosylation patterns of the antigen binding proteins described herein are modified to enhance ADCC and CDC effector function.

The antigen binding protein may be engineered to control or alter the glycosylation pattern, e.g., by deleting and/or adding one or more glycosylation sites. The creation of glycosylation sites can e.g., be accomplished by introducing the corresponding enzymatic recognition sequence into the amino acid sequence of the antigen binding protein.

In some embodiments, the antigen binding protein is PEGylated. PEGylation may alter the pharmacodynamic and pharmacokinetic properties of a protein. Additionally, PEGylation may reduce the immunogenicity by shielding the PEGylated antigen binding protein from the immune system and/or alter its pharmacokinetics by, e.g., increasing the in vivo stability of the antigen binding protein, protecting it from proteolytic degradation, extending its half-life and by altering its biodistribution. Typically, polyethylene-glycol (PEG) of an appropriate molecular weight is covalently attached to the protein. Similar effects may be achieved using PEG mimetics, e.g., HESylating, XTENylating or PASylating the antigen binding protein. HESylation utilizes hydroxyethyl starch ("HES") derivatives. During PASylation, the antigen binding protein is linked to conformationally disordered polypeptide sequences composed of the amino acids proline (P), alanine (A) and serine (S).

In certain embodiments, the antigen binding protein (e.g., the multispecific antigen binding protein) is linked to or combined with a detectable label, a therapeutic agent or a PK modifying moiety. For example, the antigen binding protein can be labelled with or conjugated to a second moiety which attributes one or more ancillary functions to the antigen binding protein. For example, the second moiety may have an additional immunological effector function, be effective in drug targeting or useful for detection. The second moiety can, e.g., be chemically linked or fused genetically to the antigen binding protein using known methods in the art. As used herein, the term "label" refers to any substance or ion which is indicative of the presence of the antigen binding protein when detected or measured by physical or chemical means, either directly or indirectly. For example, the label may be directly detectable by, without being limited to, light absorbance, fluorescence, reflectivity, light scatter, phosphorescence, or luminescence properties, molecules or ions detectable by their radioactive properties or molecules or ions detectable by their nuclear magnetic resonance or paramagnetic properties. Examples of indirect detection include light absorbance or fluorescence; for example, various enzymes which cause appropriate substrates to convert, e.g., from non-light absorbing to light absorbing molecules, or from non-fluorescent to fluorescent molecules. A labelled antigen binding protein is particularly useful for in vitro and in vivo detection or diagnostic purposes. For example, an antigen binding protein labelled with a suitable radioisotope, enzyme, fluorophore or chromophore can be detected by radioimmunoassay (RIA), enzyme-linked immunosorbent assay (ELISA), or flow cytometry-based single cell analysis (e.g., FACS analysis), respectively. Similarly, the nucleic acids and/or vectors disclosed herein can be labeled for detection or diagnostic purposes, e.g., using labelled fragments thereof as probes in hybridization assays.

Non-limiting examples of second moieties include radio-isotopes (35S, 32P, 14C, 18F, and/or 125I), apoenzymes, enzymes (e.g., alkaline phosphatase, horseradish peroxidase, beta-galactosidase and/or angiogenin), co-factors, peptide moieties (e.g., a HIS-tag), proteins (e.g. lectin, serum albumin), carbohydrates (e.g., mannose-6-phosphate tags), fluorophores (e.g., fluorescein isothiocyanate (FITC)), phycoerythrin, green/blue/red or other fluorescent proteins, allophycocyanin (APC), chromophores, vitamins (e.g., biotin), chelators, antimetabolites (e.g., methotrexate), toxins (e.g. a cytotoxic drug, or a radiotoxin).

In one aspect, the invention relates to drug conjugates (in particular antibody-drug conjugates ADCs) comprising the antigen binding proteins described herein, e.g., a monovalent or a multispecific antigen binding protein described herein, conjugated to a toxin which further enhances efficient killing of specific cells, such as e.g., MAGE-A4 positive cells. The toxin moiety is typically a small molecular weight moiety, such as anthracycline toxins, taxol, gramicidin D and/or colchicine which may be linked via a peptide linker to the antigen binding protein.

The toxin may be conjugated non-site-specifically or site-specifically to the antigen binding protein. Non-site-specific conjugation typically involves the use of chemical linkers, e.g., with maleimide functionality, that mediate conjugation to lysine or cysteine amino acid side chains of the antigen binding protein or to the amino-group of the N-terminus. Site-specific conjugation may be achieved using chemical, chemo-enzymatic, or enzymatic conjugations known in the art, e.g., employing bifunctional linkers, bacterial transglutaminase or sortase enzymes, linkers allowing Pictet-Spengler chemistry on formyl-glycine forming enzyme modified antigen binding proteins, or glycan-remodeled antigen binding proteins.

Methods of Administering Antigen Binding Proteins

Methods of preparing and administering antigen binding proteins of the disclosure (such as the multispecific antigen binding protein described above) as well as the nucleic acids described herein, the vectors described herein, the host cell described herein or the compositions described herein to a subject are well known to or are readily determined by those skilled in the art. The route of administration of the antigen binding proteins of the current disclosure may e.g., be oral, parenteral, by inhalation, or topical. The term parenteral as used herein includes intravenous, intraarterial, intraperitoneal, intramuscular, subcutaneous, rectal or vaginal administration. The term intraocular as used herein includes, but is not limited to, subconjunctival, intravitreal, retrobulbar, or intracameral. The term topical as used herein includes, but is not limited to, administration with liquid or solution eye drops, emulsions (e.g., oil-in-water emulsions), suspensions, and ointments.

While all these forms of administration are clearly contemplated as being within the scope of the current disclosure, a form for administration would be a solution for injection. Usually, a suitable pharmaceutical composition for injection may comprise a buffer (e.g., acetate, phosphate or citrate buffer), a surfactant (e.g., polysorbate), optionally a stabilizer agent (e.g., human albumin), etc. However, in other methods compatible with the teachings herein, the modified antibodies can be delivered directly to the site of the adverse cellular population thereby increasing the exposure of the diseased tissue to the therapeutic agent.

Effective doses of the compositions of the present disclosure, for the treatment of the related conditions vary depending upon many different factors, including means of administration, target site, physiological state of the patient, whether the patient is human or an animal, other medications administered, and whether treatment is prophylactic or therapeutic. Usually, the patient is a human, but non-human mammals, including transgenic mammals, can also be treated. Treatment dosages may be titrated using routine methods known to those of skill in the art to optimize safety and efficacy.

As previously discussed, the antigen binding proteins of the present disclosure (e.g., the multispecific antigen binding protein), conjugates or recombinants thereof may be administered in a pharmaceutically effective amount for the in vivo treatment of mammalian disorders. In this regard, it will be appreciated that the disclosed antigen binding proteins will be formulated to facilitate administration and promote stability of the active agent.

Pharmaceutical compositions in accordance with the present disclosure typically include a pharmaceutically acceptable, non-toxic, sterile carrier such as physiological saline, nontoxic buffers, preservatives and the like. For the purposes of the instant application, a pharmaceutically effective amount of the antigen binding proteins (such as the multispecific antigen binding protein) shall be held to mean an amount sufficient to achieve effective binding to an antigen and to achieve a benefit, e.g., to ameliorate symptoms of a disease or disorder or to detect a substance or a cell. In the case of tumor cells, the antigen binding proteins will typically be capable of interacting with selected immunoreactive antigens on neoplastic or immunoreactive cells and provide for an increase in the death of those cells. Of course, the pharmaceutical compositions of the present disclosure may be administered in single or multiple doses to provide for a pharmaceutically effective amount of the modified binding polypeptide.

In keeping with the scope of the present disclosure, the antigen binding proteins of the disclosure (such as the multispecific antigen binding protein described above) may be administered to a human or other animal in accordance with the aforementioned methods of treatment in an amount sufficient to produce a therapeutic or prophylactic effect. The antigen binding proteins of the disclosure can be administered to such human or other animal in a conventional dosage form prepared by combining the antigen binding proteins of the disclosure with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of antigen binding proteins described in the current disclosure may prove to be particularly effective. Similarly, the nucleic acids described herein, the vectors described herein, the host cell cells described herein (in particular the immune cells bearing a CAR) or the compositions described herein may be administered to a human or other animal in accordance with the methods of treatment described above in an amount sufficient to produce a therapeutic or prophylactic effect.

"Efficacy" or "in vivo efficacy" as used herein refers to the response to a therapy by the pharmaceutical composition of the disclosure, using e.g., standardized response criteria. The success or in vivo efficacy of the therapy using a pharmaceutical composition of the disclosure refers to the effectiveness of the composition for its intended purpose, i.e., the ability of the composition to cause its desired effect. The in vivo efficacy may be monitored by established standard methods for the specific diseases. In addition, various disease specific clinical chemistry parameters and other established standard methods may be used.

In some embodiments, the compounds and cells described herein are administered in combination with one or more different pharmaceutical compounds. Generally, therapeutic use of the compounds and cells described herein may be in combination with one or more therapies selected from the group of antibody therapy, chemotherapy, cytokine therapy, dendritic cell therapy, gene therapy, hormone therapy, laser light therapy, radiation therapy or vaccine therapy.

Chimeric Antigen Receptors

In one aspect, the disclosure provides chimeric antigen receptors (CARs) and immune cells engineered to express such CARs, comprising the antigen binding protein sequences described herein. As used herein, the term "chimeric antigen receptor" or "CAR" refers to a receptor that is capable of activating an immune cell in response to antigen binding. CARs are recombinant membrane spanning molecules and are advantageously expressed on immune cells. Their structure typically comprises (i) an extracellular domain (ectodomain or antibody domain), (ii) a transmembrane domain and (iii) a cytoplasmic domain (endodomain or intracellular signaling domain).

The ectodomain (i.e., antibody domain) typically comprises a scFv but other formats may also be used. A spacer connects the ectodomain and the transmembrane domain, which in turn is connected to an endodomain. Upon binding of the ectodomain to the antigen, the receptors cluster and an activation signal is transmitted to the cell which results in initiation of an immune response. First generation CARs have a simply structured endodomain comprising CD3-zeta. To increase the activation signal, a co-stimulatory domain was added in the second-generation CARs; and third generation CARs include two or more co-stimulatory domains (Maus M V et al (2014) Blood, 123: 2625-2635). Said co-stimulatory domains may be selected from the group consisting of CD28, OX40 and/or 4-1BB. Apart from CD3-zeta, other ITAM-containing domains have been explored including the Fc receptor for IgE-γ domain.

In certain embodiments, the CAR comprises a scFv comprising the amino acid sequence of SEQ ID NO: 61, SEQ ID NO: 62, SEQ ID NO: 63 and/or SEQ ID NO: 64, or a variant thereof that is at least about 90%, 95%, 96%, 97%, 98% or 99% identical to the amino acid sequence of SEQ ID NO: SEQ ID NO: 61, SEQ ID NO: 62, SEQ ID NO: 63 and/or SEQ ID NO: 64, respectively.

Suitable immune cells engineered to express such CARs include, without being limited to, T cells, Natural Killer T (NKT) cells, natural killer (NK) cells, human embryonic stem cells, hematopoietic stem cells (HSC) or induced pluripotent stem cells (iPS). Such T cell may be a cytotoxic T lymphocyte (CTL), a regulatory T lymphocyte, an inflammatory T-lymphocytes, or a helper T-lymphocyte or a gamma-delta T cell. The T cell may be a CD4+ or CD8+ or a mixed population of CD4+ and CD8+ cells.

In one aspect, the disclosure provides a chimeric antigen receptor (CAR) that specifically recognizes a peptide-MHC, comprising: i) an antigen binding protein identified from the nucleic acid libraries or methods described herein; ii) a transmembrane domain; and iii) an intracellular signaling domain.

In certain embodiments, the transmembrane domain is selected from the group consisting of an artificial hydrophobic sequence and transmembrane domains of a type I transmembrane protein, an alpha, beta or zeta chain of a T cell receptor, CD28, CD3 epsilon, CD45, CD4, CD5, CD8, CD9, CD16, CD22, CD33, CD37, CD64, CD80, CD86, CD134, CD137, and CD154.

In certain embodiments, the intracellular signaling domain is selected from the group consisting of cytoplasmic signaling domains of a human CD3 zeta chain, FcγRIII, a cytoplasmic tail of an Fc receptor, an immunoreceptor tyrosine-based activation motif (ITAM) bearing cytoplasmic receptors, TCR zeta, FcR gamma, FcR beta, CD3 gamma, CD3 delta, CD3 epsilon, CD5, CD22, CD79a, CD79b, and CD66d.

The antibody domain may be any of the antigen binding proteins outlined above. Thus, in certain embodiments, the antibody domain comprises an antibody variable light domain (VL) comprising an amino acid sequence represented by the formula LFR1-LCDR1-LFR2-LCDR2-LFR3-LCDR3-LFR4. In certain embodiments, the antibody domain comprises an antibody variable heavy domain (VH) comprising an amino acid sequence represented by the formula HFR1-HCDR1-HFR2-HCDR2-HFR3-HCDR3-HFR4. In certain embodiments, the antibody domain comprises an scFv as described herein.

Methods of Treating Cancer

Provided herein are methods of treating cancer with the antigen binding proteins and in particular with the multispecific antigen binding proteins of the disclosure (e.g., a MAGE-A4 pMHC antigen binding protein). The methods may be used to treat patients having any tumor type in which at least some of the cancer cells express a MAGE-A4 antigen displayed on a pMHC, such as GVYDGREHTV (SEQ ID NO: 3)—HLA-A*02:01 complex. Such MAGE-A4 positive cancers or cancer cells can be assessed using any method known in the art, including, but are not limited to, detecting RNA expression levels or histological methods such as Immunohistochemistry (IHC).

In some embodiments, the MAGE-A4 positive cancer is selected from the group consisting of bladder cancer, breast cancer, colorectal cancer, gastric cancer, head and neck cancer, lung cancer, melanoma, esophageal carcinoma, ovarian cancer, renal cancer, synovial sarcoma, and a tumor with squamous cell histology. In certain embodiments, the cancer is of squamous origin. Experimental data showed that squamous cancers which had both MAGE-A4 mRNA highest prevalence and median expression. In certain embodiments, the cancer is selected from the group consisting of head & neck squamous cancer (HNSC), head and neck squamous cell carcinoma (HNSCC), non-small cell lung carcinoma (NSCLC), in particular squamous NSCLC, triple negative breast cancer, urothelial carcinoma, high-grade endometrial cancers including uterine carcinosarcoma (UCS; in particular UCEC subgroup), myxoid/round cell liposarcoma, gastric or gastroesophageal junction (GEJ) adenocarcinoma, epithelial ovarian cancer, such as high grade serous ovarian carcinoma, synovial sarcoma, bladder urothelial carcinoma (BLCA), in particular transitional cell carcinoma, testicular germ cell tumors (TGCT) and cervical squamous carcinoma (CESC).

The antigen binding proteins described herein also comprise binding specificity for certain related MAGE pMHC targets, in particular a MAGE-A8 derived GLYDGREHSV (SEQ ID NO: 71) HLA-A*02 complex. and/or a MAGE-B4 derived GIYDGKRHLI (SEQ ID NO: 72 #) HLA-A*02 complex. Accordingly, the disclosure provides a method of treating such a related MAGE-pMHC positive cancer.

In one aspect, the disclosure provides the use of the antigen binding protein described herein, the multispecific antigen binding protein described herein, or the pharmaceutical composition described herein, in the manufacture of a medicament.

In another aspect, the disclosure provides the use of the antigen binding protein described herein, the CAR described herein, the immune cell described herein, the multispecific antigen binding protein described herein, or the pharmaceutical composition described herein, for use in the treatment of a disease, in particular cancer.

In another aspect, the disclosure provides a method of treating a MAGE-A4 pMHC-expressing cancer in a patient in need thereof comprising administering to the patient a therapeutically effective amount of the antigen binding protein described herein, the CAR described herein, the immune cell described herein, the multispecific antigen binding protein described herein, or the pharmaceutical composition described herein.

In certain aspects, patients eligible for treatment with a MAGE-A4 antagonist are selected based on RNA sequencing and/or immunohistochemistry (IHC), such as for detection of total MAGE-A4.

In certain aspects, patients eligible for treatment with a MAGE-A4 antagonist described herein (e.g., the antigen binding protein described herein, the CAR described herein, the immune cell described herein, the multispecific antigen binding protein described herein, or the pharmaceutical composition described herein) are selected based on an immunohistological method comprising the sequential steps of:

(i) obtaining a tumor sample from a patient;
(ii) adding an anti-MAGEA4 detection antibody to the sample;
(iii) incubating said detection antibody and the sample;

(iv) detecting said detection antibody bound to the sample; and (v) selecting the patient for treatment with a MAGE-A4 antagonist if said detection antibody is bound by the sample.

In certain embodiments, the detection antibody is OTI1F9, E7O1U or an antigen binding protein described herein. The OTI1F9 detection antibody is further described in WO2019171064A1. In vitro over-expression experiments demonstrated that E7O1U only bound to MAGE-A4 whereas OTI1F9 cross-reacted widely with MAGE-A3, -A6, -A8, -A10, -A11 and -A12. E7O1U is therefore more specific than OTI1F9 Thus, in certain embodiments, the anti-MAGE-A4 detection antibody is E7O1U. For example, E7O1U is commercially available as MAGE-A4 (E7O1U) XP Rabbit mAb.

In certain embodiments, the MAGE-A4 antagonist is the antigen binding protein described herein, the CAR described herein, the immune cell described herein, the multispecific antigen binding protein described herein, or the pharmaceutical composition described herein.

Kits

Also contemplated are kits comprising at least one nucleic acid library or antigen binding protein, including the multispecific antigen binding protein, or the pharmaceutical composition as described herein, typically together with a packaged combination of reagents with instructions. In one embodiment, the kit includes a composition containing an effective amount of said antigen binding protein in unit dosage form. Such kit may comprise a sterile container comprising the composition; non-limiting examples of such containers include, without being limited to, vials, ampoules, bottles, tubes, syringes, blister-packs. In some embodiments, the composition is a pharmaceutical composition and the containers are made of a material suitable for holding medicaments. In one embodiment, the kit may comprise in a first container the antigen binding protein in lyophilized form and a second container with a diluent (e.g., sterile water) for reconstitution or dilution of the antigen binding protein. In some embodiments, said diluent is a pharmaceutically acceptable diluent. In one embodiment, the kit is for diagnostic purposes and the antigen binding protein is formulated for diagnostic applications. In one embodiment, the kit is for therapeutic purposes and the antigen binding protein is formulated for therapeutic applications.

Typically, the kit will further comprise a separate sheet, pamphlet or card supplied in or with the container with instructions for use. If the kit is intended for pharmaceutical use, it may further comprise one or more of the following: information for administering the composition to a subject having a related disease or disorder and a dosage schedule, description of the therapeutic agent, precautions, warnings, indications, counter-indications, overdosage information and/or adverse reactions.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1—Production of pMHC Antigen for Animal Immunization

MHC class I heavy chain and β2m were cloned into a pET-24D(+) vector using standard molecular biology techniques (J Biol Chem. 1995 Jan. 13; 270(2):971-7). E. coli BL-21 (DE3) were transformed with the expression vectors according to the supplier's protocols. Protein expression was performed for 16-18 hours at 37° C. with 220 rpm shaking in MagicMedium (Invitrogen), as described by the supplier. Cells were harvested and lysed with BugBuster (Invitrogen) and the inclusion bodies were washed twice with TBS supplemented with 0.5% LDAO and twice with TBS. Such prepared inclusion bodies were solubilized in a denaturing buffer (8 M urea, 100 mM Tris-HCl pH 8) using 5 mL buffer per 1 g inclusion body pellet. Refolding and purification of the MHC with the target peptides (HLA-A*02:01 extracellular domain, human β2m, and MAGE-A4 peptide 230-239) was performed essentially as described by Rodenko et al. (2006). The amino acid sequences for each component of the pMHC antigen are recited below in Table 1.

TABLE 1

| Amino Acid Sequences Of pMHC Antigen Components | |
|---|---|
| Sequence ID | Sequence |
| HLA-A*02:01 extracellular domain SEQ ID NO: 1 | GSHSMRYFFTSVSRPGRGEPRFIAVGYVDDTQFV RFDSDAASQRMEPRAPWIEQEGPEYWDGETRKV KAHSQTHRVDLGTLRGYYNQSEAGSHTVQRMY GCDVGSDWRFLRGYHQYAYDGKDYIALKEDLR SWTAADMAAQTTKHKWEAAHVAEQLRAYLEG TCVEWLRRYLENGKETLQRTDAPKTHMTHHAV SDHEATLRCWALSFYPAEITLTWQRDGEDQTQD TELVETRPAGDGTFQKWAAVVVPSGQEQRYTCH VQHEGLPKPLTLRWE |
| human β2m SEQ ID NO: 2 | IQRTPKIQVYSRHPAENGKSNFLNCYVSGFHPSDI EVDLLKNGERIEKVEHSDLSFSKDWSFYLLYYTE FTPTEKDEYACRVNHVTLSQPKIVKWDRDM |
| MAGE-A4$_{230-239}$ SEQ ID NO: 3 | GVYDGREHTV |

Example 2—Rabbit Immunization

To generate antibodies able to specifically recognize the target peptide in the context of the HLA-A*02:01 complex, 3 New Zealand white rabbits were immunized with the recombinantly produced HLA-A*02:01/MAGE-A4 complex. Each animal received at different timepoints 4 injections of the HLA-A*02:01/MAGE-A4 complex with complete or incomplete Freund's adjuvant. The immune response of the animals was tested in ELISA to quantify anti-pMHC antibodies present in serum samples of the immunized animals.

Example 3—Construction of Immune Libraries Derived from Rabbits

ScFv antibody cDNA libraries were constructed from the RNA extracted from isolated PBMCs and spleen lymphocytes from rabbits via PCR amplification. Coding sequences for the variable light (VL) and heavy (VH) domains were amplified separately and linked through a series of overlap PCR steps to give the final scFv products. The amplified DNA sequences coding for the scFvs from rabbits were digested using appropriate restriction enzymes and subsequently ligated into the phagemid vectors. The phagemid vectors were transformed into E. coli TG1 electrocompetent cells which are well suited for antibody phage display library creation. These processes resulted in two antibody libraries comprising a diversity of $5.2 \times 10^8$ with a sequence accuracy of 87.5% for the kappa-based library and $2.0 \times 10^9$ with an accuracy of 91.7% for the lambda-based library.

Example 4—Screening of Rabbit Derived Immune Libraries

Rabbit-derived immune libraries were screened for HLA-A*02:01/MAGE-A4 specific binders. Briefly, three rounds of phage display biopanning against HLA-A*02:01/MAGE-A4 antigen were performed, before the libraries were screened for specific hits. Screening was performed with a monoclonal phage ELISA against specific, i.e., HLA-A*02:01/MAGE-A4 and unspecific, i.e., HLA-A*02:01/peptide mix targets. The control HLA-A*02:01/peptide mix complex comprised an HLA-A*02:01 complex loaded with a mixture of 49 unrelated peptides. Signal ratio from the specific target binding to the unspecific binding was calculated to determine hits binding specifically to the target. Identified hits were expressed as chimeric Fabs.

Example 5—Expression of Antibodies as Monovalent Monospecific Fabs

The monovalent monospecific antibodies were expressed in a Fab format. The rabbit variable domains were paired with human constant domains (heavy chain and kappa light chain) to generate the chimeric Fabs, which bind to the target pMHC. The amino acid sequences of the constant domains are recited below in Table 2.

TABLE 2

Amino Acid Sequences For Generating Chimeric Fabs

| Sequence ID | Sequence |
|---|---|
| Human constant kappa SEQ ID NO: 4 | RTVAAPSVFIFPPSDEQLKSGTASVVCLLNNFYPR EAKVQWKVDNALQSGNSQESVTEQDSKDSTYSL SSTLTLSKADYEKHKVYACEVTHQGLSSPVTKSF NRGEC |
| Human constant heavy SEQ ID NO: 5 | ASTKGPSVFPLAPSSKSTSGGTAALGCLVKDYFPE PVTVSWNSGALTSGVHTFPAVLQSSGLYSLSSVVT VPSSSLGTQTYICNVNHKPSNTKVDKKVEPKSC |

Synthetic genes encoding different antibody chains (i.e., heavy chain and light chain) were constructed at Twist Bioscience Corporation and were separately cloned into the expression vectors for transient expression in HEK 293 6E cells. Expression vector DNA was prepared using conventional plasmid DNA purification methods (for example Qiagen HiSpeed plasmid maxi kit, cat. #12662).

The antigen binding proteins were expressed by transient co-transfection of the respective mammalian expression vectors in HEK293-6E cells, which were cultured in suspension using polyethylenimine (PEI 40 kD linear). The HEK293-6E cells were seeded at $1.7 \times 10^6$ cells/mL in Freestyle F17 medium supplemented with 2 mM L-Glutamine. The DNA for every mL of the final production volume was prepared by adding DNA and PEI separately to 50 µL medium without supplement. Both fractions were mixed, vortexed and rested for 15 minutes, resulting in a DNA:PEI ratio of 1:2.5 (1 µg DNA/mL cells). The cells and DNA/PEI mixture were put together and then transferred into an appropriate container which was placed in a shaking device (37° C., 5% CO2, 80% RH). After 24 hours, 25 µL of Tryptone N1 was added for every mL of final production volume.

After 7 days, cells were harvested by centrifugation and sterile filtered. For the affinity purification of Fab-based constructs, the supernatant was loaded on a CaptureSelect™ CH1-XLcolumn (Thermo Fisher Scientific) equilibrated with 6 CV PBS (pH 7.4). After a washing step with the same buffer, the antigen binding protein was eluted from the column by step elution with 100 mM citric acid (pH 3.0). The fractions with the desired antigen binding protein were immediately neutralized by 1 M Tris Buffer (pH 9.0) at 1:10 ratio, then pooled, dialyzed against PBS buffer and concentrated by centrifugation. Purity of the proteins was assessed by SDS-PAGE and size-exclusion HPLC.

Example 6—Characterization of Hits

Figure 1B:
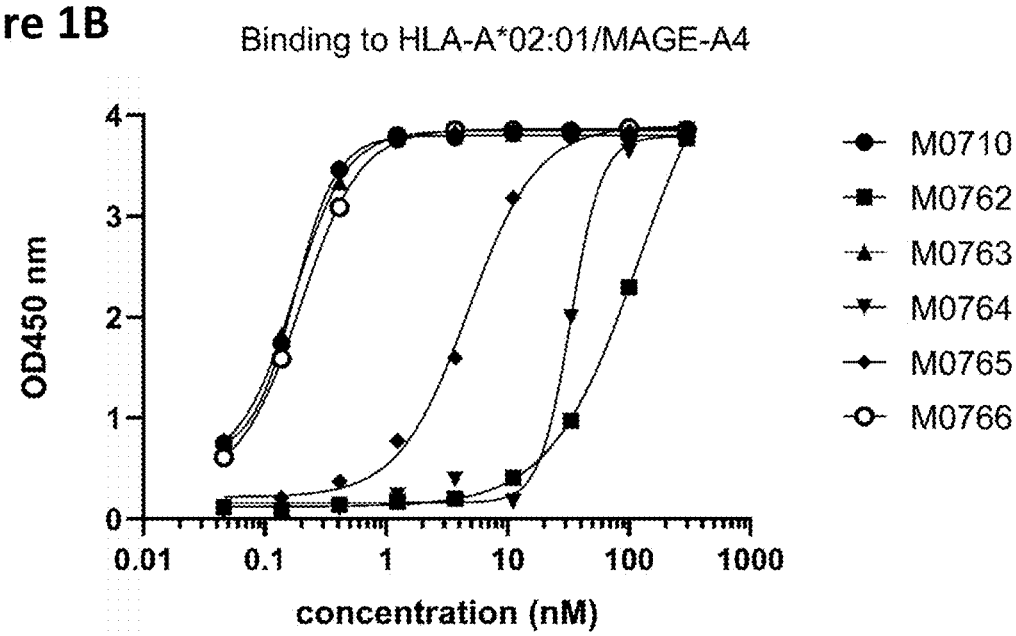
Figure 1C:
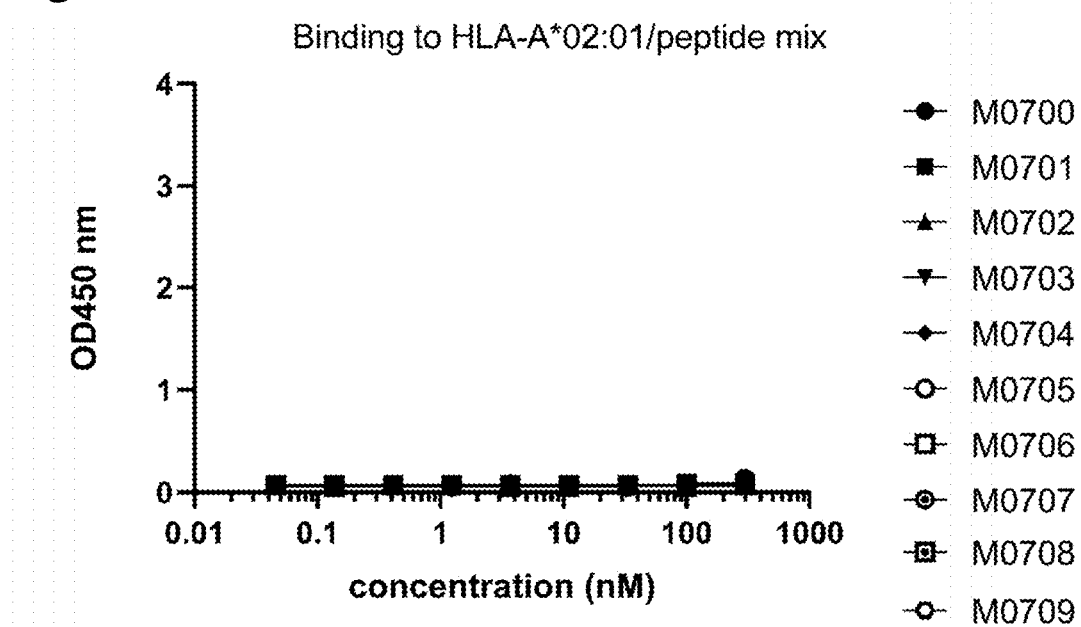
Figure 1D:
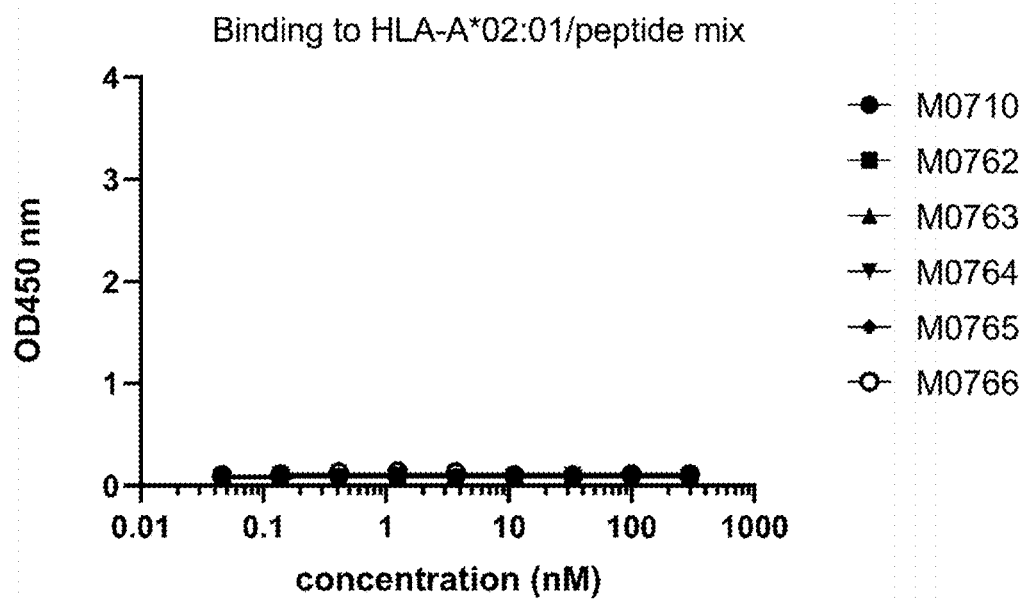

Hits were evaluated for their ability to bind HLA-A*02:01/MAGE-A4 complex and a control HLA-A*02:01/peptide mix complex in a direct binding ELISA assay. Briefly, 96 well ELISA plates were coated with HLA-A*02:01/MAGE-A4 complex or control HLA-A*02:01 complex. Serial dilutions of antigen binding proteins in a Fab format were added to the plate and detected by an anti-kappa light chain-HRP (Invitrogen) followed by goat anti-rabbit IgG (H+L) HRP (Southern Biotech). Binders were considered for further characterization when showing high binding to HLA-A*02:01/MAGE-A4 complex and no binding to control HLA-A*02:01/peptide mix complex. Binding of the selected antibodies M0700, M0701, M0703, M0704, M0705, M0706, M0707, M0708, M0709, M0710, M0762, M0763, M0764, M0765 and M0766 to HLA-A*02:01/MAGE-A4 complex, as determined by ELISA, is shown in FIGS. 1A and 1B. Respectively, binding to the negative control complex HLA-A*02:01/peptide mix, as determined by ELISA, is shown in FIGS. 1C and 1D. All tested molecules showed specific binding to the HLA-A*02:01/MAGE-A4 complex and no binding to the control HLA-A*02:01/peptide mix complex.

Figure 2A:
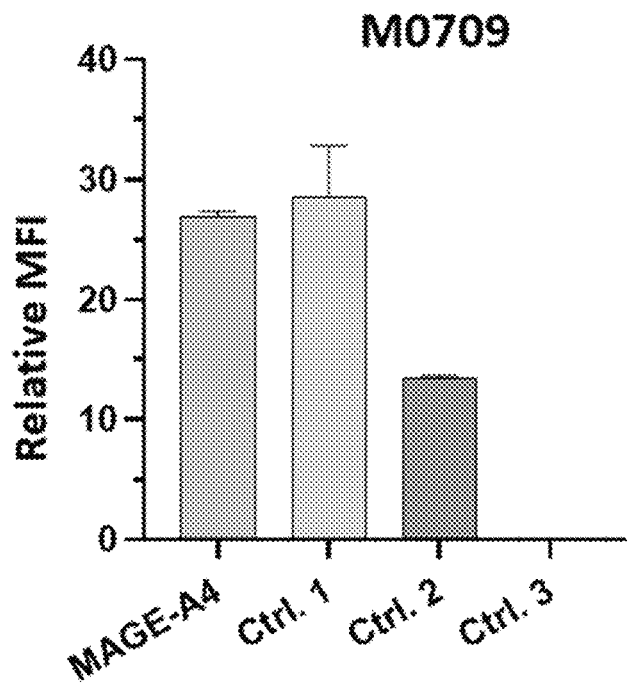
FIGS. 2A-2B show binding of antibodies M0709 (FIG. 2A) and M0763 (FIG. 2B) to T2 cells displaying MAGE-A4 or control peptides 1, 2 and 3.
Figure 2B:
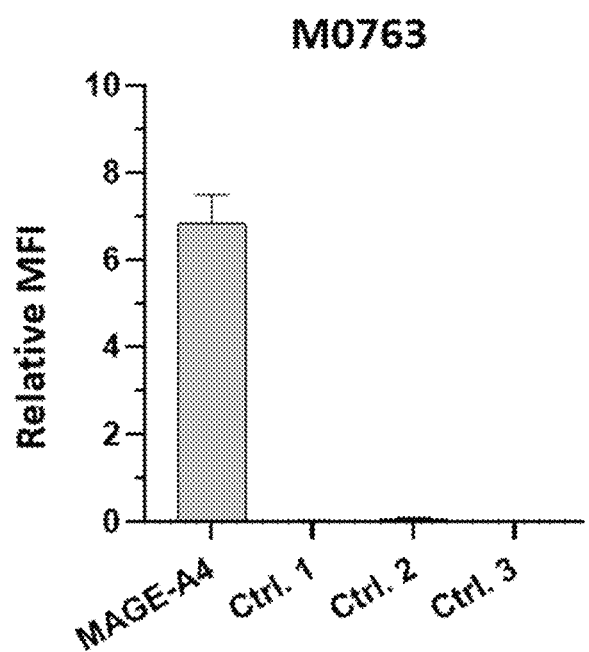

Binding of the specific antibodies M0709 and M0763 to the HLA-A*02:01/MAGE-A4 complex presented on cells was determined. Briefly, T-B hybrid T2 cells were incubated with serum-free RPMI1640 medium containing MAGE-A4 or control peptides. Control peptides constituted sequences with high identity to MAGE-A4 and had previously been identified in healthy human tissues, i.e., Ctrl.1 (GLADGRTHTV; SEQ ID NO: 68), Ctrl.2 (GLYDGPVHEV; SEQ ID NO: 69) and Ctrl.3 (GVFDGLHTV; SEQ ID NO: 70) (US20180171024, incorporated herein by reference). Peptide loading efficiency was verified by using the ratio between median fluorescent intensity (MFI) of HLA-A*02:01-binding antibody BB7.2 on peptide loaded T2 cells and MFI of unloaded T2 cells (>1). T2 cells were incubated with each of the specific antibodies followed by fluorophore-labeled detection antibodies (anti-kappa light chain). The cells were fixed and fluorescence was measured by flow cytometry. Binding and specificity of M0709 and M0763 to the T2 cells displaying MAGE-A4 or control peptides 1, 2 and 3 is presented in FIGS. 2A-2B. Both tested molecules showed binding to the HLA-A*02:01/MAGE-A4 displayed on the T2 cells. Moreover, M0763 showed a very high specificity for the MAGE-A4 peptide and did not show binding to any of the control peptides displayed by the HLA-A*02:01 on T2 cells. M0709 showed lower specificity than M0763 and was also binding control peptide 1 and 2.

Example 7—Optimization of M0763

Figure 3A:
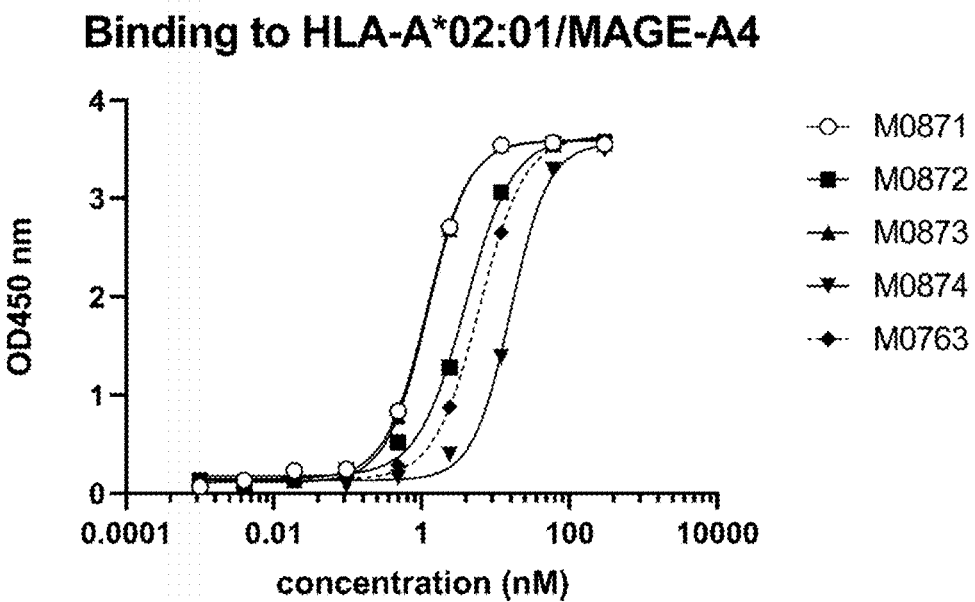
FIGS. 3A-3B show binding of humanized M0763 variants to HLA-A*02:01/MAGE-A4 (FIG. 3A) or control complex HLA-A*02:01/peptide mix (FIG. 3B), as determined by direct ELISA.
Figure 3B:
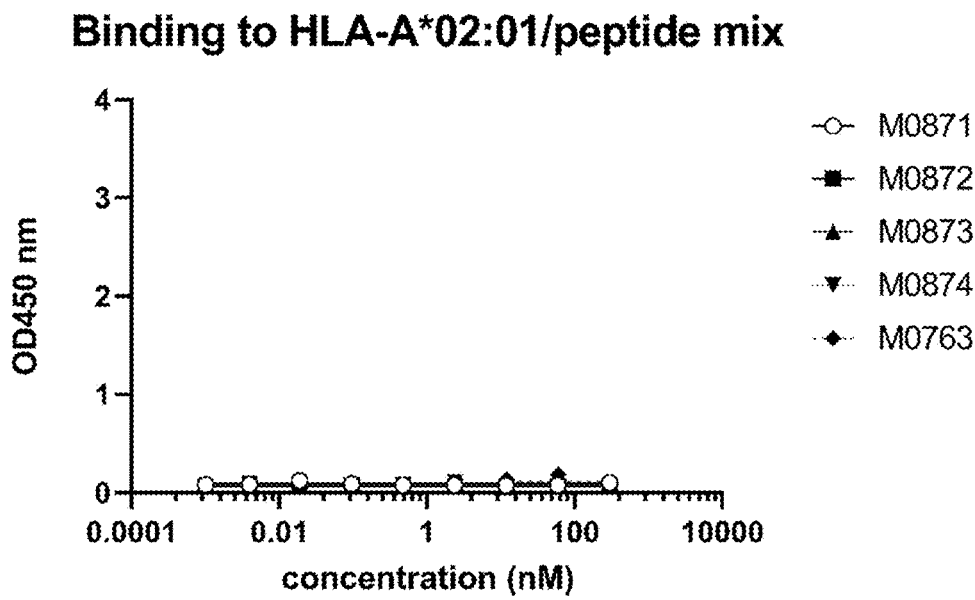

The rabbit antibody designated M0763 was humanized by CDR grafting. Briefly, human V gene germlines displaying high sequence identity to M0763 VH and VL, i.e., IMGT_hVH_3_23 and IMGT_hVL_3-1, respectively were selected as CDR acceptor scaffolds. Resulting humanized antibodies M0871-M874 retained HLA-A*02:01/MAGE-A4 binding, as determined by direct ELISA (as described in Example 6) with EC50 values of 1.18-16.02 nM and showed no binding to the HLA-A*02:01/peptide mix negative control (FIGS. 3A-3B).

In the next step of optimization, M0873 was subjected to affinity maturation. Briefly, multiple antibody libraries were designed to span the entire length of all 6 CDRs, randomizing 3 consecutive amino acids at the time. The libraries were generated using primers for site saturation mutagenesis. Therefore, the three amino acid positions targeted for randomization contained one of 19 possible amino acid variations. After electroporation into *E. coli* TG-1 cells, the diversity of the libraries was determined by plating the libraries on agar plates using serial dilutions of the transfected TG-1 cells. The number of colonies growing on the plates was used as indication of library diversity assuming one inserted plasmid in each *E. coli* colony. Additionally, library quality was evaluated by sequencing a sample of 10 clones per library.

Libraries comprising site saturation mutagenesis in the light chain were combined into one library and libraries comprising site saturation mutagenesis in the heavy chain were combined into another library. The two resulting libraries for randomized CDRs in light and heavy chains were subjected to affinity selection, henceforth referred as biopanning against the HLA-A*02:01/MAGE-A4 complex. The HLA-A*02:01/MAGE-A4 specific phage libraries were submitted to panning (selection) on antigen adsorbed on to polystyrene tubes or plates. Briefly, three rounds of phage display biopanning against HLA-A*02:01/MAGE-A4 antigen were performed, before the libraries were screened for hits. Screening was performed with a monoclonal phage ELISA against specific, i.e., HLA-A*02:01/MAGE-A4 and unspecific, i.e., HLA-A*02:01/peptide mix targets.

Phage displayed antibody clones were then categorized into high, medium and low signal in ELISA for the target complex protein and for the HLA-A*02:01 in complex with unrelated peptides. Clones with high binding signal for the target complex and low binding to the HLA-A*02:01/peptide mix complexes were sequenced. Sequence analysis facilitated the identification of unique clones which were then selected to expressed recombinantly in bispecific format anti-CD3 Fab×anti-MAGE-A4 scFv. The resulting constructs were then evaluated in SPR for binding affinity to HLA-A*02:01/MAGE-A4 complex (Table 3).

TABLE 3

Binding Affinity Values to HLA-A2/MAGE-A4 Complex for Variant Antibodies

| Monovalent | Affinity $K_D$ (nM) |
|---|---|
| M1036 | 4.90 |
| M1037 | 0.40 |
| M1038 | 3.60 |
| M1040 | 0.45 |
| M1041 | 0.24 |
| M1051 | 5.00 |
| M1086 | 7.02 |
| M1087 | 0.82 |
| M1088 | 3.90 |
| M1089 | 1.34 |
| M1090 | 1.80 |
| M1096 | 3.23 |
| M1097 | 0.99 |
| M1098 | 1.73 |
| M1099 | 2.13 |
| M1100 | 0.66 |
| M1101 | 1.69 |
| M1105 | 4.12 |
| M1107 | 1.45 |
| M1108 | 19.00 |
| M1109 | 11.70 |
| M1110 | 9.65 |
| M1111 | 0.65 |
| M1112 | 35.90 |
| M1113 | 15.30 |
| M1114 | 1.18 |
| M1115 | 0.48 |
| M1116 | 3.88 |
| M1117 | 4.20 |
| M1119 | 0.91 |
| M1120 | 1.21 |
| M1121 | 6.53 |
| M1122 | 0.75 |
| M1089 | 0.79 |
| M1123 | 0.79 |
| M1124 | 0.65 |
| M1125 | 0.89 |
| M1127 | 0.89 |
| M1128 | 1.32 |
| M1129 | 0.46 |
| M1130 | 2.20 |
| M1131 | 3.20 |
| M1132 | 4.10 |
| M1133 | 12.40 |
| M1134 | 4.20 |
| M1135 | 2.40 |
| M1136 | 2.70 |
| M1137 | 2.20 |
| M1138 | 3.10 |
| M1139 | 2.10 |
| M1140 | 2.80 |
| M1141 | 1.20 |
| M1142 | 2.90 |
| M1143 | 2.40 |
| M1144 | 2.30 |
| M1145 | 2.10 |
| M1169 | 3.20 |
| M1171 | 4.40 |
| M1172 | 1.50 |
| M1176 | 6.00 |
| M1177 | 4.20 |
| M1178 | 8.30 |
| M1202 | 3.90 |
| M1253 | 2.55 |
| M1297 | 0.09 |
| M1298 | 0.07 |
| M1299 | 0.05 |
| M1300 | 0.12 |
| M1301 | 0.12 |
| M1302 | 0.60 |
| M1309 | 0.09 |
| M1310 | 0.35 |
| M0763 | 44.00 |

Affinity characterization of anti-HLA-A*02:01/MAGE-A4×CD3 bispecific antibodies of Table 3 was performed by surface plasmon resonance (SPR) using a Biacore™ T200 Device (Cytiva). To determine the affinity of the bispecific antibodies to the HLA-A*02:01/MAGE-A4 complex, a streptavidin chip (SAHC30M, XanTec) was coated according to the manufacturer's instructions with 500 RU HLA-A*02:01 in complex with the MAGE-A4 peptide. To determine the affinity of the bispecific antibodies to CD3, a HC30M chip (XanTec) was coated according to the manufacturer's instructions with 400 RU of CD3 heterodimer (Acro Biosystems). Uncoated channels were used for referencing. Data fitting was performed using a 1:1 Langmuir model. Affinity matured clones resulted in binding affinities as low as two-digit picomolar, which was almost 1000-fold improved binding affinity compared to the parental M0763 antibody.

Affinity matured M1041 was optimized by further humanization and stabilization of the anti-HLA-A*02:01/MAGE-A4 binding scFv arm. Rabbit originating residues in VH FR1 were further mutated by incorporating amino acid substitutions S2V and V4L, yielding M1067. M1067 was further modified by incorporating mutations in VH FR3, i.e., amino acid substitutions K71R and T73N, and in CDR-L3, i.e., amino acid substitution L97A, yielding M1402. Each optimization step improved the human sequence identity score, thermostability and affinity to the target antigen, as indicated in Table 4. Thermostability of the bispecific antibodies was measured using a differential scanning fluorimetry (DSF), as described in the Protein Thermal Shift manual MAN4461806B from Applied Biosystems (Thermo Fisher).

TABLE 4

Characteristics of stabilized and humanized variants of M1041.

| Molecule | Affinity to HLA-A*02:01/ MAGE-A4 [pM] | Melting temperature [° C.] | Human sequence identity anti-HLA-A*02:01/ MAGE-A4 scFv [%] | |
|---|---|---|---|---|
| | | | VL | VH |
| M1041 | 250 | 59.9 | 89.8 | 77.8 |
| M1067 | 120 | 63.6 | 89.8 | 79.6 |
| M1402 | 110 | 68.0 | 89.8 | 81.5 |

Simultaneously, M1067 was further modified to obtain a more stable molecule with lower affinity to HLA-A*02:01/MAGE-A4 antigen by incorporating a mutation in VH FR2, i.e., amino acid substitution Y47W, yielding M1068. M1067 and M1068 were compared for stability at various concentrations and during a prolonged incubation at 4° C. and at 37° C. in PBS pH 7.4. Stability was assessed by SEC-HPLC quantification of the target protein monomer, and the corresponding data is presented in Table 5. M1068 showed superior stability to M1067 and retained >90% monomeric content upon two-week incubation at all tested concentrations and incubation temperatures.

TABLE 5

Stability of M1067 and M1068

| Molecule | Concentration [mg/mL] | Incubation temperature [° C.] | Stability [% monomer target protein] Incubation time | | | |
|---|---|---|---|---|---|---|
| | | | 0 days | 3 days | 7 days | 14 days |
| M1067 | 1.02 | 4 | 94.1 | 94.7 | 96.9 | 94.6 |
| | | 37 | | 83.5 | 82.6 | 80.4 |
| | 5.13 | 37 | 91.6 | 79.2 | 78.9 | 77.3 |
| M1068 | 0.97 | 4 | 98.2 | 98.8 | 98.8 | 98.5 |
| | | 37 | | 98.7 | 98.2 | 97.1 |
| | 4.98 | 4 | 95.7 | 96.0 | 96.0 | 94.5 |
| | | 37 | | 96.4 | 94.7 | 93.2 |
| | 10.37 | 37 | 92.8 | 94.1 | 93.5 | 91.7 |

M1068 was further subjected to affinity maturation, as described previously. Affinity maturation campaign resulted in generation of novel CDR-L3 and CDR-H3 sequences with distinct properties. Molecules containing these novel CDR sequences included M1302, M1382 and M1386, and they all showed improved affinity to HLA-A*02:01/MAGE-A4 antigen with $K_D$ values of 0.6 nM, 0.23 nM and 0.15 nM, respectively, compared to a $K_D$ of 1.0 nM for M1068. M1302 was additionally optimized for human sequence content and stabilization. A different human germline VL framework, i.e., IMGT_hVL_3-19 was selected for grafting CDR-L1, -L2 and -L3 of M1302, resulting in M1312. IMGT_hVL_3-19 showed a similar high sequence similarity to M0763 VL sequence, as previously selected IMGT_hVL_3-1, however IMGT_hVL_3-19 provided the molecule with improved biophysical properties. M1312 was further humanized by incorporating mutations in VH FR3, i.e., amino acid substitutions K71R and T73N, yielding M1394. Final humanization of M1394 comprised substitutions in CDR-H2, i.e., amino acid substitutions S61D, W62S and A63V, VL FR1, i.e., amino acid substitutions S1Q and E3V, and in CDR-L3, i.e., amino acid substitution L97A, resulting in M1396. Each incorporated substitution improved the human sequence identity score and/or stability of the molecule, as shown in Table 6.

TABLE 6

Characteristics of stabilized and humanized variants of M1068.

| Molecule | Affinity to HLA-A*02:01/ MAGE-A4 [nM] | Melting temperature (Tm) [° C.] | Human sequence identity anti-HLA-A*02:01/ MAGE-A4 scFv [%] | |
|---|---|---|---|---|
| | | | VL | VH |
| M1068 | 1.0 | 64.9 | 89.8 | 82.4 |
| M1302 | 0.6 | 55.7 | 89.8 | 82.4 |
| M1312 | 0.8 | 74.4 | 89.8 | 82.4 |
| M1394 | 1.4 | 74.6 | 89.8 | 84.3 |
| M1396 | 1.6 | 76.6 | 87.8 | 87.0 |

Example 8—Production of Monovalent and Bivalent pMHC-Targeting T Cell Engagers Monovalent bispecific antigen binding proteins were expressed by transient co-transfection in HEK293-6E cells. Cells were cultured in suspension using polyethylenimine (PEI 40 kD linear). HEK293-6E cells were seeded at $1.7 \times 10^6$ cells/mL in Freestyle F17 medium supplemented with 2 mM L-Glutamine. DNA and PEI were added separately to 50 µL medium without supplement. Both fractions were mixed at 1:2.5 DNA:PEI ratio, vortexed and rested for 15 minutes. Cells and DNA/PEI mixture were combined (1 µg DNA/mL cells) and incubated at 37° C., 5% CO2, 80% RH. After 24 hours, cells were supplemented with Tryptone N1 at 25 µL per mL production volume. After 7 days, cells were harvested by centrifugation and the supernatant was sterile filtered. The antigen binding proteins were purified by an affinity chromatography from the supernatant. Supernatant was loaded on a CaptureSelect™ CH1-XL column (Thermo Fisher Scientific) equilibrated with 6 CV PBS (pH 7.4). After a washing step with the same buffer, protein was eluted from the column by step elution with 100 mM Citric acid (pH 3.0). Fractions with the desired antigen binding protein were immediately neutralized by 1 M Tris Buffer (pH 9.0) at 1:10 ratio. Size exclusion chromatography was performed as an additional purification step. Samples were run on the Superdex 200 10/300 GL column with PBS (pH7.4) as a running buffer. Collected fractions were analyzed by SE-HPLC for monomer content and pooled accordingly. Final protein purity was assessed by SDS-PAGE and SE-HPLC.

Bivalent bispecific antigen binding proteins were produced by transient co-transfection in CHO-K1 cells. The genes for HC and LC were expressed using a 2:1 vector ratio in shake flask cultures for 7 days. The target proteins were captured from the clarified, sterile-filtered culture supernatants by affinity chromatography and an Amsphere A3 resin (JSR Life Science). The captured antigen binding proteins were further polished by strong cation exchange chromatography (CEC) over a Source 30S resin (Cytiva) and hydrophobic interaction chromatography (HIC) over a Toyopearl PPG-600M resin (Tosoh Bioscience). An Amicon stirred cell (Merck) was applied for transferring the target proteins into the final buffer (130 mM NaCl, 10 mM sodium phosphate, pH 6.5).

Example 9—Dual pMHC-Targeting T Cell Engagers

Figure 4:
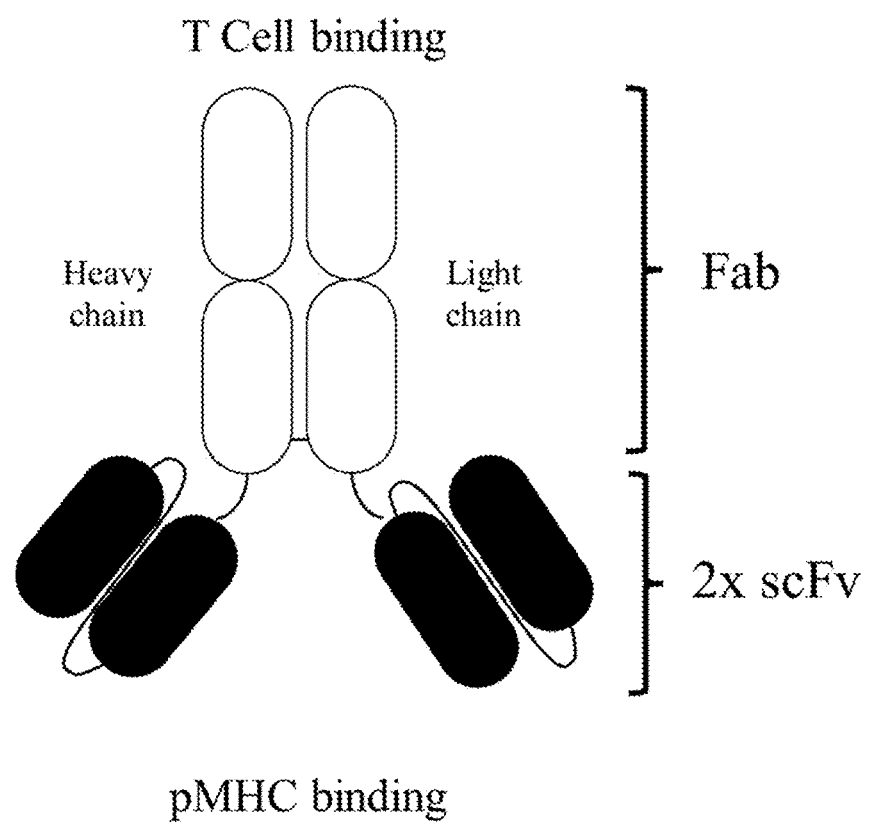
FIG. 4 depicts a schematic of one embodiment of the bispecific antibody of the invention. The represented embodiment comprises an anti-CD3 Fab fragment and two single chain antibody fragments (scFv) which specifically bind target peptides presented on MHC complexes. The pMHC binding scFvs may be linked to the C-termini of the CH1- and CL-domains via a glycine-serine flexible linker.

Antigen binding proteins were designed with two binding domains targeting a specific pMHC and a Fab binding domain targeting CD3 as a T cell recruiting domain. FIG. 4 depicts a schematic of an exemplary bispecific antigen binding protein with a Fab T cell binding domain (e.g., an anti-CD3 Fab) and two pMHC binding domains in an scFv format (e.g., each pMHC binding domain specifically binds to the same target pMHC molecule on the surface of a tumor cell). These dual pMHC-targeting T cell engagers function by recruiting a T cell to a tumor cell expressing the target pMHC molecule on the surface.

Figure 5A:
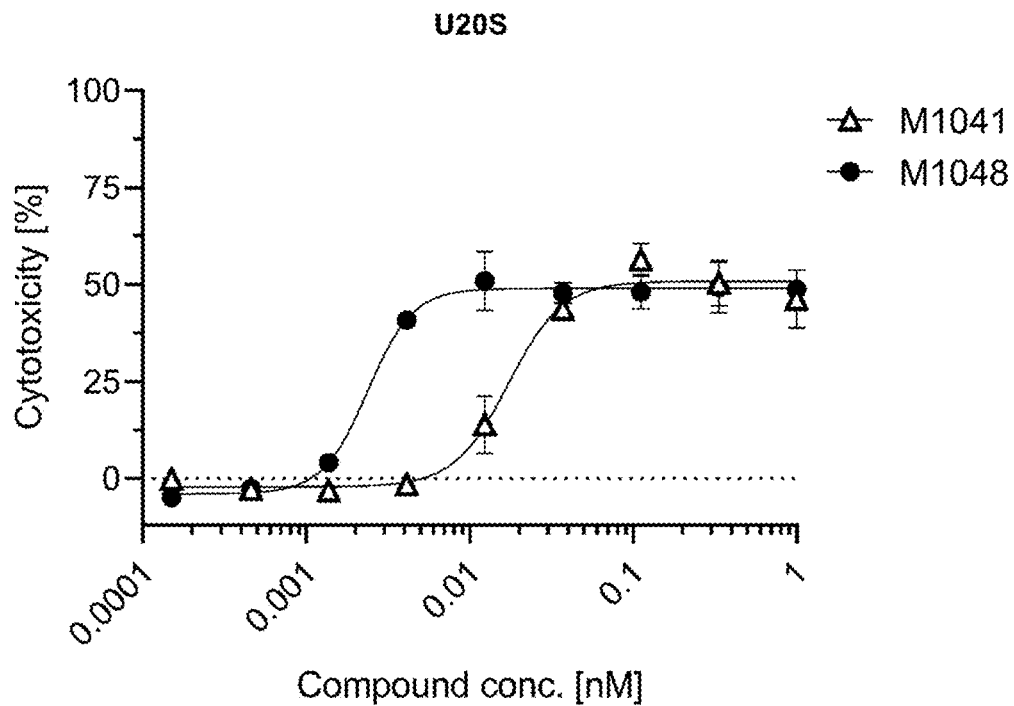
FIGS. 5A-5D show cytotoxicity of dual T cell engager M1048 and its monovalent counterpart M1041 in MAGE-A4-positive HLA-A*02:01-positive U2OS cancer cells (FIG. 5A) and MAGE-A4-negative HLA-A*02:01-positive SK-MEL-30 (FIG. 5B), MDA-MB-231 (FIG. 5C) and PANC-1 (FIG. 5D) cancer cells.
Figure 5B:
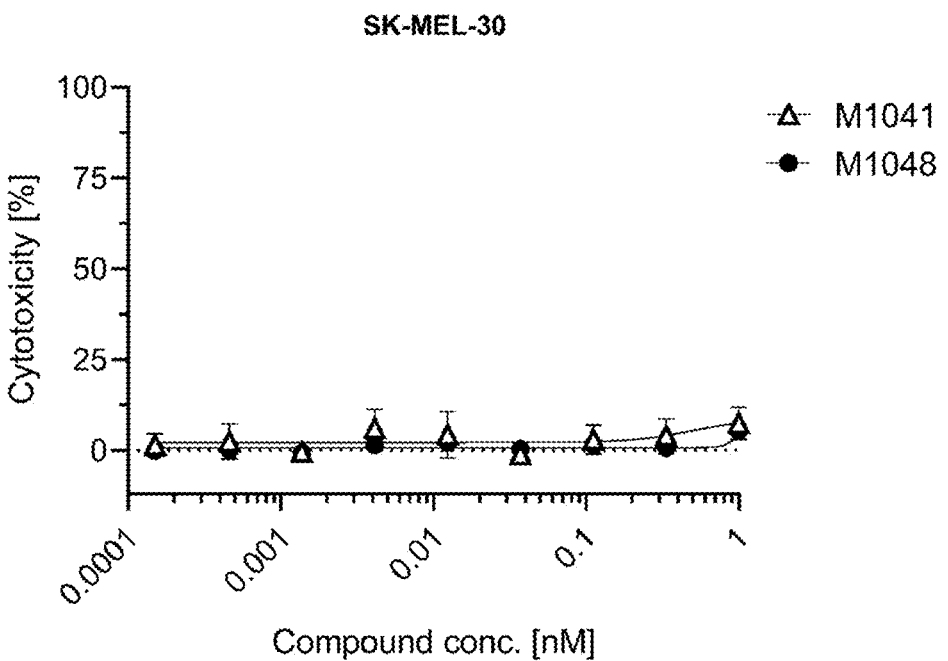
Figure 5C:
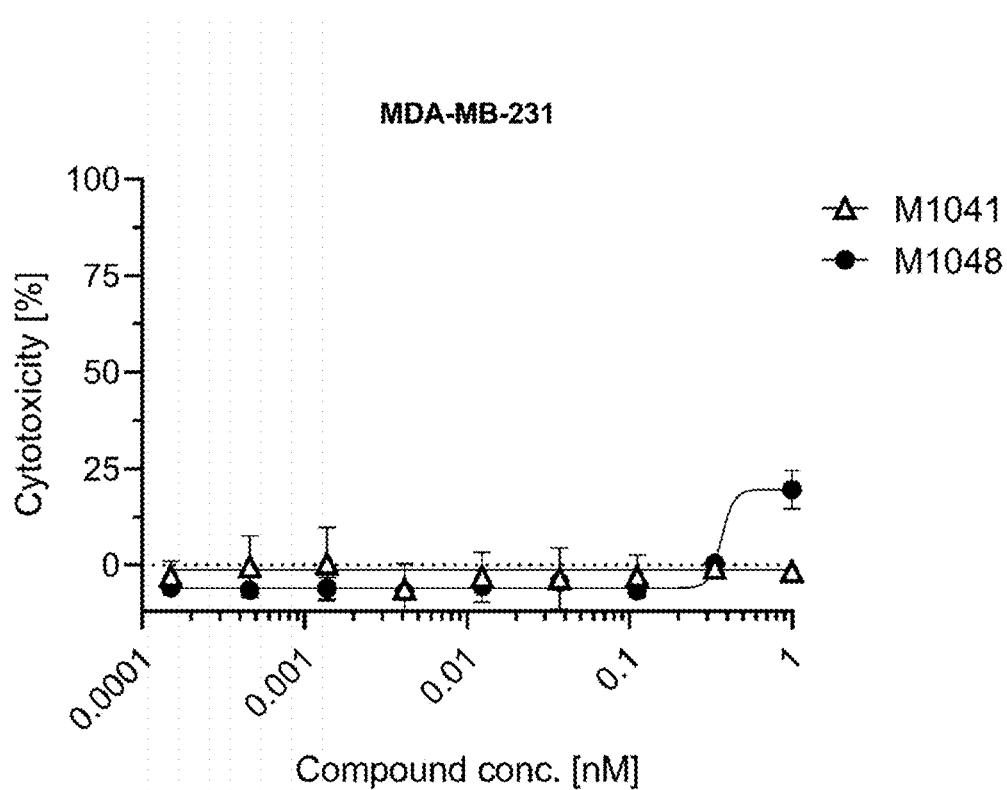
Figure 5D:
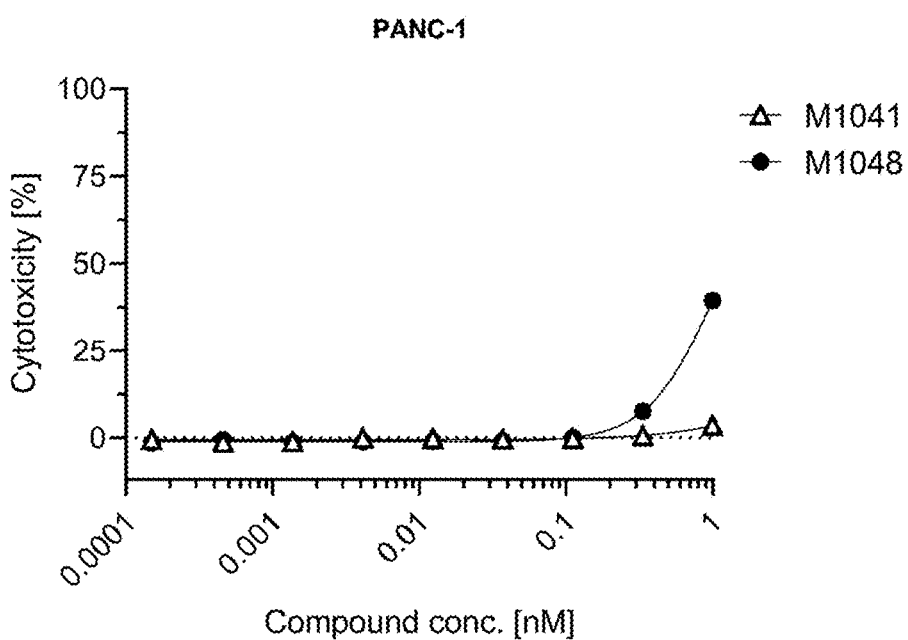

To test the functionality of the dual pMHC-targeting T cell engagers, two identical scFv antigen binding proteins with binding specificity to pMHC-MAGE-A4 were linked to an anti-CD3 Fab, with one scFv linked to the Fab heavy chain (HC) and one scFv linked to the Fab light chain (LC). The CD3 Fab possesses a binding affinity of 10 nM KD for CD3 and each pMHC-MAGE-A4 scFv possesses a binding affinity of 250 pM KD for pMHC-MAGE-A4. This multispecific antigen binding protein was designated "anti-MAGE-A4 dual engager" or simply "dual engager". Dual engager M1048 and its monovalent counterpart M1041 were compared for efficacy and safety in LDH assay. MAGE-A4-positive HLA-A*02:01-positive osteosarcoma cell line U2OS and three MAGE-A4-negative HLA-A*02:01-positive cell lines SK-MEL-30, MDA-MB-231 and PANC-1 were incubated with human PBMCs at an E:T ratio of 10:1. Cancer cell killing was measured at various concentrations of the monovalent T-cell engager M1041 and dual T-cell engager M1048. Cytotoxicity was quantified by colorimetric absorbance measurements of the amount of LDH released from damaged cells into the medium after 48 h (FIGS. 5A-5C). Dual T-cell engager M1048 showed superior cancer cell killing than its monovalent counterpart M1041. Simultaneously, M1048 showed comparably low cytotoxicity on the antigen-negative cancer cells SK-MEL-30, MDA-MB-231 and PANC-1 to its monovalent counterpart M1041, with higher cytotoxicity of M1048 observed only at the highest tested compound concentration of 1 nM in PANC-1 and MDA-MB-231 cell lines. Overall, data showed superiority of the dual T cell engager over its monovalent counterpart with about a 10-fold increase in antigen-positive cancer cell killing potency of a dual pMHC-targeting T cell engager and comparable low cytotoxicity in antigen negative cancer cell lines.

Example 10—Characterization of Optimized Anti-HLA-A*02:01/MAGE-A4×CD3 Dual pMHC-Targeting T Cell Engagers Optimized variants of M1041, i.e., M1382, M1386, M1396 and M1402 were reformatted into the dual pMHC T cell engager format, resulting in molecules M1383, M1387, M1397 and M1403, respectively. Molecule production showed a comparable titer for both M1397 and M1403. After purification according to a standardized protocol, M1397 showed considerably lower amounts of charge variants than M1403.

Figure 6A:
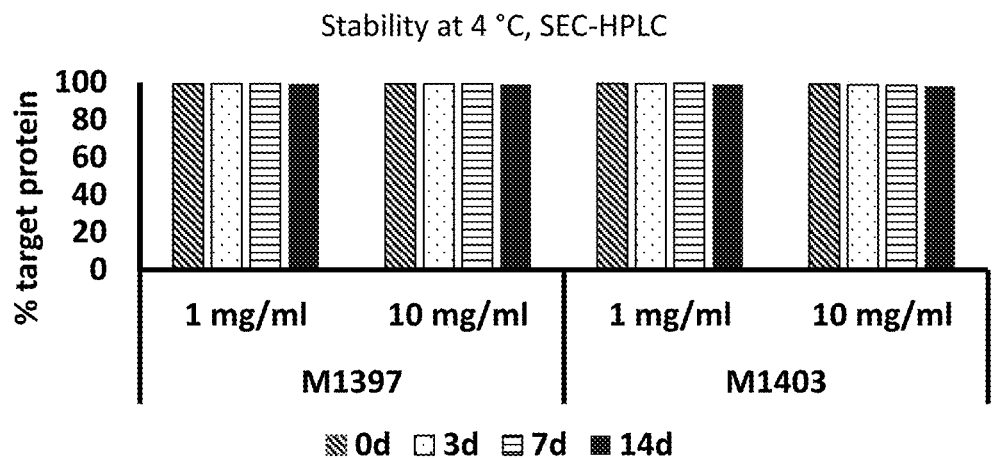
FIGS. 6A-6B show the stability of dual engagers M1397 and M1403 in PBS over 0, 3, 7 and 14 days as determined by SEC-HPLC.
Figure 6B:
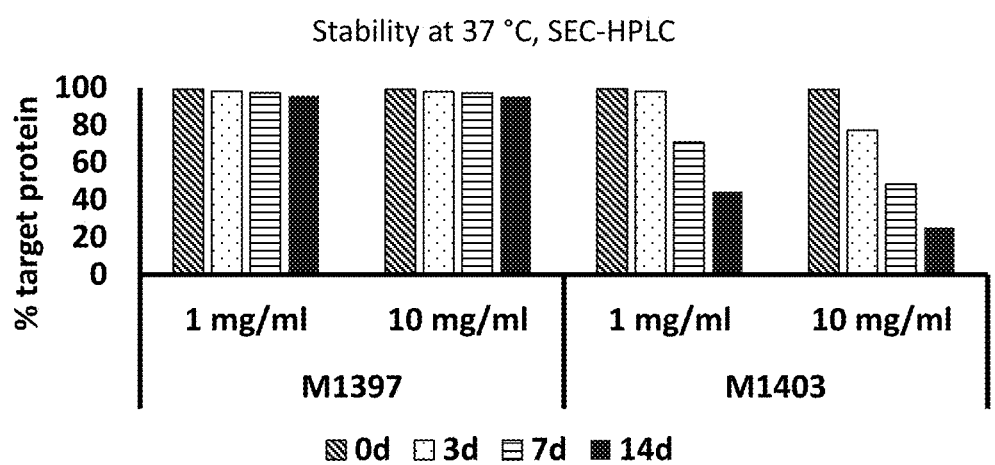

M1403 and M1397 were tested for stability at 1 mg/mL and 10 mg/mL concentrations during a prolonged incubation at 4° C. and at 37° C. in 10 mM phosphate buffer pH 6.0 supplemented with 130 mM NaCl. Stability was assessed by SEC-HPLC quantification of the target protein monomer, and the corresponding data is presented in FIGS. 6A-6B. Both molecules M1397 and M1403 showed good stability in 10 mM phosphate buffer pH 6.0 supplemented with 130 mM NaCl at 4° C. for 14 days retaining >98% target protein monomeric content at both tested concentrations. M1397 showed superior stability to M1403 when incubated at 37° C. retaining >95% target protein monomeric content at both tested concentrations.

M1397 and M1403 were subjected to a detailed biophysical characterization using dynamic light scattering (DLS). Briefly, molecule cumulant radius (average size of the particles) and polydispersity index (PDI) were determined by DLS using the Prometheus Panta instrument. Samples were mixed and 0.1 µm filtered before measurement. Analysis was performed at 20° C. and at 100% DLS laser power. Data was analyzed with the PR Panta Analysis (x64) software. Thermostability of the dual engagers M1397 and M1403 was measured using differential scanning fluorimetry (DSF). For this purpose, the samples were diluted to a concentration of 1 mg/ml. Temperature increased by 1° C./min from 20-95° C. Data was analyzed with the PR Panta Analysis (x64) software. Thermostability including onset of protein unfolding (Tonset), melting Temperature™ and aggregation temperature (Tagg) was determined. Resulting data is presented in Table 7. M1397 showed a very favorable thermostability profile with unfolding onset at 47.01° C. and a two-step unfolding process. The first transition occurred at 53.33° C., corresponding to scFv domain unfolding and the second at 72.47° C., corresponding to the Fab domain unfolding. M1403 showed onset of unfolding at >10° C. lower temperature than M1397 and a three-step unfolding process.

TABLE 7

Thermostability and cumulant analysis of M1397 and M1403.

| Molecule | $T_{onset}$ [° C.] | $T_m$ peak 1 [° C.] | $T_m$ peak 2 [° C.] | $T_m$ peak 3 [° C.] | $T_{agg}$ [° C.] | Cumulant radius [nm] | Cumulant PDI |
|---|---|---|---|---|---|---|---|
| M1397 | 47.01 | 53.33 | — | 72.47 | 55.22 | 4.76 | 0.08 |
| M1403 | 36.41 | 46.76 | 52.52 | 73.97 | 52.83 | 4.79 | 0.09 |

Figure 7A:
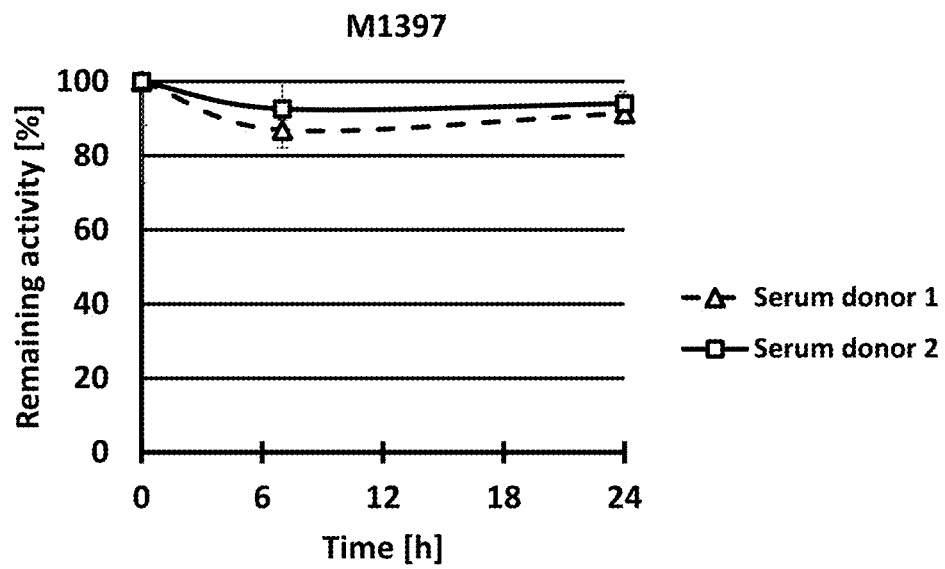
FIGS. 7A-7B show the stability of dual engagers M1397 (FIG. 7A) and M1403 (FIG. 7B) in human serum at 37° C.
Figure 7B:
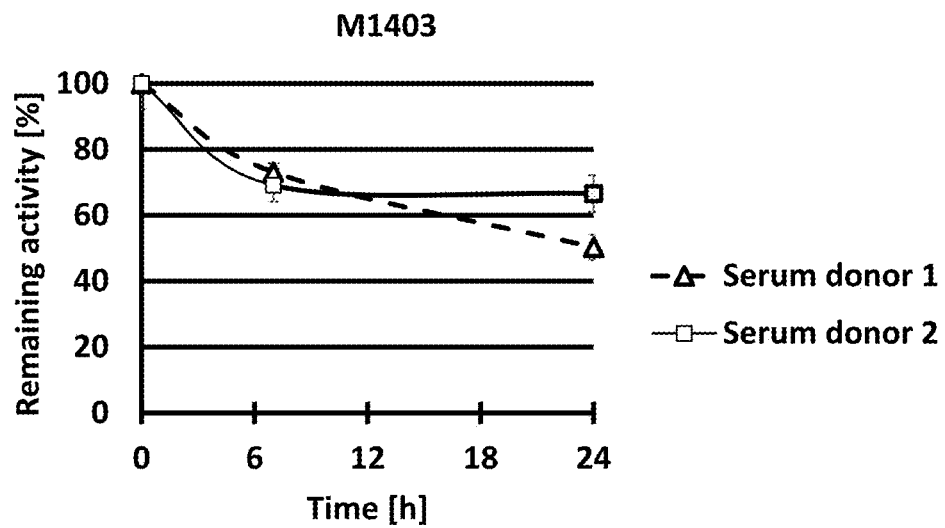
Figure 8A:
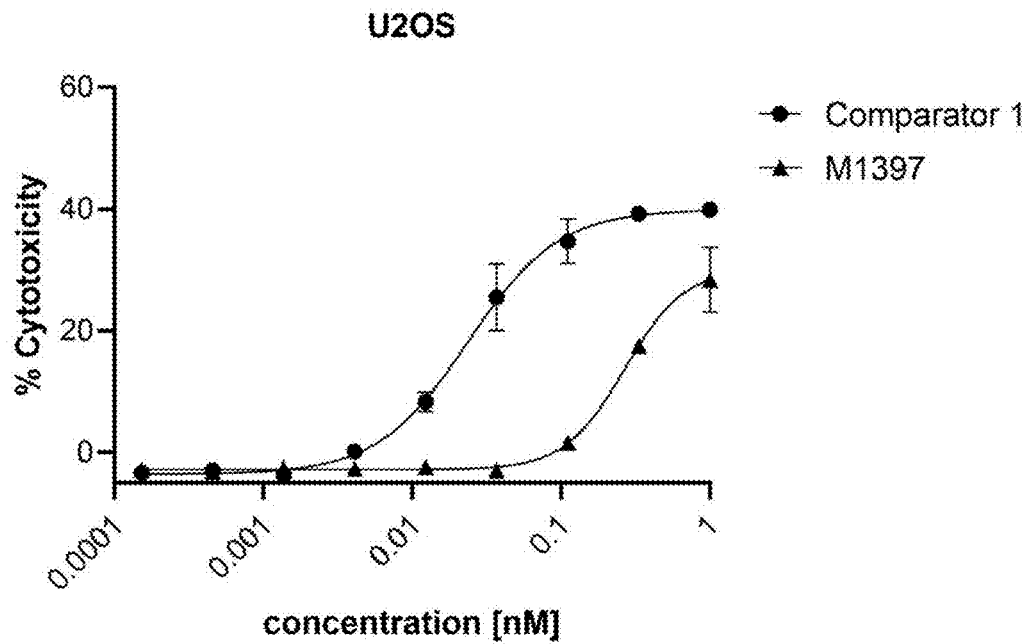
FIGS. 8A-8K show cytotoxicity of dual engagers M1397 and M1403 or Comparator 1 in MAGE-A4-positive HLA-A*02:01-positive cancer cells (FIG. 8A-E) and MAGE-A4-negative HLA-A*02:01-positive cancer cells (FIG. 8F-K).
Figure 8B:
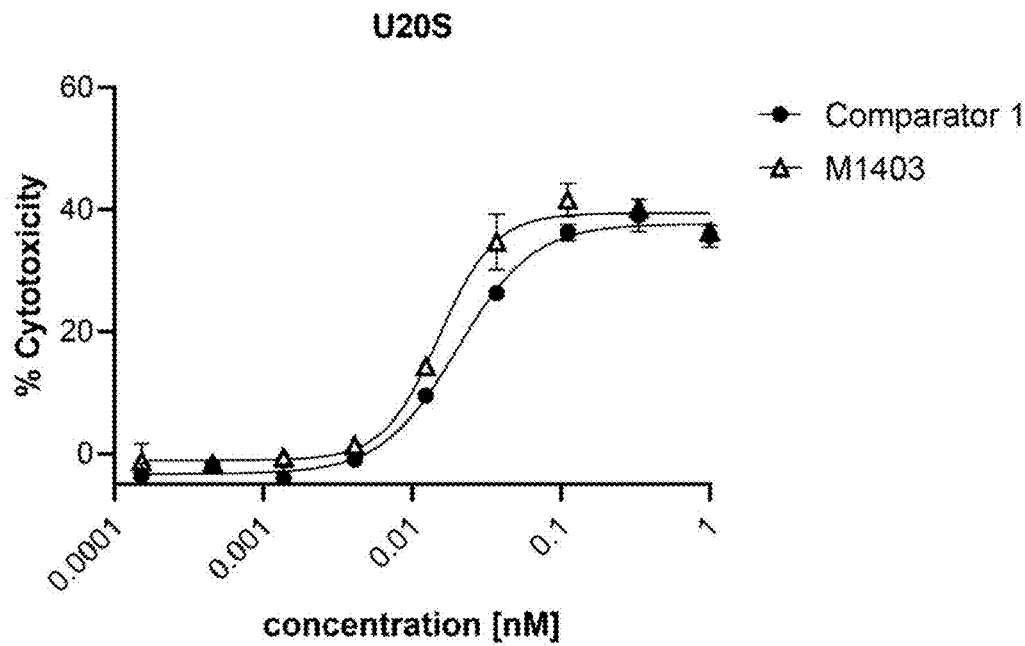
Figure 8C:
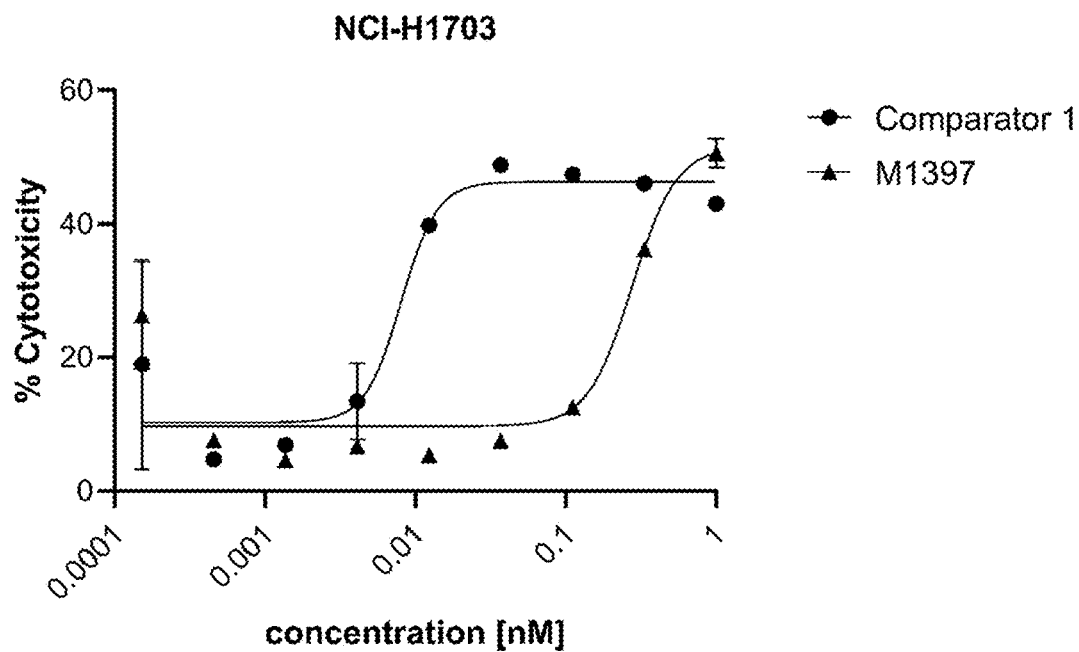
Figure 8D:
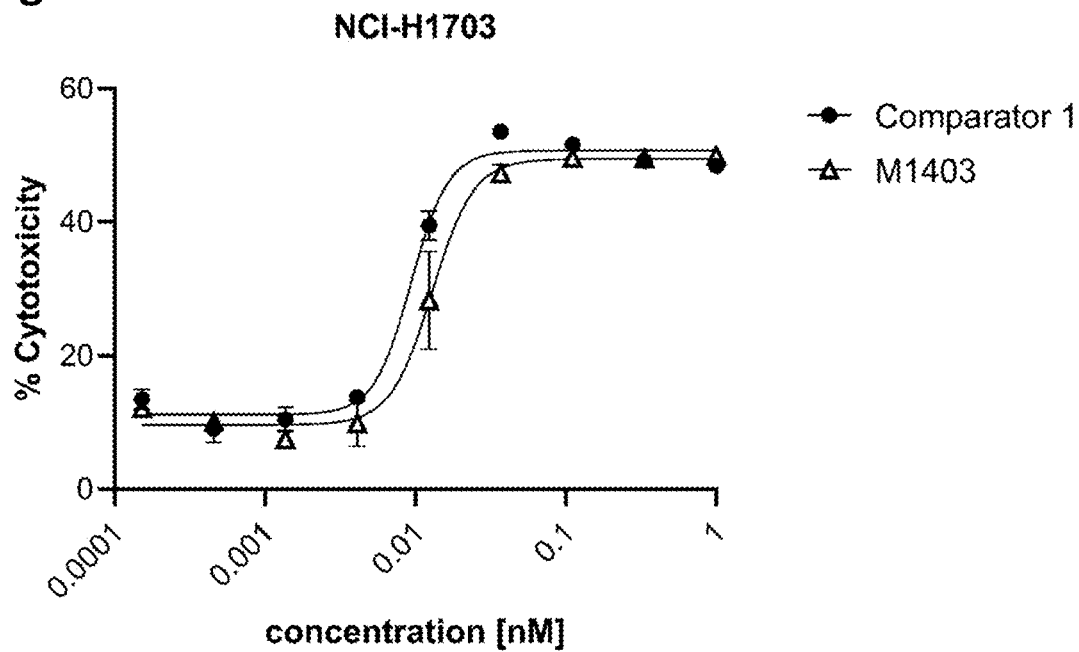
Figure 8E:
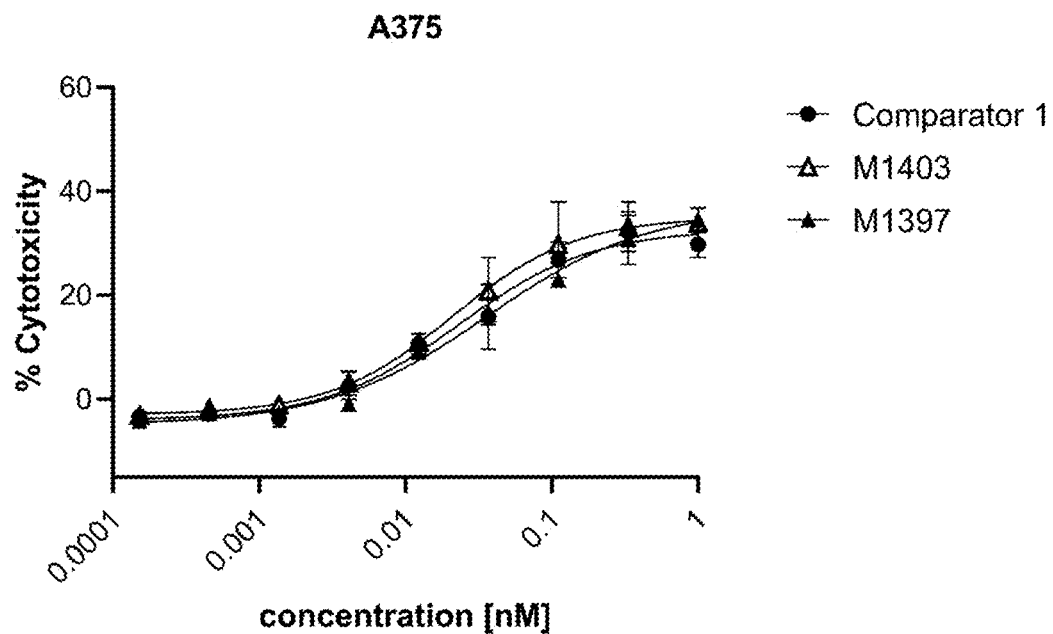
Figure 8F:
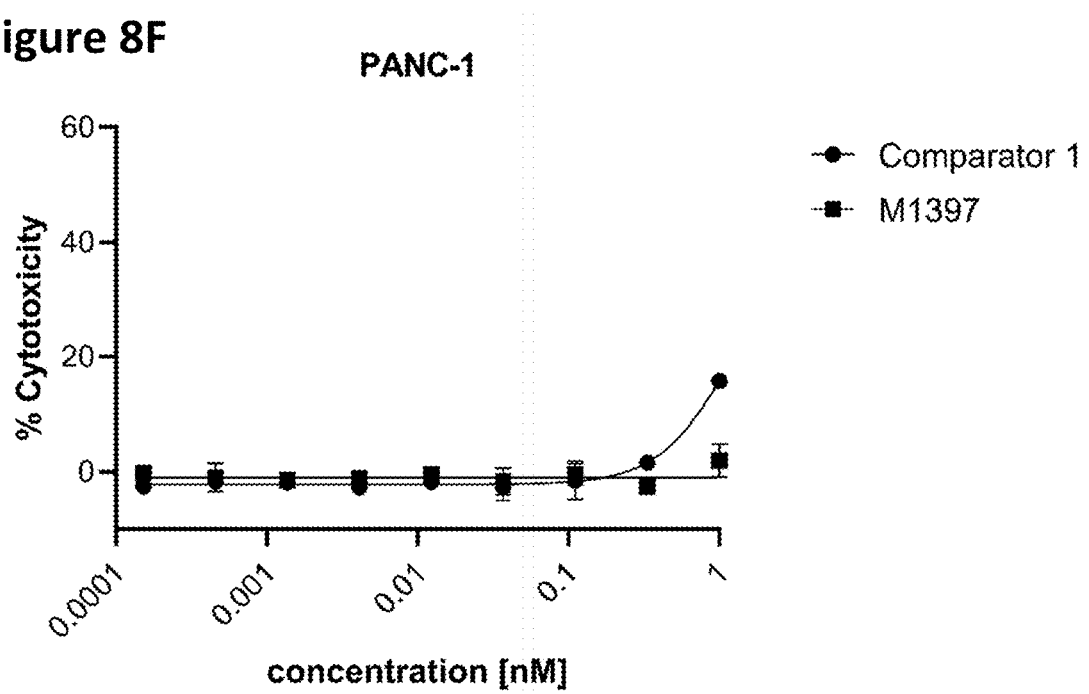
Figure 8G:
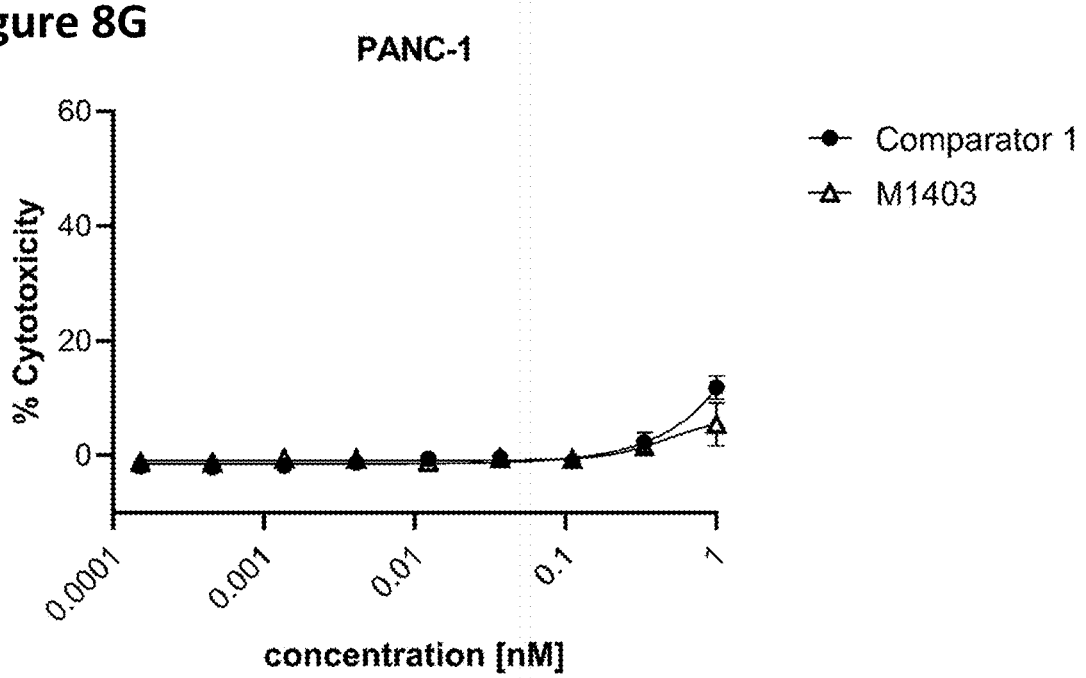
Figure 8H:
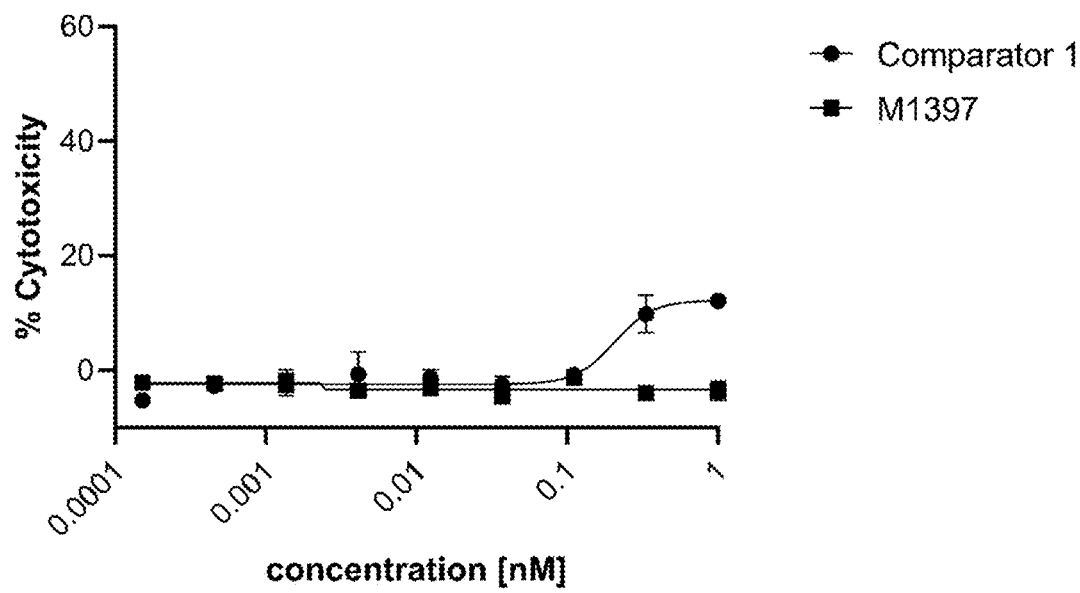
Figure 8I:
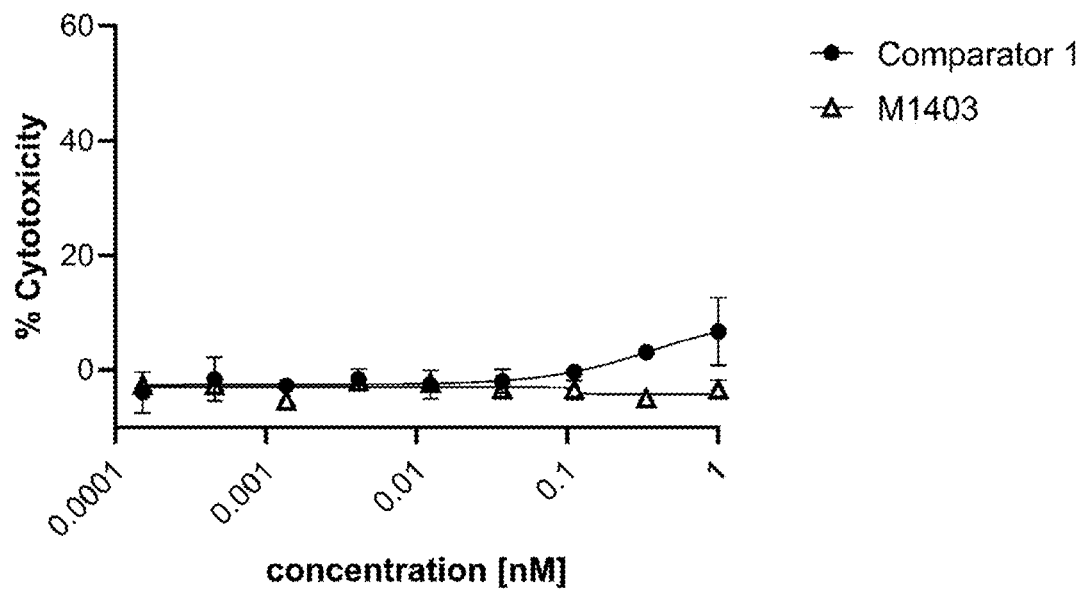
Figure 8J:
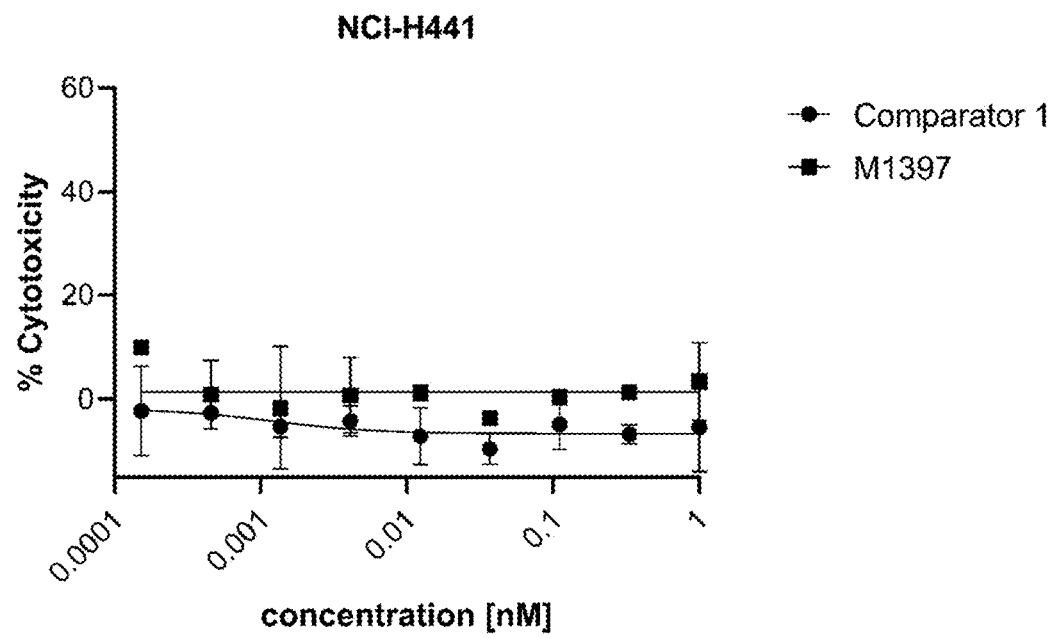
Figure 8K:
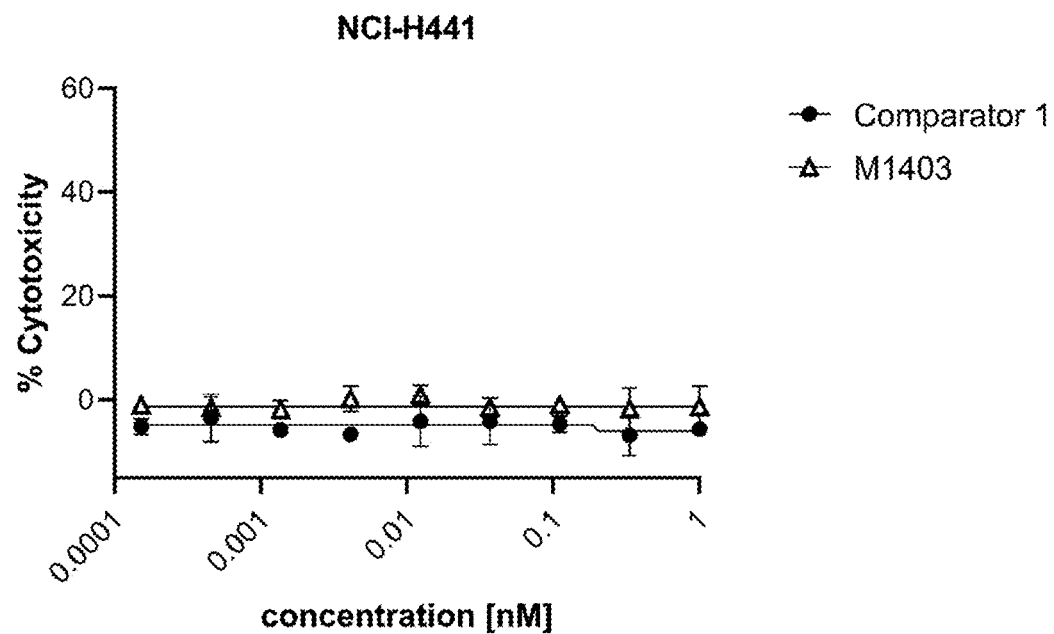
Figure 9A:
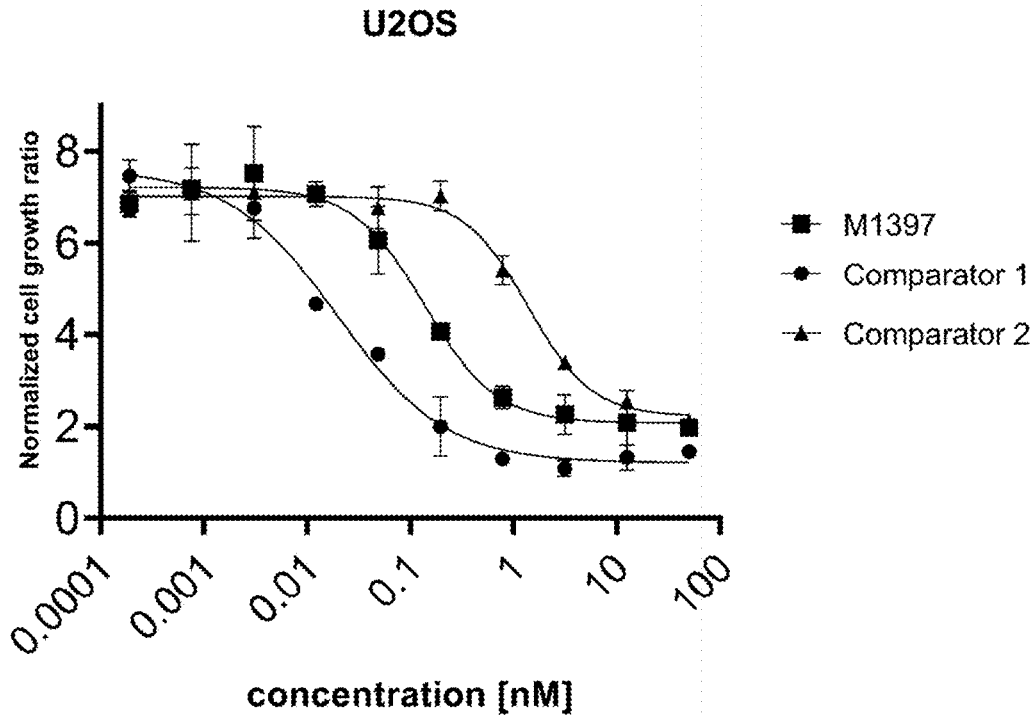
FIGS. 9A-9D show cancer cell killing mediated by dual engager M1397, Comparator 1 or Comparator 2 on MAGE-A4-positive HLA-A*02:01-positive cancer cell lines U2OS and NCI-H1703 (FIGS. 9A and 9B, respectively), and MAGE-A4-negative HLA-A*02:01-positive cancer cell lines PANC-1 and SKMEL-30 (FIGS. 9C and 9D, respectively).
Figure 9B:
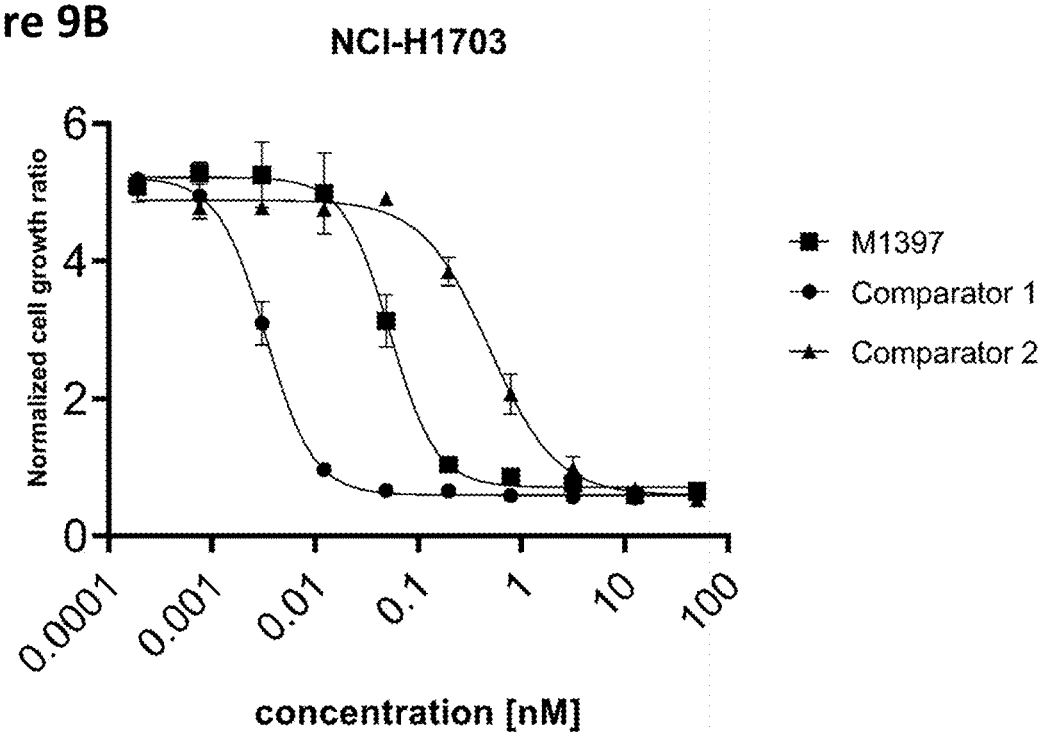
Figure 9C:
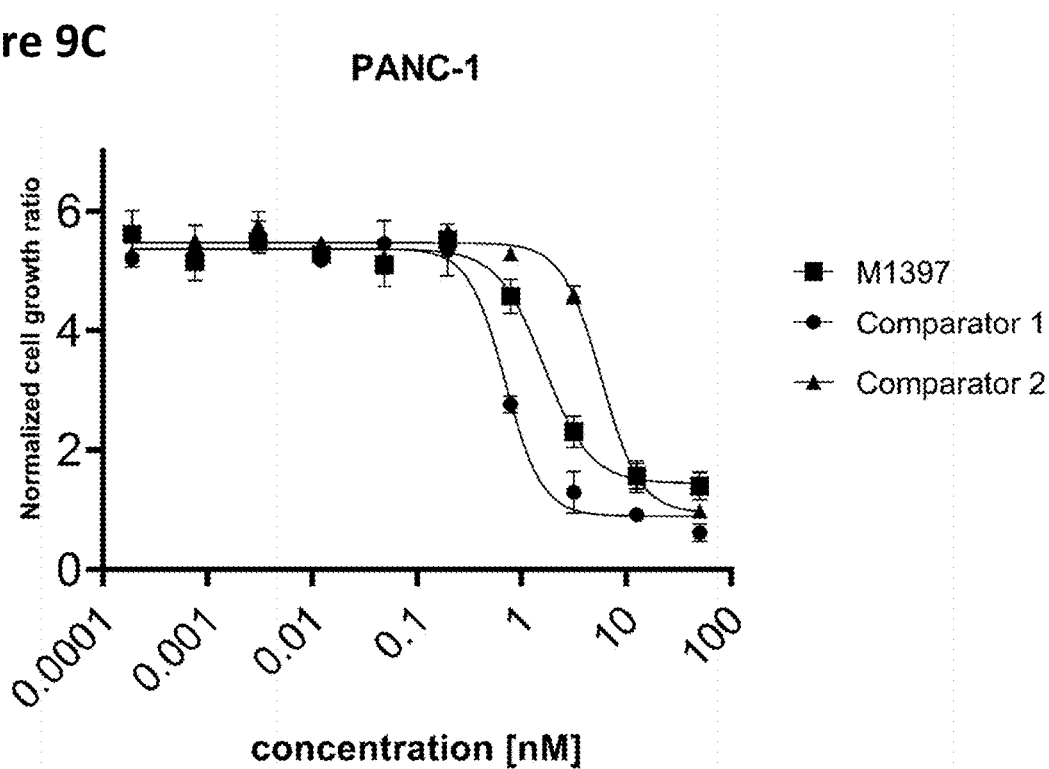
Figure 9D:
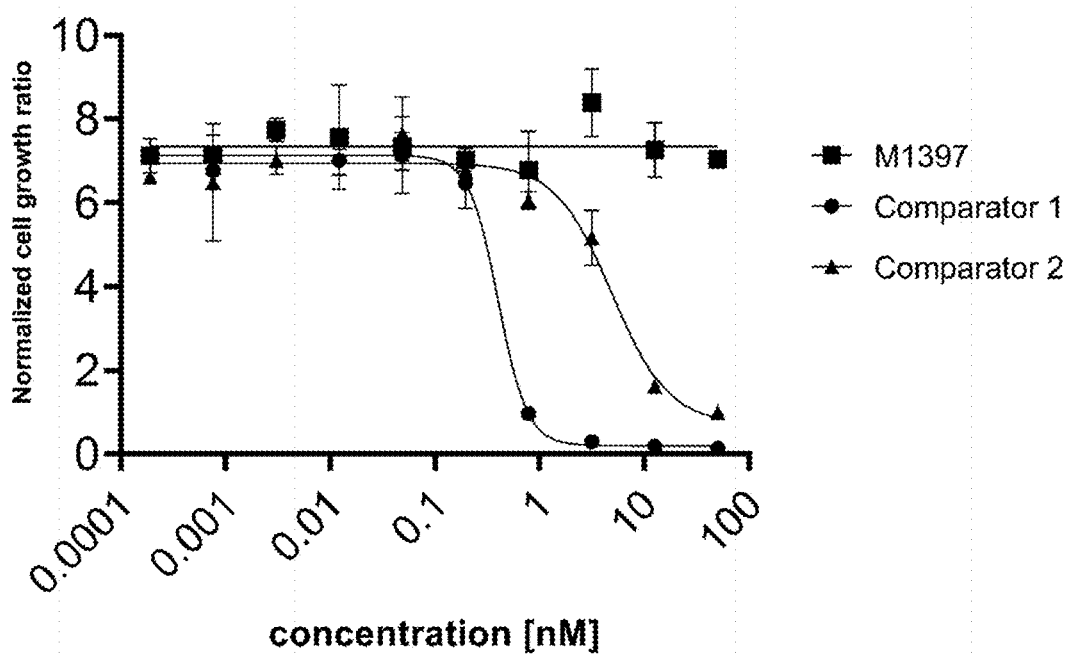
Figure 10A:
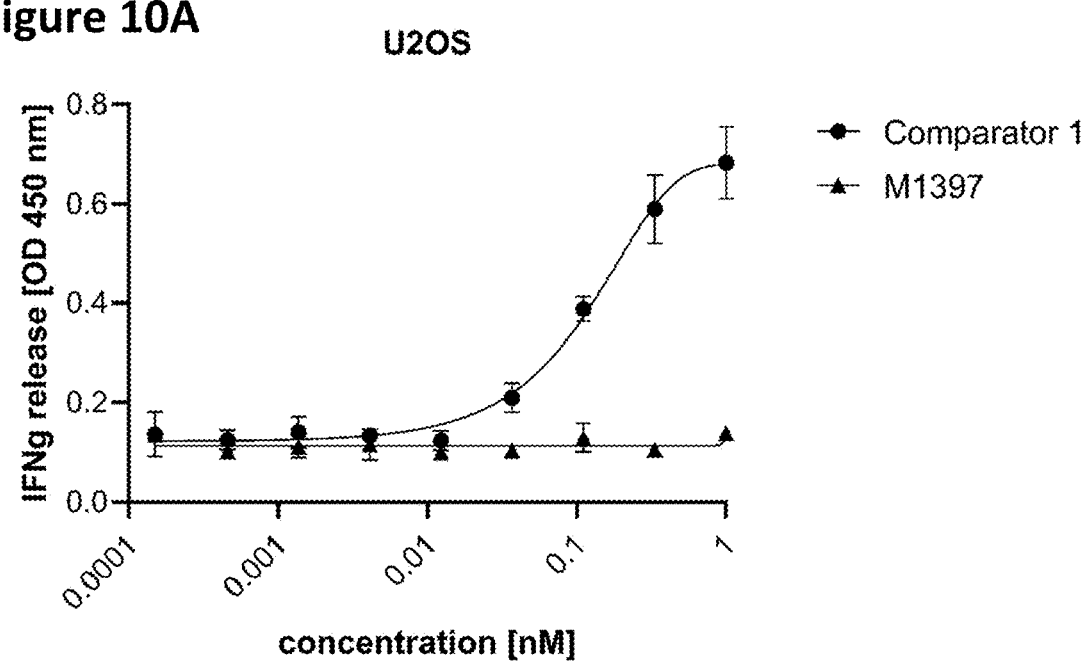
FIGS. 10A-10J shows IFN gamma release upon treatment with dual T cell engagers M1397 and M1403 or Comparator 1 in MAGE-A4-positive HLA-A*02:01-positive cancer cells (FIG. 10A: M1397 and Comparator 1 in U2OS.
Figure 10B:
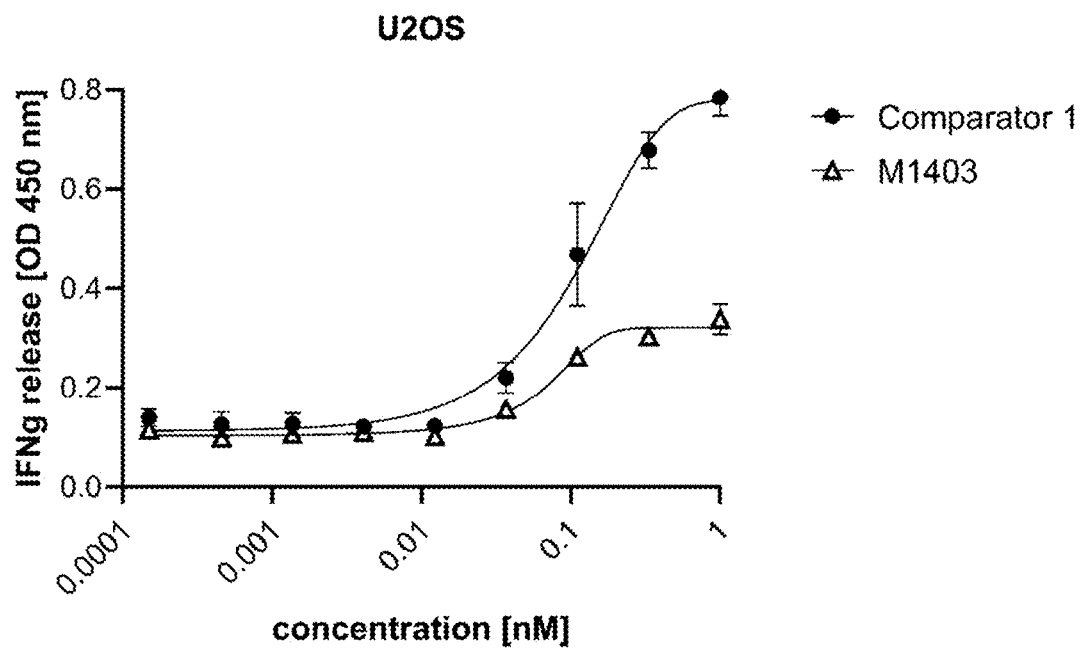
Figure 10C:
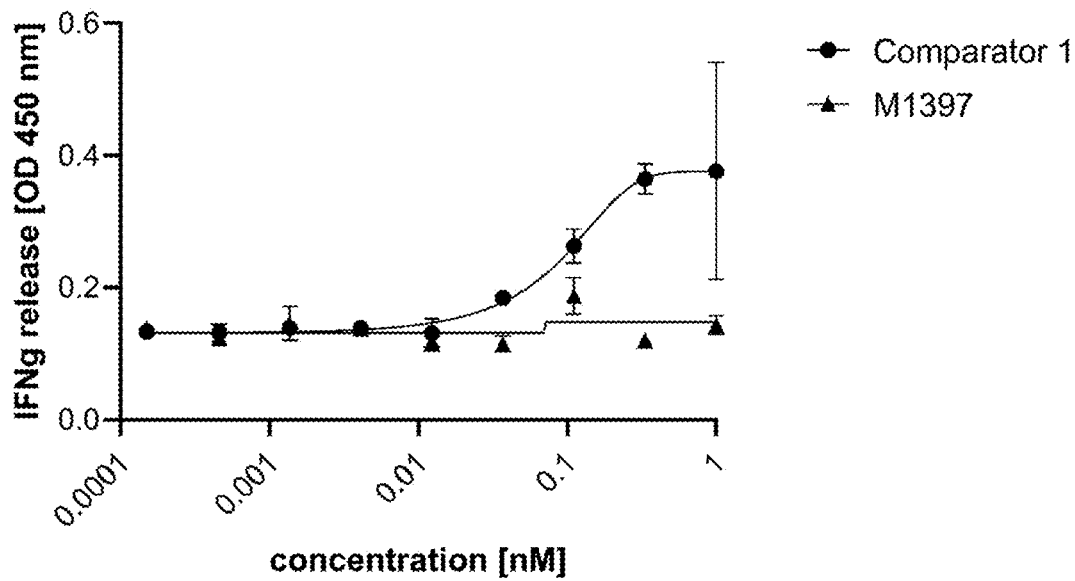
Figure 10D:
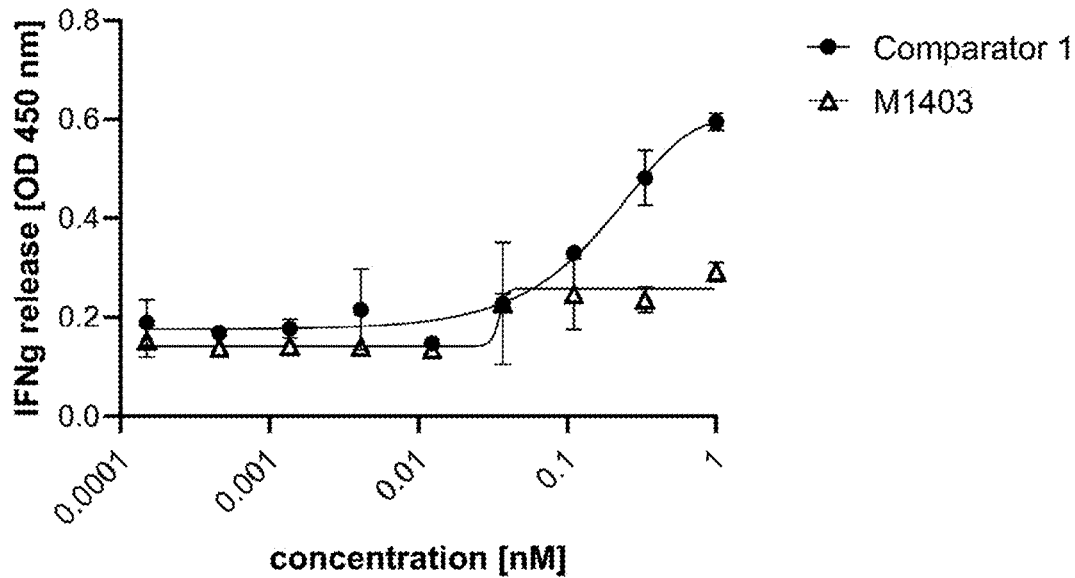
Figure 10E:
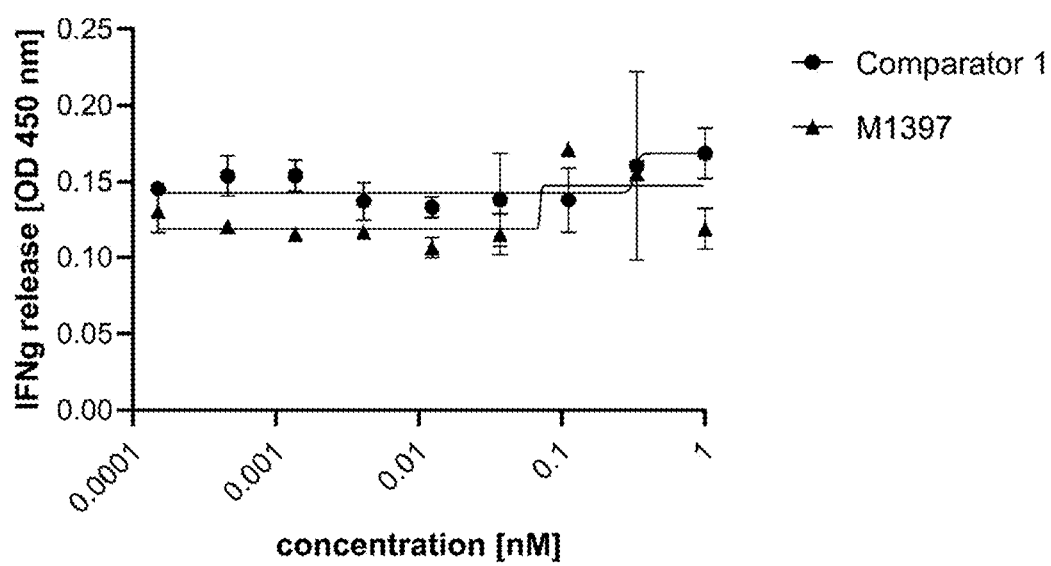
Figure 10F:
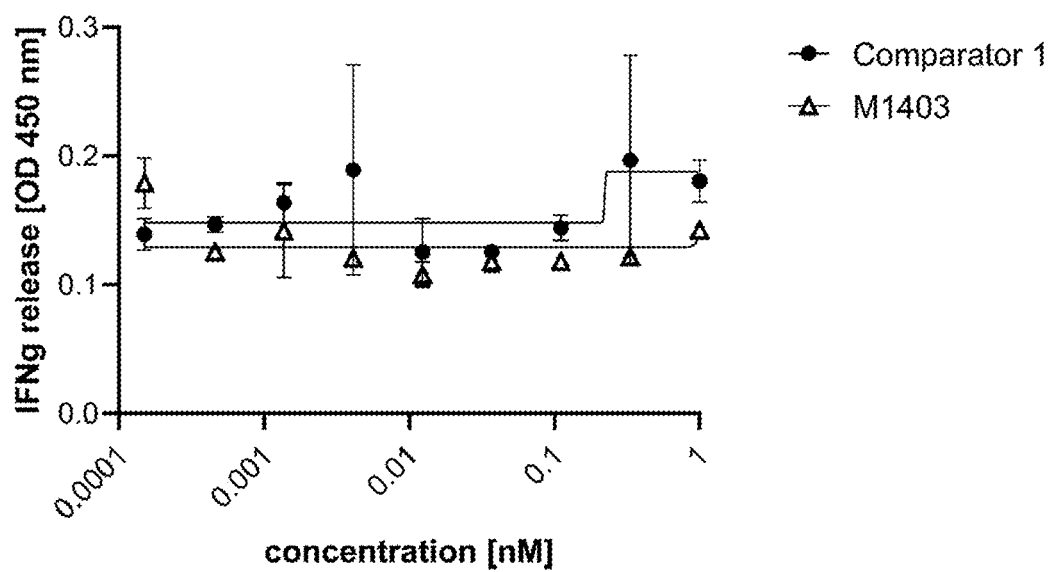
Figure 10G:
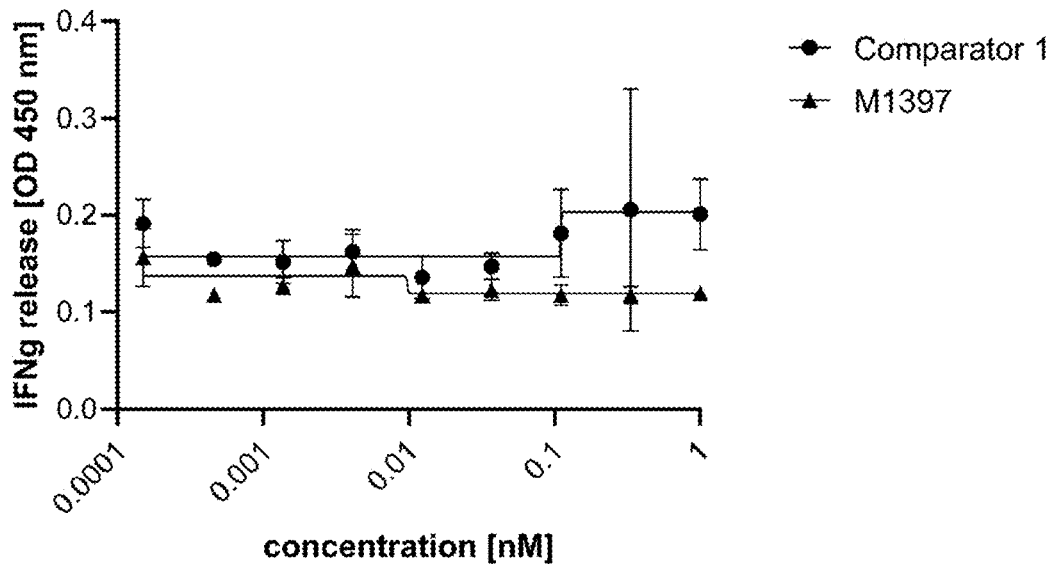
Figure 10H:
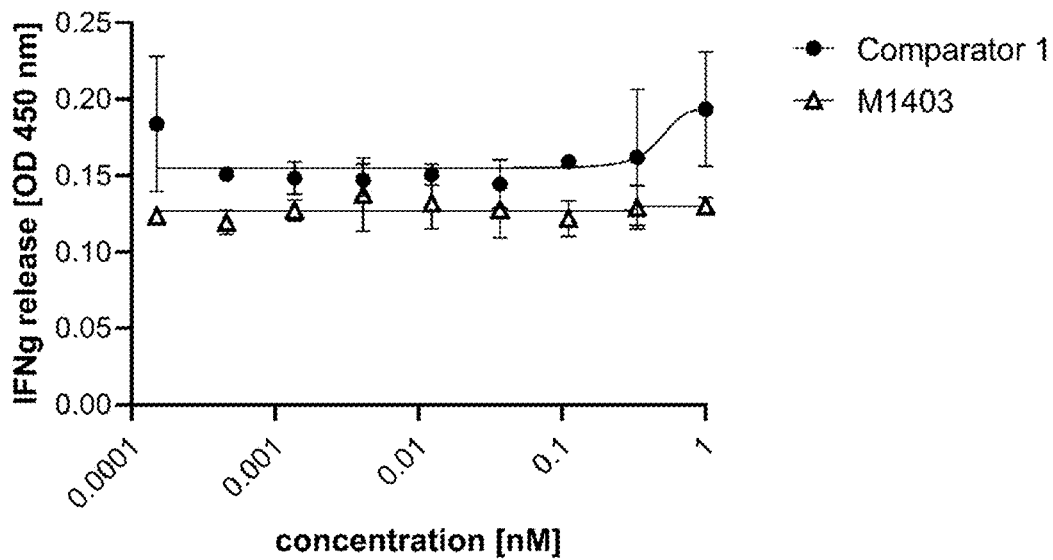
Figure 10I:
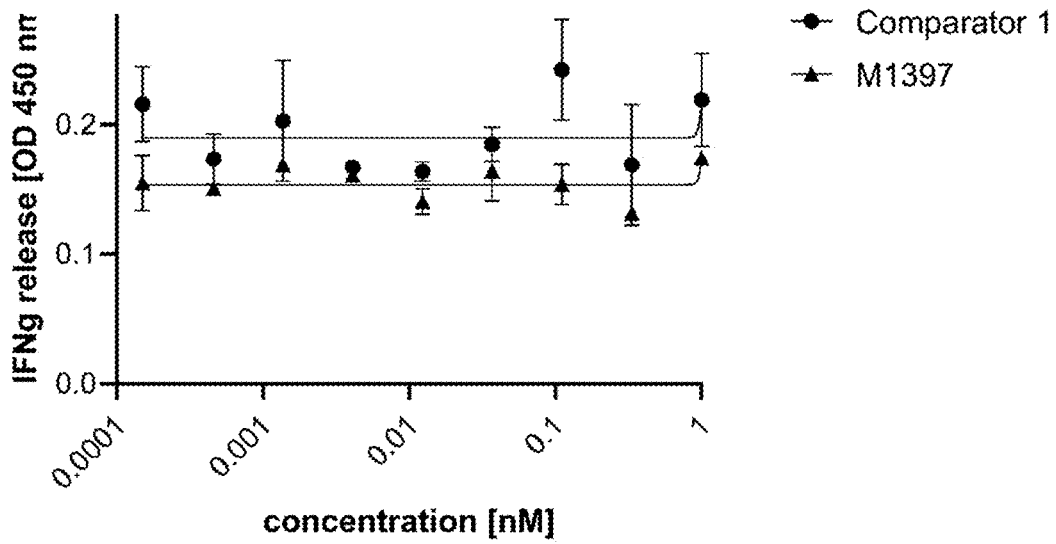
Figure 10J:
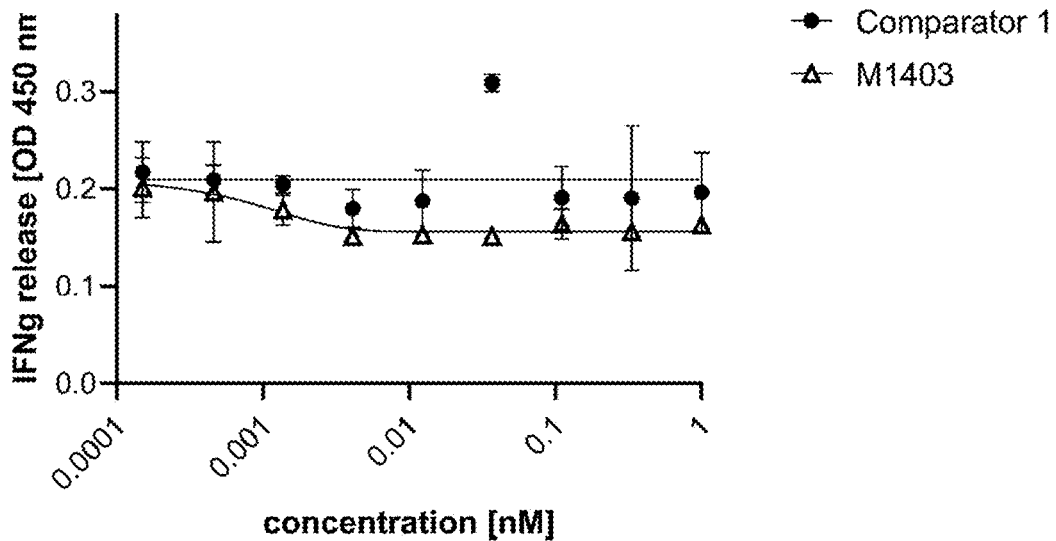
Figure 11A:
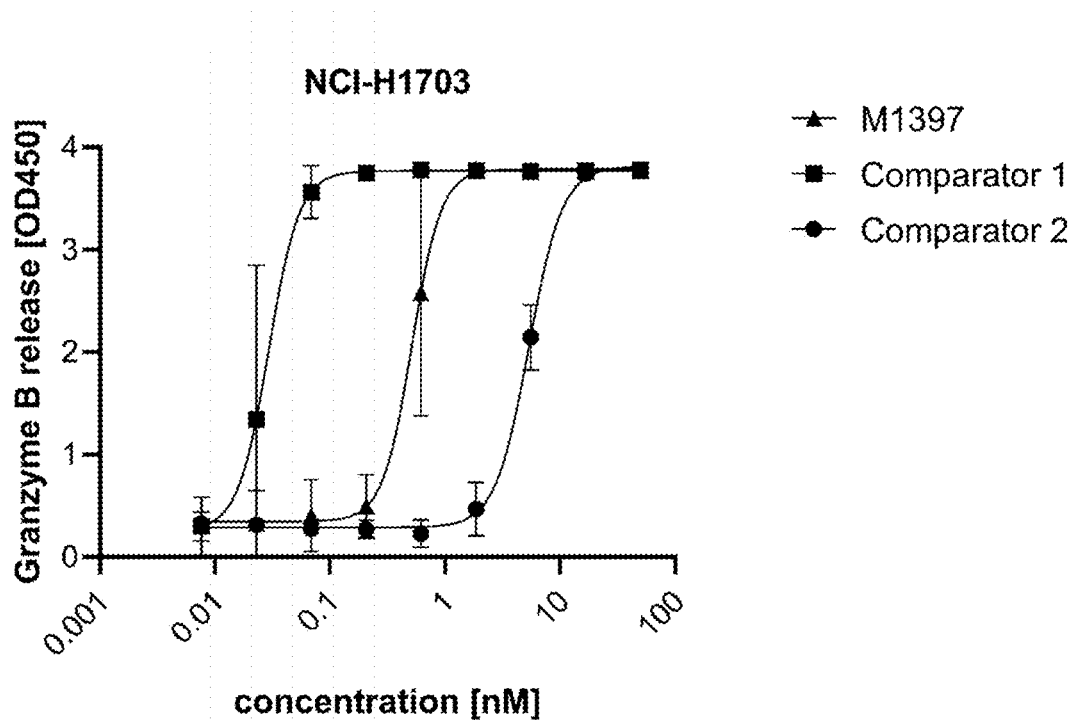
FIGS. 11A-11D show Granzyme B (FIG. 11A-B) and IFN gamma release (FIG. 11C-D) as a measure of T cell activation upon treatment with dual engager M1397, Comparator 1 or Comparator 2 in MAGE-A4-positive HLA-A*02:01-positive cancer cells NCI-H1703 (FIGS. 11A and 11C) and MAGE-A4-negative HLA-A*02:01-positive cancer cells SKMEL-30 (FIGS. 11B and 11D).
Figure 11B:
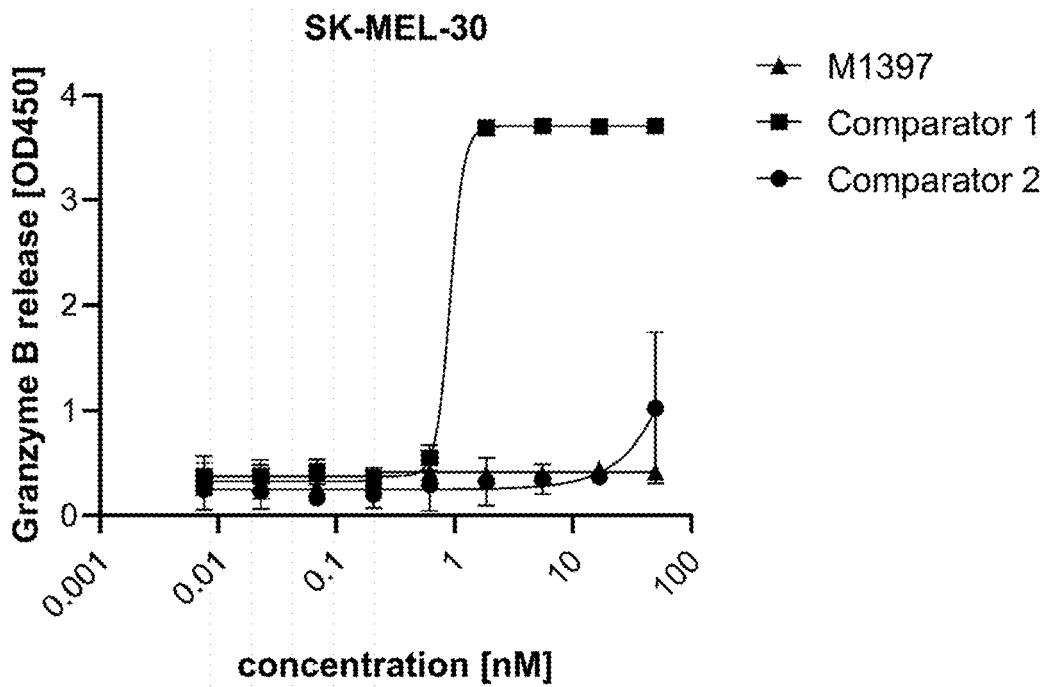
Figure 11C:
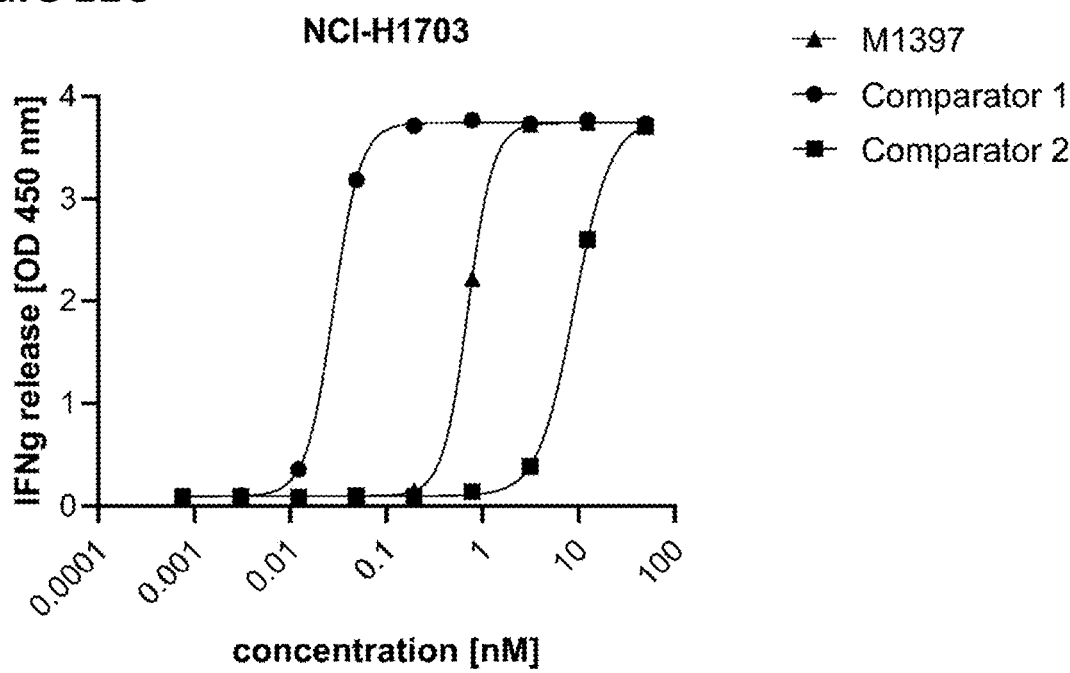
Figure 11D:
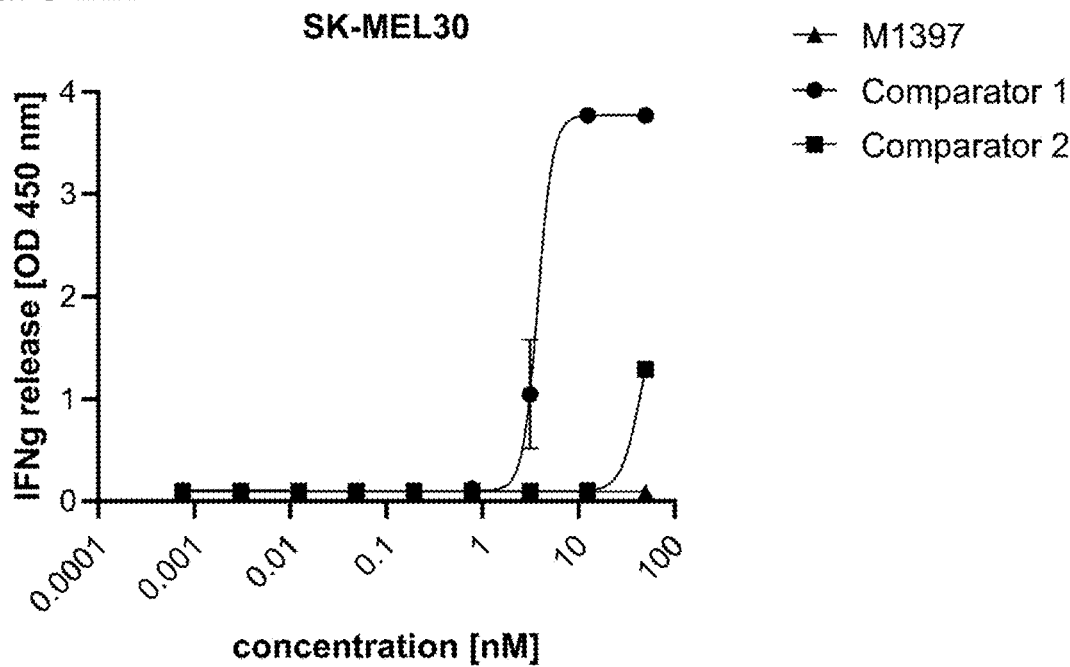
Figure 12A:
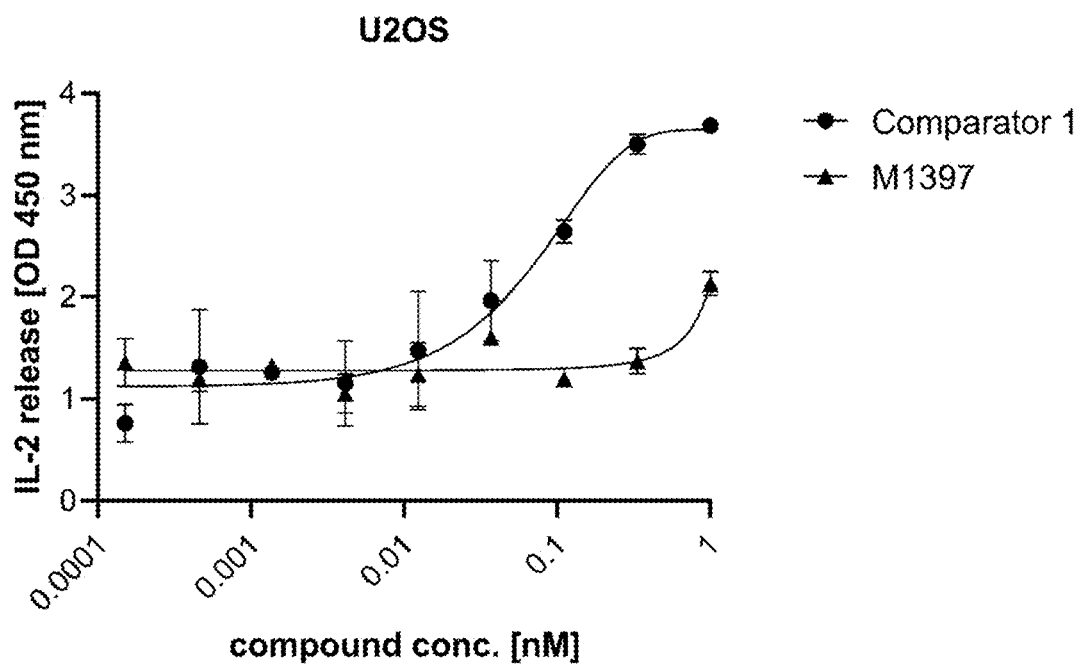
FIGS. 12A-12L show cytokine release in MAGE-A4-positive HLA-A*02:01-positive U2OS and MAGE-A4-negative HLA-A*02:01-positive PANC-1 cells upon treatment with dual T cell engagers M1397 or M1403 and Comparator 1. IL-2 (FIGS. 12A to 12D), IL-6 (FIGS. 12G-12H) and TNF alpha (FIGS. 12I-12L) were quantified.
Figure 12B:
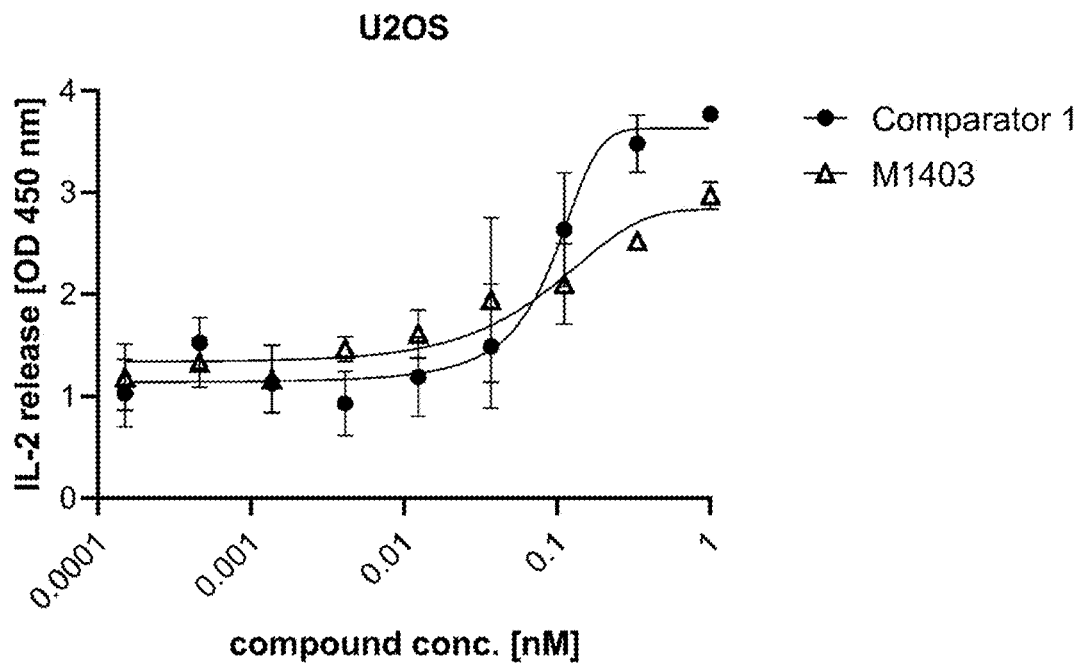
Figure 12C:
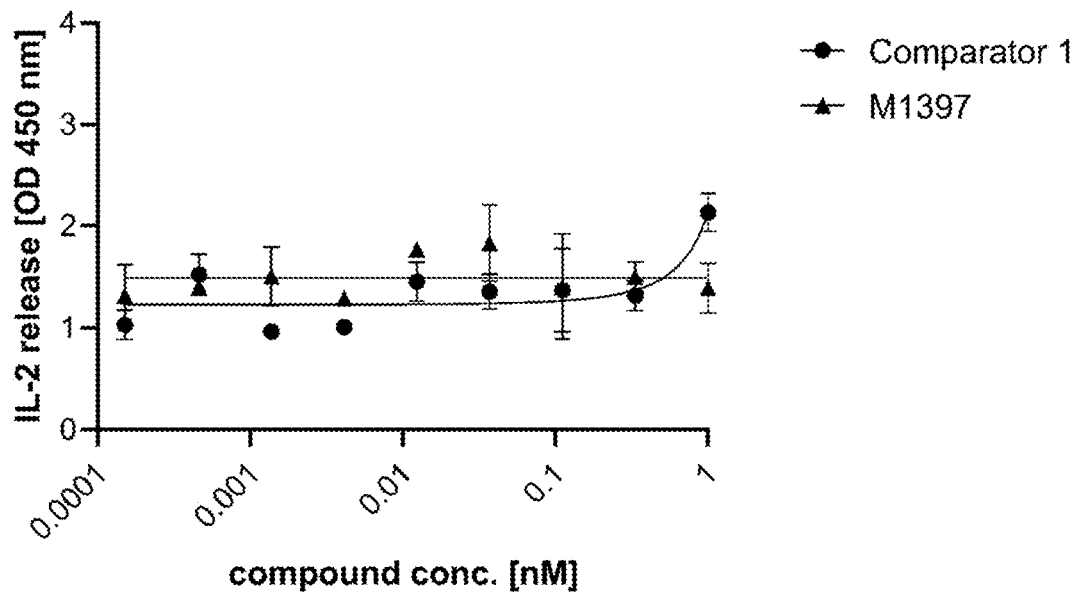
Figure 12D:
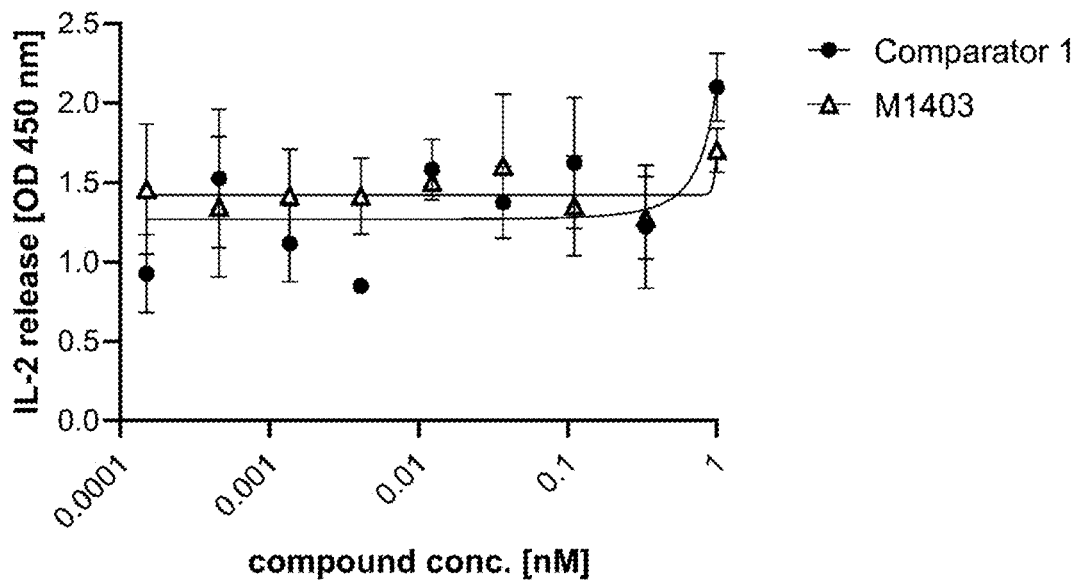
Figure 12E:
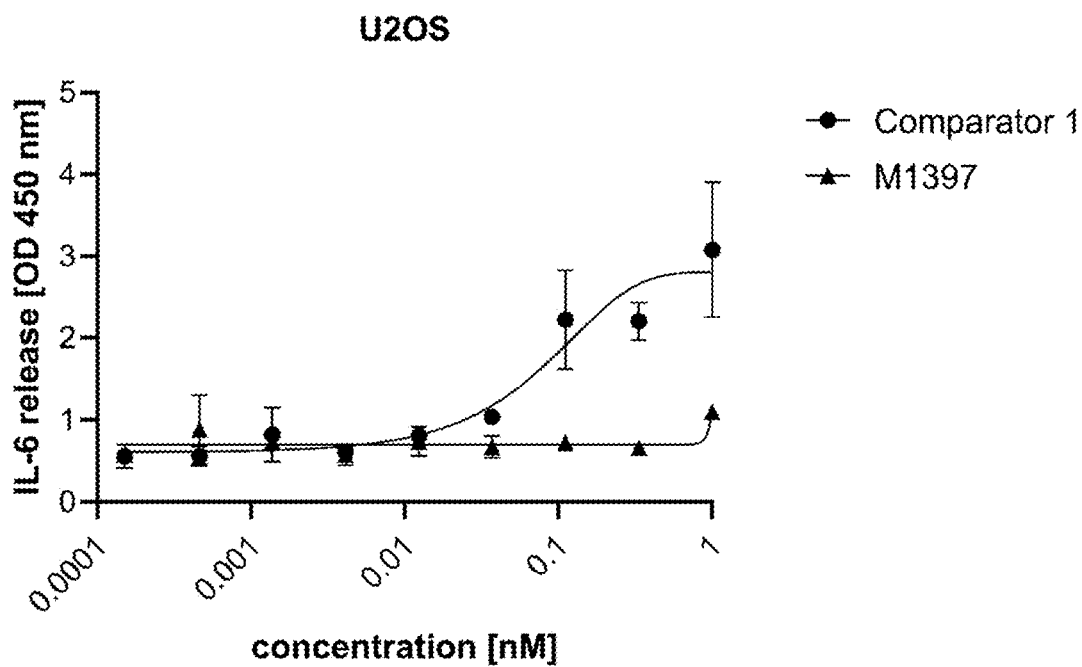
Figure 12F:
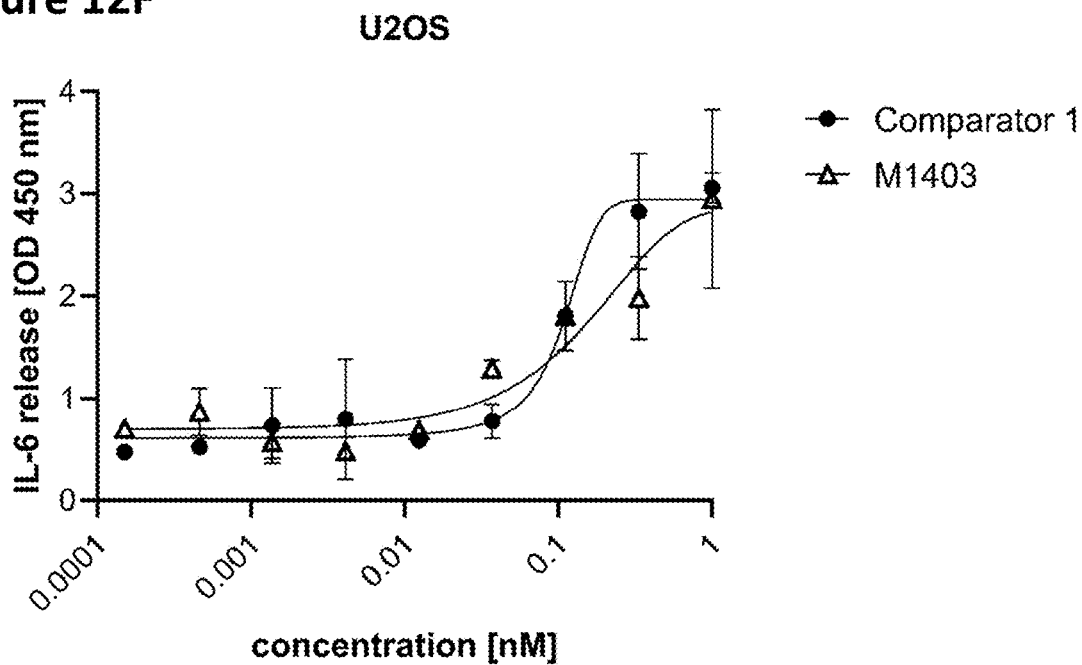
Figure 12G:
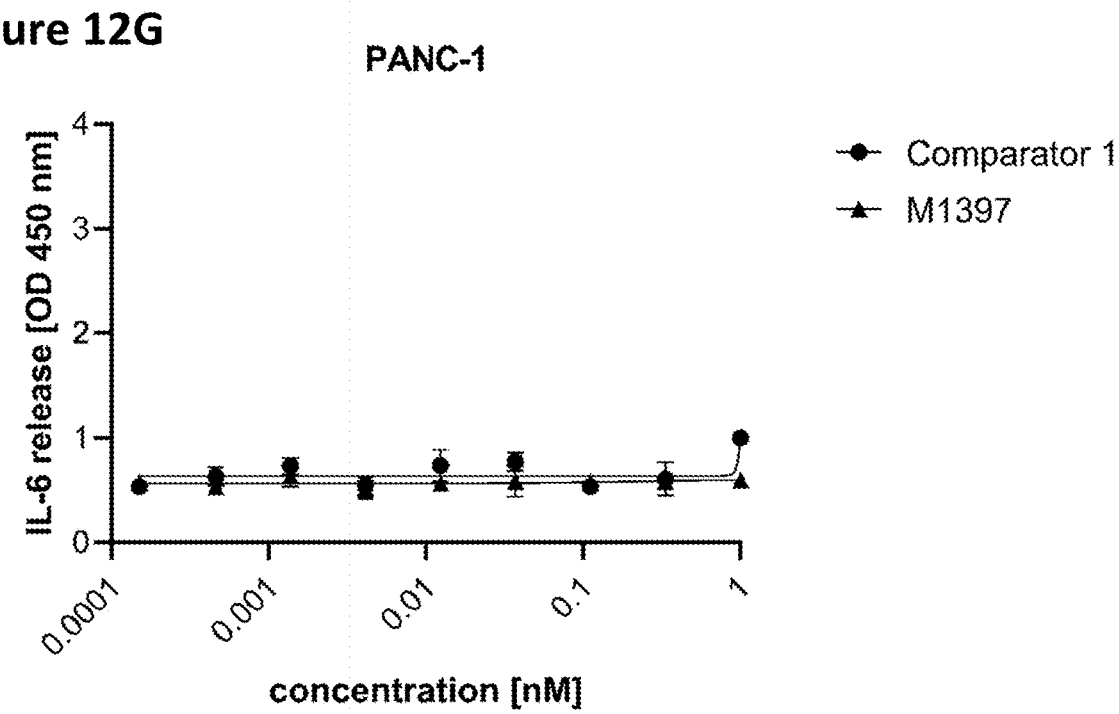
Figure 12H:
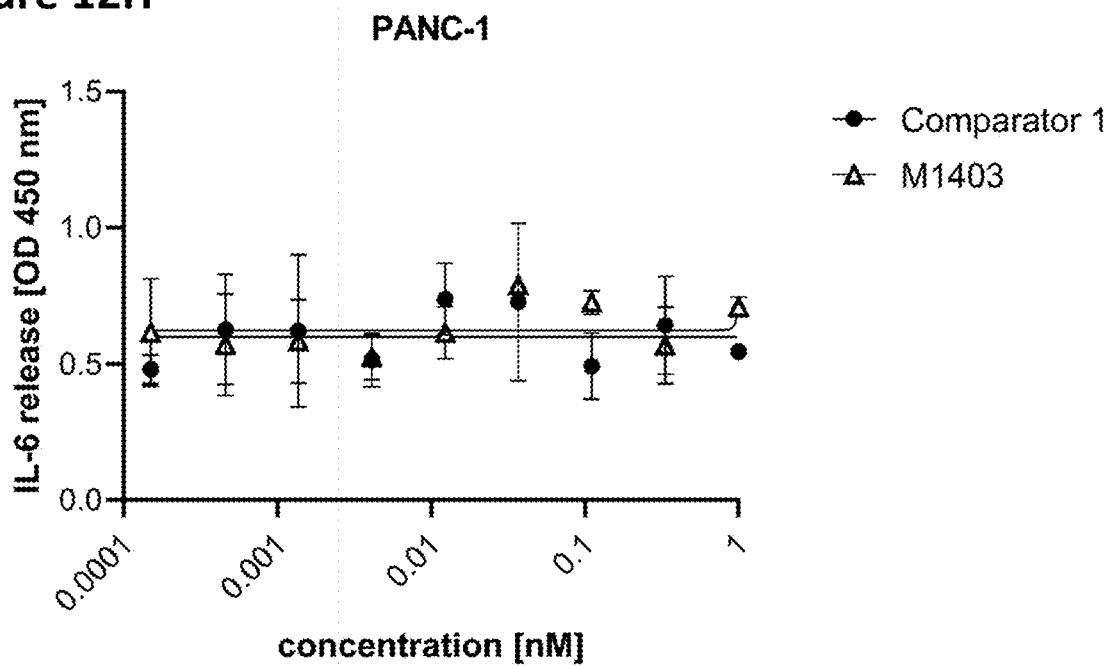
Figure 12I:
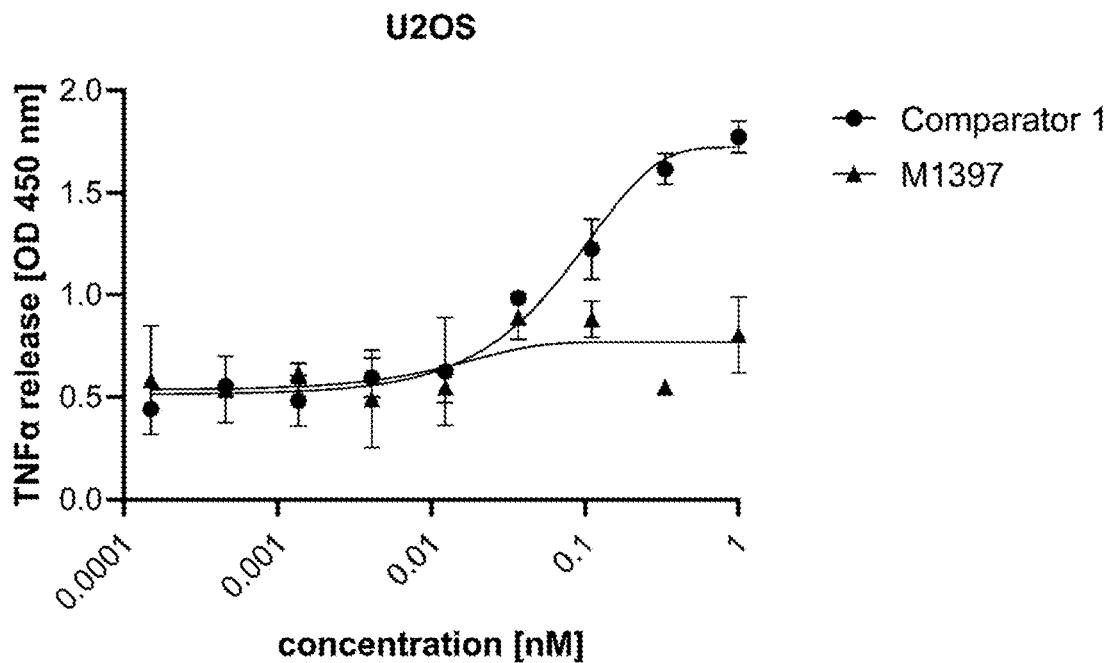
Figure 12J:
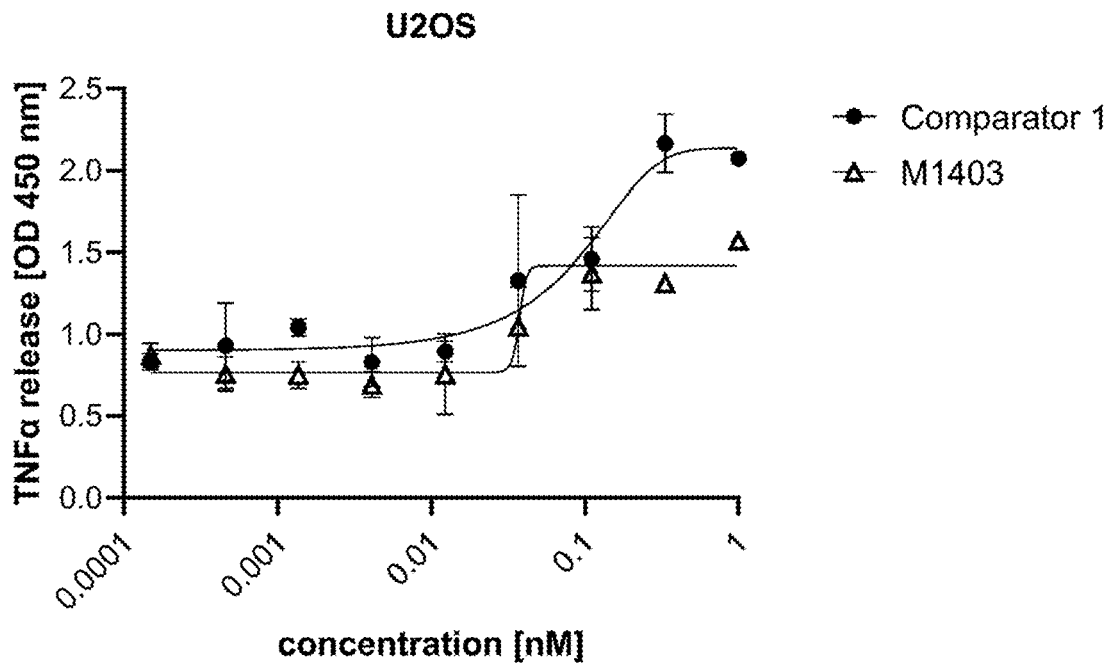
Figure 12K:
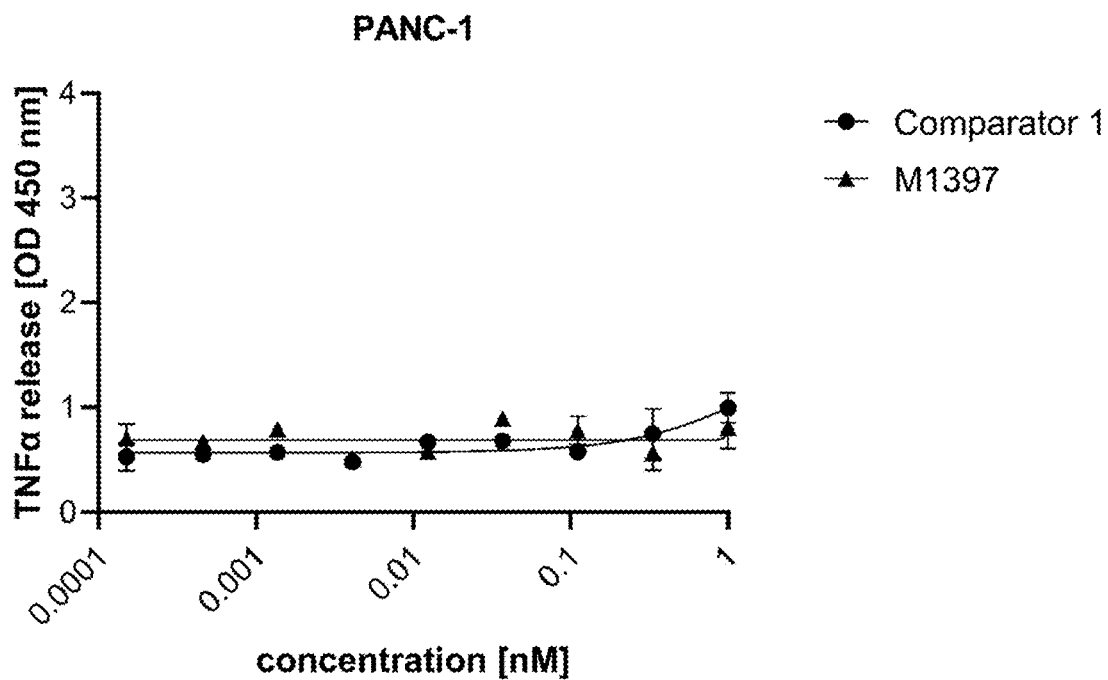
Figure 12L:
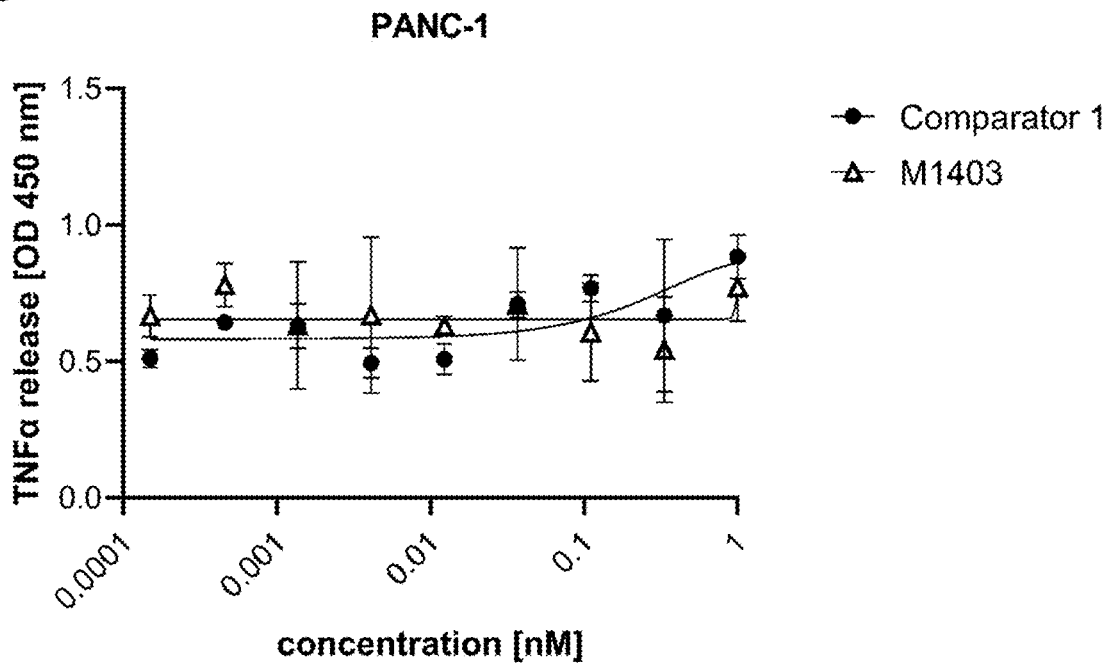

Human serum stability of M1397 and M1403 was measured. Briefly, human serum was prepared by centrifugation at of whole clotted blood 2'000×g. The resulting supernatant was designated serum and was directly frozen and stored at −80° C. The sterile filtered samples were diluted in serum to a concentration of 100 ug/ml. The incubation was performed in sterile Eppendorf tubes in a humid $CO_2$ incubator at 8% CO2 and at 37° C. A reference sample (T0) was taken before the incubation started and after 7 h and 24 h serum incubated samples were collected. The samples were directly quantified by SPR. The SPR quantification was performed on a Biacore T200 instrument. The HLA-A*02:01/MAGE-A4 binding molecules were quantified by an SPR assay where HLA-A*02:01/MAGE-A4 was used as ligand and the serum samples were injected after a 1:100 dilution in SPR running buffer. The samples were evaluated over a direct comparison of the signal height after the serum sample injection. A relative decrease of the binding signal compared to the T0 sample was calculated. Corresponding results are presented in FIGS. 7A-7B.

Example 11—Production of Comparator Molecules: Soluble TCR-Anti-CD3 Fusion Protein (Comparator 1) and TCR-Like CD3 T-Cell Bispecific Antibody (Comparator 2)

DNA sequences encoding extracellular regions of the alpha (SEQ ID NO: 59) and beta (SEQ ID NO: 60) chains of soluble TCR-anti-CD3 fusion (Comparator 1) were separately cloned into pET-24D(+) vector using standard molecular biology techniques (J Biol Chem. 1995 Jan. 13; 270(2):971-7). E. coli BL-21 (DE3) were transformed with the expression vectors according to the supplier's protocols. Protein expression was performed for 16-18 hours at 37° C. with 220 rpm shaking in MagicMedium (Invitrogen), as described by the supplier. Cells were harvested, resuspended in TBS and lysed via lysozyme treatment and sonication. Inclusion bodies were washed twice with TBS supplemented with Triton-$X_{100}$ (50 mM Tris-HCl pH 8.1, 0.5% Triton-X100, 100 mM NaCl, 10 mM NaEDTA) and twice with TBS (50 mM Tris, 100 mM NaCl, 10 mM EDTA, pH 8.1). Such prepared inclusion bodies were solubilized in a denaturing buffer (9M Urea, 0.5M Gua, 25 mM Tris, 1.25 mM EDTA, pH 8.1). Solubilized inclusion bodies from alpha chain and beta chain-anti-CD3 scFv fusion were combined and mixed with reducing agent at final DTT concentration of 20 mM. Solubilized and reduced inclusion bodies were slowly mixed with the refolding buffer (4M Urea, 400 mM L-Arg, 2 mM EDTA, 100 mM Tris, 10 mM L-Cysteine, 2.5 mM L-Cystine, pH 8.1) and incubated at room temperature overnight. Molecule was captured from a diluted and pH adjusted refolding solution by anion exchange chromatography using POROS 50HQ column. Molecule was eluted by applying a gradient of 0-500 mM NaCl in 20 mM Tris pH 8.1 over 50 column volumes on Akta® purifier device (Cytiva). Size exclusion chromatography was performed as an additional purification step. Samples were run on HiLoad Superdex 75, 26/600 column with PBS (pH7.4) as a running buffer. Collected fractions were analyzed by SE-HPLC for monomer content and pooled accordingly. Final protein purity was assessed by SDS-PAGE and SE-HPLC.

TCR-like CD3 T-cell bispecific antibody (Comparator 2, SEQ ID NO: 65, SEQ ID NO: 66, SEQ ID NO: 67) was expressed by transient co-transfection in HEK293-6E cells. Cells were cultured in suspension using polyethylenimine (PEI 40 kD linear). HEK293-6E cells were seeded at 1.7× $10^6$ cells/mL in Freestyle F17 medium supplemented with 2 mM L-Glutamine. DNA and PEI were added separately to 50 µL medium without supplement. Both fractions were mixed at 1:2.5 DNA:PEI ratio, vortexed and rested for 15 minutes. Cells and DNA/PEI mixture were combined (1 µg DNA/mL cells) and incubated at 37° C., 5% $CO_2$, 80% RH. After 24 hours, cells were supplemented with Tryptone N1 at 25 µL per mL production volume. After 7 days, cells were harvested by centrifugation and the supernatant was sterile filtered. The antigen binding proteins were purified by an affinity chromatography from the supernatant. Supernatant was loaded on a CaptureSelect™ CH1-XL column (Thermo Fisher Scientific) equilibrated with 6 CV PBS (pH 7.4). After a washing step with the same buffer, protein was eluted from the column by step elution with 100 mM Citric acid (pH 3.0). Fractions with the desired antigen binding protein were immediately neutralized by 1 M Tris Buffer (pH 9.0) at 1:10 ratio. Size exclusion chromatography was performed as an additional purification step. Samples were run on the Superdex 200 10/300 GL column with PBS (pH7.4) as a running buffer. Collected fractions were analyzed by SE-HPLC for monomer content and pooled accordingly. Final protein purity was assessed by SDS-PAGE and SE-HPLC.

Example 12—In Vitro Efficacy of the Optimized Dual pMHC-Targeting T Cell Engagers Dual engager M1048 showed improved efficacy in in vitro cytotoxicity assays, compared to its monovalent counterpart M1041. Optimized variants of M1041, i.e., M1402 and M1396 were reformatted into dual engager format, yielding M1403 and M1397, respectively. Optimized variants of M1048, i.e., M1403 and M1397 possessed higher human sequence content, higher stability and/or higher affinity. Dual pMHC targeting T cell engagers M1403 and M1397 were compared for efficacy and safety in LDH assay. In addition, dual T cell engagers M1397 and M1403 were compared to two comparator antigen binding molecules, i.e., Comparator 1 and Comparator 2. Comparator 1 is composed of a soluble affinity-enhanced TCR with binding specificity for the same pMHC-MAGE-A4 antigen with a $K_D$ value of 87 μM, linked to an anti-CD3 scFv with a binding affinity of 1 nM. Comparator 1 is monovalent for the target pMHC and CD3, while the dual engagers are bivalent for the target pMHC and monovalent for CD3. Comparator 1 is described in further detail in US20190092834, incorporated herein by reference. Comparator 2 is a bispecific TCR-like antibody specific for the same pMHC-MAGE-A4 antigen linked to an anti-CD3 Fab. Comparator 2 is bivalent for the target pMHC, monovalent for CD3 and contains an Fc domain for half-life extension. Comparator 2 is described in further detail in US20210230278A1, incorporated herein by reference.

As shown in FIGS. 9A-9D, percent cancer cell killing in several MAGE-A4-positive HLA-A*02:01-positive cell lines, i.e., U2OS (osteosarcoma), NCI-H1703 (lung squamous cell carcinoma) and A375 (melanoma), and MAGE-A4-negative HLA-A*02:01-positive cell lines, i.e., PANC1 (pancreatic cancer), MDA-MB-231 (breast cancer) and NCI-H441 (lung adenocarcinoma) was measured. Cancer cell lines were incubated with the dual engagers M1397, M1403 or Comparator 1 and human PBMCs at an E:T ratio of 10:1. Cytotoxicity at various concentrations of the three different antigen binding proteins was quantified by colorimetric absorbance measurements of the amount of LDH released from damaged cells into the medium after 48 h for all cell lines with exception of NCI-H1703. Cytotoxicity in NCI-H1703 was determined by CellTiter-Glo assay (Promega), according to the instructions provided by the kit manufacturer. Data shows comparable cell killing mediated by the dual engager M1403 compared to Comparator 1 for all tested MAGE-A4-positive HLA-A*02:01-positive cell lines, while M1397 showed lower efficacy. In addition, lower cancer cell killing was observed for both dual T cell engagers, compared to the Comparator 1 for all tested MAGE-A4-negative HLA-A*02:01-positive cancer cell lines, especially for M1397, indicating a better therapeutic window of M1397 and M1403.

In addition, cell killing mediated by M1397, Comparator 1 and Comparator 2 was analyzed in a time-resolved manner using the IncuCyte S3 system. Briefly, antigen-positive target cells (NCI-H1703 and U2OS) and antigen-negative target cells (SKMEL-30 and PANC-1) were transduced with Nuclight Red lentivirus (Sartorius) to stably express the NucLight Red fluorescent protein. Cancer cells were seeded at the density of 1.5×10³ cells per well in a sterile 384-well flat bottom adhesion tissue culture plate overnight at 37° C. and 5% $CO_2$ in an incubator. Molecules M1397, Comparator 1 and Comparator 2 were added at the indicated concentrations (range of 0.2 μM to 50 nM). PBMCs were added as effector cells to each well at an E:T ratio of 10:1. The plate was imaged by fluorescent microscopy to monitor cell growth for 72 h. The degree of cell killing was quantified by comparing the fold growth ratio of fluorescent targets cancer cells over time, relative to their number at time 0. As depicted in FIGS. 9A-9D, M1397 showed a superior potency on both tested antigen-positive cancer cells lines than Comparator 2 and lower potency than Comparator 1. Furthermore, M1397 showed superior safety than both comparators on SK-MEL-30 antigen-negative cancer cell line and similar safety profile as both comparators on PANC-1 antigen-negative cancer cell line.

As shown in FIGS. 10A-10J, release of pro-inflammatory cytokine IFN gamma was measured in several MAGE-A4-positive HLA-A*02:01-positive cell lines, i.e., U2OS (osteosarcoma) and NCI-H1703 (lung squamous cell carcinoma), and MAGE-A4-negative HLA-A*02:01-positive cell lines, i.e., PANC1 (pancreatic ductal adenocarcinoma), MDA-MB-231 (breast adenocarcinoma) and NCI-H441 (lung adenocarcinoma). Cells were incubated with the dual engagers or Comparator 1 and human PBMCs at an E:T ratio of 10:1. IFN gamma was measured at various concentrations of the three antigen binding proteins after 24 h incubation. Data shows that the dual engagers induced lower levels of the pro-inflammatory cytokine IFN gamma in both antigen-positive (FIGS. 10A-10D) and antigen-negative cell lines (FIG. 10E-J), indicating a lower potential for inducing a cytokine storm syndrome.

Next, M1397, Comparator 1 and Comparator 2 were further compared in Granzyme B and IFN gamma release assays as a measure of T cell activation properties. Briefly, antigen-positive (NCI-H1703) and antigen negative (SK-MEL-30) cancer cell lines were incubated with M1397, Comparator 1 or Comparator 2 at the indicated concentrations (range of 7.6 μM to 50 nM) and human PBMCs at an E:T ratio of 5:1. Granzyme B and IFN gamma levels were measured after 24 h incubation and the corresponding results are shown in FIGS. 11A-11B and 11C-11D, respectively. M1397 showed a superior safety profile than both comparators with no Granzyme B or IFN gamma release when tested on antigen-negative cell line SK-MEL-30. Moreover, M1397 induced higher Granzyme B and IFN gamma release than Comparator 2 on antigen-positive cell line and lower Granzyme B and IFN gamma release than Comparator 1 on both antigen-positive and antigen-negative cell lines.

As shown in FIGS. 12A-12L, IL-2, IL-6 and TNF alpha cytokine release in MAGE-A4-positive HLA-A*02:01-positive U2OS and MAGE-A4-negative HLA-A*02:01-positive PANC-1 cells was measured. Dual engagers M1397 and M1403 or Comparator 1 at various concentrations were incubated with the cancer cells and human PBMCs at an E:T ratio of 10:1. Cytokines IL-2, IL-6 and TNF alpha were measured after 24 h incubation. Data shows that both dual engagers M1397 and M1403 induced lower levels of the pro-inflammatory cytokines, indicating a lower potential for inducing a cytokine storm syndrome.

Example 13—In Vitro Safety of the Optimized Dual pMHC-Targeting T Cell Engagers

Potential off-target binding to the MAGE-A4 similar physiologically-relevant peptides by monovalent counterparts of M1397 and M1403, i.e., M1396 and M1402, respectively, was investigated by SPR. Control peptides constituted sequences with high identity to MAGE-A4 and had previously been identified in healthy human tissues, i.e., Ctrl.1 (GLADGRTHTV; SEQ ID NO: 68), Ctrl.2 (GLYDGPVHEV; SEQ ID NO: 69) and Ctrl.3 (GVFDGLHTV; SEQ ID NO: 70) (US20180171024, incorporated herein by reference). Corresponding data is presented in Table 8.

TABLE 8

Binding of M1396 and M1402 to HLA-A*02:01 in complex with physiologically-relevant control peptides with high identity to MAGE-A4.

| Molecule | Affinity to HLA-A*02:01/ MAGE-A4 [nM] | Affinity to HLA-A*02:01/ Ctrl. 1 [nM] | Affinity to HLA-A*02:01/ Ctrl. 2 [nM] | Affinity to HLA-A*02:01/ Ctrl. 3 [nM] |
|---|---|---|---|---|
| M1396 | 1.6 | 127 | 121 | no binding |
| M1402 | 0.11 | 12 | 6.2 | 761 |

Figure 13A:
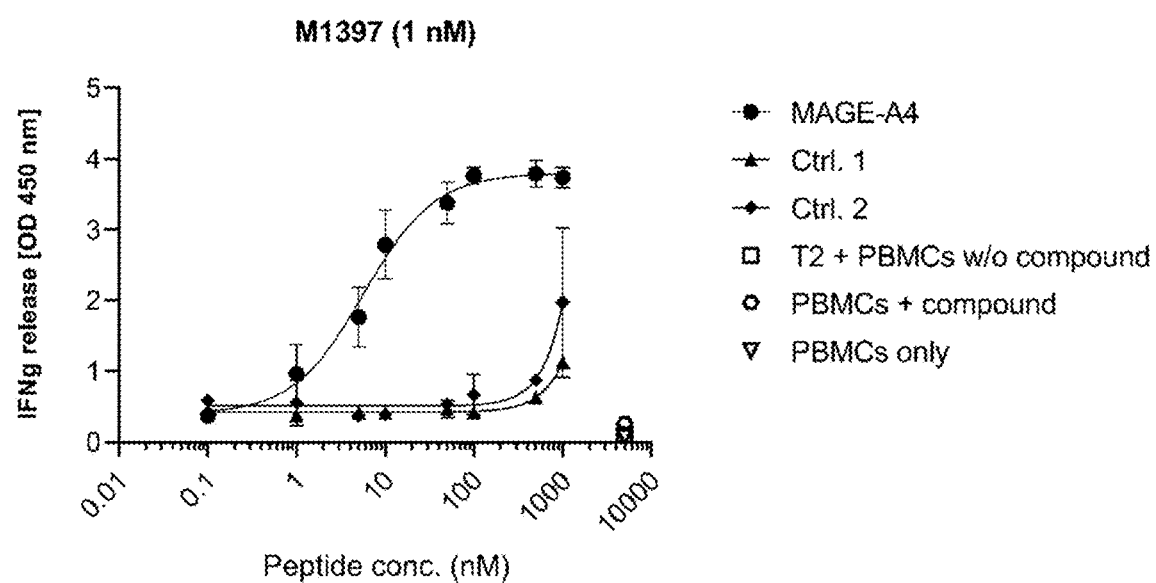
FIGS. 13A-13C show IFN-gamma expression upon incubation of a TAP-deficient T2 cells pulsed with MAGE-A4 or physiologically relevant highly similar peptides Ctrl.1 or Ctrl.2 with PBMCs as effector cells and dual engager M1397 (FIG. 13A), Comparator 1 (FIG. 13B) or Comparator 2 (FIG. 13C). Controls employed T2 cells with PBMCs only, PBMCs with tested compounds and PBMCs only.
Figure 13B:
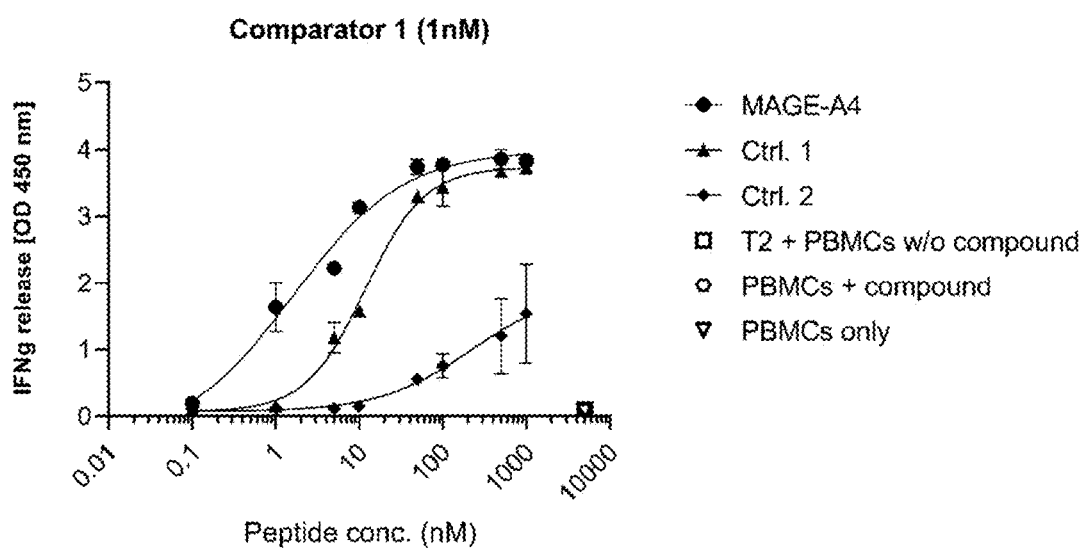
Figure 13C:
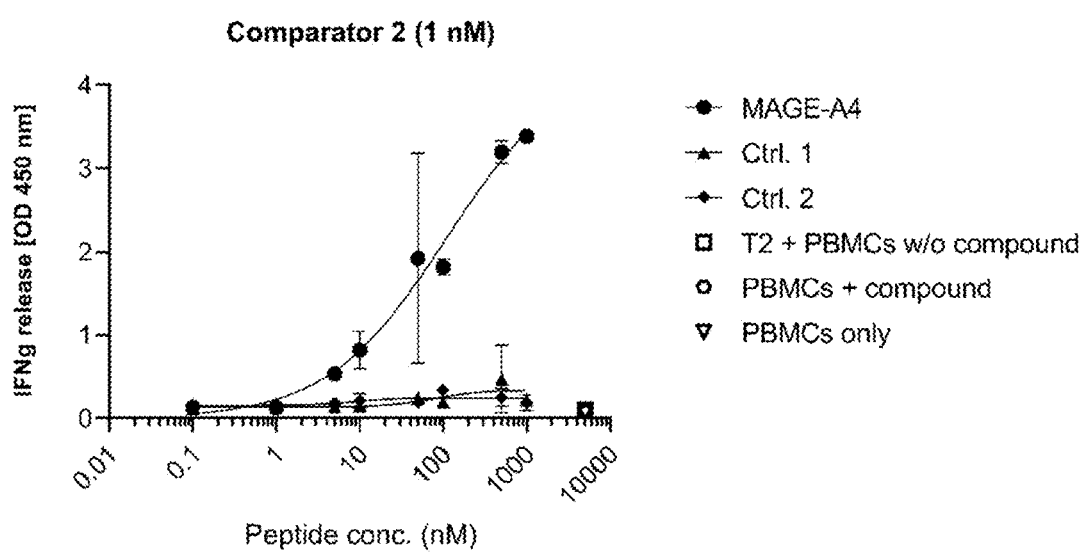
Figure 14A:
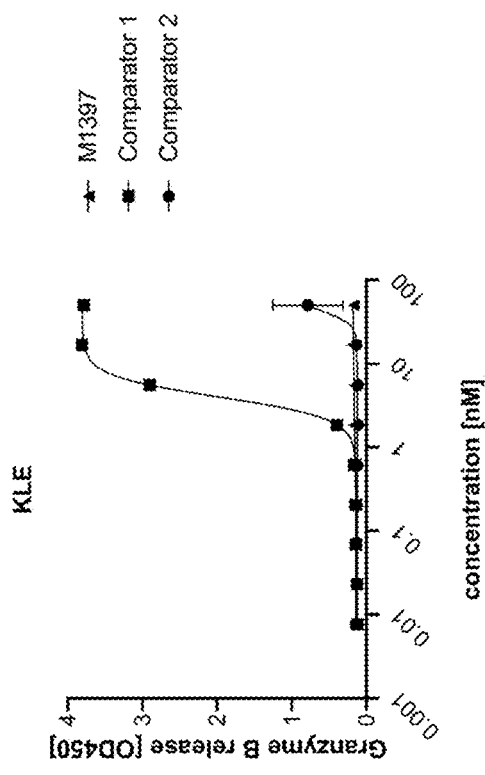
Figure 14B:
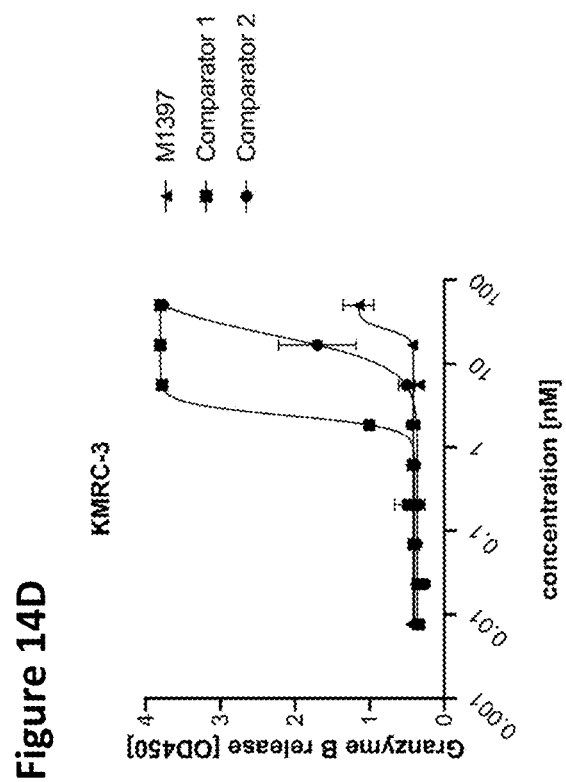
Figure 14C:
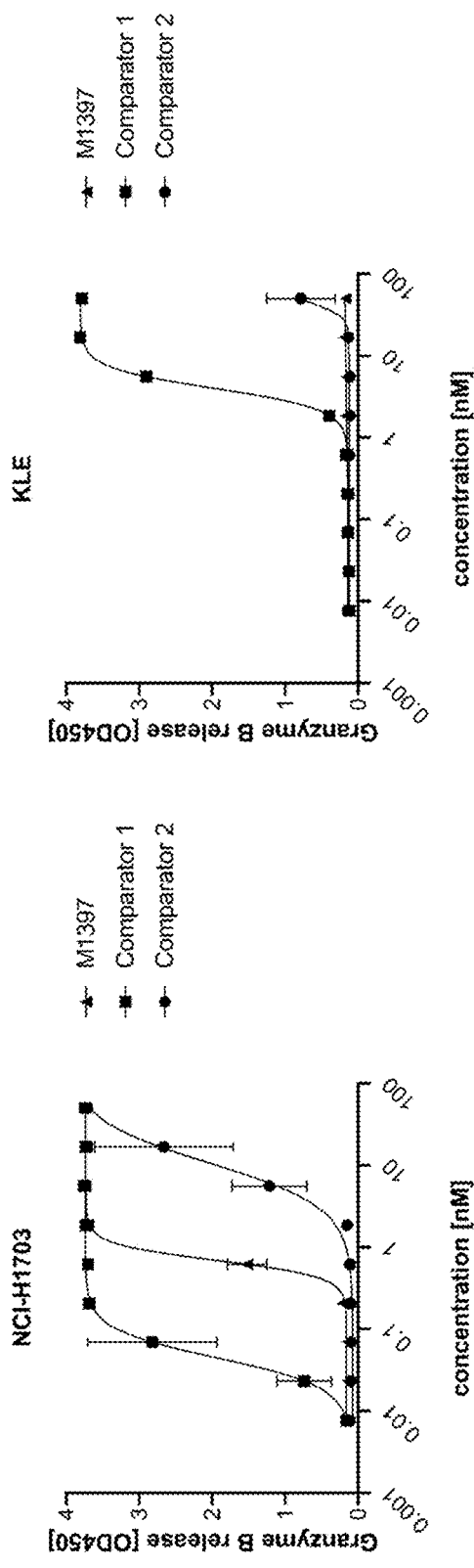
Figure 14D:
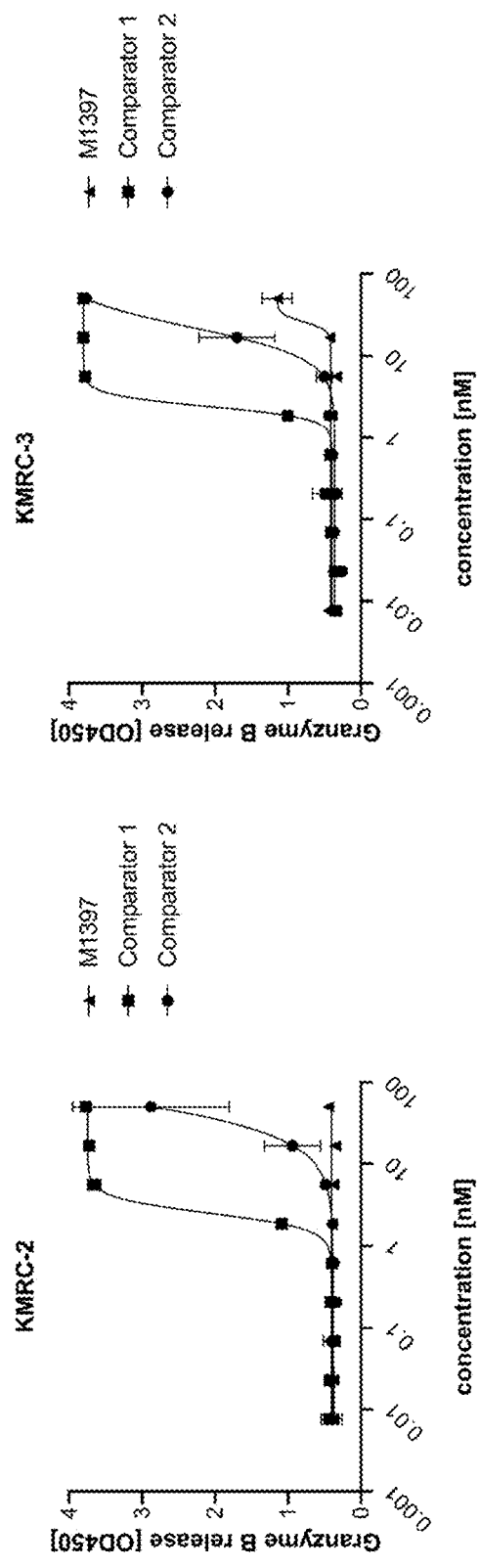
Figure 16A:
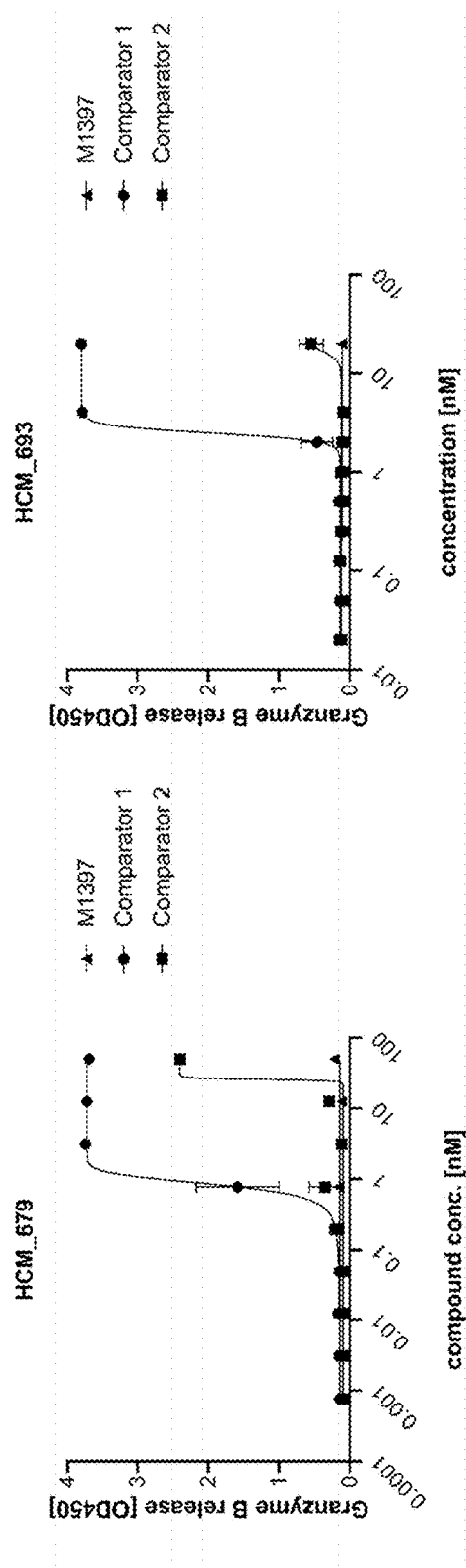
FIGS. 16A-16M show safety of dual engager M1397, Comparator 1 and Comparator 2 in various HLA-A*02:01-positive primary cells.
Figure 16B:
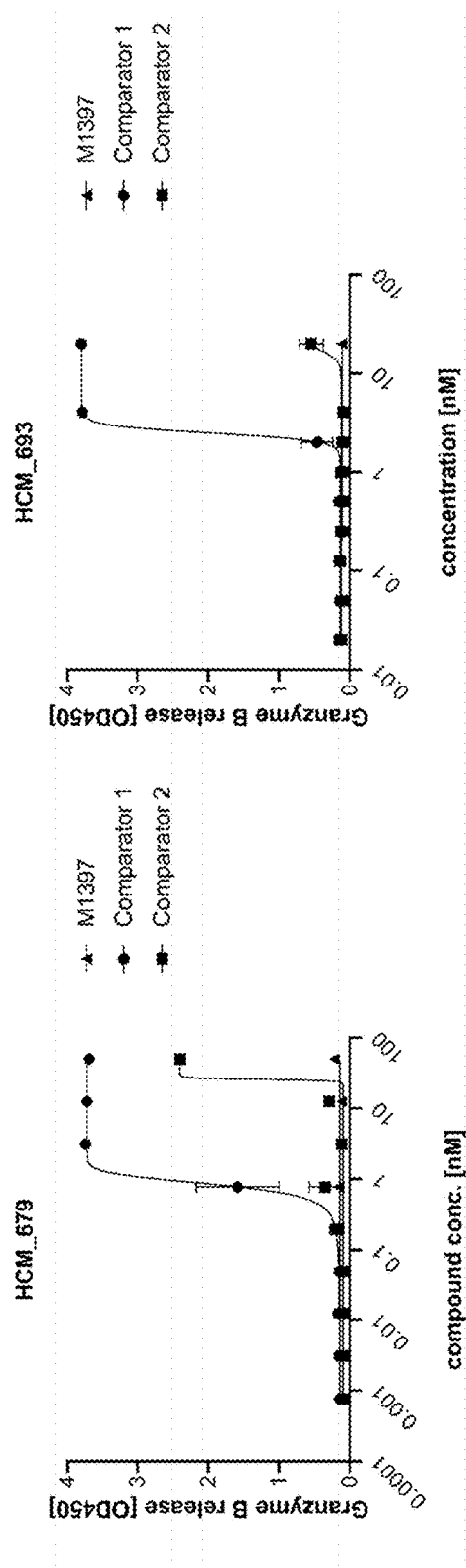
Figure 16C:
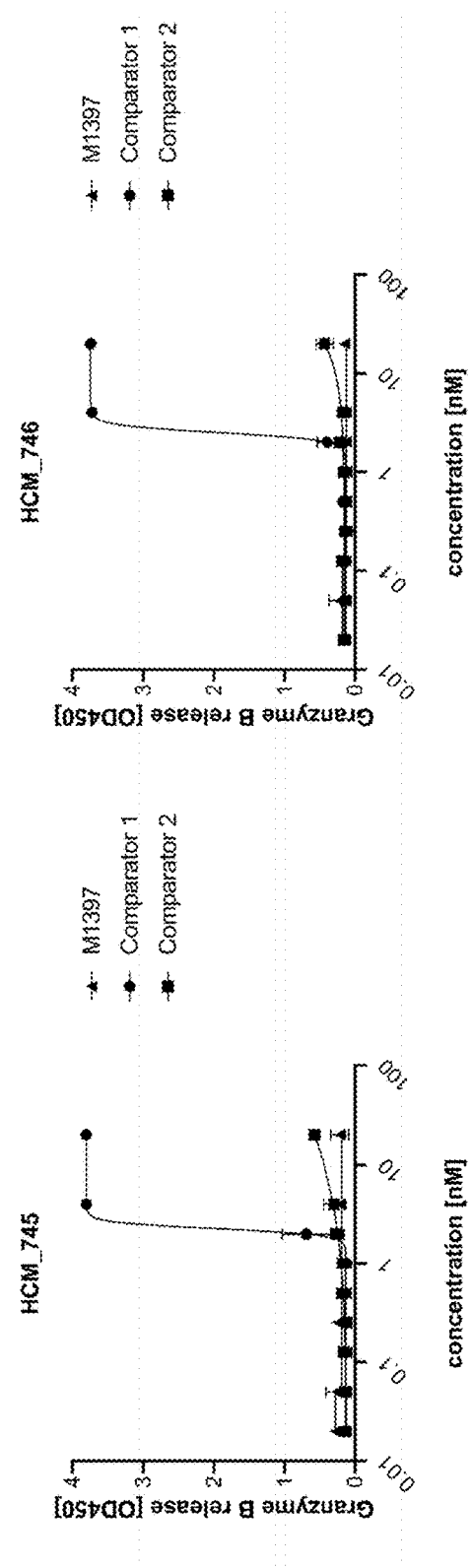
Figure 16D:
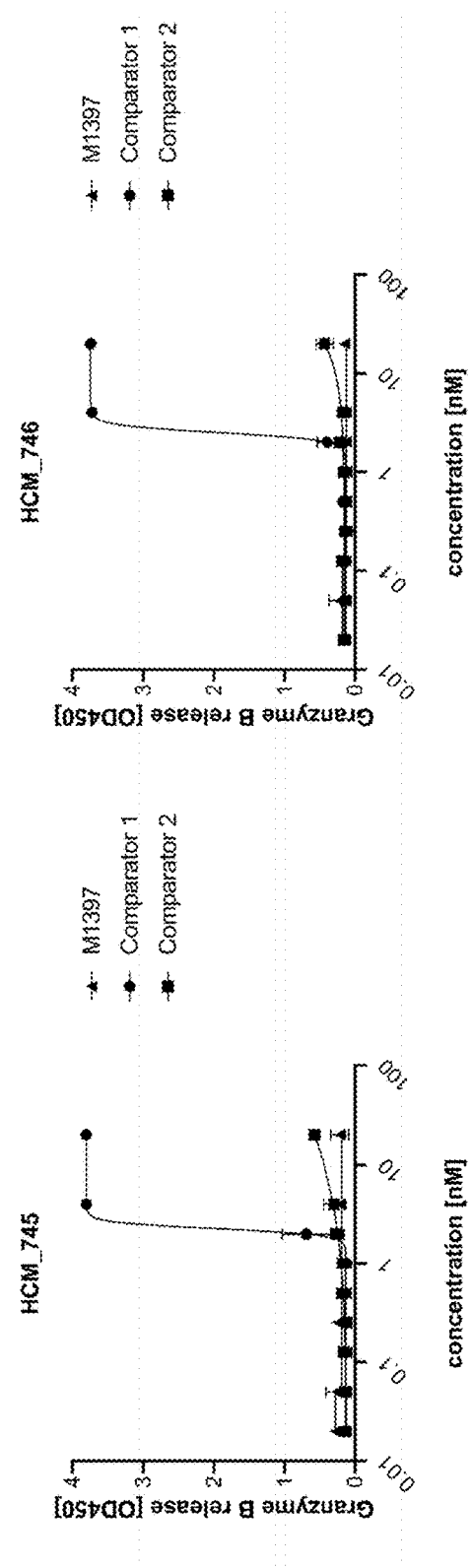
Figure 16E:
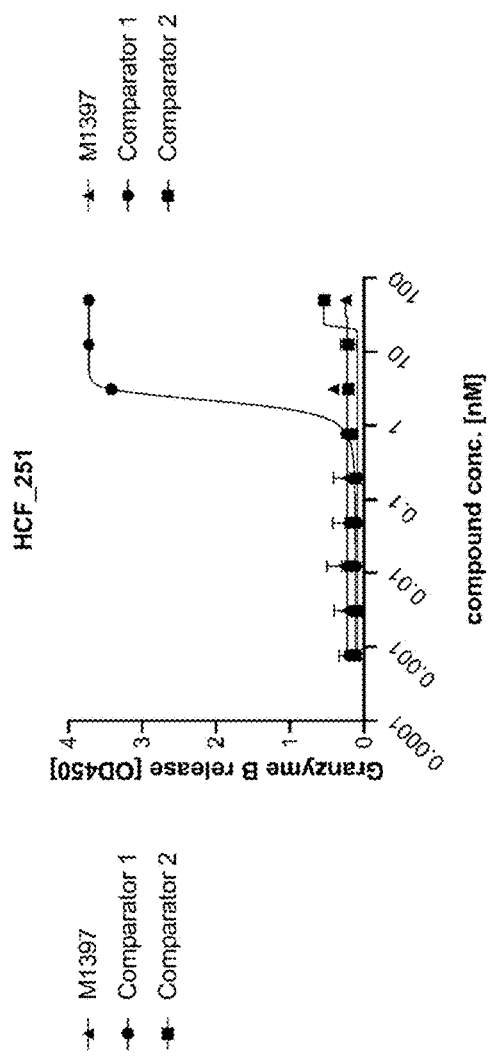
Figure 16F:
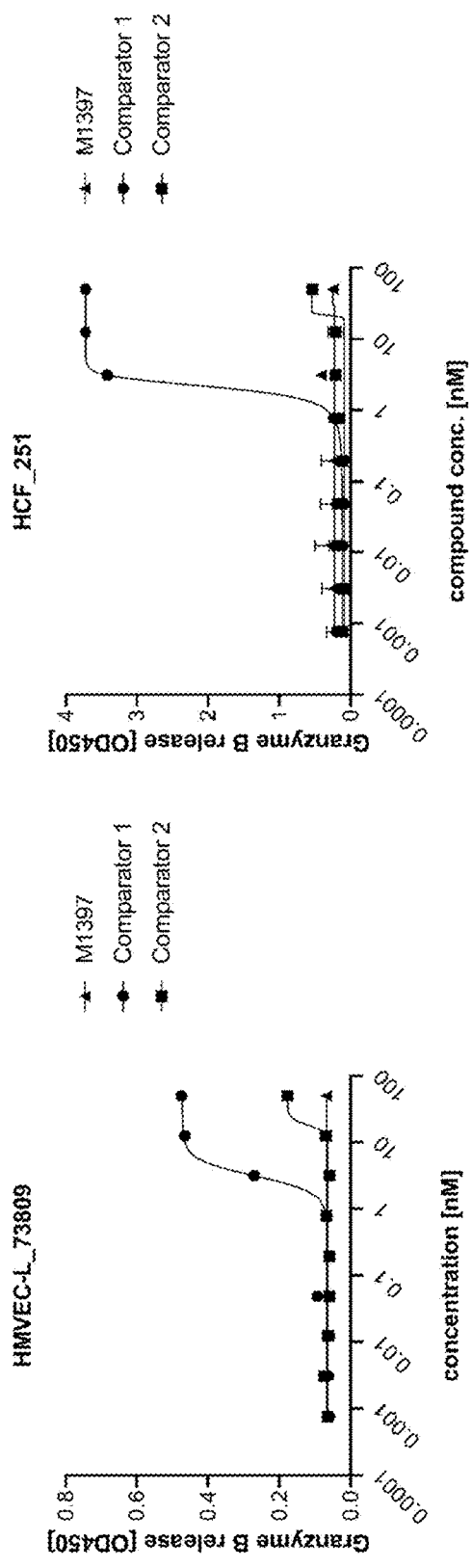
Figure 16G:
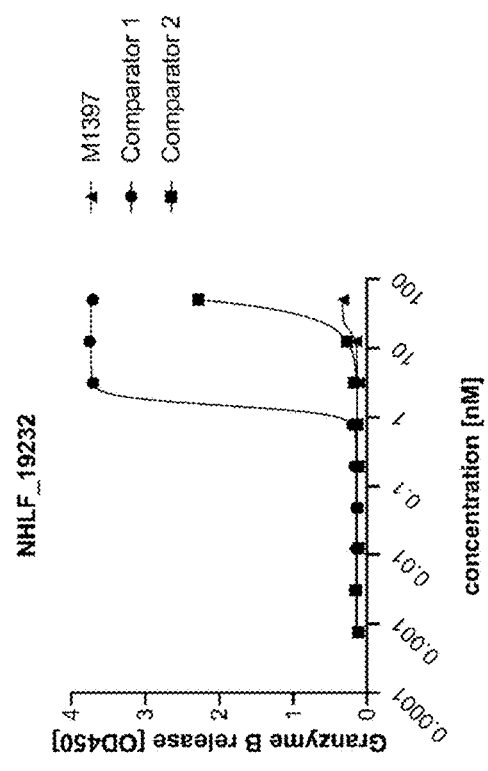
Figure 16H:
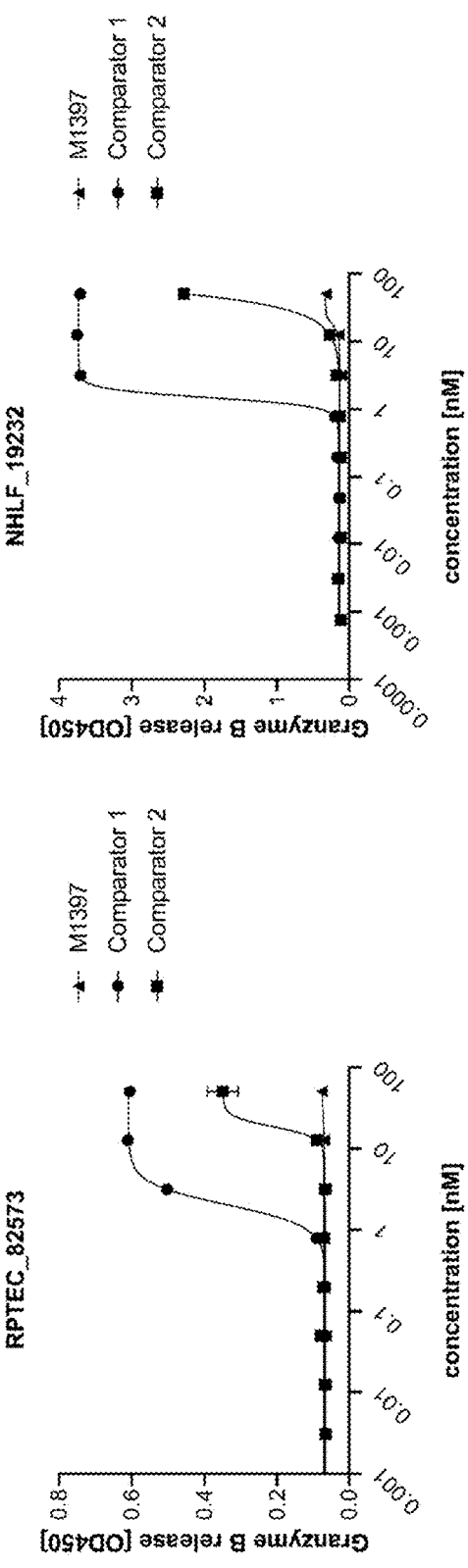
Figure 16I:
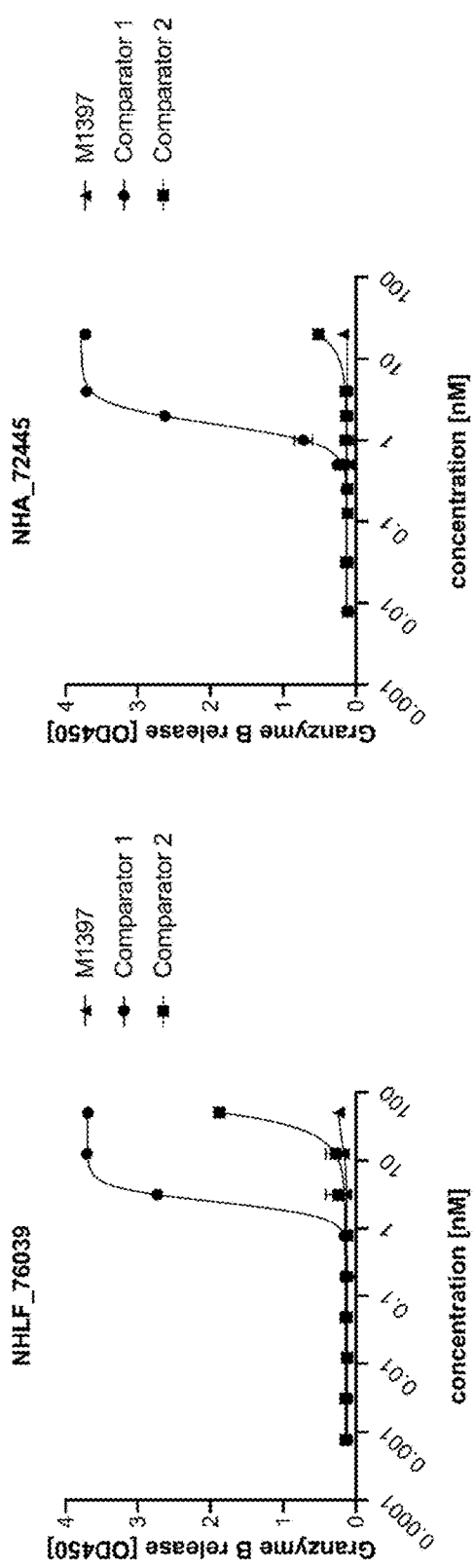
Figure 16J:
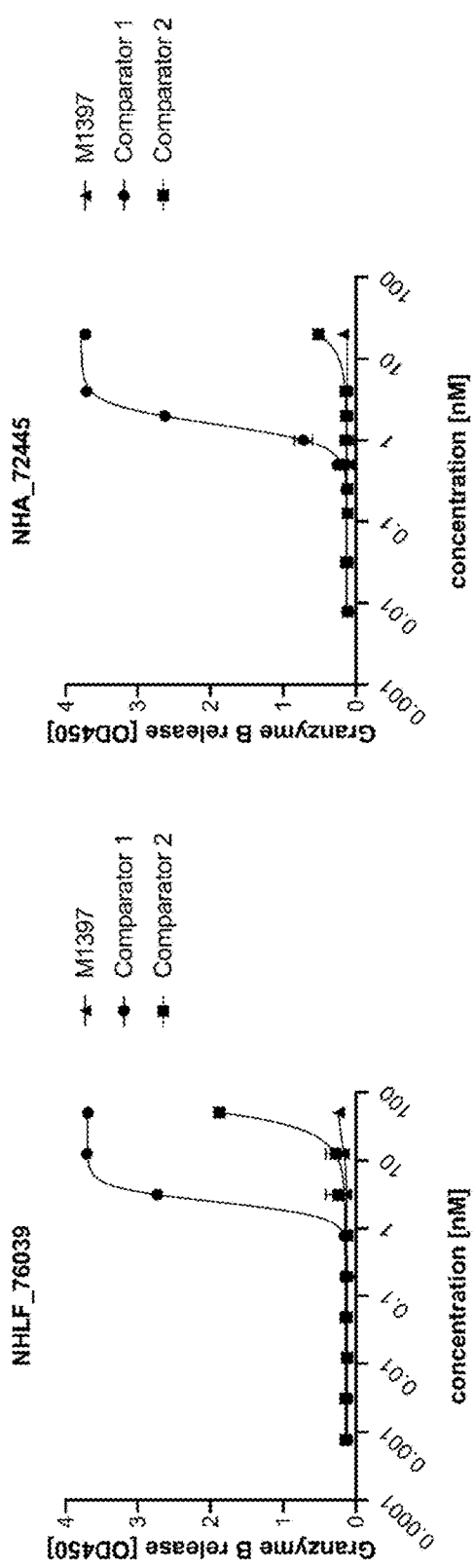
Figure 16K:
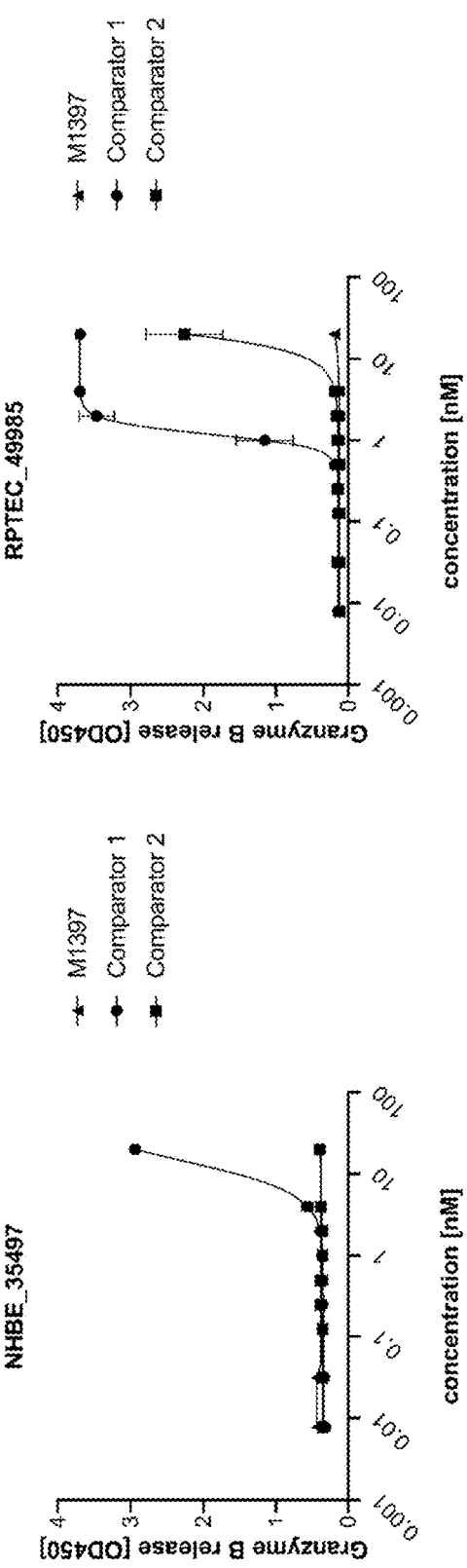
Figure 16L:
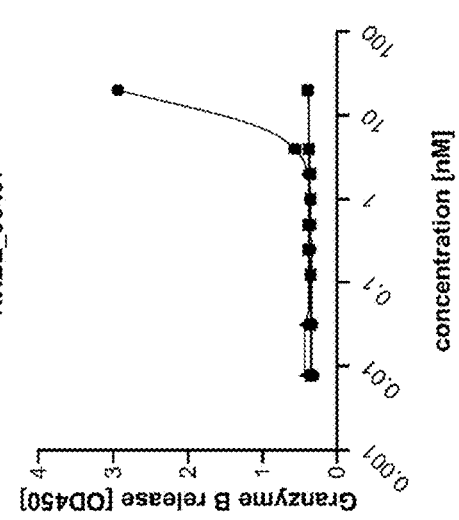
Figure 16M:
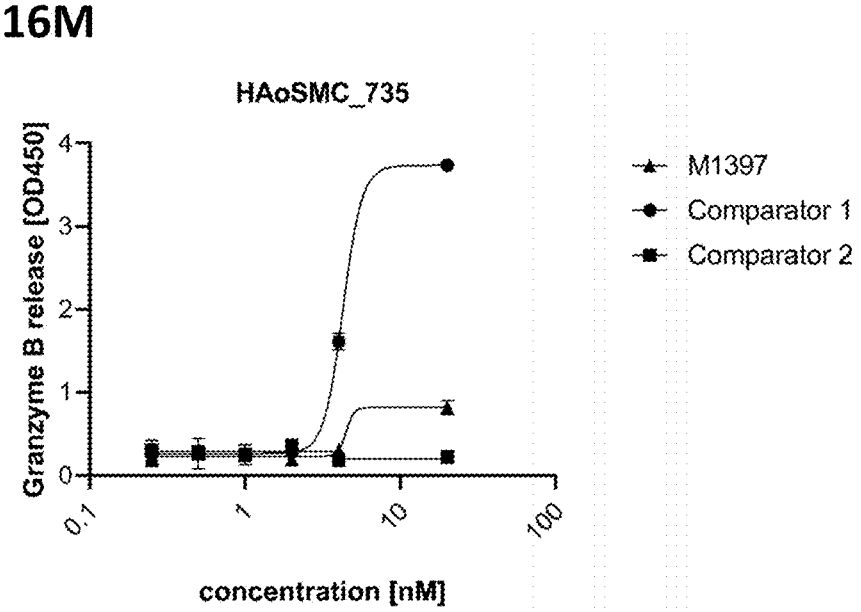

To determine the potency and safety of M1397, Comparator 1 or Comparator 2, T cell activation in the presence of the target HLA-A2/MAGE-A4, or physiologically relevant control peptide antigens HLA-A2/Ctrl.1 and HLA-A2/Ctrl. 2 was determined. Briefly, TAP-deficient T2 cells were incubated with serum-free RPMI1640 medium containing peptides MAGE-A4 (SEQ ID NO: 3), Ctrl.1 (SEQ ID NO: 61) and Ctrl.2 (SEQ ID NO: 62) at indicated concentrations (range of 0.1 nM to 1000 nM) overnight. Then, cells were washed in serum-free RPMI 1640 medium and co-incubated with PBMCs (E:T 5:1) and M1397, Comparator 1 or Comparator 2 at a concentration of 1 nM for 24 h. T cell activation was determined by quantification of IFN-gamma in the cell supernatants and is shown in FIGS. 13A-13C. Consistently, M1397 showed a very good T cell activation profile with EC50 of 5.75 nM when tested on T2 cells pulsed with the target peptide MAGE-A4 and a favorable safety window to the two tested control peptides, where IFN gamma release was only observed at the highest tested peptide concentration of 1 μM. Comparator 1 showed an inferior safety profile, compared to M1397 with increased T cell activation in the presence of off-target HLA-A2/Ctrl.1 antigen, while Comparator 2 showed inferior T cell activation properties, compared to M1397 with EC50 of 105.8 nM on T2 cells pulsed with the target peptide MAGE-A4.

To determine safety of M1397, a panel of various antigen-negative cancer cell lines was tested for compound-induced T cell activation by determining Granzyme B release. Briefly, antigen-negative cancer cell lines KLE (endometrial carcinoma), LNCaP (Lymph Node Carcinoma of the Prostate), KMRC-2 (clear cell renal cell carcinoma), KMRC-3 (clear cell renal cell carcinoma), 639-V (urothelial bladder cancer), EKVX (lung adenocarcinoma) and HCT116 (colorectal carcinoma) were incubated with M1397, Comparator 1 or Comparator 2 at indicated concentrations (range of 7.6 μM to 50 nM) and human PBMCs at an E:T ratio of 5:1. Antigen-positive cell line NCI-H1703 served as a positive control. Granzyme B levels were measured after 24 h incubation and the corresponding results are shown in FIGS. 14A-14H. M1397 showed a superior safety profile than Comparator 1 and Comparator 2 molecules on all tested antigen-negative cancer cell lines.

For in vitro safety experiments, various primary cell types and PBMCs from healthy human donors were co-cultured with compound for 24 h and the supernatant was subsequently analyzed for Granzyme B released from the effector cells as a function of cell-mediated cytotoxicity. Target cells included human cardiac microvascular endothelial cells (HMVEC-C), normal human bronchial epithelial (NHBE) and normal human astrocytes (NHA). Target cells were prepared in assay medium (RPMI 1640 containing 10% FBS and 1% penicillin-streptomycin) and plated at 20,000 cells per well in a volume of 50 μL assay medium. PBMCs effector cells were plated at 100,000 cells per well in a volume of 50 μL assay medium. Varying concentrations of compounds M1397, M1403 or Comparator 1, spanning the anticipated clinically relevant range, were added to the plated wells in 15 μL assay volume. The final assay medium was made up to 150 μL per well. Positive control wells included ImmunoCult Human CD3/CD28 T Cell Activator. Negative control wells included target and effector cells alone or PBMCs alone with the maximum concentration of compound. All reactions were performed in duplicates. The plates were incubated for 24 h at 37° C./5% $CO_2$. Supernatants were collected and analyzed by human Granzyme B ELISA kit (MabTech) according to the manufacturer's instructions. Corresponding results are depicted in FIGS. 15A-15C. M1397 and M1403 showed a superior safety profile, compared to the soluble TCR bispecific Comparator 1 molecule.

Further safety assessment of M1397 in relation to Comparator 1 and Comparator 2 was performed by testing a broader panel of primary cells originating from various essential tissues, i.e., human aortic smooth muscle cells (HAoSMC_735), human lung microvascular endothelial cells (HMVEC-L_73809), renal proximal tubule epithelial cells (RPTEC_49985 and RPTEC_82573), bronchial epithelial cells (NHBE_35497), normal human lung fibroblasts (NHLF_19232 and NHLF_76039), normal human astrocytes (NHA_72445), human cardiac myocytes (HCM_679, HCM_693, HCM_745, HCM_746) and human cardiac fibroblasts (HCF_251). The assay was performed essentially as described above, with altered compound concentration range (maximum tested concentration 50 nM) and excluding the ImmunoCult Human CD3/CD28 T Cell Activator positive control. Data is shown in FIGS. 16A-16M. M1397 showed a favorable and superior safety profile that both comparators on the tested primary cells.

Example 14—In Vivo Efficacy in a Cell Line-Derived Mouse NSCLC Xenograft Model

The antitumor activity of M1397 at doses ranging from 0.5 to 5.0 mg/kg was evaluated in a mouse cell-line derived xenograft model derived using the human NSCLC cell line, NCI-H1703, which expresses MAGE-A4 and HLA-A*02:01.

Immunodeficient female NCG mice were engrafted subcutaneously (SC) with $5 \times 10^6$ cells of the human squamous NSCLC cell line NCI-H1703, which expresses MAGE-A4 and HLA-A*02:01. Once tumors reached a mean size of 120 $mm^3$, the mice were randomized and implanted intraperitoneally with $1 \times 10^7$ human peripheral blood mononuclear cells (PBMCs) from two healthy, treatment naïve donors. Treatment with M1397 started on the following day with daily intravenous doses ranging from 0.5 to 5 mg/kg/day for up to 28 days. Three mice per PBMC donor and per dosing or vehicle (phosphate-buffered saline) group were evaluated twice per week with caliper and body weight measurements.

Figure 17:
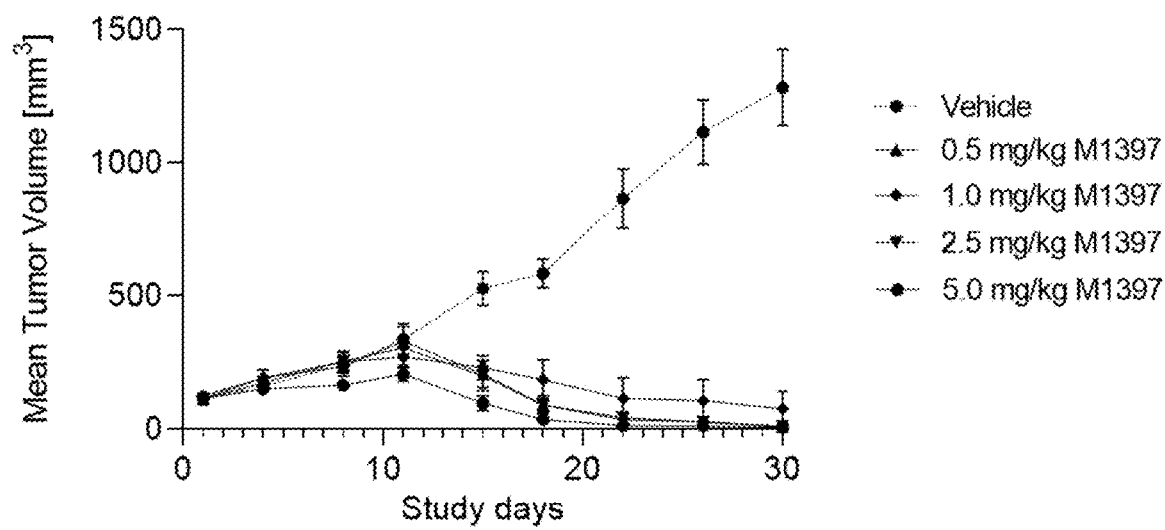
FIG. 17 shows the in vivo efficacy of M1397 in the cell line-derived mouse NSCLC xenograft model detailed in Example 14. Mean tumor volume over the study period at various dosages of the active compound are shown.

Strong tumor growth inhibition was seen in all M1397 groups, with the majority of mice showing full tumor eradication at the end of the study (FIG. 17). Modest signs of graft versus-host disease were noted after Day 18 in all groups, including the vehicle control group. M1397 was well tolerated throughout the study and constant body weights were observed.

| ID | Sequence |
|---|---|
| Consensus CDRH2 SEQ ID NO: 6 | IVSSGGTTYYAX$_1$X$_2$X$_3$KG, wherein X$_1$ corresponds to amino acid S or D, X$_2$ corresponds to amino acid W or S, and X$_3$ corresponds to amino acid A or V |
| Consensus CDRH3 SEQ ID NO: 7 | DLYYGPX$_4$TX$_5$YX$_6$X$_7$X$_8$NL, wherein X$_4$ corresponds to amino acid T, N, or S, X$_5$ corresponds to amino acid D or is absent, X$_6$ corresponds to amino acid S or F, X$_7$ corresponds to amino acid A or V, and X$_8$ corresponds to amino acid F or A |
| Consensus CDRL3 SEQ ID NO: 8 | ATX$_9$X$_{10}$X$_{11}$SGSNFQX$_{12}$, wherein X$_9$ corresponds to amino acid S or R, X$_{10}$ corresponds to amino acid D or P, X$_{11}$ corresponds to amino acid G, S, or F, and X$_{12}$ corresponds to amino acid L or A |
| M1397 Heavy Chain SEQ ID NO: 9 | EVQLVESGGGLVQPGGSLRLSCAASGFTFSTYAMNWVRQAPG KGLEWVGRIRSKYNNYATYYADSVKGRFTISRDDSKNTLYLQ MNSLRAEDTAVYYCVRHGNFGDSYVSWFAYWGQGTLVTVS SASTKGPSVFPLAPSSKSTSGGTAALGCLVKDYFPEPVTVSWN SGALTSGVHTFPAVLQSSGLYSLSSVVTVPSSSLGTQTYICNVN HKPSNTKVDKRVEPKSCGGGGSQSVLTQDPAVSALGQTVRI TCTADTLSRSYASWYQQKPGQAPVLVIYRDTSRPSGIPDRFSG SSSGNTASLTITGAQAEDEADYYCATRPSSGSNFQAFGGGTKL TVLGGGGGSGGGGSGGGGSGGGGSEVQLLESGGGSVQPGGSL RLSCTVSGFSLSNYAMSWVRQAPGKGLEWIGIVSSGGTTYYA DSVKGRFTISRDNSKNTVYLQMNSLRAEDTASYYCAKDLYYG PNTDYSAANLWGQGTSVTVSS |
| M1397 Anti-MAGE-A4 pMHC VH SEQ ID NO: 10 | EVQLLESGGGSVQPGGSLRLSCTVSGFSLSNYAMSWVRQAPG KGLEWIGIVSSGGTTYYADSVKGRFTISRDNSKNTVYLQMNS LRAEDTASYYCAKDLYYGPNTDYSAANLWGQGTSVTVSS |
| M1397 Anti-MAGE-A4 pMHC HCDR1 SEQ ID NO: 11 | SNYAMS |
| M1397 Anti-MAGE-A4 pMHC HCDR2 SEQ ID NO: 12 | IVSSGGTTYYADSVKG |
| M1397 Anti-MAGE-A4 pMHC HCDR3 SEQ ID NO: 13 | DLYYGPNTDYSAANL |
| M1397 Light Chain SEQ ID NO: 14 | QAVVTQEPSLTVSPGGTVTLTCGSSTGAVTTSNYANWVQQKP GKSPRGLIGGTNKRAPGVPARFSGSLLGGKAALTISGAQPEDE ADYYCALWYSNHWVFGGGTKLTVLGQPKAAPSVTLFPPSSEE LQANKATLVCLISDFYPGAVTVAWKADSSPVKAGVETTTPSK QSNNKYAASSYLSLTPEQWKSHRSYSCQVTHEGSTVEKTVAP TECSGGGGSQSVLTQDPAVSALGQTVRITCTADTLSRSYAS WYQQKPGQAPVLVIYRDTSRPSGIPDRFSGSSSGNTASLTITGA QAEDEADYYCATRPSSGSNFQAFGGGTKLTVLGGGGGSGGG GSGGGGSGGGGSEVQLLESGGGSVQPGGSLRLSCTVSGFSLSN YAMSWVRQAPGKGLEWIGIVSSGGTTYYADSVKGRFTISRDN SKNTVYLQMNSLRAEDTASYYCAKDLYYGPNTDYSAANLW GQGTSVTVSS |
| M1397 Anti-MAGE-A4 pMHC VL SEQ ID NO: 15 | QSVLTQDPAVSVALGQTVRITCTADTLSRSYASWYQQKPGQA PVLVIYRDTSRPSGIPDRFSGSSSGNTASLTITGAQAEDEADYY CATRPSSGSNFQAFGGGTKLTVLG |
| M1397 Anti-MAGE-A4 pMHC | TADTLSRSYAS |

SEQUENCES

| ID | Sequence |
|---|---|
| LCDR1 SEQ ID NO: 16 M1397 Anti-MAGE-A4 pMHC LCDR2 SEQ ID NO: 17 | RDTSRPS |
| M1397 Anti-MAGE-A4 pMHC LCDR3 SEQ ID NO: 18 | ATRPSSGSNFQA |
| M1383 Heavy Chain SEQ ID NO: 19 | EVQLVESGGGLVQPGGSLRLSCAASGFTFSTYAMNWVRQAPG KGLEWVGRIRSKYNNYATYYADSVKGRFTISRDDSKNTLYLQ MNSLRAEDTAVYYCVRHGNFGDSYVSWFAYWGQGTLVTVS SASTKGPSVFPLAPSSKSTSGGTAALGCLVKDYFPEPVTVSWN SGALTSGVHTFPAVLQSSGLYSLSSVVTVPSSSLGTQTYICNVN HKPSNTKVDKRVEPKSCGGGGSQSVLTQDPAVSVALGQTVRI TCTADTLSRSYASWYQQKPGQAPVLVIYRDTSRPSGIPDRFSG SSSGNTASLTITGAQAEDEADYYCATRPSSGSNFQLFGCGTKL TVLGGGGSGGGGSGGGGSGGGGSEVQLLESGGGSVQPGGSL RLSCTVSGFSLSNYAMSWVRQAPGKCLEWIGIVSSGGTTYYA DSVKGRFTISRDNSKNTVYLMNSLRAEDTASYYCAKDLYYG PSTYFVANLWGQGTSVTSS |
| M1383 Anti-MAGE-A4 pMHC VH SEQ ID NO: 20 | EVQLLESGGGSVQPGGSLRLSCTVSGFSLSNYAMSWVRQAPG KCLEWIGIVSSGGTTYYADSVKGRFTISRDNSKNTVYLMNS LRAEDTASYYCAKDLYYGPSTYFVANLWGQGTSVTSS |
| M1383 Anti-MAGE-A4 pMHC HCDR1 SEQ ID NO: 21 | SNYAMS |
| M1383 Anti-MAGE-A4 pMHC HCDR2 SEQ ID NO: 22 | IVSSGGTTYYADSVKG |
| M1383 Anti-MAGE-A4 pMHC HCDR3 SEQ ID NO: 23 | DLYYGPSTYFVANL |
| M1383 Light Chain SEQ ID NO: 24 | QAVVTQEPSLTVSPGGTVTLTCGSSTGAVTTSNYANWVQQKP GKSPRGLIGGTNKRAPGVPARFSGSLLGGKAALTISGAQPEDE ADYYCALWYSNHWVFGGGTKLTVLGQPKAAPSVTLFPPSSEE LQANKATLVCLISDFYPGAVTVAWKADSSPVKAGVETTTPSK QSNNKYAASSYLSLTPEQWKSHRSYSCQVTHEGSTVEKTVAP TECSGGGGSQSVLTQDPAVSVALGQTVRITCTADTLSRSYAS WYQQKPGQAPVLVIYRDTSRPSGIPDRFSGSSSGNTASLTITGA QAEDEADYYCATRPSSGSNFQLFGCGTKLTVLGGGGSGGG GSGGGGSGGGGSEVQLLESGGGSVQPGGSLRLSCTVSGFSLSN YAMSWVRQAPGKCLEWIGIVSSGGTTYYADSVKGRFTISRDN SKNTVYLMNSLRAEDTASYYCAKDLYYGPSTYFVANLWGQ GTSVTSS |
| M1383 Anti-MAGE-A4 pMHC VL | QSVLTQDPAVSVALGQTVRITCTADTLSRSYASWYQQKPGQA PVLVIYRDTSRPSGIPDRFSGSSSGNTASLTITGAQAEDEADYY CATRPSSGSNFQLFGCGTKLTVLG |

| ID | Sequence |
|---|---|
| SEQ ID NO: 25<br>M1383 Anti-MAGE-A4 pMHC LCDR1 | TADTLSRSYAS |
| SEQ ID NO: 26<br>M1383 Anti-MAGE-A4 pMHC LCDR2 | RDTSRPS |
| SEQ ID NO: 27<br>M1383 Anti-MAGE-A4 pMHC LCDR3 | ATRPSSGSNFQL |
| SEQ ID NO: 28<br>M1387 Heavy Chain | EVQLVESGGGLVQPGGSLRLSCAASGFTFSTYAMNWVRQAPG KGLEWVGRIRSKYNNYATYYADSVKGRFTISRDDSKNTLYLQ MNSLRAEDTAVYYCVRHGNFGDSYVSWFAYWGQGTLVTVS SASTKGPSVFPLAPSSKSTSGGTAALGCLVKDYFPEPVTVSWN SGALTSGVHTFPAVLQSSGLYSLSSVVTVPSSSLGTQTYICNVN HKPSNTKVDKRVEPKSCGGGGSSYELTQPPSVSVSPGQTASITC TADTLSRSYASWYQQKPGQSPVLVIYRDTSRPSGIPERFSGSN SGNTATLTISGTQAMDEADYYCATRDFSGSNFQLFGCGTKLT VLGGGGSGGGGSGGGGSGGGGSEVQLLESGGGSVQPGGSLR LSCTVSGFSLSNYAMSWVRQAPGKCLEWIGIVSSGGTTYYAS WAKGRFTISKDTSKNTVYLQMNSLRAEDTASYYCAKDLYYG PTTYSAANLWGQGTSVTVSS |
| SEQ ID NO: 29<br>M1387 Anti-MAGE-A4 pMHC VH | EVQLLESGGGSVQPGGSLRLSCTVSGFSLSNYAMSWVRQAPG KCLEWIGIVSSGGTTYYASWAKGRFTISKDTSKNTVYLQMNS LRAEDTASYYCAKDLYYGPTTYSAANLWGQGTSVTVSS |
| SEQ ID NO: 30<br>M1387 Anti-MAGE-A4 pMHC HCDR1 | SNYAMS |
| SEQ ID NO: 31<br>M1387 Anti-MAGE-A4 pMHC HCDR2 | IVSSGGTTYYASWAKG |
| SEQ ID NO: 32<br>M1387 Anti-MAGE-A4 pMHC HCDR3 | DLYYGPTTYSAANL |
| SEQ ID NO: 33<br>M1387 Light Chain | QAVVTQEPSLTVSPGGTVTLTCGSSTGAVTTSNYANWVQQKP GKSPRGLIGGTNKRAPGVPARFSGSLLGGKAALTISGAQPEDE ADYYCALWYSNHWVFGGGTKLTVLGQPKAAPSVTLFPPSSEE LQANKATLVCLISDFYPGAVTVAWKADSSPVKAGVETTTPSK QSNNKYAASSYLSLTPEQWKSHRSYSCQVTHEGSTVEKTVAP TECSGGGGSSYELTQPPSVSVSPGQTASITCTADTLSRSYASW YQQKPGQSPVLVIYRDTSRPSGIPERFSGSNSGNTATLTISGTQ |

| ID | Sequence |
|---|---|
| | AMDEADYYATRDFSGSNFQLFGCGTKLTVLGGGGSGGGG<br>SGGGGSGGGGSEVQLLESGGGSVQPGGSLRLSCTVSGFSLSNY<br>AMSWVRQAPGKCLEWIGIVSSGGTTYYASWAKGRFTISKDTS<br>KNTVYLQMNSLRAEDTASYYCAKDLYYGPTTYSAANLWGQ<br>GTSVTVSS |
| M1387 Anti-<br>MAGE-A4<br>pMHC VL<br>SEQ ID NO:<br>35 | SYELTQPPSVSVSPGQTASITCTADTLSRSYASWYQQKPGQSP<br>VLVIYRDTSRPSGIPERFSGSNSGNTATLTISGTQAMDEADYYC<br>ATRDFSGSNFQLFGCGTKLTVLG |
| M1387<br>Anti-<br>MAGE-A4<br>pMHC<br>LCDR1<br>SEQ ID NO:<br>36 | TADTLSRSYAS |
| M1387<br>Anti-<br>MAGE-A4<br>pMHC<br>LCDR2<br>SEQ ID NO:<br>37 | RDTSRPS |
| M1387<br>Anti-<br>MAGE-A4<br>pMHC<br>LCDR3<br>SEQ ID NO:<br>38 | ATRDFSGSNFQL |
| M1403<br>Heavy Chain<br>SEQ ID NO:<br>39 | EVQLVESGGGLVQPGGSLRLSCAASGFTFSTYAMNWVRQAPG<br>KGLEWVGRIRSKYNNYATYYADSVKGRFTISRDDSKNTLYLQ<br>MNSLRAEDTAVYYCVRHGNFGDSYVSWFAYWGQGTLVTVS<br>SASTKGPSVFPLAPSSKSTSGGTAALGCLVKDYFPEPVTVSWN<br>SGALTSGVHTFPAVLQSSGLYSLSSVVTVPSSSLGTQTYICNVN<br>HKPSNTKVDKRVEPKSCGGGGSSYELTQPPSVSVSPGQTASITC<br>TADTLSRSYASWYQQKPGQSPVLVIYRDTSRPSGIPERFSGSN<br>SGNTATLTISGTQAMDEADYYCATRPSSGSNFQAFGGGTKLT<br>VLGGGGGSGGGGSGGGGSGGGGSEVQLLESGGGSVQPGGSL<br>RLSCTVSGFSLSNYAMSWVRQAPGKGLEYIGIVSSGGTTYYA<br>SWAKGRFTISRDNSKNTVYLQMNSLRAEDTASYYCAKDLYY<br>GPTTYSAFNLWGQGTSVTVSS |
| M1403 Anti-<br>MAGE-A4<br>pMHC VH<br>SEQ ID NO:<br>40 | EVQLLESGGGSVQPGGSLRLSCTVSGFSLSNYAMSWVRQAPG<br>KGLEYIGIVSSGGTTYYASWAKGRFTISRDNSKNTVYLQMNS<br>LRAEDTASYYCAKDLYYGPTTYSAFNLWGQGTSVTVSS |
| M1403<br>Anti-<br>MAGE-A4<br>pMHC<br>HCDR1<br>SEQ ID NO:<br>41 | SNYAMS |
| M1403<br>Anti-<br>MAGE-A4<br>pMHC<br>HCDR2<br>SEQ ID NO:<br>42 | IVSSGGTTYYASWAKG |
| M1403<br>Anti-<br>MAGE-A4<br>pMHC | DLYYGPTTYSAFNL |

| ID | Sequence |
|---|---|
| HCDR3 SEQ ID NO: 43 | |
| M1403 Light Chain SEQ ID NO: 44 | QAVVTQEPSLTVSPGGTVTLTCGSSTGAVTTSNYANWVQQKPGKSPRGLIGGTNKRAPGVPARFSGSLLGGKAALTISGAQPEDEADYYCALWYSNHWVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECSGGGGSSYELTQPPSVSVSPGQTASITCTADTLSRSYASWYQQKPGQSPVLVIYRDTSRPSGIPERFSGSNSGNTATLTISGTQAMDEADYYCATRPSSGSNFQAFGGGTKLTVLGGGGGSGGGGSGGGGSGGGGSEVQLLESGGGSVQPGGSLRLSCTVSGFSLSNYAMSWVRQAPGKGLEYIGIVSSGGTTYYASWAKGRFTISRDNSKNTVYLQMNSLRAEDTASYYCAKDLYYGPTTYSAFNLWGQGTSVTVSS |
| M1403 Anti-MAGE-A4 pMHC VL SEQ ID NO: 45 | SYELTQPPSVSVSPGQTASITCTADTLSRSYASWYQQKPGQSPVLVIYRDTSRPSGIPERFSGSNSGNTATLTISGTQAMDEADYYCATRPSSGSNFQAFGGGTKLTVLG |
| M1403 Anti-MAGE-A4 pMHC LCDR1 SEQ ID NO: 46 | TADTLSRSYAS |
| M1403 Anti-MAGE-A4 pMHC LCDR2 SEQ ID NO: 47 | RDTSRPS |
| M1403 Anti-MAGE-A4 pMHC LCDR3 SEQ ID NO: 48 | ATRPSSGSNFQA |
| Anti-CD3 Heavy Chain SEQ ID NO: 49 | EVQLVESGGGLVQPGGSLRLSCAASGFTFSTYAMNWVRQAPGKGLEWVGRIRSKYNNYATYYADSVKGRFTISRDDSKNTLYLQMNSLRAEDTAVYYCVRHGNFGDSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC |
| Anti-CD3 VH SEQ ID NO: 50 | EVQLVESGGGLVQPGGSLRLSCAASGFTFSTYAMNWVRQAPGKGLEWVGRIRSKYNNYATYYADSVKGRFTISRDDSKNTLYLQMNSLRAEDTAVYYCVRHGNFGDSYVSWFAYWGQGTLVTVSS |
| Anti-CD3 HCDR1 SEQ ID NO: 51 | STYAMN |
| Anti-CD3 HCDR2 SEQ ID NO: 52 | RIRSKYNNYATYYADSVKG |
| Anti-CD3 HCDR3 SEQ ID NO: 53 | HGNFGDSYVSWFAY |
| Anti-CD3 | QAVVTQEPSLTVSPGGTVTLTCGSSTGAVTTSNYANWVQQKP |

SEQUENCES

| ID | Sequence |
|---|---|
| Light Chain SEQ ID NO: 54 | GKSPRGLIGGTNKRAPGVPARFSGSLLGGKAALTISGAQPEDE ADYYCALWYSNHWVFGGGTKLTVLGQPKAAPSVTLFPPSSEE LQANKATLVCLISDFYPGAVTVAWKADSSPVKAGVETTTPSK QSNNKYAASSYLSLTPEQWKSHRSYSCQVTHEGSTVEKTVAP TECS |
| Anti-CD3 VL SEQ ID NO: 55 | QAVVTQEPSLTVSPGGTVTLTCGSSTGAVTTSNYANWVQQKP GKSPRGLIGGTNKRAPGVPARFSGSLLGGKAALTISGAQPEDE ADYYCALWYSNHWVFGGGTKLTVLG |
| Anti-CD3 LCDR1 SEQ ID NO: 56 | GSSTGAVTTSNYAN |
| Anti-CD3 LCDR2 SEQ ID NO: 57 | GTNKRAP |
| Anti-CD3 LCDR3 SEQ ID NO: 58 | ALWYSNHWV |
| Comparator 1 Alpha Chain SEQ ID NO: 59 | MANQVEQSPQSLIILEGKNVTLQCNYTVSPFSNLRWYKQDTGR GPVSLTILTFSENTKSNGRYTATLDADTKQSSLHITASQLSDSA SYICVVNSAQGLYIPTFGRGTSLIVHPYIQKPDPAVYQLRDSKS SDKSVCLFTDFDSQTNVSQSKDSDVYITDKCVLDMRSMDFKS NSAVAWSNKSDFACANAFNNSIIPEDT |
| Comparator 1 Beta Chain SEQ ID NO: 60 | MAIQMTQSPSSLSASVGDRVTITCRASQDIRNYLNWYQQKPGK APKLLIYYTSRLESGVPSRFSGSGSGTDYTLTISSLQPEDFATYY CQQGNTLPWTFGQGTKVEIKGGGGSGGGGSGGGGSGGGGSG GGGSEVQLVESGGGLVQPGGSLRLSCAASGYSFTGYTMNWVR QAPGKGLEWVALINPYKGVSTYNQKFKDRFTISVDKSKNTAY LQMNSLRAEDTAVYYCARSGYYGDSDWYFDVWGQGTLVTV SSGGGGSDVKVTQSSRYLVKRTGEKVFLECVQDLDHENMFW YRQDPDGLGLRLIYFSRFATGKEKGDIPEGYSVSREKKERFSLILE SASTNQTSMYLCASSSDQNSGDPYEQYFGPGTRLTVTEDLKNV FPPEVAVFEPSEAEISHTQKATLVCLATGFYPDHVELSWWVNG KEVHSGVCTDPQPLKEQPALNDSRY ALSSRLRVSATFWQDPR NHFRCQVQFYGLSENDEWTQDRAKPVTQIVSAEAWGRAD |
| MAGE-A4 scFv of M1397 SEQ ID NO: 61 | QSVLTQDPAVSVALGQTVRITCTADTLSRSYASWYQQKPGQA PVLVIYRDTSRPSGIPDRFSGSSSGNTASLTITGAQAEDEADYY CATRPSSGSNFQAFGGGTKLTVLGGGGGSGGGGSGGGGSGGG GSEVQLLESGGGSVQPGGSLRLSCTVSGFSLSNYAMSWVRQA PGKGLEWIGIVSSGGTTYYADSVKGRFTISRDNSKNTVYLQMN SLRAEDTASYYCAKDLYYGPNTDYSAANLWGQGTSVTVSS |
| MAGE-A4 scFv of M1383 SEQ ID NO: 62 | QSVLTQDPAVSVALGQTVRITCTADTLSRSYASWYQQKPGQA PVLVIYRDTSRPSGIPDRFSGSSSGNTASLTITGAQAEDEADYY CATRPSSGSNFQLFGCGTKLTVLGGGGGSGGGGSGGGGSGGG GSEVQLLESGGGSVQPGGSLRLSCTVSGFSLSNYAMSWVRQA PGKCLEWIGIVSSGGTTYYADSVKGRFTISRDNSKNTVYLQMN SLRAEDTASYYCAKDLYYGPSTYFVANLWGQGTSVTVSS |
| MAGE-A4 scFv of M1387 SEQ ID NO: 63 | SYELTQPPSVSVSPGQTASITCTADTLSRSYASWYQQKPGQSPV LVIYRDTSRPSGIPERFSGSNSGNTATLTISGTQAMDEADYYCA TRDFSGSNFQLFGCGTKLTVLGGGGGSGGGGSGGGGSGGGGS EVQLLESGGGSVQPGGSLRLSCTVSGFSLSNYAMSWVRQAPG KCLEWIGIVSSGGTTYYASWAKGRFTISKDTSKNTVYLQMNSL RAEDTASYYCAKDLYYGPTTYSAANLWGQGTSVTVSS |
| MAGE-A4 scFv of M1403 SEQ ID NO: 64 | SYELTQPPSVSVSPGQTASITCTADTLSRSYASWYQQKPGQSPV LVIYRDTSRPSGIPERFSGSNSGNTATLTISGTQAMDEADYYCA TRPSSGSNFQAFGGGTKLTVLGGGGGSGGGGSGGGGSGGGG SEVQLLESGGGSVQPGGSLRLSCTVSGFSLSNYAMSWVRQAP GKGLEYIGIVSSGGTTYYASWAKGRFTISRDNSKNTVYLQMNS LRAEDTASYYCAKDLYYGPTTYSAFNLWGQGTSVTVSS |
| Comparator 2 heavy | AQLVESGGGLVQPGGSLRLSCAASAYFSFKAMSWVRQAPGKG LEWVGSISPSGGSTYYNDNVLGRFTISRDNSKNTLYLQMNSLR |

SEQUENCES

| ID | Sequence |
|---|---|
| chain 1 SEQ ID NO: 65 | AEDTAVYYCAKDVGFFDEWGQGTLVTVSSASTKGPSVFPLAP SSKSTSGGTAALGCLVEDYFPEPVTVSWNSGALTSGVHTFPAV LQSSGLYSLSSVVTVPSSSLGTQTYICNVNHKPSNTKVDEKVEP KSCDGGGSGGGGSDIQMTQSPSSLSASVGDRVTITCRASQDI RNYLNWYQQKPGKAPKLLIYYTSRLESGVPSRFSGSGSGTDYT LTISSLQPEDFATYYCQQGNTLPWTFGQGTKVEIKSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTKV DKKVEPKSCDKTHTCPPCPAPEAAGGPSVFLFPPKPKDTLMISR TPEVTCVVVDVSHEDPEVKFNWYVDGVEVHNAKTKPREEQY NSTYRVVSVLTVLHQDWLNGKEYKCKVSNKALGAPIEKTISK AKGQPREPQVYTLPPCRDELTKNQVSLWCLVKGFYPSDIAVE WESNGQPENNYKTTPPVLDSDGSFFLYSKLTVDKSRWQQGNV FSCSVMHEALHNHYTQKSLSLSP |
| Comparator 2 heavy chain 2 SEQ ID NO: 66 | AQLVESGGGLVQPGGSLRLSCAASAYFSFKAMSWVRQAPGKG LEWVGSISPSGGSTYYNDNVLGRFTISRDNSKNTLYLQMNSLR AEDTAVYYCAKDVGFFDEWGQGTLVTVSSASTKGPSVFPLAP SSKSTSGGTAALGCLVEDYFPEPVTVSWNSGALTSGVHTFPAV LQSSGLYSLSSVVTVPSSSLGTQTYICNVNHKPSNTKVDEKVEP KSCDKTHTCPPCPAPEAAGGPSVFLFPPKPKDTLMISRTPEVTC VVVDVSHEDPEVKFNWYVDGVEVHNAKTKPREEQYNSTYRV VSVLTVLHQDWLNGKEYKCKVSNKALGAPIEKTISKAKGQPR EPQVCTLPPSRDELTKNQVSLSCAVKGFYPSDIAVEWESNGQP ENNYKTTPPVLDSDGSFFLVSKLTVDKSRWQQGNVFSCSVMH EALHNHYTQKSLSLSP |
| Comparator 2 light chain SEQ ID NO: 67 | DIQMTQSPSSLSASVGDRVTITCRASQSISSYLAWYQQKPGKAP KLLIYDASIRDIGVPSRFSGSGSGTDFTLTISSLQPEDFATYYCQ QYSSYPYTFGQGTKLEIKRTVAAPSVFIFPPSDRKLKSGTASVV CLLNNFYPREAKVQWKVDNALQSGNSQESVTEQDSKDSTYSL SSTLTLSKADYEKHKVYACEVTHQGLSSPVTKSFNRGEC |

---

SEQUENCE LISTING

```
Sequence total quantity: 88
SEQ ID NO: 1           moltype = AA  length = 275
FEATURE                Location/Qualifiers
source                 1..275
                       mol_type = protein
                       organism = synthetic construct
SEQUENCE: 1
GSHSMRYFFT SVSRPGRGEP RFIAVGYVDD TQFVRFDSDA ASQRMEPRAP WIEQEGPEYW   60
DGETRKVKAH SQTHRVDLGT LRGYYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPAGDGT  240
FQKWAAVVVP SGQEQRYTCH VQHEGLPKPL TLRWE                            275

SEQ ID NO: 2           moltype = AA  length = 99
FEATURE                Location/Qualifiers
source                 1..99
                       mol_type = protein
                       organism = synthetic construct
SEQUENCE: 2
IQRTPKIQVY SRHPAENGKS NFLNCYVSGF HPSDIEVDLL KNGERIEKVE HSDLSFSKDW   60
SFYLLYYTEF TPTEKDEYAC RVNHVTLSQP KIVKWDRDM                         99

SEQ ID NO: 3           moltype = AA  length = 10
FEATURE                Location/Qualifiers
source                 1..10
                       mol_type = protein
                       organism = synthetic construct
SEQUENCE: 3
GVYDGREHTV                                                          10

SEQ ID NO: 4           moltype = AA  length = 107
FEATURE                Location/Qualifiers
source                 1..107
                       mol_type = protein
                       organism = synthetic construct
SEQUENCE: 4
```

```
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 5              moltype = AA   length = 103
FEATURE                   Location/Qualifiers
source                    1..103
                          mol_type = protein
                          organism = synthetic construct
SEQUENCE: 5
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSC                     103

SEQ ID NO: 6              moltype = AA   length = 16
FEATURE                   Location/Qualifiers
source                    1..16
                          mol_type = protein
                          organism = synthetic construct
VARIANT                   12
                          note = corresponds to amino acid S or D
VARIANT                   13
                          note = corresponds to amino acid W or S
VARIANT                   14
                          note = corresponds to amino acid A or V
SEQUENCE: 6
IVSSGGTTYY AXXXKG                                                   16

SEQ ID NO: 7              moltype = AA   length = 15
FEATURE                   Location/Qualifiers
source                    1..15
                          mol_type = protein
                          organism = synthetic construct
VARIANT                   7
                          note = corresponds to amino acid T, N, or S
VARIANT                   9
                          note = corresponds to amino acid D or is absent
VARIANT                   11
                          note = corresponds to amino acid S or F
VARIANT                   12
                          note = corresponds to amino acid A or V
VARIANT                   13
                          note = corresponds to amino acid F or A
SEQUENCE: 7
DLYYGPXTXY XXXNL                                                    15

SEQ ID NO: 8              moltype = AA   length = 12
FEATURE                   Location/Qualifiers
source                    1..12
                          mol_type = protein
                          organism = synthetic construct
VARIANT                   3
                          note = corresponds to amino acid S or R
VARIANT                   4
                          note = corresponds to amino acid D or P
VARIANT                   5
                          note = corresponds to amino acid G, S, or F
VARIANT                   12
                          note = corresponds to amino acid L or A
SEQUENCE: 8
ATXXXSGSNF QX                                                       12

SEQ ID NO: 9              moltype = AA   length = 486
FEATURE                   Location/Qualifiers
source                    1..486
                          mol_type = protein
                          organism = synthetic construct
SEQUENCE: 9
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KRVEPKSCGG GGSQSVLTQD   240
PAVSVALGQT VRITCTADTL SRSYASWYQQ KPGQAPVLVI YRDTSRPSGI PDRFSGSSSG   300
NTASLTITGA QAEDEADYYC ATRPSSGSNF QAFGGGTKLT VLGGGGGSGG GGSGGGGSGG   360
GGSEVQLLES GGGSVQPGGS LRLSCTVSGF SLSNYAMSWV RQAPGKGLEW IGIVSSGGTT   420
YYADSVKGRF TISRDNSKNT VYLQMNSLRA EDTASYYCAK DLYYGPNTDY SAANLWGQGT   480
SVTVSS                                                              486

SEQ ID NO: 10             moltype = AA   length = 123
FEATURE                   Location/Qualifiers
source                    1..123
```

```
                            mol_type = protein
                            organism = synthetic construct
SEQUENCE: 10
EVQLLESGGG SVQPGGSLRL SCTVSGFSLS NYAMSWVRQA PGKGLEWIGI VSSGGTTYYA         60
DSVKGRFTIS RDNSKNTVYL QMNSLRAEDT ASYYCAKDLY YGPNTDYSAA NLWGQGTSVT        120
VSS                                                                      123

SEQ ID NO: 11               moltype = AA  length = 6
FEATURE                     Location/Qualifiers
source                      1..6
                            mol_type = protein
                            organism = synthetic construct
SEQUENCE: 11
SNYAMS                                                                     6

SEQ ID NO: 12               moltype = AA  length = 16
FEATURE                     Location/Qualifiers
source                      1..16
                            mol_type = protein
                            organism = synthetic construct
SEQUENCE: 12
IVSSGGTTYY ADSVKG                                                         16

SEQ ID NO: 13               moltype = AA  length = 15
FEATURE                     Location/Qualifiers
source                      1..15
                            mol_type = protein
                            organism = synthetic construct
SEQUENCE: 13
DLYYGPNTDY SAANL                                                          15

SEQ ID NO: 14               moltype = AA  length = 473
FEATURE                     Location/Qualifiers
source                      1..473
                            mol_type = protein
                            organism = synthetic construct
SEQUENCE: 14
QAVVTQEPSL TVSPGGTVTL TCGSSTGAVT TSNYANWVQQ KPGKSPRGLI GGTNKRAPGV         60
PARFSGSLLG GKAALTISGA QPEDEADYYC ALWYSNHWVF GGGTKLTVLG QPKAAPSVTL        120
FPPSSEELQA NKATLVCLIS DFYPGAVTVA WKADSSPVKA GVETTTPSKQ SNNKYAASSY        180
LSLTPEQWKS HRSYSCQVTH EGSTVEKTVA PTECSGGGGS QSVLTQDPAV SVALGQTVRI        240
TCTADTLSRS YASWYQQKPG QAPVLVIYRD TSRPSGIPDR FSGSSSGNTA SLTITGAQAE        300
DEADYYCATR PSSGSNFQAF GGGTKLTVLG GGGGSGGGGS GGGGSGGGGS EVQLLESGGG        360
SVQPGGSLRL SCTVSGFSLS NYAMSWVRQA PGKGLEWIGI VSSGGTTYYA DSVKGRFTIS        420
RDNSKNTVYL QMNSLRAEDT ASYYCAKDLY YGPNTDYSAA NLWGQGTSVT VSS               473

SEQ ID NO: 15               moltype = AA  length = 110
FEATURE                     Location/Qualifiers
source                      1..110
                            mol_type = protein
                            organism = synthetic construct
SEQUENCE: 15
QSVLTQDPAV SVALGQTVRI TCTADTLSRS YASWYQQKPG QAPVLVIYRD TSRPSGIPDR         60
FSGSSSGNTA SLTITGAQAE DEADYYCATR PSSGSNFQAF GGGTKLTVLG                  110

SEQ ID NO: 16               moltype = AA  length = 11
FEATURE                     Location/Qualifiers
source                      1..11
                            mol_type = protein
                            organism = synthetic construct
SEQUENCE: 16
TADTLSRSYA S                                                              11

SEQ ID NO: 17               moltype = AA  length = 7
FEATURE                     Location/Qualifiers
source                      1..7
                            mol_type = protein
                            organism = synthetic construct
SEQUENCE: 17
RDTSRPS                                                                    7

SEQ ID NO: 18               moltype = AA  length = 12
FEATURE                     Location/Qualifiers
source                      1..12
                            mol_type = protein
                            organism = synthetic construct
SEQUENCE: 18
ATRPSSGSNF QA                                                             12
```

| | | |
|---|---|---|
| SEQ ID NO: 19 | moltype = AA length = 485 | |
| FEATURE | Location/Qualifiers | |
| source | 1..485 | |
| | mol_type = protein | |
| | organism = synthetic construct | |
| SEQUENCE: 19 | | |
| EVQLVESGGG LVQPGGSLRL SCAASGFTFS TYAMNWVRQA PGKGLEWVGR IRSKYNNYAT | | 60 |
| YYADSVKGRF TISRDDSKNT LYLQMNSLRA EDTAVYYCVR HGNFGDSYVS WFAYWGQGTL | | 120 |
| VTVSSASTKG PSVFPLAPSS KSTSGGTAAL GCLVKDYFPE PVTVSWNSGA LTSGVHTFPA | | 180 |
| VLQSSGLYSL SSVVTVPSSS LGTQTYICNV NHKPSNTKVD KRVEPKSCGG GGSQSVLTQD | | 240 |
| PAVSVALGQT VRITCTADTL SRSYASWYQQ KPGQAPVLVI YRDTSRPSGI PDRFSGSSSG | | 300 |
| NTASLTITGA QAEDEADYYC ATRPSSGSNF QLFGCGTKLT VLGGGGGSGG GGSGGGGSGG | | 360 |
| GGSEVQLLES GGGSVQPGGS LRLSCTVSGF SLSNYAMSWV RQAPGKCLEW IGIVSSGGTT | | 420 |
| YYADSVKGRF TISRDNSKNT VYLQMNSLRA EDTASYYCAK DLYYGPSTYF VANLWGQGTS | | 480 |
| VTVSS | | 485 |
| | | |
| SEQ ID NO: 20 | moltype = AA length = 122 | |
| FEATURE | Location/Qualifiers | |
| source | 1..122 | |
| | mol_type = protein | |
| | organism = synthetic construct | |
| SEQUENCE: 20 | | |
| EVQLLESGGG SVQPGGSLRL SCTVSGFSLS NYAMSWVRQA PGKCLEWIGI VSSGGTTYYA | | 60 |
| DSVKGRFTIS RDNSKNTVYL QMNSLRAEDT ASYYCAKDLY YGPSTYFVAN LWGQGTSVTV | | 120 |
| SS | | 122 |
| | | |
| SEQ ID NO: 21 | moltype = AA length = 6 | |
| FEATURE | Location/Qualifiers | |
| source | 1..6 | |
| | mol_type = protein | |
| | organism = synthetic construct | |
| SEQUENCE: 21 | | |
| SNYAMS | | 6 |
| | | |
| SEQ ID NO: 22 | moltype = AA length = 16 | |
| FEATURE | Location/Qualifiers | |
| source | 1..16 | |
| | mol_type = protein | |
| | organism = synthetic construct | |
| SEQUENCE: 22 | | |
| IVSSGGTTYY ADSVKG | | 16 |
| | | |
| SEQ ID NO: 23 | moltype = AA length = 14 | |
| FEATURE | Location/Qualifiers | |
| source | 1..14 | |
| | mol_type = protein | |
| | organism = synthetic construct | |
| SEQUENCE: 23 | | |
| DLYYGPSTYF VANL | | 14 |
| | | |
| SEQ ID NO: 24 | moltype = AA length = 472 | |
| FEATURE | Location/Qualifiers | |
| source | 1..472 | |
| | mol_type = protein | |
| | organism = synthetic construct | |
| SEQUENCE: 24 | | |
| QAVVTQEPSL TVSPGGTVTL TCGSSTGAVT TSNYANWVQQ KPGKSPRGLI GGTNKRAPGV | | 60 |
| PARFSGSLLG GKAALTISGA QPEDEADYYC ALWYSNHWVF GGGTKLTVLG QPKAAPSVTL | | 120 |
| FPPSSEELQA NKATLVCLIS DFYPGAVTVA WKADSSPVKA GVETTTPSKQ SNNKYAASSY | | 180 |
| LSLTPEQWKS HRSYSCQVTH EGSTVEKTVA PTECSGGGGS QSVLTQDPAV SVALGQTVRI | | 240 |
| TCTADTLSRS YASWYQQKPG QAPVLVIYRD TSRPSGIPDR FSGSSSGNTA SLTITGAQAE | | 300 |
| DEADYYCATR PSSGSNFQLF GCGTKLTVLG GGGSGGGGS GGGGSGGGGS EVQLLESGGG | | 360 |
| SVQPGGSLRL SCTVSGFSLS NYAMSWVRQA PGKCLEWIGI VSSGGTTYYA DSVKGRFTIS | | 420 |
| RDNSKNTVYL QMNSLRAEDT ASYYCAKDLY YGPSTYFVAN LWGQGTSVTV SS | | 472 |
| | | |
| SEQ ID NO: 25 | moltype = AA length = 110 | |
| FEATURE | Location/Qualifiers | |
| source | 1..110 | |
| | mol_type = protein | |
| | organism = synthetic construct | |
| SEQUENCE: 25 | | |
| QSVLTQDPAV SVALGQTVRI TCTADTLSRS YASWYQQKPG QAPVLVIYRD TSRPSGIPDR | | 60 |
| FSGSSSGNTA SLTITGAQAE DEADYYCATR PSSGSNFQLF GCGTKLTVLG | | 110 |
| | | |
| SEQ ID NO: 26 | moltype = AA length = 11 | |
| FEATURE | Location/Qualifiers | |
| source | 1..11 | |
| | mol_type = protein | |
| | organism = synthetic construct | |

```
SEQUENCE: 26
TADTLSRSYA S                                                              11

SEQ ID NO: 27           moltype = AA   length = 7
FEATURE                 Location/Qualifiers
source                  1..7
                        mol_type = protein
                        organism = synthetic construct
SEQUENCE: 27
RDTSRPS                                                                    7

SEQ ID NO: 28           moltype = AA   length = 12
FEATURE                 Location/Qualifiers
source                  1..12
                        mol_type = protein
                        organism = synthetic construct
SEQUENCE: 28
ATRPSSGSNF QL                                                             12

SEQ ID NO: 29           moltype = AA   length = 485
FEATURE                 Location/Qualifiers
source                  1..485
                        mol_type = protein
                        organism = synthetic construct
SEQUENCE: 29
EVQLVESGGG LVQPGGSLRL SCAASGFTFS TYAMNWVRQA PGKGLEWVGR IRSKYNNYAT          60
YYADSVKGRF TISRDDSKNT LYLQMNSLRA EDTAVYYCVR HGNFGDSYVS WFAYWGQGTL         120
VTVSSASTKG PSVFPLAPSS KSTSGGTAAL GCLVKDYFPE PVTVSWNSGA LTSGVHTFPA         180
VLQSSGLYSL SSVVTVPSSS LGTQTYICNV NHKPSNTKVD KRVEPKSCGG GGSSYELTQP         240
PSVSVSPGQT ASITCTADTL SRSYASWYQQ KPGQSPVLVI YRDTSRPSGI PERFSGSNSG         300
NTATLTISGT QAMDEADYYC ATRDFSGSNF QLFGCGTKLT VLGGGGGSGG GGSGGGGSGG         360
GGSEVQLLES GGGSVQPGGS LRLSCTVSGF SLSNYAMSWV RQAPGKCLEW IGIVSSGGTT         420
YYASWAKGRF TISKDTSKNT VYLQMNSLRA EDTASYYCAK DLYYGPTTYS AANLWGQGTS         480
VTVSS                                                                    485

SEQ ID NO: 30           moltype = AA   length = 122
FEATURE                 Location/Qualifiers
source                  1..122
                        mol_type = protein
                        organism = synthetic construct
SEQUENCE: 30
EVQLLESGGG SVQPGGSLRL SCTVSGFSLS NYAMSWVRQA PGKCLEWIGI VSSGGTTYYA          60
SWAKGRFTIS KDTSKNTVYL QMNSLRAEDT ASYYCAKDLY YGPTTYSAAN LWGQGTSVTV        120
SS                                                                       122

SEQ ID NO: 31           moltype = AA   length = 6
FEATURE                 Location/Qualifiers
source                  1..6
                        mol_type = protein
                        organism = synthetic construct
SEQUENCE: 31
SNYAMS                                                                     6

SEQ ID NO: 32           moltype = AA   length = 16
FEATURE                 Location/Qualifiers
source                  1..16
                        mol_type = protein
                        organism = synthetic construct
SEQUENCE: 32
IVSSGGTTYY ASWAKG                                                         16

SEQ ID NO: 33           moltype = AA   length = 14
FEATURE                 Location/Qualifiers
source                  1..14
                        mol_type = protein
                        organism = synthetic construct
SEQUENCE: 33
DLYYGPTTYS AANL                                                           14

SEQ ID NO: 34           moltype = AA   length = 472
FEATURE                 Location/Qualifiers
source                  1..472
                        mol_type = protein
                        organism = synthetic construct
SEQUENCE: 34
QAVVTQEPSL TVSPGGTVTL TCGSSTGAVT TSNYANWVQQ KPGKSPRGLI GGTNKRAPGV          60
PARFSGSLLG GKAALTISGA QPEDEADYYC ALWYSNHWVF GGGTKLTVLG QPKAAPSVTL         120
FPPSSEELQA NKATLVCLIS DFYPGAVTVA WKADSSPVKA GVETTTPSKQ SNNKYAASSY         180
LSLTPEQWKS HRSYSCQVTH EGSTVEKTVA PTECSGGGGS SYELTQPPSV SVSPGQTASI         240
```

```
TCTADTLSRS YASWYQQKPG QSPVLVIYRD TSRPSGIPER FSGSNSGNTA TLTISGTQAM    300
DEADYYCATR DFSGSNFQLF GCGTKLTVLG GGGGSGGGGS GGGGSGGGGS EVQLLESGGG    360
SVQPGGSLRL SCTVSGFSLS NYAMSWVRQA PGKCLEWIGI VSSGGTTYYA SWAKGRFTIS    420
KDTSKNTVYL QMNSLRAEDT ASYYCAKDLY YGPTTYSAAN LWGQGTSVTV SS            472

SEQ ID NO: 35           moltype = AA  length = 110
FEATURE                 Location/Qualifiers
source                  1..110
                        mol_type = protein
                        organism = synthetic construct
SEQUENCE: 35
SYELTQPPSV SVSPGQTASI TCTADTLSRS YASWYQQKPG QSPVLVIYRD TSRPSGIPER    60
FSGSNSGNTA TLTISGTQAM DEADYYCATR DFSGSNFQLF GCGTKLTVLG               110

SEQ ID NO: 36           moltype = AA  length = 11
FEATURE                 Location/Qualifiers
source                  1..11
                        mol_type = protein
                        organism = synthetic construct
SEQUENCE: 36
TADTLSRSYA S                                                         11

SEQ ID NO: 37           moltype = AA  length = 7
FEATURE                 Location/Qualifiers
source                  1..7
                        mol_type = protein
                        organism = synthetic construct
SEQUENCE: 37
RDTSRPS                                                              7

SEQ ID NO: 38           moltype = AA  length = 12
FEATURE                 Location/Qualifiers
source                  1..12
                        mol_type = protein
                        organism = synthetic construct
SEQUENCE: 38
ATRDFSGSNF QL                                                        12

SEQ ID NO: 39           moltype = AA  length = 486
FEATURE                 Location/Qualifiers
source                  1..486
                        mol_type = protein
                        organism = synthetic construct
SEQUENCE: 39
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL    120
VTVSSASTKG PSVFPLAPSS KSTSGGTAAL GCLVKDYFPE PVTVSWNSGA LTSGVHTFPA    180
VLQSSGLYSL SSVVTPSSS LGTQTYICNV NHKPSNTKVD KRVEPKSCGG GGSSYELTQP     240
PSVSVSPGQT ASITCTADTL SRSYASWYQQ KPGQSPVLVI YRDTSRPSGI PERFSGSNSG    300
NTATLTISGT QAMDEADYYC ATRPSSGSNF QAFGGGTKLT VLGGGGGSG GGGSGGGGS     360
GGGSEVQLLE SGGGSVQPGG SLRLSCTVSG FSLSNYAMSW VRQAPGKGLE YIGIVSSGGT    420
TYYASWAKGR FTISRDNSKN TVYLQMNSLR AEDTASYYCA KDLYYGPTTY SAFNLWGQGT    480
SVTVSS                                                               486

SEQ ID NO: 40           moltype = AA  length = 122
FEATURE                 Location/Qualifiers
source                  1..122
                        mol_type = protein
                        organism = synthetic construct
SEQUENCE: 40
EVQLLESGGG SVQPGGSLRL SCTVSGFSLS NYAMSWVRQA PGKGLEYIGI VSSGGTTYYA    60
SWAKGRFTIS RDNSKNTVYL QMNSLRAEDT ASYYCAKDLY YGPTTYSAFN LWGQGTSVTV    120
SS                                                                   122

SEQ ID NO: 41           moltype = AA  length = 6
FEATURE                 Location/Qualifiers
source                  1..6
                        mol_type = protein
                        organism = synthetic construct
SEQUENCE: 41
SNYAMS                                                               6

SEQ ID NO: 42           moltype = AA  length = 16
FEATURE                 Location/Qualifiers
source                  1..16
                        mol_type = protein
                        organism = synthetic construct
SEQUENCE: 42
IVSSGGTTYY ASWAKG                                                    16
```

```
SEQ ID NO: 43            moltype = AA  length = 14
FEATURE                  Location/Qualifiers
source                   1..14
                         mol_type = protein
                         organism = synthetic construct
SEQUENCE: 43
DLYYGPTTYS AFNL                                                        14

SEQ ID NO: 44            moltype = AA  length = 473
FEATURE                  Location/Qualifiers
source                   1..473
                         mol_type = protein
                         organism = synthetic construct
SEQUENCE: 44
QAVVTQEPSL TVSPGGTVTL TCGSSTGAVT TSNYANWVQQ KPGKSPRGLI GGTNKRAPGV       60
PARFSGSLLG GKAALTISGA QPEDEADYYC ALWYSNHWVF GGGTKLTVLG QPKAAPSVTL      120
FPPSSEELQA NKATLVCLIS DFYPGAVTVA WKADSSPVKA GVETTTPSKQ SNNKYAASSY      180
LSLTPEQWKS HRSYSCQVTH EGSTVEKTVA PTECSGGGGS SYELTQPPSV SVSPGQTASI      240
TCTADTLSRS YASWYQQKPG QSPVLVIYRD TSRPSGIPER FSGSNSGNTA TLTISGTQAM      300
DEADYYCATR PSSGSNFQAF GGGTKLTVLG GGGGSGGGG SGGGGSGGGG SEVQLLESGG       360
GSVQPGGSLR LSCTVSGFSL SNYAMSWVRQ APGKGLEYIG IVSSGGTTYY ASWAKGRFTI      420
SRDNSKNTVY LQMNSLRAED TASYYCAKDL YYGPTTYSAF NLWGQGTSVT VSS             473

SEQ ID NO: 45            moltype = AA  length = 110
FEATURE                  Location/Qualifiers
source                   1..110
                         mol_type = protein
                         organism = synthetic construct
SEQUENCE: 45
SYELTQPPSV SVSPGQTASI TCTADTLSRS YASWYQQKPG QSPVLVIYRD TSRPSGIPER       60
FSGSNSGNTA TLTISGTQAM DEADYYCATR PSSGSNFQAF GGGTKLTVLG                 110

SEQ ID NO: 46            moltype = AA  length = 11
FEATURE                  Location/Qualifiers
source                   1..11
                         mol_type = protein
                         organism = synthetic construct
SEQUENCE: 46
TADTLSRSYA S                                                            11

SEQ ID NO: 47            moltype = AA  length = 7
FEATURE                  Location/Qualifiers
source                   1..7
                         mol_type = protein
                         organism = synthetic construct
SEQUENCE: 47
RDTSRPS                                                                  7

SEQ ID NO: 48            moltype = AA  length = 12
FEATURE                  Location/Qualifiers
source                   1..12
                         mol_type = protein
                         organism = synthetic construct
SEQUENCE: 48
ATRPSSGSNF QA                                                           12

SEQ ID NO: 49            moltype = AA  length = 228
FEATURE                  Location/Qualifiers
source                   1..228
                         mol_type = protein
                         organism = synthetic construct
SEQUENCE: 49
EVQLVESGGG LVQPGGSLRL SCAASGFTFS TYAMNWVRQA PGKGLEWVGR IRSKYNNYAT       60
YYADSVKGRF TISRDDSKNT LYLQMNSLRA EDTAVYYCVR HGNFGDSYVS WFAYWGQGTL      120
VTVSSASTKG PSVFPLAPSS KSTSGGTAAL GCLVKDYFPE PVTVSWNSGA LTSGVHTFPA      180
VLQSSGLYSL SSVVTVPSSS LGTQTYICNV NHKPSNTKVD KRVEPKSC                   228

SEQ ID NO: 50            moltype = AA  length = 125
FEATURE                  Location/Qualifiers
source                   1..125
                         mol_type = protein
                         organism = synthetic construct
SEQUENCE: 50
EVQLVESGGG LVQPGGSLRL SCAASGFTFS TYAMNWVRQA PGKGLEWVGR IRSKYNNYAT       60
YYADSVKGRF TISRDDSKNT LYLQMNSLRA EDTAVYYCVR HGNFGDSYVS WFAYWGQGTL      120
VTVSS                                                                  125

SEQ ID NO: 51            moltype = AA  length = 6
```

```
FEATURE                 Location/Qualifiers
source                  1..6
                        mol_type = protein
                        organism = synthetic construct
SEQUENCE: 51
STYAMN                                                                    6

SEQ ID NO: 52           moltype = AA  length = 19
FEATURE                 Location/Qualifiers
source                  1..19
                        mol_type = protein
                        organism = synthetic construct
SEQUENCE: 52
RIRSKYNNYA TYYADSVKG                                                      19

SEQ ID NO: 53           moltype = AA  length = 14
FEATURE                 Location/Qualifiers
source                  1..14
                        mol_type = protein
                        organism = synthetic construct
SEQUENCE: 53
HGNFGDSYVS WFAY                                                           14

SEQ ID NO: 54           moltype = AA  length = 215
FEATURE                 Location/Qualifiers
source                  1..215
                        mol_type = protein
                        organism = synthetic construct
SEQUENCE: 54
QAVVTQEPSL TVSPGGTVTL TCGSSTGAVT TSNYANWVQQ KPGKSPRGLI GGTNKRAPGV          60
PARFSGSLLG GKAALTISGA QPEDEADYYC ALWYSNHWVF GGGTKLTVLG QPKAAPSVTL          120
FPPSSEELQA NKATLVCLIS DFYPGAVTVA WKADSSPVKA GVETTTPSKQ SNNKYAASSY          180
LSLTPEQWKS HRSYSCQVTH EGSTVEKTVA PTECS                                    215

SEQ ID NO: 55           moltype = AA  length = 110
FEATURE                 Location/Qualifiers
source                  1..110
                        mol_type = protein
                        organism = synthetic construct
SEQUENCE: 55
QAVVTQEPSL TVSPGGTVTL TCGSSTGAVT TSNYANWVQQ KPGKSPRGLI GGTNKRAPGV          60
PARFSGSLLG GKAALTISGA QPEDEADYYC ALWYSNHWVF GGGTKLTVLG                    110

SEQ ID NO: 56           moltype = AA  length = 14
FEATURE                 Location/Qualifiers
source                  1..14
                        mol_type = protein
                        organism = synthetic construct
SEQUENCE: 56
GSSTGAVTTS NYAN                                                           14

SEQ ID NO: 57           moltype = AA  length = 7
FEATURE                 Location/Qualifiers
source                  1..7
                        mol_type = protein
                        organism = synthetic construct
SEQUENCE: 57
GTNKRAP                                                                   7

SEQ ID NO: 58           moltype = AA  length = 9
FEATURE                 Location/Qualifiers
source                  1..9
                        mol_type = protein
                        organism = synthetic construct
SEQUENCE: 58
ALWYSNHWV                                                                 9

SEQ ID NO: 59           moltype = AA  length = 200
FEATURE                 Location/Qualifiers
source                  1..200
                        mol_type = protein
                        organism = synthetic construct
SEQUENCE: 59
MANQVEQSPQ SLIILEGKNV TLQCNYTVSP FSNLRWYKQD TGRGPVSLTI LTFSENTKSN          60
GRYTATLDAD TKQSSLHITA SQLSDSASYI CVVNSAQGLY IPTFGRGTSL IVHPYIQKPD          120
PAVYQLRDSK SSDKSVCLFT DFDSQTNVSQ SKDSDVYITD KCVLDMRSMD FKSNSAVAWS          180
NKSDFACANA FNNSIIPEDT                                                     200

SEQ ID NO: 60           moltype = AA  length = 506
```

```
FEATURE                 Location/Qualifiers
source                  1..506
                        mol_type = protein
                        organism = synthetic construct
SEQUENCE: 60
MAIQMTQSPS SLSASVGDRV TITCRASQDI RNYLNWYQQK PGKAPKLLIY YTSRLESGVP    60
SRFSGSGSGT DYTLTISSLQ PEDFATYYCQ QGNTLPWTFG QGTKVEIKGG GGSGGGGSGG   120
GGSGGGGSGG GGSEVQLVES GGGLVQPGGS LRLSCAASGY SFTGYTMNWV RQAPGKGLEW   180
VALINPYKGV STYNQKFKDR FTISVDKSKN TAYLQMNSLR AEDTAVYYCA RSGYYGDSDW   240
YFDVWGQGTL VTVSSGGGGS DVKVTQSSRY LVKRTGEKVF LECVQDLDHE NMFWYRQDPG   300
LGLRLIYFSR FATGKEKGDI PEGYSVSREK KERFSLILES ASTNQTSMYL CASSSDQNSG   360
DPYEQYFGPG TRLTVTEDLK NVFPPEVAVF EPSEAEISHT QKATLVCLAT GFYPDHVELS   420
WWVNGKEVHS GVCTDPQPLK EQPALNDSRY ALSSRLRVSA TFWQDPRNHF RCQVQFYGLS   480
ENDEWTQDRA KPVTQIVSAE AWGRAD                                       506

SEQ ID NO: 61           moltype = AA  length = 253
FEATURE                 Location/Qualifiers
source                  1..253
                        mol_type = protein
                        organism = synthetic construct
SEQUENCE: 61
QSVLTQDPAV SVALGQTVRI TCTADTLSRS YASWYQQKPG QAPVLVIYRD TSRPSGIPDR    60
FSGSSSGNTA SLTITGAQAE DEADYYCATR PSSGSNFQAF GGGTKLTVLG GGGGSGGGGS   120
GGGGSGGGGS EVQLLESGGG SVQPGGSLRL SCTVSGFSLS NYAMSWVRQA PGKGLEWIGI   180
VSSGGTTYYA DSVKGRFTIS RDNSKNTVYL QMNSLRAEDT ASYYCAKDLY YGPNTDYSAA   240
NLWGQGTSVT VSS                                                     253

SEQ ID NO: 62           moltype = AA  length = 252
FEATURE                 Location/Qualifiers
source                  1..252
                        mol_type = protein
                        organism = synthetic construct
SEQUENCE: 62
QSVLTQDPAV SVALGQTVRI TCTADTLSRS YASWYQQKPG QAPVLVIYRD TSRPSGIPDR    60
FSGSSSGNTA SLTITGAQAE DEADYYCATR PSSGSNFQLF GCGTKLTVLG GGGGSGGGGS   120
GGGGSGGGGS EVQLLESGGG SVQPGGSLRL SCTVSGFSLS NYAMSWVRQA PGKCLEWIGI   180
VSSGGTTYYA DSVKGRFTIS RDNSKNTVYL QMNSLRAEDT ASYYCAKDLY YGPSTYFVAN   240
LWGQGTSVTV SS                                                      252

SEQ ID NO: 63           moltype = AA  length = 252
FEATURE                 Location/Qualifiers
source                  1..252
                        mol_type = protein
                        organism = synthetic construct
SEQUENCE: 63
SYELTQPPSV SVSPGQTASI TCTADTLSRS YASWYQQKPG QSPVLVIYRD TSRPSGIPER    60
FSGSNSGNTA TLTISGTQAM DEADYYCATR DFSGSNFQLF GCGTKLTVLG GGGGSGGGGS   120
GGGGSGGGGS EVQLLESGGG SVQPGGSLRL SCTVSGFSLS NYAMSWVRQA PGKCLEWIGI   180
VSSGGTTYYA SWAKGRFTIS KDTSKNTVYL QMNSLRAEDT ASYYCAKDLY YGPTTYSAAN   240
LWGQGTSVTV SS                                                      252

SEQ ID NO: 64           moltype = AA  length = 253
FEATURE                 Location/Qualifiers
source                  1..253
                        mol_type = protein
                        organism = synthetic construct
SEQUENCE: 64
SYELTQPPSV SVSPGQTASI TCTADTLSRS YASWYQQKPG QSPVLVIYRD TSRPSGIPER    60
FSGSNSGNTA TLTISGTQAM DEADYYCATR PSSGSNFQLF GGGTKLTVLG GGGGSGGGGS   120
SGGGSGGGG SEVQLLESGG GSVQPGGSLR LSCTVSGFSL SNYAMSWVRQ APGKGLEYIG   180
IVSSGGTTYY ASWAKGRFTI SRDNSKNTVY LQMNSLRAED TASYYCAKDL YYGPTTYSAF   240
NLWGQGTSVT VSS                                                     253

SEQ ID NO: 65           moltype = AA  length = 665
FEATURE                 Location/Qualifiers
source                  1..665
                        mol_type = protein
                        organism = synthetic construct
SEQUENCE: 65
AQLVESGGGL VQPGGSLRLS CAASAYFSFK AMSWVRQAPG KGLEWVGSIS PSGGSTYYND    60
NVLGRFTISR DNSKNTLYLQ MNSLRAEDTA VYYCAKDVGF FDEWGQGTLV TVSSASTKGP   120
SVFPLAPSSK STSGGTAALG CLVEDYFPEP VTVSWNSGAL TSGVHTFPAV LQSSGLYSLS   180
SVVTVPSSSL GTQTYICNVN HKPSNTKVDE KVEPKSCDGG GGGGGGSDI QMTQSPSSLS   240
ASVGDRVTIT CRASQDIRNY LNWYQQKPGK APKLLIYYTS RLESGVPSRF SGSGSGTDYT   300
LTISSLQPED FATYYCQQGN TLPWTFGQGT KVEIKSSAST KGPSVFPLAP SSKSTSGGTA   360
ALGCLVKDYF PEPVTVSWNS GALTSGVHTF PAVLQSSGLY SLSSVVTVPS SSLGTQTYIC   420
NVNHKPSNTK VDKKVEPKSC DKTHTCPPCP APEAAGGPSV FLFPPKPKDT LMISRTPEVT   480
CVVVDVSHED PEVKFNWYVD GVEVHNAKTK PREEQYNSTY RVVSVLTVLH QDWLNGKEYK   540
CKVSNKALGA PIEKTISKAK GQPREPQVYT LPPCRDELTK NQVSLWCLVK GFYPSDIAVE   600
```

```
WESNGQPENN YKTTPPVLDS DGSFFLYSKL TVDKSRWQQG NVFSCSVMHE ALHNHYTQKS    660
LSLSP                                                               665

SEQ ID NO: 66           moltype = AA  length = 442
FEATURE                 Location/Qualifiers
source                  1..442
                        mol_type = protein
                        organism = synthetic construct
SEQUENCE: 66
AQLVESGGGL VQPGGSLRLS CAASAYFSFK AMSWVRQAPG KGLEWVGSIS PSGGSTYYND    60
NVLGRFTISR DNSKNTLYLQ MNSLRAEDTA VYYCAKDVGF FDEWGQGTLV TVSSASTKGP    120
SVFPLAPSSK STSGGTAALG CLVEDYFPEP VTVSWNSGAL TSGVHTFPAV LQSSGLYSLS    180
SVVTVPSSSL GTQTYICNVN HKPSNTKVDE KVEPKSCDKT HTCPPCPAPE AAGGPSVFLF    240
PPKPKDTLMI SRTPEVTCVV VDVSHEDPEV KFNWYVDGVE VHNAKTKPRE EQYNSTYRVV    300
SVLTVLHQDW LNGKEYKCKV SNKALGAPIE KTISKAKGQP REPQVCTLPP SRDELTKNQV    360
SLSCAVKGFY PSDIAVEWES NGQPENNYKT TPPVLDSDGS FFLVSKLTVD KSRWQQGNVF    420
SCSVMHEALH NHYTQKSLSL SP                                            442

SEQ ID NO: 67           moltype = AA  length = 214
FEATURE                 Location/Qualifiers
source                  1..214
                        mol_type = protein
                        organism = synthetic construct
SEQUENCE: 67
DIQMTQSPSS LSASVGDRVT ITCRASQSIS SYLAWYQQKP GKAPKLLIYD ASIRDIGVPS    60
RFSGSGSGTD FTLTISSLQP EDFATYYCQQ YSSYPYTFGQ GTKLEIKRTV AAPSVFIFPP    120
SDRKLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 68           moltype = AA  length = 10
FEATURE                 Location/Qualifiers
source                  1..10
                        mol_type = protein
                        organism = synthetic construct
SEQUENCE: 68
GLADGRTHTV                                                          10

SEQ ID NO: 69           moltype = AA  length = 10
FEATURE                 Location/Qualifiers
source                  1..10
                        mol_type = protein
                        organism = synthetic construct
SEQUENCE: 69
GLYDGPVHEV                                                          10

SEQ ID NO: 70           moltype = AA  length = 9
FEATURE                 Location/Qualifiers
source                  1..9
                        mol_type = protein
                        organism = synthetic construct
SEQUENCE: 70
GVFDGLHTV                                                           9

SEQ ID NO: 71           moltype = AA  length = 10
FEATURE                 Location/Qualifiers
source                  1..10
                        mol_type = protein
                        organism = synthetic construct
SEQUENCE: 71
GLYDGREHSV                                                          10

SEQ ID NO: 72           moltype = AA  length = 10
FEATURE                 Location/Qualifiers
source                  1..10
                        mol_type = protein
                        organism = synthetic construct
SEQUENCE: 72
GIYDGKRHLI                                                          10

SEQ ID NO: 73           moltype = AA  length = 25
FEATURE                 Location/Qualifiers
source                  1..25
                        mol_type = protein
                        organism = synthetic construct
REPEAT                  1..25
                        note = This sequence may encompass 1-5 "Gly GLy Gly Gly
                        Ser" repeating units
SEQUENCE: 73
GGGGSGGGGS GGGGSGGGGS GGGGS                                         25
```

```
SEQ ID NO: 74            moltype = AA  length = 5
FEATURE                  Location/Qualifiers
source                   1..5
                         mol_type = protein
                         organism = synthetic construct
SEQUENCE: 74
GGGGS                                                                     5

SEQ ID NO: 75            moltype = AA  length = 15
FEATURE                  Location/Qualifiers
source                   1..15
                         mol_type = protein
                         organism = synthetic construct
SEQUENCE: 75
GGGGSGGGGS GGGGS                                                         15

SEQ ID NO: 76            moltype = AA  length = 20
FEATURE                  Location/Qualifiers
source                   1..20
                         mol_type = protein
                         organism = synthetic construct
SEQUENCE: 76
GGGGSGGGGS GGGGSGGGGS                                                    20

SEQ ID NO: 77            moltype = AA  length = 21
FEATURE                  Location/Qualifiers
source                   1..21
                         mol_type = protein
                         organism = synthetic construct
SEQUENCE: 77
GGGGSGGGGS GGGGSGGGGA S                                                  21

SEQ ID NO: 78            moltype = AA  length = 21
FEATURE                  Location/Qualifiers
source                   1..21
                         mol_type = protein
                         organism = synthetic construct
SEQUENCE: 78
GGGGGSGGGG SGGGGSGGGG S                                                  21

SEQ ID NO: 79            moltype = AA  length = 5
FEATURE                  Location/Qualifiers
source                   1..5
                         mol_type = protein
                         organism = synthetic construct
SEQUENCE: 79
DGGGS                                                                     5

SEQ ID NO: 80            moltype = AA  length = 5
FEATURE                  Location/Qualifiers
source                   1..5
                         mol_type = protein
                         organism = synthetic construct
SEQUENCE: 80
TGEKP                                                                     5

SEQ ID NO: 81            moltype = AA  length = 4
FEATURE                  Location/Qualifiers
source                   1..4
                         mol_type = protein
                         organism = synthetic construct
SEQUENCE: 81
GGRR                                                                      4

SEQ ID NO: 82            moltype = AA  length = 14
FEATURE                  Location/Qualifiers
source                   1..14
                         mol_type = protein
                         organism = synthetic construct
SEQUENCE: 82
EGKSSGSGSE SKVD                                                          14

SEQ ID NO: 83            moltype = AA  length = 18
FEATURE                  Location/Qualifiers
source                   1..18
                         mol_type = protein
                         organism = synthetic construct
SEQUENCE: 83
```

```
KESGSVSSEQ LAQFRSLD                                                              18

SEQ ID NO: 84            moltype = AA  length = 8
FEATURE                  Location/Qualifiers
source                   1..8
                         mol_type = protein
                         organism = synthetic construct
SEQUENCE: 84
GGRRGGGS                                                                         8

SEQ ID NO: 85            moltype = AA  length = 9
FEATURE                  Location/Qualifiers
source                   1..9
                         mol_type = protein
                         organism = synthetic construct
SEQUENCE: 85
LRQRDGERP                                                                        9

SEQ ID NO: 86            moltype = AA  length = 12
FEATURE                  Location/Qualifiers
source                   1..12
                         mol_type = protein
                         organism = synthetic construct
SEQUENCE: 86
LRQKDGGGSE RP                                                                   12

SEQ ID NO: 87            moltype = AA  length = 18
FEATURE                  Location/Qualifiers
source                   1..18
                         mol_type = protein
                         organism = synthetic construct
SEQUENCE: 87
GSTSGSGKPG SGEGSTKG                                                             18

SEQ ID NO: 88            moltype = AA  length = 5
FEATURE                  Location/Qualifiers
source                   1..5
                         mol_type = protein
                         organism = synthetic construct
SEQUENCE: 88
EPKSC                                                                            5
```

What is claimed:

1. An antigen binding protein which specifically binds to Melanoma-Associated Antigen A4 (MAGE-A4) peptide-MHC (pMHC), comprising:
   an antibody heavy chain variable (VH) domain comprising an amino acid sequence that is at least about 90% identical to the amino acid sequence of SEQ ID NO: 10, and comprises an HCDR1 sequence comprising the amino acid sequence of SNYAMS (SEQ ID NO: 11), an HCDR2 sequence comprising the amino acid sequence of IVSSGGTTYYADSVKG (SEQ ID NO: 12), and an HCDR3 sequence comprising the amino acid sequence of DLYYGPNTDYSAANL (SEQ ID NO: 13), and
   an antibody light chain variable (VL) domain comprising an amino acid sequence that is at least about 90% identical to the amino acid sequence of SEQ ID NO: 15 and comprises an LCDR1 sequence comprising the amino acid sequence of TADTLSRSYAS (SEQ ID NO: 16), an LCDR2 sequence comprising the amino acid sequence of RDTSRPS (SEQ ID NO: 17), and an LCDR3 sequence comprising the amino acid sequence of ATRPSSGSNFQA (SEQ ID NO: 18).

2. The antigen binding protein of claim 1, wherein said MAGE-A4 pMHC complex is a GVYDGREHTV (SEQ ID NO: 3) HLA-A*02 complex.

3. The antigen binding protein of claim 1, being a full-length immunoglobulin or an antibody fragment.

4. The antigen binding protein of claim 3, wherein the antibody fragment is a Fab, a Fab', a F(ab')₂, a scFv, or a Fv fragment.

5. A multispecific antigen binding protein comprising the antigen binding protein of claim 1.

6. The multispecific antigen binding protein of claim 5, further comprising at least one additional binding domain of an antibody.

7. The multispecific antigen binding protein of claim 6, wherein said at least one additional binding domain of an antibody is an immune cell engager.

8. The multispecific antigen binding protein of claim 7, wherein the immune cell engager is a CD3-binding domain.

9. The multispecific antigen binding protein of claim 7, wherein the immune cell engager is a CD16a-binding domain.

10. A kit comprising the antigen binding protein of claim 1.

11. A pharmaceutical composition comprising the antigen binding protein of claim 1, and a pharmaceutically acceptable buffer.

12. The antigen binding protein of claim 1, comprising a VH domain comprising the amino acid sequence of SEQ ID NO: 10, and a VL domain comprising the amino acid sequence of SEQ ID NO: 15.

13. A multispecific antigen binding protein comprising:
   a) a first antigen binding domain of an antibody which specifically binds to CD3;
   b) a second antigen binding domain which specifically binds to Melanoma-Associated Antigen A4 (MAGE-A4) peptide-MHC (pMHC), the second antigen binding domain comprising:

b1) an antibody heavy chain variable (VH) domain comprising an amino acid sequence that is at least about 90% identical to the amino acid sequence of SEQ ID NO: 10, and comprises an HCDR1 sequence comprising the amino acid sequence of SNYAMS (SEQ ID NO: 11), an HCDR2 sequence comprising the amino acid sequence of IVSSGGTTYYADSVKG (SEQ ID NO: 12), and an HCDR3 sequence comprising the amino acid sequence of DLYYGPNTDYSAANL (SEQ ID NO: 13), and b2) an antibody light chain variable (VL) domain comprising an amino acid sequence that is at least about 90% identical to the amino acid sequence of SEQ ID NO: 15 and comprises an LCDR1 sequence comprising the amino acid sequence of TADTLSRSYAS (SEQ ID NO: 16), an LCDR2 sequence comprising the amino acid sequence of RDTSRPS (SEQ ID NO: 17), and an LCDR3 sequence comprising the amino acid sequence of ATRPSSGSNFQA (SEQ ID NO: 18); and c) a third antigen binding domain which specifically binds to MAGE-A4 pMHC, said third antigen binding domain comprising:

c1) a VH domain comprising an amino acid sequence that is at least about 90% identical to the amino acid sequence of SEQ ID NO: 10, and comprises an HCDR1 sequence comprising the amino acid sequence of SNYAMS (SEQ ID NO: 11), an HCDR2 sequence comprising the amino acid sequence of IVSSGGTTYYADSVKG (SEQ ID NO: 12), and an HCDR3 sequence comprising the amino acid sequence of DLYYGPNTDYSAANL (SEQ ID NO: 13), and c2) a VL domain comprising an amino acid sequence that is at least about 90%/o identical to the amino acid sequence of SEQ ID NO: 15 and comprises an LCDR1 sequence comprising the amino acid sequence of TADTLSRSYAS (SEQ ID NO: 16), an LCDR2 sequence comprising the amino acid sequence of RDTSRPS (SEQ ID NO: 17), and an LCDR3 sequence comprising the amino acid sequence of ATRPSSG-SNFQA (SEQ ID NO: 18).

14. The multispecific antigen binding protein of claim 13, wherein the multispecific antigen binding protein does not comprise an Fc domain.

15. The multispecific antigen binding protein of claim 13, wherein the CD3 antigen binding domain comprises:

a1) a VH comprising an HCDR1 sequence comprising the amino acid sequence of STYAMN (SEQ ID NO: 51), an HCDR2 sequence comprising the amino acid sequence of RIRSKYNNYATYYADSVKG (SEQ ID NO: 52), and an HCDR3 sequence comprising the amino acid sequence of HGNFGDSYVSWFAY (SEQ ID NO: 53); and a2) a VL comprising an LCDR1 sequence comprising the amino acid sequence of GSSTGAVTTSNYAN (SEQ ID NO: 56), an LCDR2 sequence comprising the amino acid sequence of GTNKRAP (SEQ ID NO: 57), and an LCDR3 sequence comprising the amino acid sequence of ALWYSNHWV (SEQ ID NO: 58).

16. The multispecific antigen binding protein of claim 15, wherein the CD3 antigen binding domain comprises
a VH comprising an amino acid sequence that is at least about 90% identical to the amino acid sequence of SEQ ID NO: 49, and
a VL comprising an amino acid sequence that is at least about 90% identical to the amino acid sequence of SEQ ID NO: 54.

17. The multispecific antigen binding protein of claim 16, comprising a posttranslational modification.

18. The multispecific antigen binding protein of claim 16, wherein the VH and/or the VL of the CD3 antigen binding domain comprises a pyroglutamate (pE) at amino acid position 1 instead of glutamine (Q) or glutamate (E).

19. The multispecific antigen binding protein of claim 16, wherein the VH and/or the VL of the CD3 antigen binding domain comprises an N-terminal truncation and/or a C-terminal truncation of 1, 2, 3, 4 or 5 amino acids compared to SEQ ID NO: 49 and SEQ ID NO: 54, respectively.

20. The multispecific antigen binding protein of claim 13, being linked to or combined with a functional entity.

21. The multispecific antigen binding protein of claim 20, wherein the functional entity is a detectable label, a therapeutic agent or a PK modifying moiety.

22. The multispecific antigen binding protein of claim 13, wherein:
the second antigen binding domain comprising a VH domain comprising the amino acid sequence of SEQ ID NO: 10, and a VL domain comprising the amino acid sequence of SEQ ID NO: 15; and
the third antigen binding domain comprising a VH domain comprising the amino acid sequence of SEQ ID NO: 10, and a VL domain comprising the amino acid sequence of SEQ ID NO: 15.

23. The multispecific antigen binding protein of claim 13, wherein:
the first antigen binding domain comprises a VH domain comprising the amino acid sequence of SEQ ID NO: 50, and a VL domain comprising the amino acid sequence u der of SEQ ID NO: 55;
the second antigen binding domain comprising a VH domain comprising the amino acid sequence of SEQ ID NO: 10, and a VL domain comprising the amino acid sequence of SEQ ID NO: 15; and
the third antigen binding domain comprising a VH domain comprising the amino acid sequence of SEQ ID NO: 10, and a VL domain comprising the amino acid sequence of SEQ ID NO: 15.

24. The multispecific antigen binding protein of claim 13, wherein the first antigen binding domain is a Fab comprising a heavy chain and a light chain, the second antigen binding domain is an scFv, and the third antigen binding domain is an scFv.

25. The multispecific antigen binding protein of claim 24, wherein the second antigen binding domain is operatively linked via an amino acid linker to the C-terminus of the Fab heavy chain, and the third antigen binding domain is operatively linked to the C-terminus of the Fab light chain.

26. The multispecific antigen binding protein of claim 25, wherein the amino acid linker comprises GGGGS (SEQ ID NO: 74), GGGGSGGGGSGGGGS (SEQ ID NO: 75), GGGGSGGGGSGGGGSGGGGS (SEQ ID NO: 76), GGGGSGGGGSGGGGSGGGGAS (SEQ ID NO: 77), or GGGGGSGGGGSGGGGSGGGGS (SEQ ID NO: 78).

27. A kit comprising the multispecific antigen binding protein of claim 13.

28. A pharmaceutical composition comprising the multispecific antigen binding protein of claim 13, and a pharmaceutically acceptable buffer.

29. The multispecific antigen binding protein of claim 15, wherein the CD3 antigen binding domain comprises
a VH comprising an amino acid sequence that is at least about 90% identical to the amino acid sequence of SEQ ID NO: 50, and a VL comprising an amino acid sequence that is at least about 90% identical to the amino acid sequence of SEQ ID NO: 55.

30. The multispecific antigen binding protein of claim 29, comprising a posttranslational modification.

31. The multispecific antigen binding protein of claim 29, wherein the VH and/or the VL of the CD3 antigen binding domain comprises a pyroglutamate (pE) at amino acid position 1 instead of glutamine (Q) or glutamate (E).

32. The multispecific antigen binding protein of claim 29, wherein the VH and/or the VL of the CD3 antigen binding domain comprises an N-terminal truncation and/or a C-terminal truncation of 1, 2, 3, 4 or 5 amino acids compared to SEQ ID NO: 50 and SEQ ID NO: 55, respectively.

33. A multispecific antigen binding protein binding to GVYDGREHTV (SEQ ID NO: 3) HLA-A*02 complex and to CD3 comprising a first polypeptide chain comprising the amino acid sequence set forth in SEQ ID NO: 9, of a variant thereof being at least 90% identical to SEQ ID NO: 9, and a second polypeptide chain comprising the amino acid sequence set forth in SEQ ID NO: 14, or a variant thereof being at least 90% identical to SEQ ID NO: 14, wherein:
   i) the first polypeptide chain comprises:
   ia) an antigen binding domain binding to the GVYDGREHTV (SEQ ID NO: 3) HLA-A*02 complex, comprising an HCDR1 sequence comprising the amino acid sequence of SNYAMS (SEQ ID NO: 11), an HCDR2 sequence comprising the amino acid sequence of IVSSGGTTYYADSVKG (SEQ ID NO: 12), and an HCDR3 sequence comprising the amino acid sequence of DLYYGPNTDYSAANL (SEQ ID NO: 13) and an LCDR1 sequence comprising the amino acid sequence of TADTLSRSYAS (SEQ ID NO: 16), an LCDR2 sequence comprising the amino acid sequence of RDTSRPS (SEQ ID NO: 17), and an LCDR3 sequence comprising the amino acid sequence of ATRPSSG-SNFQA (SEQ ID NO: 18); and
   ib) an antibody heavy chain variable (VH) domain of a CD3 antigen binding domain, comprising an HCDR1 sequence comprising the amino acid sequence of STYAMN (SEQ ID NO: 51), an HCDR2 sequence comprising the amino acid sequence of RIRSKYN-NYATYYADSVKG (SEQ ID NO: 52), and an HCDR3 sequence comprising the amino acid sequence of HGNFGDSYVSWFAY (SEQ ID NO: 53); and
   ii) the second polypeptide chain comprises:
   iia) an antigen binding domain binding to the GVYDGREHTV (SEQ ID NO: 3) HLA-A*02 complex, comprising an HCDR1 sequence comprising the amino acid sequence of SNYAMS (SEQ ID NO: 11), an HCDR2 sequence comprising the amino acid sequence of IVSSGGTTYYADSVKG (SEQ ID NO: 12), and an HCDR3 sequence comprising the amino acid sequence of DLYYGPNTDYSAANL (SEQ ID NO: 13) and an LCDR1 sequence comprising the amino acid sequence of TADTLSRSYAS (SEQ ID NO: 16), an LCDR2 sequence comprising the amino acid sequence of RDTSRPS (SEQ ID NO: 17), and an LCDR3 sequence comprising the amino acid sequence of ATRPSSG-SNFQA (SEQ ID NO: 18); and
   iib) an antibody light chain variable (VL) domain of a CD3 antigen binding domain, comprising an LCDR1 sequence comprising the amino acid sequence of GSSTGAVTTSNYAN (SEQ ID NO: 56), an LCDR1 sequence comprising the amino acid sequence of GTNKRAP (SEQ ID NO: 57), and an LCDR3 sequence comprising the amino acid sequence of ALWYSNHWV (SEQ ID NO: 58).

34. The multispecific antigen binding protein of claim 33, comprising a posttranslational modification.

35. The multispecific antigen binding protein of claim 33, wherein the first polypeptide chain and/or the second polypeptide chain comprises a pyroglutamate (pE) at amino acid position 1 instead of glutamine (Q) or glutamate (E).

36. The multispecific antigen binding protein of claim 33, wherein the first polypeptide chain and/or the second polypeptide chain comprises an N-terminal truncation and/or a C-terminal truncation of 1, 2, 3, 4 or 5 amino acids compared to SEQ ID NO: 9 and SEQ ID NO: 14, respectively.

37. A kit comprising the multispecific antigen binding protein of claim 33.

38. A pharmaceutical composition comprising the multispecific antigen binding protein of claim 33, and a pharmaceutically acceptable buffer.

39. The multispecific antigen binding protein of claim 33, wherein the first polypeptide chain comprises the amino acid sequence set forth in SEQ ID NO: 9 and the second polypeptide chain comprises the amino acid sequence set forth in SEQ ID NO: 14.

40. The multispecific antigen binding protein of claim 33, wherein the first polypeptide chain consists of the amino acid sequence set forth in SEQ ID NO: 9 and the second polypeptide chain consists of the amino acid sequence set forth in SEQ ID NO: 14.

* * * * *